United States Patent
Shamloo et al.

(10) Patent No.: US 11,173,144 B2
(45) Date of Patent: Nov. 16, 2021

(54) ADRENERGIC RECEPTOR MODULATING COMPOUNDS AND METHODS OF USING THE SAME

(71) Applicant: The Board of Trustees of the Leland Stanford Junior University, Stanford, CA (US)

(72) Inventors: Mehrdad Shamloo, Stanford, CA (US); Alam Jahangir, San Jose, CA (US); Bitna Yi, San Mateo, CA (US); Andrew Kelley Evans, Essex Junction, VT (US); Michael John Green, Half Moon Bay, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 196 days.

(21) Appl. No.: 16/099,802

(22) PCT Filed: May 12, 2017

(86) PCT No.: PCT/US2017/032505
§ 371 (c)(1),
(2) Date: Nov. 8, 2018

(87) PCT Pub. No.: WO2017/197324
PCT Pub. Date: Nov. 16, 2017

(65) Prior Publication Data
US 2020/0237724 A1    Jul. 30, 2020

Related U.S. Application Data

(60) Provisional application No. 62/336,370, filed on May 13, 2016.

(51) Int. Cl.
| | | |
|---|---|---|
| *A61K 31/416* | (2006.01) | |
| *A61K 31/138* | (2006.01) | |
| *A61K 31/216* | (2006.01) | |
| *A61P 25/28* | (2006.01) | |
| *A61P 11/00* | (2006.01) | |
| *A61P 29/00* | (2006.01) | |
| *A61P 35/00* | (2006.01) | |
| *A61K 31/397* | (2006.01) | |
| *A61K 31/4453* | (2006.01) | |
| *A61K 31/5377* | (2006.01) | |

(52) U.S. Cl.
CPC .......... *A61K 31/416* (2013.01); *A61K 31/138* (2013.01); *A61K 31/216* (2013.01); *A61K 31/397* (2013.01); *A61K 31/4453* (2013.01); *A61K 31/5377* (2013.01); *A61P 11/00* (2018.01); *A61P 25/28* (2018.01); *A61P 29/00* (2018.01); *A61P 35/00* (2018.01)

(58) Field of Classification Search
CPC ... A61K 31/416; A61K 31/138; A61K 31/216
See application file for complete search history.

(56) References Cited

U.S. PATENT DOCUMENTS

| 4,143,149 A | * | 3/1979 | Wiedemann | .............. A61P 9/00 514/406 |
| 4,346,093 A | * | 8/1982 | Friebe | ....................... A61P 9/00 514/359 |
| 5,098,996 A | | 3/1992 | Jacobson et al. | |
| 2006/0247311 A1 | | 11/2006 | Fraser et al. | |

FOREIGN PATENT DOCUMENTS

| EP | 0 042 593 A1 | 12/1981 |
| JP | S 54-22364 | 2/1979 |
| JP | S 55-120559 | 9/1980 |
| JP | S 55-167263 | 12/1980 |
| JP | H 9-510964 | 11/1997 |
| JP | 2004-534772 | 11/2004 |
| JP | 2008-521805 | 6/2008 |
| WO | WO 2001/07026 | 2/2001 |
| WO | WO 2001/007026 A2 | 2/2001 |
| WO | WO 2001/078709 A2 | 10/2001 |
| WO | WO 2010/099217 A1 | 9/2010 |
| WO | WO 2011/133226 A2 | 10/2011 |
| WO | WO 2015/126915 A2 | 8/2015 |

OTHER PUBLICATIONS

Extended European Search Report dated Mar. 25, 2020, regarding EP 17 79 6976.
Groszek, G. et al.: "*Synthesis and adrenolytic activity of 1-(1H-indol-4-yloxy)-3-{[2-(2-methoxypheno xy)ethyl]amino}propan-2-ol and its enantiomers. Part I*"; Eur. J. Med. Chem., Feb. 1, 2009, 44(2), 809-817, XP025950212.
International Search Report dated Sep. 21, 2017, regarding PCT/US2017/032505.
Partial Supplementary European Search Report dated Dec. 17, 2019, regarding EP 17 79 6976.
Bednarski et al., "Synthesis and Pharmacological Activity of a New Series of 1-(1H-Indol-4-yloxy)-3-(2-(2-methoxyphenoxy)ethylamino)-propan-2-ol Analogs", Arch. Pharm. Chem. Life Sci, 349:211-223, Jan. 2016.

(Continued)

*Primary Examiner* — Karen Cheng
(74) *Attorney, Agent, or Firm* — DLA Piper LLP (US)

(57) ABSTRACT

Adrenergic receptor modulating compounds and methods of using the same are provided. Also provided are methods of treating a subject for a disease or condition associated with an adrenergic receptor including administering a therapeutically effective amount of the subject compound. Aspects of the disclosure include a method of modulating an inflammatory pathway in a cell, such as the production of TNF-alpha in the cell. The method can include contacting a cell with β1-selective adrenergic receptor modulating compound to selectively activate a cAMP pathway over a beta-arrestin pathway in the cell. Pharmaceutical compositions and kits which include the subject compounds are provided.

11 Claims, 39 Drawing Sheets

(56) References Cited

OTHER PUBLICATIONS

Groszek et al., "Synthesis and adrenolytic activity of 1-(1H-indol-4-yloxy)-3-{[2-(2-methoxyphenoxy)ethyl]amino} propan-2-ol and its enantiomers. Part 1", European Journal of Medicinal Chemistry 44(2009):809-817, Jul. 2008.

JP Office Action in Japanese Application No. 2018-559812, dated Mar. 9, 2021, 13 pages (with English translation).

Registry (STN) [online, Date: Dec. 7, 2011, search date: Feb. 12, 2021, CAS Registration No. 1350167 to 05, 3, 1350159-6, 1349694-62, and CAS Registry No. 06 to 7, 1349433-74-4, 1349209-80-8, 1348892-06-7, 1348447-94-8, 1348443-86-6, 1348340-50-0, 1347818-20-5, 1347436-35-4. 1347126-82-2. 1161069-04-0. 1028281-12-0. 14 pages.

Tejani-Butt et al., Structural derivatives of pindolol: relationship between in vivo and in vitro potencies for their interaction with central beta-adrenergic receptors, Life Sciences 41(8):995-1002, Jun. 1987.

* cited by examiner

ADRENERGIC RECEPTOR MODULATING COMPOUNDS AND METHODS OF USING THE SAME

CROSS-REFERENCE

This application claims the benefit of U.S. Provisional Patent Application No. 62/336,370, filed May 13, 2016, which application is incorporated herein by reference in its entirety.

STATEMENT OF GOVERNMENTAL SUPPORT

This invention was made with Government support under contract TR001085 awarded by the National Institutes of Health. The Government has certain rights in the invention.

INTRODUCTION

Adrenergic receptors (ADRs) are G-protein coupled receptors (GPCR) that are widely expressed throughout the body and play an important role in regulating multiple physiological processes including cognition, stress-related behavior, inflammation, and smooth muscle contraction/dilation, cardiac muscle contraction, airway reactivity and cognition. In addition, adrenergic receptors are associated with a number of diseases. There exist multiple subtypes.

Because these subtypes are expressed in distinct patterns and involved in different physiological processes, ligands that can selectively target one subtype have therapeutic potential for multiple diseases. However, discovery of subtype-selective ligands has been challenging due to a high level of sequence homology shared by these subtypes. As a class of G-protein coupled receptor, adrenergic receptors signal via G protein- and beta-arrestin-dependent pathways. G protein- or beta-arrestin signaling can mediate different physiological responses.

Adrenergic receptors mediate the central and peripheral effects of noradrenaline (NA) and adrenaline. Multiple subtypes of ADRs exist. Each subtype is expressed in distinct patterns and involved in different physiological processes. Therefore, ligands that selectively target one subtype are valuable both as research tools to identify the roles of different ADR subtypes and as therapeutic agents for multiple diseases related to dysfunction of the NA and adrenaline systems.

SUMMARY

Adrenergic receptor modulating compounds and methods of using the same are provided. Also provided are methods of treating a subject for a disease or condition associated with an adrenergic receptor including administering a therapeutically effective amount of the subject compound. Aspects of the disclosure include a method of modulating an inflammatory pathway in a cell, such as the production of TNF-alpha in the cell. The method can include contacting a cell with a β1-selective adrenergic receptor modulating compound to selectively activate a cAMP pathway over a beta-arrestin pathway in the cell. Pharmaceutical compositions and kits which include the subject compounds are provided.

BRIEF DESCRIPTION OF THE DRAWINGS

The invention is best understood from the following detailed description when read in conjunction with the accompanying drawings. The patent or application file contains at least one drawing executed in color. It is emphasized that, according to common practice, the various features of the drawings are not to-scale. On the contrary, the dimensions of the various features are arbitrarily expanded or reduced for clarity. Included in the drawings are the following figures.

DEFINITIONS

Figure 1:
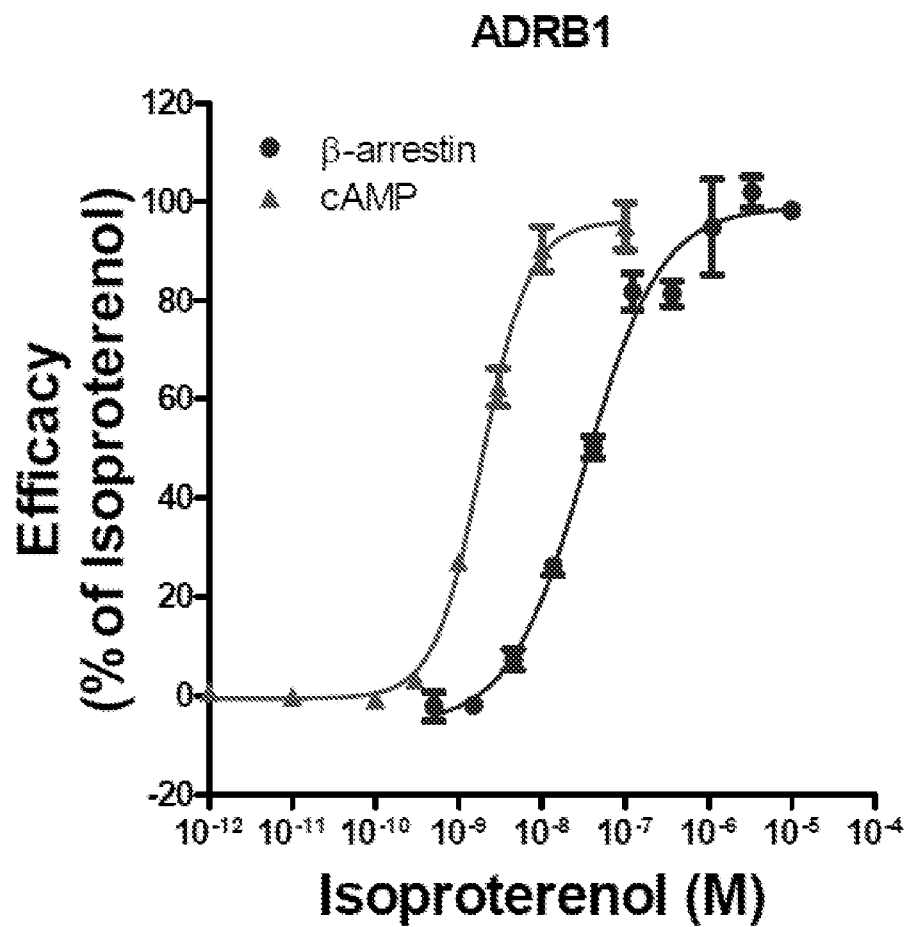
FIG. 1 illustrates the control compound isoproterenol activates both cAMP and β-arrestin pathways in a cell.

Unless defined otherwise, all technical and scientific terms used herein have the same meaning as is commonly understood by one of skill in the art to which this invention belongs. All patents and publications referred to herein are incorporated by reference. As used in the specification and claims, the singular form "a", "an" and "the" include plural references unless the context clearly dictates otherwise.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2$CH—), n-butyl ($CH_3CH_2CH_2CH_2$—), isobutyl (($CH_3)_2$CHCH_2$—), sec-butyl (($CH_3)(CH_3CH_2)$CH—), t-butyl (($CH_3)_3$C—), n-pentyl ($CH_3CH_2CH_2CH_2CH_2$—), and neopentyl (($CH_3)_3$CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cydoalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cydoalkenyl, substituted cydoalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocydooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cydoalkenyl, substituted cydoalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocydooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cydoalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O) substituted alkyl, N R$^{20}$C(O)cycloalkyl, —NR$^{20}$C(O) substituted cycloalkyl, —NR$^{20}$C(O)cycloalkenyl, —NR$^{20}$C(O) substituted cycloalkenyl, —NR$^{20}$C(O) alkenyl, —NR$^{20}$C(O) substituted alkenyl, —NR$^{20}$C(O) alkynyl, —NR$^{20}$C(O) substituted alkynyl, —NR$^{20}$C(O)aryl, —NR$^{20}$C(O) substituted aryl, —NR$^{20}$C(O)heteroaryl, —NR$^{20}$C(O) substituted heteroaryl, —NR$^{20}$C(O)heterocyclic, and —NR$^{20}$C(O) substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cydoalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cydoalkenyl, substituted cydoalkenyl, aryl, substituted aryl, heteroaryl, substituted heteroaryl, heterocyclic, and substituted heterocyclic are as defined herein.

"Aminocarbonylamino" refers to the group —NR$^{21}$C(O) NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O) O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cydoalkyl, cycloalkenyl, substituted cydoalkenyl, heteroaryl, substituted heteroaryl, heterocydic, substituted heterocydic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cydoalkyl, cycloalkenyl, substituted cycloalkenyl, heteroaryl, substituted heteroaryl, heterocydic, and substituted heterocydic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocydooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cydoalkyl, —C(O)O-substituted cydoalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocydic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O— alkyl, —O—C(O)O-substituted alkyl, —O—C(O)O-alkenyl, —O—C(O)O-substituted alkenyl, —O—C(O)O— alkynyl, —O—C(O)O-substituted alkynyl, —O—C(O)O-aryl, —O—C(O)O-substituted aryl, —O—C(O)O— cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cydopropyl, cyclobutyl, cydopentyl, cyclooctyl, and the like, or multiple ring structures such as adamantanyl, and the like.

The term "substituted cydoalkyl" refers to cycloalkyl groups having from 1 to 5 substituents, or from 1 to 3 substituents, selected from alkyl, substituted alkyl, alkoxy, substituted alkoxy, cycloalkyl, substituted cydoalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocydooxy, thiol, thioalkoxy, substituted thioalkoxy, aryl, aryloxy, heteroaryl, heteroaryloxy, heterocydyl, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cydoalkenyl" refers to cycloalkenyl groups having from 1 to 5 substituents, or from 1 to 3 substituents, selected from alkoxy, substituted alkoxy, cydoalkyl, substituted cycloalkyl, cycloalkenyl, substituted cydoalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocydooxy, thiol, thioalkoxy, substituted thioalkoxy, aryl, aryloxy, heteroaryl, heteroaryloxy, heterocydyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cydoalkenyl, substituted alkyl, substituted alkoxy, substituted alkenyl, substituted alkynyl, substituted cydoalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocydooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$— substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocyde," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cydoalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cydoalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocydyloxy" refers to the group —O-heterocyclyl.

The term "heterocyclylthio" refers to the group heterocydic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (═O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$— substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (═S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocydooxy" refers to the group heterocydyl-S— wherein the heterocyclyl group is as defined herein inducing optionally substituted heterocydyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$ M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$ (M$^+$)$_2$, —P(O)(OR$^{70}$)O$^-$ M$^+$, —P(O)(OR$^{70}$)$_2$, —C(O)R$^{70}$, —C(S)R$^{70}$, —C(NR$^{70}$)R$^{70}$, —C(O)O$^-$ M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O.M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$ M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cydoalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$ M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —P(O)(OR$^{70}$)O$^-$ M$^+$, —P(O)(OR$^{70}$)$_2$, —C(O)R$^{70}$, —C(S)R$^{70}$, —C(NR$^{70}$)R$^{70}$, —CO$_2^-$ M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$ M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$ M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$ M$^+$, —OS(O)$_2$OR$^{70}$, —P(O)(O$^-$)$_2$(M$^+$)$_2$, —P(O)(OR$^{70}$)O$^-$ M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

As used herein, the term "linker" or "linkage" refers to a linking moiety that connects two groups and has a backbone of 100 atoms or less in length. A linker or linkage may be a covalent bond that connects two groups or a chain of between 1 and 100 atoms in length, for example of 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, poly(ethylene glycol); ethers, thioethers, tertiary amines, alkyls, which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable. A linker may be deuterated.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human subjects, especially mammalian subjects.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

When describing the compounds, compositions, methods and processes of this invention, the following terms have the meanings defined herein, unless otherwise indicated.

DETAILED DESCRIPTION

As summarized above, adrenergic receptor modulating compounds and methods of using the same are provided. Also provided are methods of treating a subject for a disease or condition associated with an adrenergic receptor including administering a therapeutically effective amount of the subject compound. Aspects of the disclosure include a method of modulating inflammatory response and production of TNF-alpha in a cell, including contacting a cell with a β1-selective adrenergic receptor modulating compound to selectively activate a cAMP pathway over a beta-arrestin pathway in the cell. Pharmaceutical compositions and kits which include the subject compounds are provided.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Modulation of Adrenergic Receptors

The present disclosure provides adrenergic receptor modulating compounds and salts thereof, and solvate, hydrate and/or prodrug forms thereof, and compositions including the same. Also provided are methods that find use in the modulation of the activity of a target adrenergic receptor. As used herein, the terms "adrenergic receptor" is used to refer to members of a family of G-protein coupled receptors that are involved in transmitting signals and regulating various processes within a variety of different cells. Adrenergic receptors can be classified into two main groups, alpha and beta, with several subtypes within each group. α-Adrenergic receptors include subtypes α1 and α2. β-Adrenergic receptors include the subtypes β1, β2 and β3, which are linked to Gs proteins (although in some cases β2 also couples to Gi), which in turn can be linked to adenylate cyclase. In some cases, agonist binding to an adrenergic receptor of interest can cause a rise in the intracellular concentration of the messenger cyclic adenosine monophosphate (cAMP) and mediate a variety of intracellular events, e.g., via a cAMP-dependent pathway. Adrenergic receptor family members of interest which may be targeted using the subject compounds include, but are not limited to, β1-adrenergic receptors, β2-adrenergic receptors, β3-adrenergic receptors, α1-adrenergic receptors and α2-adrenergic receptors. In some cases, the target adrenergic receptor is one that is implicated in a disease of interest.

In further describing the various aspects of the invention, the function and structure of various embodiments of adrenergic receptor modulating compounds are described first in greater detail, followed by a description of methods and applications in which the compounds finds use.

Compounds that Modulate Adrenergic Receptor Activity

As summarized above, aspects of the present disclosure include adrenergic receptor modulating compounds. The adrenergic receptor modulating compounds are compounds which modulate the activity of a target adrenergic receptor in a sample upon contact with the sample or components thereof. In some embodiments, the subject compound modulates a β1-adrenergic receptor. In some embodiments, the subject compound modulates a β2-adrenergic receptor. In some embodiments, the subject compound modulates a β3-adrenergic receptor. In some embodiments, the subject compound modulate an α1-adrenergic receptor. In some embodiments, the subject compound modulate an α2-adrenergic receptors.

Depending on the particular adrenergic receptor of interest and its activity and function in a cell, it can be desirable to activate the receptor with a partial or full agonist. As such, modulation of adrenergic receptor activity can include partial or full agonism of activity. The subject compounds may modulate adrenergic receptor activity by activating the activity of the receptor. In some instances, the subject compound is a partial agonist.

In other cases, it can be desirable to block the activity and function of the adrenergic receptor in a cell using an antagonist. The present disclosure provides adrenergic receptor modulating compounds that can have antagonist activity at an adrenergic receptor of interest. In some cases, the subject compounds can partially or fully block the acitvity of an adrenergic receptor of interest.

In some cases, by modulating the activity of an adrenergic receptor is meant that an activity related to the adrenergic receptor in a cell is activated by 10% or more, such as 20% or more, 30% or more, 40% or more, 50% or more, 60% or more, 70% or more, 80% or more, 90% or more, 100% or more, 200% or or even more relative to a control, e.g., a cell not contacted with the compound of interest.

In some cases, by modulating the activity of an adrenergic receptor is meant partial agonism of the adrenergic receptor in a cell, e.g., where the subject compound achieves 10% activation or more of the receptor, such as 20% or more, 30% or more, 40% or more, 50% or more, 60% or more, 70% or more, 80% or more, or 90% or more, relative to a control, e.g., a receptor that is fully activated. Partial agonism may be assessed using any convenient methods, such as a cell based assay using a known full agonist as a 100% activation control, where the relative maximum activation of the receptor can be measured relative to the full agonist (see e.g., FIG. 2A).

In some cases, by modulating the activity of an adrenergic receptor is meant that an activity related to the adrenergic receptor in a cell is inhibited by 10% or more, such as 20% or more, 30% or more, 40% or more, 50% or more, 60% or more, 70% or more, 80% or more, 90% or more, or even more relative to a control, e.g., a cell not contacted with the compound of interest.

Any convenient methods can be utilized in assessing and classifying the subject compounds ability to modulation of the activity of adrenergic receptor in a sample. In some cases, modulation of the activity of the target adrenergic receptor may be assessed by observing a signal of the cAMP pathway. Modulation of the signals and activities of the adrenergic receptor of interest can be assessed using any convenient methods, such as any convenient functional GPCR cell based assay for an adrenergic receptor of interest and assays described in the Examples section herein, e.g., a cell based cAMP assay using fluorescence energy transfer (FRET) technology or cardiovascular assessment. In some instances, the types of cells in which the subject compounds exhibit activity are ones that include an adrenergic receptor of interest.

Structural Features

An adrenergic receptor modulating compound can include a substituted phenyl group linked to a terminal group via an amino glycerol-containing linker. In some cases, the substituted phenyl group includes substituents that define a fused 5 membered ring. In some cases, the substituted phenyl group includes a single ring (i.e., the phenyl ring) that is substituted with up to five individual unconnected substitutents. In some cases, the substituted phenyl group includes a single ring (i.e., the phenyl ring) that is substituted with 2, 3, 4 or 5 individual unconnected substitutents. The adrenergic receptor modulating compound can include a 5-6 fused bicyclic heterocycle linked to a terminal group via an amino glycerol-containing linker. The 5-6 fused bicyclic heterocycle can include a phenyl ring fused to a five membered heterocycle that includes at least one nitrogen atom. As such, the 5-6 fused bicyclic heterocycle can be a heteroaryl. The fused five membered heterocycle can include 1, 2 or 3 nitrogen atoms, and optionally one oxygen or sulfur atom. 5-6 fused bicyclic heterocycles of interest include, but are not limited to, indazole, benzotriazole, benzoimidazole, benzooxazole, benzothiazole, benzoisothiazole, benzoisoxazole, benzothiadiazole and benzooxadiazole. In some cases, the 5-6 fused bicyclic heterocycle is an indazole or substituted indazole that is connected to the linker at a convenient position of the fused phenyl ring. The indazole group can be connected to the linker via the 4-position. In some cases, the 5-6 fused bicyclic heterocycle is an indole or substituted indole that is connected with the linker at a convenient position of the fused phenyl ring. The indole group can be connected to the linker via the 4-position. In certain instances, the compound is not xamoterol.

The amino glycerol-containing linker includes an aminoglycerol linking group. In some cases, the aminoglycerol linking group has the formula —O—CH₂CH(OH)CH₂NH— or is a substituted derivative thereof. In some cases, the aminoglycerol linking group has an (S) stereochemistry at the CH(OH) carbon. Any convenient additional linking groups can be included in the amino glycerol-containing linker to connect the 5-6 fused bicydic heterocycle to the linked terminal group. In some cases, the additional linking group has a backbone of between 1 and 20 atoms in length, such as of 1 to 10, or 2 to 6 atoms in length. The linking group may include a ring structure (e.g., a heterocycle group or a cycloalkyl group), and may include 1 or more heteroatoms, and/or may be optionally substituted. In certain instances, the linking group is selected from a carbon chain (e.g., a substituted or unsubstituted C1-C10 alkyl linker), a carbon chain including an ether, a chain including an amino or an amido functional group and a polyethyleneglycol (PEG) or modified PEG chain. In certain instances, the additional linking group includes a C1-C6 alkyl linking group, optionally substituted, that is attached to the amino group of the amino glycerol linker (e.g., as described herein). In some cases, the additional linking group that is connected to the aminoglycerol linking group via the NH— nitrogen is selected such that the —NH-nitrogen is a secondary amino group. The additional linking group is an alkyl or substituted alkyl linker, such as an alkyl or substituted alkyl linker of 1-12 carbon atoms in length, e.g., 1 to 6, or 1 to 4 atoms in length. In certain instances, the alkyl linker is deuterated, e.g., includes 1 or 2 deuterium at the carbon atom adjacent to the —NH-nitrogen.

Any convenient terminal groups may be included in the subject compounds. Terminal groups of interest which may be linked to the 5-6 fused bicyclic heterocycle include, but are not limited to, alkyl, substituted alkyl, cycloalkyl, substituted cycloalkyl, aryl, substituted aryl, heterocycle and substituted heterocycle groups.

In some embodiments, the compound is of Formula (I):

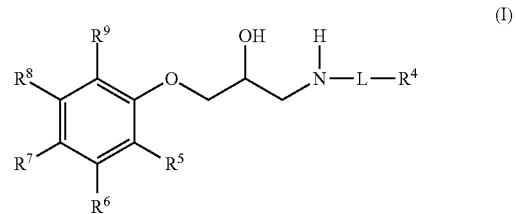

(I)

wherein:
$R^5$ to $R^9$ are independently selected from H, alkyl, substituted alkyl, halogen, hydroxyl, cyano, a fluorinated alkyl group (e.g., an alkyl group substituted with 1-6 fluoro, such as $CF_3$), alkoxyl, substituted alkoxy, OCOR', OCONR'R", where R' and R" are independently $R^5$, aryl, substituted aryl, alkyl or cycloalkyl, optionally further substituted with 1-6 fluoros, or R' and R" together with the connected N form a heterocycle or substituted heterocycle; or wherein any two of $R^5$ to $R^9$ are cyclically linked to form a fused 5 membered heterocycle ring;
L is a linker; and
$R^4$ is an alkyl, a substituted alkyl, a cydoalkyl, a substituted cycloalkyl, an aryl, a substituted aryl, a heterocycle, a substituted heterocycle, a heteroaryl or a substituted heteroaryl;
or a prodrug thereof, or a salt thereof.

In some embodiments of Formula (I), $R^7$ is OH or OP where P is a promoiety of a prodrug. In some embodiments of Formula (I), at least one of $R^5$ to $R^9$ is a halogen (e.g., at least one of $R^5$ to $R^9$ fluoro). In some embodiments of Formula (I), at least two of $R^5$ to $R^9$ is a halogen (e.g., at least one of $R^5$ to $R^9$ fluoro). In some instances, the compound is not xamoterol. In some embodiments of Formula (I), at least one of $R^6$ and $R^9$ is a halogen (e.g., at least one of $R^6$ and $R^9$ fluoro). In some embodiments of Formula (I), both $R^6$ and $R^9$ is a halogen (e.g., fluoro).

In some embodiments, the compound is of Formula (I): wherein:
$R^5$ to $R^9$ are independently selected from H, alkyl, substituted alkyl, halogen, hydroxyl, cyano, a fluorinated alkyl group (e.g., an alkyl group substituted with 1-6 fluoro, such as $CF_3$), alkoxyl, substituted alkoxy, OCOR', OCONR'R", where R' and R" are independently $R^5$, aryl, substituted aryl, alkyl or cycloalkyl, optionally further substituted with 1-6 fluoros, or R' and R" together with the connected N form a heterocycle or substituted heterocycle; or wherein any two of $R^5$ to $R^9$ are cyclically linked to form a fused 5 membered heterocycle ring;
L is a linker; and
$R^4$ is an alkyl, a substituted alkyl, a cycloalkyl, a substituted cycloalkyl, an aryl, a substituted aryl, a heterocycle, a substituted heterocycle, a heteroaryl or a substituted heteroaryl;
or a prodrug thereof, or a salt thereof.

In some embodiments of Formula (I), $R^5$, $R^6$, $R^8$ and $R^9$ are independently selected from H, alkyl, substituted alkyl, halogen, hydroxyl, cyano, a fluorinated alkyl group (e.g., an alkyl group substituted with 1-6 fluoro, such as $CF_3$), alkoxyl, substituted alkoxy, or fluorinated alkoxy (substituted with 1-6 fluoro); and $R^7$ is independently selected from $R^5$, OH, —OCOR' and —OCONR'R", where R' and R" are independently selected from aryl, substituted aryl, alkyl, substituted alkyl, cycloalkyl and substituted cydoalkyl, or R' and R" together with the connected N form a heterocyde or substituted heterocycle. In some cases, $R^7$ is a group substituted with 1-6 fluoros.

In certain embodiments, $R^7$ is not hydrogen. In certain embodiments, $R^7$ is hydroxyl. In certain embodiments, $R^7$ is alkoxy or substituted alkoxy. In certain embodiments, $R^7$ is —OCOR' where R' is alkyl, substituted alkyl, aryl, substituted aryl, heteroaryl or substituted heteroaryl.

In certain cases, at least one of $R^5$, $R^6$, $R^8$ and $R^9$ is not hydrogen. In certain instances of formula (I), $R^6$ and $R^9$ are each independently halogen. In certain instances of formula (I), $R^8$ and $R^9$ are independently fluoro or H. In some cases, at least one of $R^6$ and $R^9$ is fluoro. In certain instances of formula (I), $R^8$ and $R^9$ are independently fluoro or H, wherein at least one of $R^6$ and $R^9$ is halogen (e.g., fluoro) and $R^5$ and $R^9$ are hydrogen. In certain instances of formula (I), $R^6$ and $R^9$ are each fluoro. In certain instances of formula (I), at least one of $R^6$ and $R^8$ is H. In certain instances of formula (I), $R^6$ and $R^8$ are each H. In certain instances of formula (I), $R^8$ is H. In certain embodiments of formula (I), the compound has one of the following combination of $R^5$-$R^9$ groups:

| Embodiment | $R^5$ | $R^6$ | $R^7$ | $R^8$ | $R^9$ |
|---|---|---|---|---|---|
| 1 | H | F | OH | H | F |
| 2 | H | H | OH | H | F |
| 3 | H | F | OH | H | H |
| 4 | H | F | OP | H | F |
| 5 | H | H | OP | H | F |
| 6 | H | F | OP | H | H | where P is alkyl substituted alkyl, or a promoiety (e.g., an acyl, a substituted acyl) of a prodrug (e.g., an ester prodrug).

In some embodiments, the compound is of Formula (II):

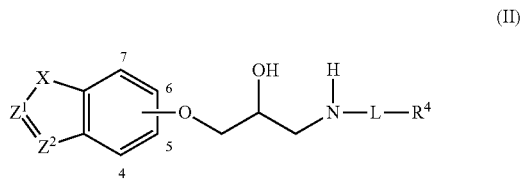

(II)

wherein:
$Z^1$ is N or $CR^1$;
$Z^2$ is N or $CR^2$;
X is $NR^3$, O or S;
$R^1$, $R^2$ and $R^3$ are each independently H, an alkyl or a substituted alkyl;
L is a linker;
$R^4$ is an alkyl, a substituted alkyl, a cydoalkyl, a substituted cycloalkyl, an aryl, a substituted aryl, a heterocycle, a substituted heterocycle, a heteroaryl or a substituted heteroaryl; and the 5-6 fused bicyclic heterocycle is optionally further substituted one or more $R^{10}$ groups independently selected from alkyl, substituted alkyl, halogen, hydroxyl, cyano, a fluorinated alkyl group (e.g., an alkyl group substituted with 1-6 fluoro, such as $CF_3$), alkoxyl, substituted alkoxy, and fluorinated alkoxy (substituted with 1-6 fluoro);

or a prodrug thereof, or a salt thereof.

In certain embodiments of Formula (II), $Z^1$ is N. In certain embodiments of Formula (II), $Z^1$ is $CR^1$. In certain embodiments of Formula (II), $Z^2$ is N. In certain embodiments of Formula (II), $Z^2$ is $CR^2$. In certain embodiments of Formula (II), X is $NR^3$. In certain embodiments of Formula (II), X is NH. In certain embodiments of Formula (II), X is O. In certain embodiments of Formula (II), X is S. In certain embodiments of Formula (II), X is $NR^3$ and $Z^1$ is N. In certain embodiments of Formula (II), X is $NR^3$ and $Z^1$ is $CR^1$. In certain embodiments of Formula (II), $Z^1$ is N, $Z^2$ is $CR^2$ and X is $NR^3$. In certain embodiments of Formula (II), $Z^1$ is $CR^1$, $Z^2$ is N and X is $NR^3$. In certain embodiments of Formula (II), $Z^1$ is N, $Z^2$ is N and X is $NR^3$.

In certain embodiments of Formula (II), $R^1$ is H. In certain embodiments of Formula (II), $R^2$ is H. In certain embodiments of Formula (II), $R^3$ is H. In certain embodiments of Formula (II), $R^1$ is an alkyl or a substituted alkyl. In certain embodiments of Formula (II), $R^2$ is an alkyl or a substituted alkyl. In certain embodiments of Formula (II), $R^2$ is methyl. In certain embodiments of Formula (II), $R^3$ is an alkyl or a substituted alkyl.

In certain embodiments of Formulae (I)-(II), $R^4$ is an alkyl or a substituted alkyl. In certain embodiments of Formulae (I)-(II), $R^4$ is a cycloalkyl or a substituted cycloalkyl. In certain embodiments of Formulae (I)-(II), $R^4$ is an aryl or a substituted aryl. In certain embodiments of Formulae (I)-(II), $R^4$ is a phenyl or a substituted phenyl. In certain embodiments of Formulae (I)-(II), $R^4$ is a heterocycle or a substituted heterocycle.

A variety of substituents of interest can be included in the subject compounds, e.g., at any one of positions number 4 to 7 of the fused phenyl ring, in the linker L, or included in any of groups $R^1$ to $R^4$ of any one of formulae (I)-(III), such as any convenient substitutent selected from halogen, —CN, —$NO_2$, —OH, —$OR_{10}$, —$C(O)R_{10}$, —$CO_2R_{10}$, —$O(CO)R_{10}$, —$C(O)NR_{10}R_{20}$, —$OC(O)NR_{10}R_{20}$, —$SR_{10}$, —$SOR_{10}$, —$SO_2R_{10}$, —$SO_2NR_{10}R_{20}$, —$NR_{10}R_{20}$, —$NR_{10}C(O)R_{20}$, —$NR_1C(O)_2R_{20}$, —$NR_1SO_2R_{20}$, —NR(CO)$NR_{20}R_{30}$, unsubstituted or substituted $C_{1-8}$ alkyl, unsubstituted or substituted $C_{2-8}$ alkenyl, unsubstituted or substituted $C_{2-8}$ alkynyl, unsubstituted or substituted $C_{3-6}$ cycloalkyl, unsubstituted or substituted $C_{6-10}$ aryl, unsubstituted or substituted 5- to 10-membered heteroaryl, and unsubstituted or substituted 3- to 10-membered heterocyclyl; where $R_{10}$, $R_{20}$ and $R_{30}$ are each independently selected from hydrogen, unsubstituted or substituted $C_{1-6}$ haloalkyl, unsubstituted or substituted $C_{1-6}$ alkyl, unsubstituted or substituted $C_{3-6}$ cycloalkyl, unsubstituted or substituted $C_{2-6}$ alkenyl, unsubstituted or substituted $C_{2-6}$ alkynyl, unsubstituted or substituted $C_{6-10}$ aryl, unsubstituted or substituted 5- to 10-membered heteroaryl, unsubstituted or substituted aryl-$C_{1-4}$ alkyl, unsubstituted or substituted aryl-$C_{1-4}$ alkyl, and unsubstituted or substituted aryloxy-$C_{1-4}$ alkyl; or two of $R_{10}$, $R_{20}$ together or $R_{10}$ and $R_{30}$ together with the atom(s) to which they are attached, may form an unsubstituted or substituted 5-, 6- or 7-membered ring.

In certain embodiments of Formulae (I)-(V), L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkylamide or substituted alkylamide group. In certain embodiments, L includes a cycloalkyl or substituted cycloalkyl group.

In certain embodiments, L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol.

In some embodiments of any of the formulae described herein (e.g., Formulae (I)-(V)), the Linker group L comprises one or more linking groups selected from —CH$_2$—, —(CH$_2$)$_2$—, —(CH$_2$)$_3$—, —(CH$_2$)$_4$—, —(CH$_2$)$_5$—, —O—, —C(=O)—, —OCH$_2$—, —O(CH$_2$)$_2$—, —O(CH$_2$)$_3$—, —O(CH$_2$)$_4$—, —O(CH$_2$)$_5$—, —SCH$_2$—, —S(CH$_2$)$_2$—, —S(CH$_2$)$_3$—, —S(CH$_2$)$_4$—, —S(CH$_2$)$_5$—, —SOCH$_2$—, —SO(CH$_2$)$_2$—, —SO(CH$_2$)$_3$—, —SO(CH$_2$)$_4$—, —SO(CH$_2$)$_5$-, —N(R)CH$_2$—, —SO$_2$CH$_2$—, —SO$_2$(CH$_2$)$_2$—, —SO$_2$(CH$_2$)$_3$—, —SO$_2$(CH$_2$)$_4$—, —SO$_2$(CH$_2$)$_5$—, —N(R)—, —N(R)(CH$_2$)$_2$—, —N(R)(CH$_2$)$_3$—, —N(R)(CH$_2$)$_4$—, —N(R)(CH$_2$)$_5$—, —N(R)(C=O)—, —(C=O)N(R)—, —CH$_2$—O—CH$_2$—, —CH$_2$—O—(CH$_2$)$_2$—, —CH$_2$—O—(CH$_2$)$_3$—, —(CH$_2$)$_2$—O—CH$_2$—, —(CH$_2$)$_2$—O—(CH$_2$)$_2$—, —(CH$_2$)$_3$—O—CH$_2$—, —(CH$_2$)$_3$—O—(CH$_2$)$_2$—, —CH$_2$—S—CH$_2$—, —CH$_2$—S—(CH$_2$)$_2$—, —CH$_2$—S—(CH$_2$)$_3$—, —(CH$_2$)$_2$—S—CH$_2$—, —(CH$_2$)$_2$—S—(CH$_2$)$_2$—, —(CH$_2$)$_3$—S—CH$_2$—, —(CH2)$_3$—S—(CH$_2$)$_2$—, —CH$_2$—SO—CH$_2$—, —CH$_2$—SO—(CH$_2$)$_2$—, —CH$_2$—SO—(CH$_2$)$_3$—, —(CH$_2$)$_2$—SO—CH$_2$—, —(CH$_2$)$_2$—SO—(CH$_2$)$_2$—, —(CH$_2$)$_3$—SO—CH$_2$—, —(CH$_2$)$_3$—SO—(CH$_2$)$_2$—, —CH$_2$—SO$_2$—CH$_2$—, —CH$_2$—SO$_2$—(CH$_2$)$_2$—, —CH$_2$—SO$_2$—(CH$_2$)$_3$—, —(CH$_2$)$_2$—SO$_2$—CH$_2$—, —(CH$_2$)$_2$—SO$_2$—(CH$_2$)$_2$—, —(CH$_2$)$_3$—SO$_2$—CH$_2$—, —(CH$_2$)$_3$—SO$_2$—(CH$_2$)$_2$—, —CH$_2$—N(R)—CH$_2$—, —CH$_2$—N(R)—(CH$_2$)$_2$—, —CH$_2$—N(R)—(CH$_2$)$_3$—, —(CH$_2$)$_2$—N(R)—CH$_2$—, —(CH$_2$)$_2$—N(R)—(CH$_2$)$_2$—, —(CH$_2$)$_3$—N(R)—CH$_2$—, and —(CH$_2$)$_3$—N(R)—(CH$_2$)$_2$—, where R is H, an alkyl (e.g., methyl) or a substituted alkyl, or a deuterated version thereof. In some embodiments of any of the formulae described herein (e.g., Formulae (I)-(V)), the Linker group L comprises one fo the following groups adjacent to the —NH— nitrogen: —CD$_2$-, —CDR— where R is alkyl or substituted alkyl. In some embodiments of Formula (I)-(III), the linker group comprises a C1-C6 alkyl linker, optionally substituted. In some embodiments of Formula (I)-(III), the linker group comprises a C1-C6 alkyl linker substituted with 1, 2 or more deuterium, e.g., at the carbon atom of the linker adjacent to the —NH— nitrogen atom. In some embodiments of Formula (I)-(III), the linker group comprises a C1-C6 alkyl linker and a linking functional group such as an amido, a carbamate, an ether, a sulfonamide, a carbonyl, a sulfonyl, an amino, a thiocarbonyl, a thiocarbamate, a thioamido, etc. In some embodiments of Formula (I)-(III), the linker group comprises a group selected from: —(CH$_2$)$_{1-6}$—N(R)—CO—, —(CH$_2$)$_{1-6}$—N(R)—CS—, —(CH$_2$)$_{1-6}$—N(R)—SO$_2$—, —(CH$_2$)$_{1-6}$—CO—, —(CH$_2$)$_{1-6}$—CS—, —(CH$_2$)$_{1-6}$—SO$_2$— —(CH$_2$)$_{1-6}$—N(R)—C(=NR)— where R is H, an alkyl or a substituted alkyl (e.g., methyl).

In some instances of Formulae (I)-(V), L is L$^1$-Z$^3$, where L$^1$ is an alkyl or substituted alkyl linking group (e.g., a C1-C6 linking group) and Z$^3$ is absent or selected from —O—, —NR—, —N(R)(C=O)—, —N(R)(SO$_2$)—, —N(R)(C=O)NR—, —N(R)(C=S)NR—, —N(R)(C=O)O—, —N(R)(C=S)O—, —O(C=O)N(R)—, —O(C=S)N(R)— and —C(=O)—NR—, wherein R is H, alkyl (e.g., methyl) or substituted alkyl.

In some instances of Formula (II), the compound has the Formula (III):

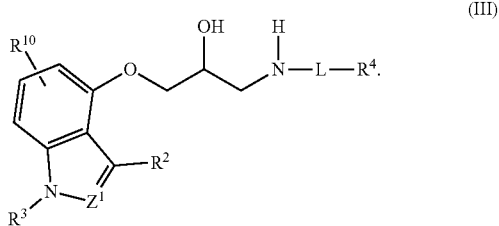

(III)

In certain embodiments of Formula (III), Z$^1$ is N. In certain embodiments of Formula (III), Z$^1$ is CR$^1$. In certain embodiments of Formula (III), Z$^1$ is CH. In certain embodiments of Formula (III), R$^2$ is H. In certain embodiments of Formula (III), R$^3$ is H. In certain embodiments of Formula (III), R$^1$ is an alkyl or a substituted alkyl. In certain embodiments of Formula (III), R$^2$ is an alkyl or a substituted alkyl. In certain embodiments of Formula (III), R$^2$ is methyl. In certain embodiments of Formula (III), R$^3$ is an alkyl or a substituted alkyl.

In certain embodiments of Formulae (I)-(III), R$^4$ is an alkyl or a substituted alkyl. In certain cases of Formulae (I)-(III), R$^4$ is a lower alkyl or substituted lower alkyl. In certain cases of Formulae (I)-(III), R$^4$ is selected from tert-butyl, isopropyl, isobutyl and isopentyl. In certain instances, the alkyl group can be further substituted, e.g., with hydroxy, alkoxy or a halogen. In some cases, L is a covalent bond and R4 is an alkyl or substituted alkyl. In certain embodiments of Formulae (I)-(III), R$^4$ is a cycloalkyl or a substituted cycloalkyl. In certain embodiments of Formulae (I)-(III), R$^4$ is an aryl or a substituted aryl. In certain embodiments of Formulae (I)-(III), R$^4$ is a phenyl or a substituted phenyl. In certain embodiments of Formulae (I)-(III), R$^4$ is a heterocycle or a substituted heterocycle. In certain embodiments of Formulae (I)-(III), R$^4$ is a morpholine. In certain embodiments of Formulae (I)-(III), R$^4$ is a heteroaryl or a substituted heteroaryl. In certain embodiments of Formulae (I)-(III), R$^4$ is a pyrazole, a substituted pyrazole, an oxazole, a substituted oxazole, thiophene, a substituted thiphene, pyridine, a substituted pyridine. In certain embodiments of Formulae (I)-(III), R$^4$ is selected from one of the following heterocycles a-l:

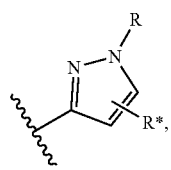

a

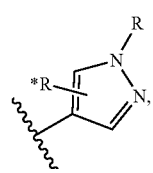

b

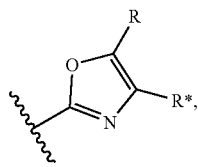

c

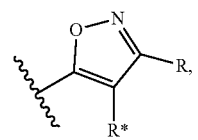

d

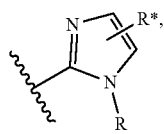

e

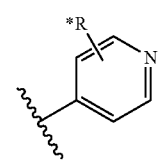

f

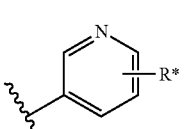

g

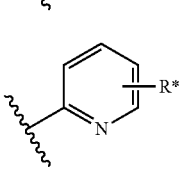

h

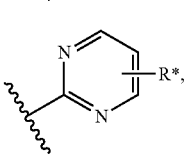

i

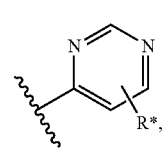

j

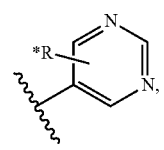

k

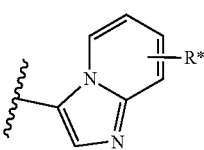

l wherein R is H, alkyl, substituted alkyl, halogen, cyano, alkoxy, substituted alkoxy; and R* is one or more optional substituents selected from alkyl, substituted alkyl, halogen, hydroxy, cyano, alkoxy, and substituted alkoxy. In certain embodiments of Formulae (I)-(III), $R^4$ is a heteroaryl or substituted heteroaryl (e.g., as described above), and L is $L^1$-Z, where $L^1$ is a C1-C6 alkyl or substituted alkyl linking group and Z is an optional linking group selected from, —NR—, —O— and —S—.

In some embodiments of formula (I), $R^4$ is selected from heterocycles a-l (e.g., as described above);

L is a covalent bond, C1-C6 alkyl or substituted C1-C6 alkyl;

$R^7$ is hydroxyl, alkoxy, substituted alkoxy, OCOR', OCONR'R", where R' and R" are independently $R^5$, aryl, substituted aryl, alkyl or cycloalkyl, optionally further substituted with 1-6 fluoros, or R' and R" together with the connected N form a heterocycle or substituted heterocycle;

$R^6$ and $R^9$ are independently fluoro or H, wherein at least one of $R^6$ and $R^9$ is fluoro; and $R^5$ and $R^8$ are hydrogen.

In some cases of Formula (III), $R^4$ is selected from heterocycles a-l (e.g., as described above); and L is a covalent bond, C1-C6 alkyl or substituted C1-C6 alkyl. In certain instances, the compound has the formula:

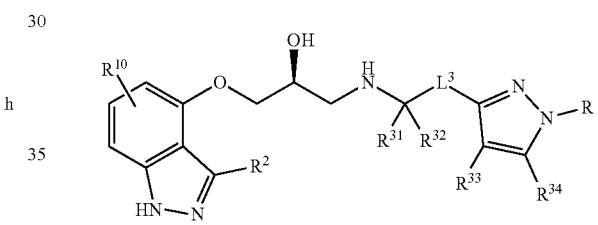

wherein:

$R^{10}$ and $R^2$ are as defined above;

$R^{33}$ and $R^{34}$ are independently selected from H, alkyl, substituted alkyl, halogen, hydroxy, cyano, alkoxy, and substituted alkoxy;

$R^{31}$ and $R^{32}$ are independently selected from H, deuterium, C1-C6 alkyl, substituted C1-C6 alkyl;

$R^2$ is a C1-C6 alkyl linker or a substituted C1-C6 alkyl linker; and $L^3$ is a covalent bond, a C1-C5 alkyl linker or a substituted C1-C5 alkyl linker. In certain cases, the compound has the structure:

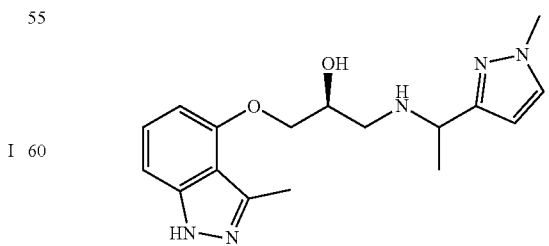

In some embodiments of Formulae (I)-(III), the compound has formula (IV) or (V):

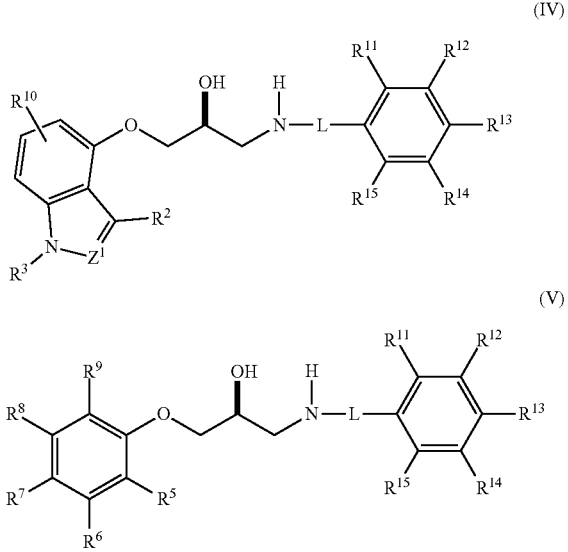

(IV)

(V)

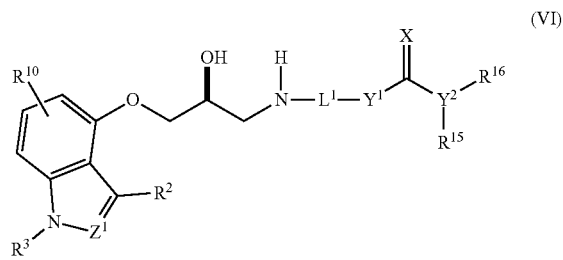

(VI)

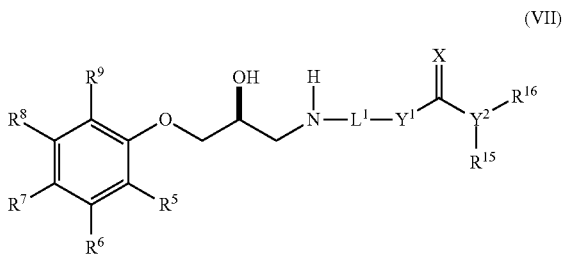

(VII)

wherein: $R^1$-$R^{10}$ and L are as defined above; and $R^{11}$-$R^{15}$ are each independently selected from H, halogen, —CN, —NO$_2$, —OH, —OR$_{10}$, —C(O)R$_{10}$, —CO$_2$R$_{10}$, —O(CO)R$_{10}$, —C(O)NR$_{10}$R$_{20}$, —OC(O)NR$_{10}$R$_{20}$, —SR$_{10}$, —SOR$_{10}$, —SO$_2$R$_{10}$, —SO$_2$NR$_{10}$R$_{20}$, —NR$_{10}$R$_{20}$, —NR$_{10}$C(O)R$_{20}$, —NR$_1$C(O)$_2$R$_{20}$, —NR$_1$SO$_2$R$_{20}$, —NR$_1$(CO)NR$_{20}$R$_{30}$, unsubstituted or substituted C$_{1-8}$ alkyl, unsubstituted or substituted C$_{2-8}$ alkenyl, unsubstituted or substituted C$_{2-8}$ alkynyl, unsubstituted or substituted C$_{3-8}$ cycloalkyl, unsubstituted or substituted C$_{6-10}$ aryl, unsubstituted or substituted 5- to 10-membered heteroaryl, and unsubstituted or substituted 3- to 10-membered heterocyclyl; where R$_{10}$, R$_{20}$ and R$_{30}$ are each independently selected from hydrogen, unsubstituted or substituted C$_{1-6}$ haloalkyl, unsubstituted or substituted C$_{1-6}$ alkyl, unsubstituted or substituted C$_{3-6}$ cycloalkyl, unsubstituted or substituted C$_{2-6}$ alkenyl, unsubstituted or substituted C$_{2-6}$ alkynyl, unsubstituted or substituted C$_{6-10}$ aryl, unsubstituted or substituted 5- to 10-membered heteroaryl, unsubstituted or substituted aryl-C$_{1-4}$ alkyl, unsubstituted or substituted aryl-C$_{1-4}$ alkyl, and unsubstituted or substituted aryloxy-C$_{1-4}$ alkyl; or two of R$_{10}$, R$_{20}$ together or R$_{10}$ and R$_{30}$ together with the atom(s) to which they are attached, may form an unsubstituted or substituted 5-, 6- or 7-membered ring.

In certain embodiments of Formula (IV), $Z^1$ is N. In certain embodiments of Formula (IV), $Z^1$ is $CR^1$. In certain embodiments of Formula (IV), $Z^1$ is CH. In certain embodiments of Formula (IV), $R^2$ is H. In certain embodiments of Formula (IV), $R^3$ is H. In certain embodiments of Formula (IV), $R^1$ is an alkyl or a substituted alkyl. In certain embodiments of Formula (IV), $R^2$ is an alkyl or a substituted alkyl. In certain embodiments of Formula (IV), $R^2$ is methyl. In certain embodiments of Formula (IV), $R^3$ is an alkyl or a substituted alkyl. In certain embodiments of Formula (IV), $Z^1$ is N, $R^2$ is methyl and $R^3$ is hydrogen.

In certain embodiments of Formula (V), $R^5$, $R^6$, $R^8$ and $R^9$ are independently selected from H, alkyl, substituted alkyl, halogen, hydroxyl, cyano, a fluorinated alkyl group (e.g., an alkyl group substituted with 1-6 fluoro, such as $CF_3$), alkoxyl, substituted alkoxy, or fluorinated alkoxy (substituted with 1-6 fluoro); and $R^7$ is independently selected from $R^5$, OH, —OCOR' and —OCONR'R", where R' and R" are independently selected from aryl, substituted aryl, alkyl, substituted alkyl, cycloalkyl and substituted cycloalkyl, or R' and R" together with the connected N form a heterocycle or substituted heterocycle. In some cases, $R^7$ is a group substituted with 1-6 fluoros. In certain embodiments, $R^7$ is not hydrogen. In certain cases, at least one of $R^5$, $R^6$, $R^8$ and $R^9$ is not hydrogen. In certain instances of formula (V), $R^6$ and $R^9$ are each independently halogen. In certain embodiments, $R^7$ is hydroxyl. In certain embodiments, $R^7$ is alkoxy or substituted alkoxy. In certain embodiments, $R^7$ is -OCOR' where R' is alkyl, substituted alkyl, aryl, substituted aryl, heteroaryl or substituted heteroaryl.

In certain cases, at least one of $R^5$, $R^6$, $R^8$ and $R^9$ is not hydrogen. In certain instances of formula (V), $R^6$ and $R^9$ are each independently halogen. In certain instances of formula (V), $R^6$ and $R^9$ are each fluoro. In certain instances of formula (V), at least one of $R^6$ and $R^8$ is H. In certain instances of formula (V), $R^6$ and $R^8$ are each H.

In certain embodiments of Formulae (I)-(III), the compound has formula (VI) or (VII):

wherein:
$R^1$-$R^{10}$ are as defined above;
$L^1$ is a linker;
$Y^1$ is absent or NR, wherein each R is independently H, an alkyl or a substituted alkyl;
X is O or S;
$Y^2$ is CH or N; and
$R^{15}$ and $R^{16}$ are independently selected from H, an alkyl and a substituted alkyl, or $R^{15}$ and $R^{16}$ are cyclically linked to form an optionally substituted cycloalkyl or heterocycle.

In certain embodiments of Formulae (VI)-(VII), $L^1$ is C1-C6 alkyl linker, optionally substituted in the backbone with 1 or 2 oxygen atoms. In certain embodiments of Formulae (VI)-(VII), $L^1$ is C1-C6 alkyl linker, optionally substituted with 1, 2 or more deuterium atoms, e.g., at the carbon atom adjacent to the —NH— nitrogen. In certain embodiments of Formulae (VI)-(VII), $L^1$ is a C2 alkyl linker. In certain embodiments of Formulae (VI)-(VII), $Y^1$ is absent. In certain embodiments of Formulae (VI)-(VII), $Y^1$ is NR, wherein each R is H, an alkyl or a substituted alkyl. In certain cases, the R of $Y^1$ is a cycloalkyl or substituted cycloalkyl, such as cyclopropyl, cyclobutyl, cyclopentyl or cyclohexyl. In certain embodiments of Formulae (VI)-(VII), $Y^1$ is NH. In certain embodiments of Formulae (VI)-(VII), X is O. In certain embodiments of Formulae (VI)-(VII), X is S. In certain embodiments of Formulae (VI)-(VII), $Y^2$ is N. In certain embodiments of Formulae (VI)-(VII), $Y^1$ is NH, X is O and $Y^2$ is N. In certain embodiments of Formulae (VI)-(VII), $Y^1$ is absent, X is O and $Y^2$ is N. In certain embodiments of Formulae (VI)-(VII), $Y^1$ is NH, X is S and $Y^2$ is N. In certain embodiments of Formulae (VI)-(VII), $Y^1$ is absent, X is S and $Y^2$ is N. In certain embodiments of Formulae (VI)-(VII), $Y^2$ is CH. In certain embodiments of Formulae (VI)-(VII), $Y^1$ is NH, X is O and $Y^2$ is CH. In certain embodiments of Formulae (VI)-(VII), $R^{15}$ and $R^{16}$ are independently selected from H, an alkyl and a substituted alkyl. In certain embodiments of Formulae (VI)-(VII), $R^{15}$ and $R^{16}$ are cyclically linked to form an optionally substituted cycloalkyl or heterocycle, such as a 4 to 6 membered cycloalkyl or heterocycle that is optionally further substituted.

In certain embodiments of Formula (VI), $Z^1$ is N. In certain embodiments of Formula (VI), $Z^1$ is $CR^1$. In certain embodiments of Formula (VI), $Z^1$ is CH. In certain embodiments of Formula (VI), $R^2$ is H. In certain embodiments of Formula (VI), $R^3$ is H. In certain embodiments of Formula (VI), $R^1$ is an alkyl or a substituted alkyl. In certain embodiments of Formula (VI), $R^2$ is an alkyl or a substituted alkyl. In certain embodiments of Formula (VI), $R^2$ is methyl. In certain embodiments of Formula (VI), $R^3$ is an alkyl or a substituted alkyl. In certain embodiments of Formula (VI), $Z^1$ is N, $R^2$ is methyl and $R^3$ is hydrogen. In certain embodiments of Formula (VI), $R^{10}$ is H. In certain instances of formula (VI), $R^{10}$ is one or more optional substituents selected from halogen, C1-C6 alkyl, substituted C1-C6 alkyl, hydroxyl, C1-C6 alkoxy and substituted C1-C6 alkoxy.

In certain embodiments of Formula (VII), $R^5$, $R^6$, $R^8$ and $R^9$ are independently selected from H, alkyl, substituted alkyl, halogen, hydroxyl, cyano, a fluorinated alkyl group (e.g., an alkyl group substituted with 1-6 fluoro, such as $CF_3$), alkoxyl, substituted alkoxy, or fluorinated alkoxy (substituted with 1-6 fluoro); and $R^7$ is independently selected from $R^5$, OH, —OCOR' and —OCONR'R", where R' and R" are independently selected from aryl, substituted aryl, alkyl, substituted alkyl, cycloalkyl and substituted cycloalkyl, or R' and R" together with the connected N form a heterocycle or substituted heterocycle. In some cases, $R^7$ is a group substituted with 1-6 fluoros. In certain embodiments, $R^7$ is not hydrogen. In certain cases, at least one of $R^5$, $R^6$, $R^8$ and $R^9$ is not hydrogen. In certain instances of formula (VII), $R^6$ and $R^9$ are each independently halogen. In certain embodiments, $R^7$ is hydroxyl. In certain embodiments, $R^7$ is alkoxy or substituted alkoxy. In certain embodiments, $R^7$ is —OCOR' where R' is alkyl, substituted alkyl, aryl, substituted aryl, heteroaryl or substituted heteroaryl.

In certain cases, at least one of $R^5$, $R^6$, $R^8$ and $R^9$ is not hydrogen. In certain instances of formula (VII), $R^6$ and $R^9$ are each independently halogen. In certain instances of formula (VII), $R^6$ and $R^9$ are independently fluoro or H, wherein at least one of $R^6$ and $R^9$ is fluoro. In certain instances of formula (VII), $R^6$ and $R^9$ are each fluoro. In certain instances of formula (VII), at least one of $R^6$ and $R^8$ is H. In certain instances of formula (VII), $R^6$ and $R^8$ are each H.

In some embodiments of Formula (VI), the compound has Formula (VIIIa) or (VIIIb):

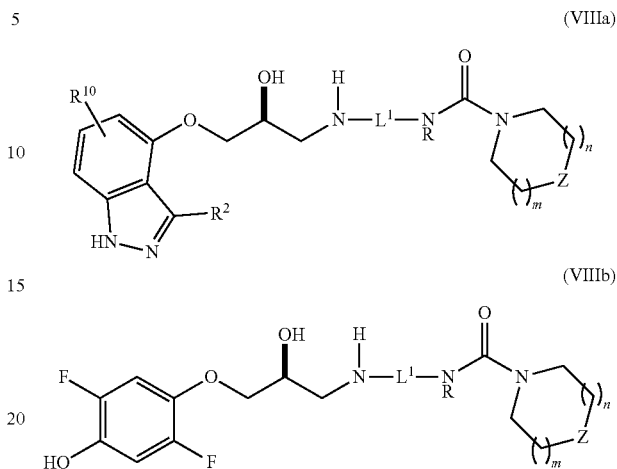

wherein L is a C1-C6 linker; Z is O, NR or CHR; m and n are independently 0 or 1; and R is H, hydroxyl, alkoxy, substituted alkoxy, alkyl, substituted alkyl, cycloalkyl or substituted cycloalkyl. In certain instances, $L^1$ is a C2-C6 alkyl linker, e.g., —$CH_2CH_2$—. In certain instances, $L^1$ is optionally substituted with 1, 2 or more deuterium atoms, e.g., at the carbon atom adjacent to the —NH— nitrogen. In certain cases, R is a lower alkyl. In certain cases, R is a cycloalkyl, e.g., a cyclopropyl, a cyclobutyl, a cyclopentyl or a cyclohexyl. In certain instances of formulae (VIIIa)-(VIIIb), Z is NR, R is alkyl or substituted alkyl and n and m are each 1. In certain instances of formulae (VIIIa)-(VIIIb), Z is CHR, R is H, hydroxyl, alkyl or substituted alkyl and n and m are each 0. In certain instances of formulae (VIIIa)-(VIIIb), Z is CHR, R is H, hydroxyl, alkoxy, substituted alkoxy, alkyl or substituted alkyl and n and m are each 1. In certain instances of formulae (VIIIa)-(VIIIb), Z is O, and n and m are each 1. In certain instances of formulae (VIIIa)-(VIIIb), n and m are each 1. In certain instances of formula (VIIIa), $R^{10}$ is one or more optional substituents selected from halogen, C1-C6 alkyl, substituted C1-C6 alkyl, hydroxyl, C1-C6 alkoxy and substituted C1-C6 alkoxy. In certain instances of formula (VIIIa), $R^2$ is a C1-C8 alkyl, such as a C1-C6 alkyl. In certain instances of formula (VIIIa), $R^2$ is methyl or ethyl.

In some embodiments of Formula (VIIIb), the compound has the structure:

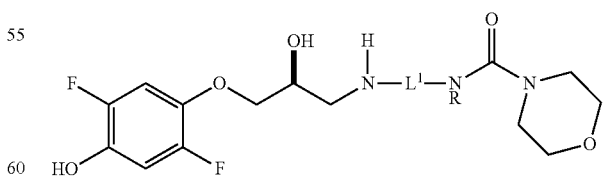

wherein $L^1$ is a C1-C6 linker (e.g., a C2-C6 alkyl linker) and R is H, alkyl, substituted alkyl, cycloalkyl or substituted cycloalkyl.

In some embodiments of Formula (VIIIa), the compound has the structure:

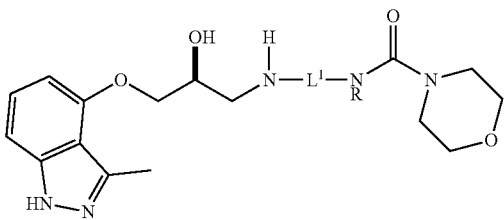

wherein $L^1$ is a C1-C6 linker (e.g., a C2-C6 alkyl linker) and R is H, alkyl, substituted alkyl, cycloalkyl or substituted cycloalkyl. In certain instances, $L^1$ is —$CH_2CH_2$—. In certain cases, R is a lower alkyl. In certain cases, R is a cycloalkyl, e.g., a cyclopropyl, a cyclobutyl, a cyclopentyl or a cyclohexyl. In some cases, R is cyclopropyl. In some cases, R is methyl.

In certain embodiments of Formula (I), the compound has Formula (IX):

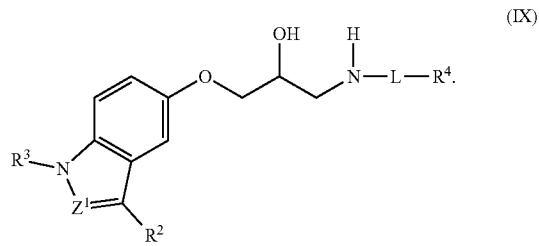

In certain embodiments of Formula (IX), $Z^1$ is N. In certain embodiments of Formula (IX), $Z^1$ is $CR^1$. In certain embodiments of Formula (IX), $Z^1$ is CH. In certain embodiments of Formula (IX), $R^2$ is H. In certain embodiments of Formula (IX), $R^3$ is H. In certain embodiments of Formula (IX), $R^1$ is an alkyl or a substituted alkyl. In certain embodiments of Formula (IX), $R^2$ is an alkyl or a substituted alkyl. In certain embodiments of Formula (IX), $R^2$ is methyl. In certain embodiments of Formula (IX), $R^3$ is an alkyl or a substituted alkyl.

In certain embodiments of Formula (IX), $R^4$ is an alkyl or a substituted alkyl. In certain embodiments of Formula (IX), $R^4$ is a cycloalkyl or a substituted cycloalkyl. In certain embodiments of Formula (IX), $R^4$ is an aryl or a substituted aryl. In certain embodiments of Formula (IX), $R^4$ is a phenyl or a substituted phenyl. In certain embodiments of Formula (IX), $R^4$ is a heterocycle or a substituted heterocycle. In certain embodiments of Formula (IX), $R^4$ is a heteroaryl or a substituted heteroaryl.

In some instances of Formula (IX), the compound has the Formula (X):

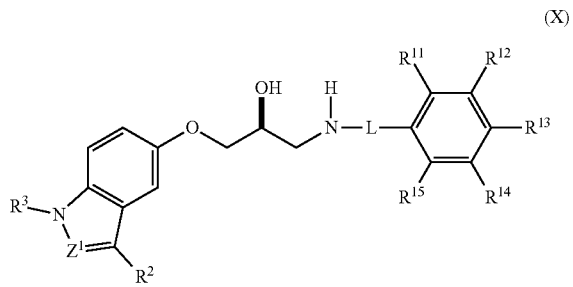

wherein: $R^1$-$R^{15}$ are each independently selected from H, halogen, —CN, —$NO_2$, —OH, —$OR_{10}$, —$C(O)R_{10}$, —$CO_2R_{10}$, —$O(CO)R_{10}$, —$C(O)NR_{10}R_{20}$, —$OC(O)NR_{10}R_{20}$, —$SR_{10}$, —$SOR_{10}$, —$SO_2R_{10}$, —$SO_2NR_{10}R_{20}$, —$NR_{10}R_{20}$, —$NR_{10}C(O)R_{20}$, —$NR_1C(O)_2R_{20}$, —$NR_1SO_2R_{20}$, —$NR_1(CO)NR_{20}R_{30}$, unsubstituted or substituted $C_{1-8}$ alkyl, unsubstituted or substituted $C_{2-8}$ alkenyl, unsubstituted or substituted $C_{2-8}$ alkynyl, unsubstituted or substituted $C_{3-8}$ cycloalkyl, unsubstituted or substituted $C_{6-10}$ aryl, unsubstituted or substituted 5- to 10-membered heteroaryl, and unsubstituted or substituted 3- to 10-membered heterocyclyl; where $R_{10}$, $R_{20}$ and $R_{30}$ are each independently selected from hydrogen, unsubstituted or substituted $C_{1-6}$ haloalkyl, unsubstituted or substituted $C_{1-6}$ alkyl, unsubstituted or substituted $C_{3-6}$ cycloalkyl, unsubstituted or substituted $C_{2-6}$ alkenyl, unsubstituted or substituted $C_{2-6}$ alkynyl, unsubstituted or substituted $C_{6-10}$ aryl, unsubstituted or substituted 5- to 10-membered heteroaryl, unsubstituted or substituted aryl-$C_{1-4}$ alkyl, unsubstituted or substituted aryl-$C_{1-4}$ alkyl, and unsubstituted or substituted aryloxy-$C_{1-4}$ alkyl; or two of $R_{10}$, $R_{20}$ together or $R_{10}$ and $R_{30}$ together with the atom(s) to which they are attached, may form an unsubstituted or substituted 5-, 6- or 7-membered ring.

In certain embodiments of Formula (X), $Z^1$ is N. In certain embodiments of Formula (X), $Z^1$ is $CR^1$. In certain embodiments of Formula (X), $Z^1$ is CH. In certain embodiments of Formula (X), $R^2$ is H. In certain embodiments of Formula (X), $R^3$ is H. In certain embodiments of Formula (X), $R^1$ is an alkyl or a substituted alkyl. In certain embodiments of Formula (X), $R^2$ is an alkyl or a substituted alkyl. In certain embodiments of Formula (X), $R^2$ is methyl. In certain embodiments of Formula (X), $R^3$ is an alkyl or a substituted alkyl. In certain embodiments of Formula (X), $Z^1$ is N, $R^2$ is methyl and $R^3$ is hydrogen.

In certain embodiments of Formulae (I)-(X), L is selected from: —$(CH_2)_n$—, —$(CH_2)_n$—O—, —$(CH_2)_n$—O—$(CH_2)_m$—, —$(CH_2CH_2O)_p$—$(CH_2)_m$—, —$(CH_2CH_2O)_p$—, —$(CH_2)_n$—CO—, —$(CH_2)_n$—O—$(CH_2)_m$—CO—, —$(CH_2CH_2O)_p$—$(CH_2)_m$—CO—, —$(CH_2)_n$—NHCO—, —$(CH_2)_n$—O—$(CH_2)_m$—NHCO—, —$(CH_2CH_2O)_p$—$(CH_2)_m$—NHCO—, wherein n is an integer from 2-6 and m and p are each independently an integer from 1-6. In certain instances, the linker (e.g., L or $L^1$) is selected from: a covalent bond, —$CH_2$—, —$(CH_2)_n$—, —$(CR_2)_n$—, —$(CH_2)_n$—O—, —$(CR_2)_n$—O—$(CR_2)_m$—, —$(CH_2CH_2O)_p$—$(CH_2)_m$—, —$(CH_2CH_2O)_p$—, —$(CR_2)_n$—CO—, —$(CR_2)_n$—O—$(CH_2)_m$—CO—, —$(CH_2CH_2O)_p$—$(CH_2)_m$—CO—, —$(CR_2)_n$—NHCO—, —$(CR_2)_n$—O—$(CH_2)_m$—NHCO— and —$(CH_2CH_2O)_p$—$(CH_2)_m$—NHCO—, wherein each R is independently H, C1-C6 alkyl or C1-C6 substituted alkyl, n is an integer from 1-6 and m and p are each independently an integer from 1-6. In certain instances, n is 2. In certain instances, n is 3. In certain instances, p is 1. In certain instances, p is 2. In certain instances, m is 2. In certain instances, m is 3. In certain instances, n+m is 6 or less. such as 5 or less, 4 or less, 3 or less. In certain instances, p+m is 6 or less. such as 5 or less, 4 or less, 3 or less.

In certain embodiments of Formula (IX), the compound has Formula (XI):

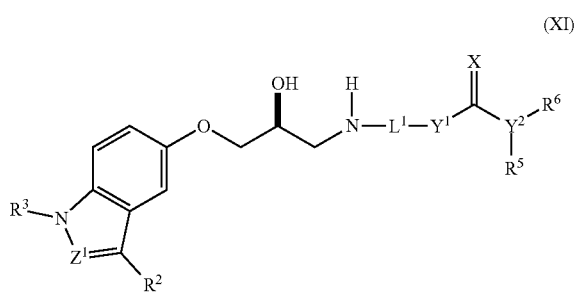

(XI)

wherein:
L¹ is a linker;
Y¹ is absent or NR, wherein each R is independently H, an alkyl or a substituted alkyl;
X is O or S;
Y² is CH or N; and
R⁵ and R⁶ are independently selected from H, an alkyl and a substituted alkyl, or R⁵ and R⁶ can be cyclically linked to form an optionally substituted cycloalkyl or heterocycle.

In certain embodiments of Formula (XI), $L^1$ is C1-C6 alkyl linker, optionally substituted in the backbone with 1 or 2 oxygen atoms. In certain embodiments of Formula (XI), $L^1$ is a C2 alkyl linker. In certain embodiments of Formula (XI), $L^1$ is C1-C6 alkyl linker substituted with 1, 2 or more deuterium, e.g., at the carbon atom of the linker adjacent to the —NH— nitrogen. In certain embodiments of Formula (XI), $Y^1$ is absent. In certain embodiments of Formula (XI), $Y^1$ is NR, wherein each R is H, an alkyl or a substituted alkyl. In certain embodiments of Formula (XI), $Y^1$ is NH. In certain embodiments of Formula (XI), X is O. In certain embodiments of Formula (XI), X is S. In certain embodiments of Formula (XI), $Y^2$ is N. In certain embodiments of Formula (XI), $Y^1$ is NH, X is O and $Y^2$ is N. In certain embodiments of Formula (XI), $Y^1$ is absent, X is O and $Y^2$ is N. In certain embodiments of Formula (XI), $Y^1$ is NH, X is S and $Y^2$ is N. In certain embodiments of Formula (XI), $Y^1$ is absent, X is S and $Y^2$ is N. In certain embodiments of Formula (XI), $Y^2$ is CH. In certain embodiments of Formula (XI), $Y^1$ is NH, X is O and $Y^2$ is CH.

In certain embodiments of Formula (XI), $Z^1$ is N. In certain embodiments of Formula (XI), $Z^1$ is $CR^1$. In certain embodiments of Formula (XI), $Z^1$ is CH. In certain embodiments of Formula (XI), $R^2$ is H. In certain embodiments of Formula (XI), $R^3$ is H. In certain embodiments of Formula (XI), $R^1$ is an alkyl or a substituted alkyl. In certain embodiments of Formula (XI), $R^2$ is an alkyl or a substituted alkyl. In certain embodiments of Formula (XI), $R^2$ is methyl. In certain embodiments of Formula (XI), $R^3$ is an alkyl or a substituted alkyl. In certain embodiments of Formula (XI), $Z^1$ is N, $R^2$ is methyl and $R^3$ is hydrogen.

In some embodiments of Formula (XI), the the compound has the structure:

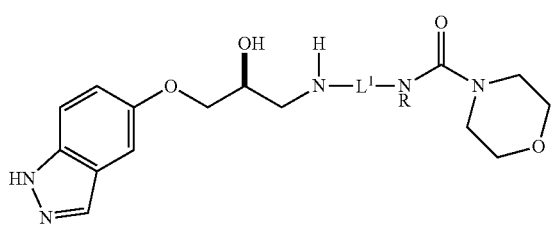

wherein $L^1$ is a C1-C6 linker and R is H, alkyl, substituted alkyl, cycloalkyl or substituted cycloalkyl. In certain instances, $L^1$ is —CH₂CH₂—. In certain cases, R is a lower alkyl. In certain cases, R is a cycloalkyl, e.g., a cyclopropyl, a cyclobutyl, a cyclopentyl or a cyclohexyl.

In some embodiments of Formulae (I)-(III) and (IX), $R^4$ is described by Formula (XII) or (XIII):

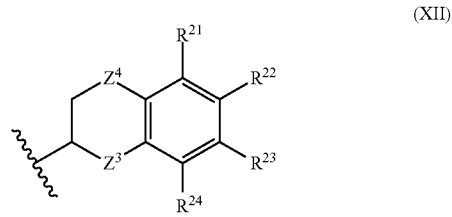

(XII)

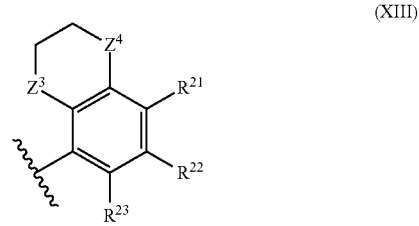

(XIII)

wherein:
$Z^3$ and $Z^4$ are independently O, CH₂ or NR, wherein R is H, an alkyl or a substituted alkyl; and
$R^{21}$-$R^{24}$ are each independently selected from H, halogen, —CN, —NO₂, —OH, —OR₁₀, —C(O)R₁₀, —CO₂R₁₀, —O(CO)R₁₀, —C(O)NR₁₀R₂₀, —OC(O)NR₁₀R₂₀, —SR₁₀, —SOR₁₀, —SO₂R₁₀, —SO₂NR₁₀R₂₀, —NR₁₀R₂₀, —NR₁₀C(O)R₂₀, —NR₁C(O)₂R₂₀, —NR₁SO₂R₂₀, —NR₁(CO)NR₂₀R₃₀, unsubstituted or substituted $C_{1-8}$ alkyl, unsubstituted or substituted $C_{2-8}$ alkenyl, unsubstituted or substituted $C_{2-8}$ alkynyl, unsubstituted or substituted $C_{3-8}$ cycloalkyl, unsubstituted or substituted $C_{6-10}$ aryl, unsubstituted or substituted 5- to 10-membered heteroaryl, and unsubstituted or substituted 3- to 10-membered heterocyclyl; where $R_{10}$, $R_{20}$ and $R_{30}$ are each independently selected from hydrogen, unsubstituted or substituted $C_{1-6}$ haloalkyl, unsubstituted or substituted $C_{1-6}$ alkyl, unsubstituted or substituted $C_{3-6}$ cycloalkyl, unsubstituted or substituted $C_{2-6}$ alkenyl, unsubstituted or substituted $C_{2-6}$ alkynyl, unsubstituted or substituted $C_{6-10}$ aryl, unsubstituted or substituted 5- to 10-membered heteroaryl, unsubstituted or substituted aryl-$C_{1-4}$ alkyl, unsubstituted or substituted aryl-$C_{1-4}$ alkyl, and unsubstituted or substituted aryloxy-$C_{1-4}$ alkyl; or two of $R_{10}$, $R_{20}$ together or $R_{10}$ and $R_{30}$ together with the atom(s) to which they are attached, may form an unsubstituted or substituted 5-, 6- or 7-membered ring.

In some embodiments of Formula (II), the compound has Formula (XIV):

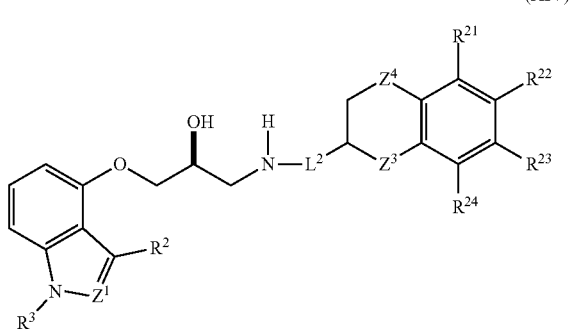

(XIV)

wherein L² is a linker. In some embodiments of Formula (XIV), L² is a C1-C6 alkyl linker, optionally substituted in the backbone with 1 or 2 oxygen atoms, e.g. L² is —(CH₂)$_q$— wherein q is an integer from 1-3; Z³ and Z⁴ are independently O, CH₂ or NR, wherein R is H, an alkyl or a substituted alkyl and R²¹-R²⁴ are as defined above. In certain embodiments of Formula (XIV), L² is C1-C6 alkyl linker substituted with 1, 2 or more deuterium, e.g., at the carbon atom of the linker adjacent to the —NH— nitrogen. In certain embodiments of Formula (XIV), Z¹ is N. In certain embodiments of Formula (XIV), Z¹ is CR¹. In certain embodiments of Formula (XIV), Z¹ is CH. In certain embodiments of Formula (XIV), R² is H. In certain embodiments of Formula (XIV), R³ is H. In certain embodiments of Formula (XIV), R¹ is an alkyl or a substituted alkyl. In certain embodiments of Formula (XIV), R² is an alkyl or a substituted alkyl. In certain embodiments of Formula (XIV), R² is methyl. In certain embodiments of Formula (XIV), R³ is an alkyl or a substituted alkyl. In some embodiments of Formula (XIV), R² is methyl, Z¹ is N and R³ is hydrogen.

In some embodiments of Formula (III), the compound has Formula (XV):

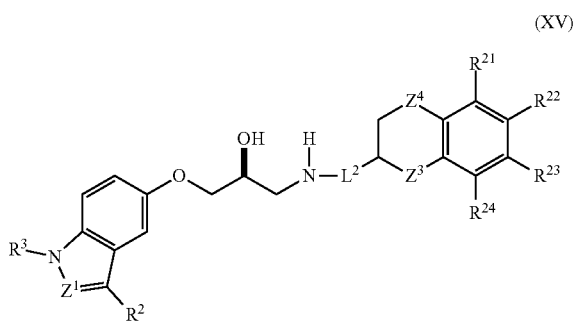

(XV)

wherein L² is a linker. In some embodiments of Formula (XV), L² is a C1-C6 alkyl linker, optionally substituted in the backbone with 1 or 2 oxygen atoms, e.g. L² is —(CH₂)$_q$— wherein q is an integer from 1-3. In certain embodiments of Formula (XV), Z¹ is N. In certain embodiments of Formula (XV), Z¹ is CR¹. In certain embodiments of Formula (XV), Z¹ is CH. In certain embodiments of Formula (XV), R² is H. In certain embodiments of Formula (XV), R³ is H. In certain embodiments of Formula (XV), R¹ is an alkyl or a substituted alkyl. In certain embodiments of Formula (XV), R² is an alkyl or a substituted alkyl. In certain embodiments of Formula (XV), R² is methyl. In certain embodiments of Formula (XV), R³ is an alkyl or a substituted alkyl. In some embodiments of Formula (XV), R² is methyl, Z¹ is N and R³ is hydrogen. In certain embodiments of Formula (XV), L² is C1-C6 alkyl linker substituted with 1, 2 or more deuterium, e.g., at the carbon atom of the linker adjacent to the —NH— nitrogen.

In some embodiments of Formulae (XV), Z⁴ is O and Z³ is CH₂. In some embodiments of Formulae (XV), Z⁴ and Z³ are each O. In some embodiments of Formulae (XV), Z⁴ is CH₂ and Z³ is O. In some embodiments of Formulae (XV), Z⁴ is CH₂ and Z³ is CH₂.

In certain instances, the compound has the following structure:

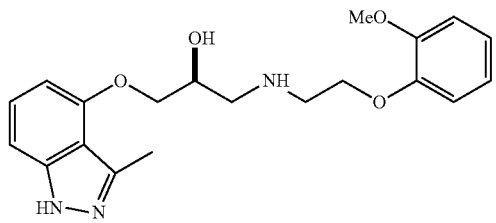

In certain instances, the compound has the following structure:

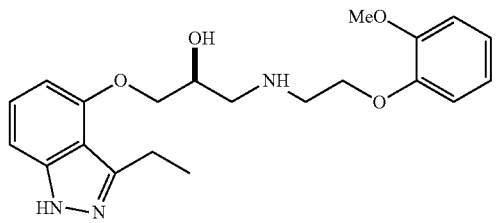

In certain instances, the compound has the following structure:

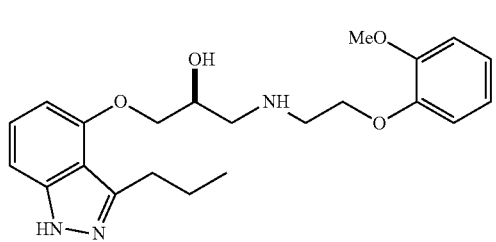

In certain instances, the compound has the following structure:

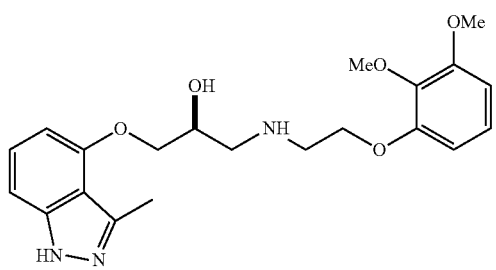

In certain instances, the compound has the following structure:

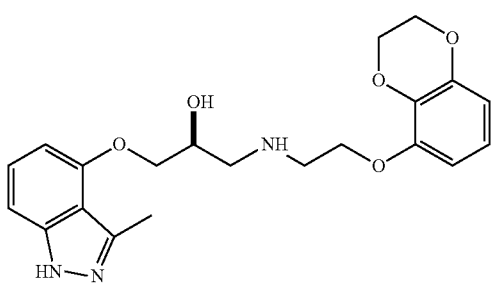

In certain instances, the compound has the following structure:

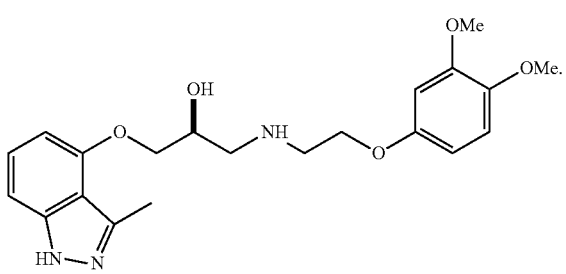 [SMILES: COc1ccc(OCCNC[C@H](O)COc2cccc3[nH]nc(C)c23)cc1OC]

In certain instances, the compound has the following structure:

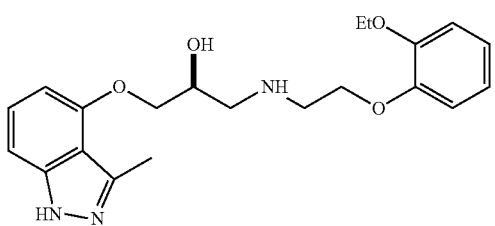

In certain instances, the compound has the following structure:

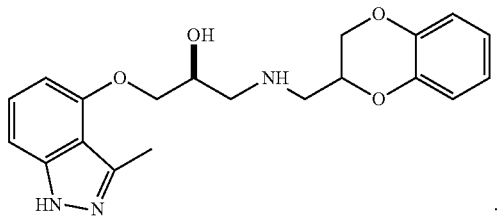 [SMILES: Cc1n[nH]c2cccc(OC[C@@H](O)CNCC3COc4ccccc4O3)c12]

In certain instances, the compound has the following structure:

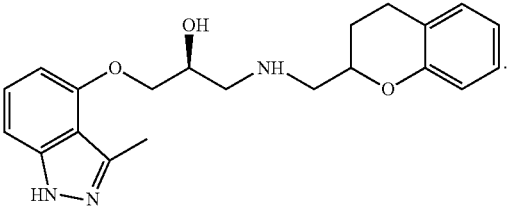 [SMILES: Cc1n[nH]c2cccc(OC[C@@H](O)CNCC3CCc4ccccc4O3)c12]

In certain instances, the compound has the following structure:

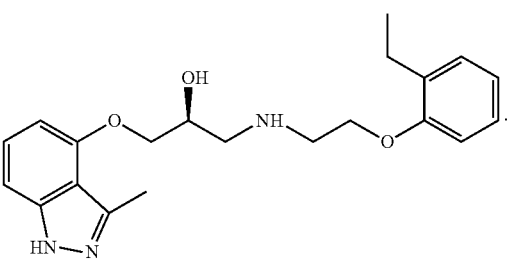 [SMILES: CCc1ccccc1OCCNC[C@H](O)COc1cccc2[nH]nc(C)c12]

In certain instances, the compound has the following structure:

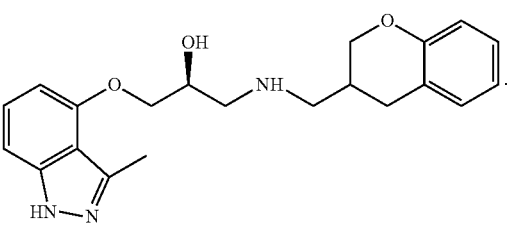 [SMILES: Cc1n[nH]c2cccc(OC[C@@H](O)CNCC3COc4ccccc4C3)c12]

In certain instances, the compound has the following structure:

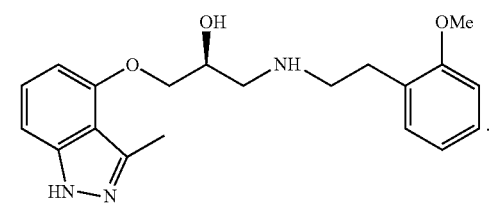 [SMILES: COc1ccccc1CCNC[C@H](O)COc1cccc2[nH]nc(C)c12]

In certain instances, the compound has the following structure:

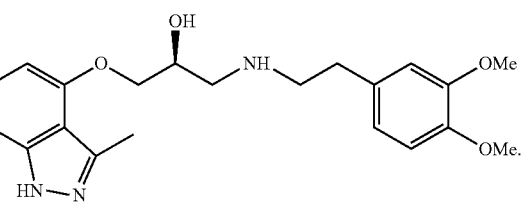

In certain instances, the compound has the following structure:

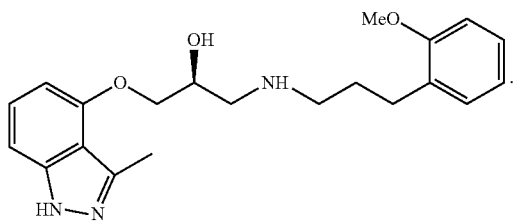 [SMILES: COc1ccccc1CCCNC[C@H](O)COc1cccc2[nH]nc(C)c12]

In certain instances, the compound has the following structure:

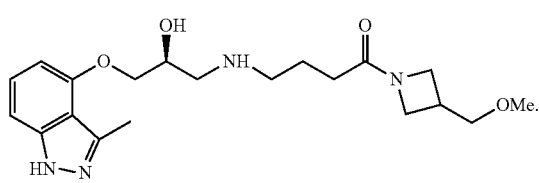 [SMILES: COCC1CN(C(=O)CCCNC[C@H](O)COc2cccc3[nH]nc(C)c23)C1]

In certain instances, the compound has the following structure:

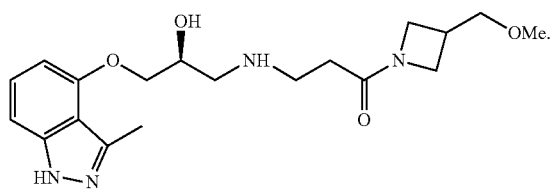 [SMILES: COCC1CN(C(=O)CCNC[C@H](O)COc2cccc3[nH]nc(C)c23)C1]

In certain instances, the compound has the following structure:

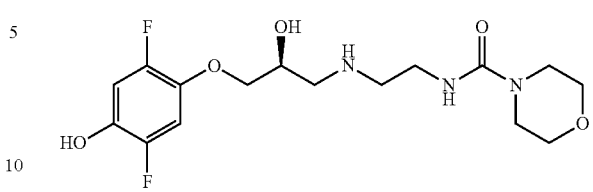

In certain instances, the compound has the following structure:

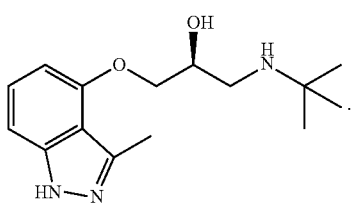 [SMILES: Cc1n[nH]c2cccc(OC[C@@H](O)CNC(C)(C)C)c12]

In some cases, the compound is a compound of Table 1. In certain instances, the compound is selected from compounds 3-6, 8 and 10 of Table 1. In certain instances, the compound is selected from compounds 24-31 of Table 1. In certain instances, the compound is selected from compounds 1-2 of Table 1. In certain instances, the compound is selected from compounds 11-21 of Table 1. In certain instances, the compound is selected from compounds 43-48 of Table 1.

TABLE 1

| Compounds of interest | |
|---|---|
| Compound No. | Compound Structure |
| 1 | |
| 2 | |
| 3 | |

US 11,173,144 B2
TABLE 1-continued
Compounds of interest
| Compound No. | Compound Structure |
|---|---|
| 4 | 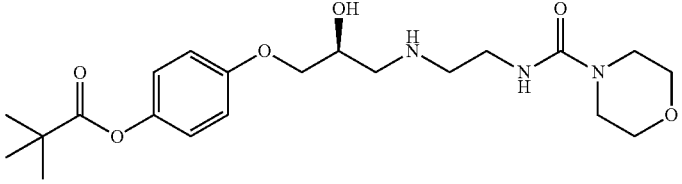 [SMILES: CC(C)(C)C(=O)Oc1ccc(OC[C@@H](O)CNCCNC(=O)N2CCOCC2)cc1] |
| 5 | 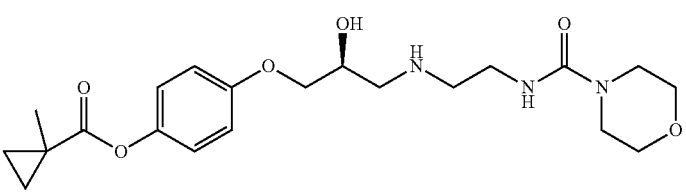 [SMILES: CC1(C(=O)Oc2ccc(OC[C@@H](O)CNCCNC(=O)N3CCOCC3)cc2)CC1] |
| 6 | 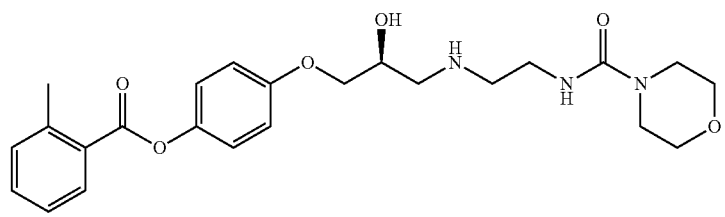 [SMILES: Cc1ccccc1C(=O)Oc1ccc(OC[C@@H](O)CNCCNC(=O)N2CCOCC2)cc1] |
| 7 | 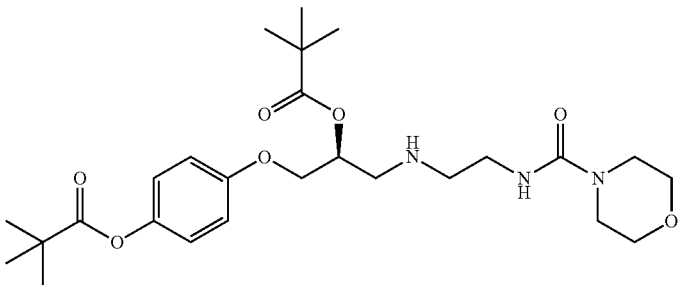 [SMILES: CC(C)(C)C(=O)Oc1ccc(OC[C@H](CNCCNC(=O)N2CCOCC2)OC(=O)C(C)(C)C)cc1] |
| 8 | 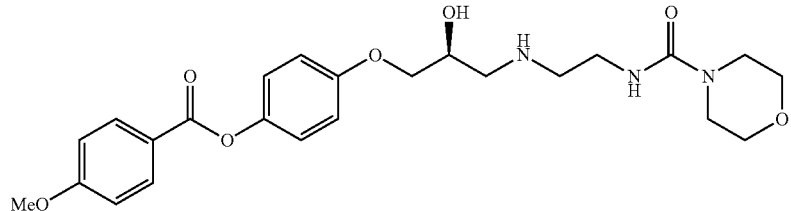 [SMILES: COc1ccc(C(=O)Oc2ccc(OC[C@@H](O)CNCCNC(=O)N3CCOCC3)cc2)cc1] |
| 9 | 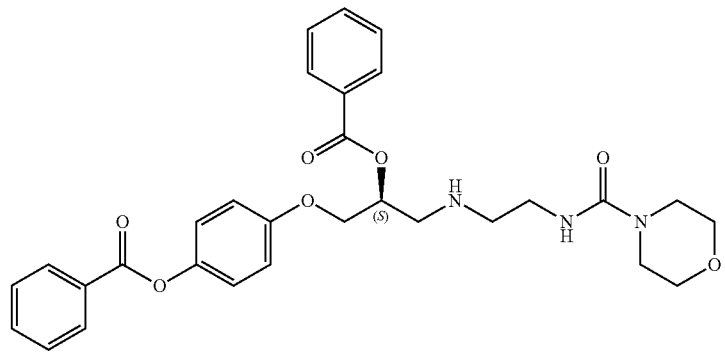 |

TABLE 1-continued

Compounds of interest

| Compound No. | Compound Structure |
|---|---|
| 10 | 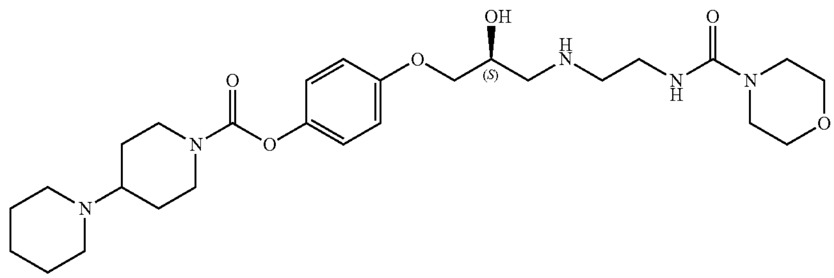 |
| 11 | 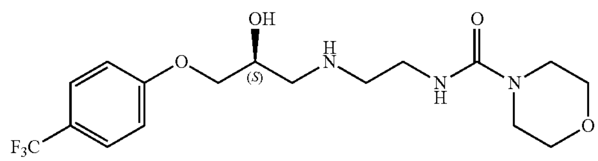 |
| 12 | 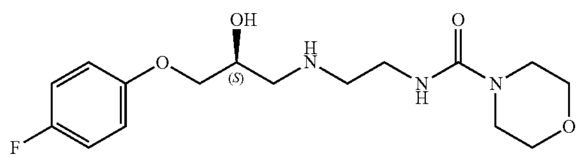 |
| 13 | 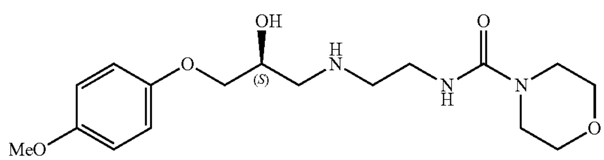 |
| 14 | 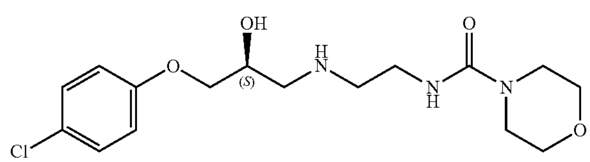 |
| 15 | 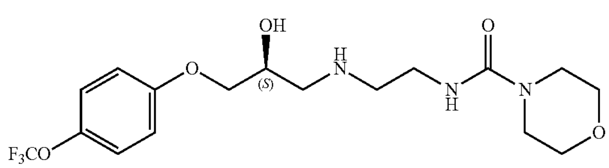 |
| 16 | 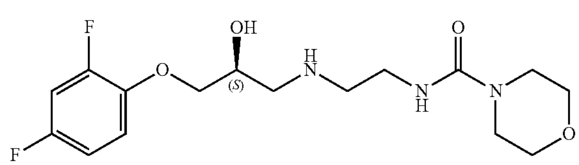 |
| 17 | 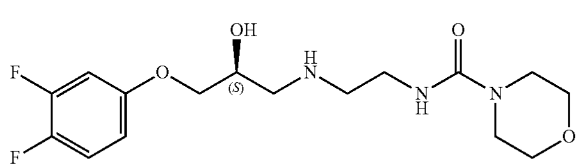 |

TABLE 1-continued

Compounds of interest

| Compound No. | Compound Structure |
| --- | --- |
| 18 | 3-fluorophenoxy-CH2-CH(OH)-CH2-NH-CH2-CH2-NH-C(O)-N(morpholine) |
| 19 | 2,5-difluorophenoxy-CH2-CH(OH)-CH2-NH-CH2-CH2-NH-C(O)-N(morpholine) |
| 20 | 3-fluoro-4-methoxyphenoxy-CH2-CH(OH)-CH2-NH-CH2-CH2-NH-C(O)-N(morpholine) |
| 21 | 3-chlorophenoxy-CH2-(S)-CH(OH)-CH2-NH-CH2-CH2-NH-C(O)-N(morpholine) |
| 22 | 3-cyanophenoxy-CH2-(S)-CH(OH)-CH2-NH-CH2-CH2-NH-C(O)-N(morpholine) |
| 23 | 2-cyanophenoxy-CH2-CH(OH)-CH2-NH-CH2-CH2-NH-C(O)-N(morpholine) |
| 24 | 4-hydroxy-3-methylphenoxy-CH2-CH(OH)-CH2-NH-CH2-CH2-NH-C(O)-N(morpholine) |
| 25 | 3-chloro-4-hydroxyphenoxy-CH2-CH(OH)-CH2-NH-CH2-CH2-NH-C(O)-N(morpholine) |

TABLE 1-continued

Compounds of interest

| Compound No. | Compound Structure |
|---|---|
| 26 | (structure) |
| 27 | (structure) |
| 28 | (structure) |
| 29 | (structure) |
| 30 | (structure) |
| 31 | (structure) |
| 32 | (structure) |

TABLE 1-continued
Compounds of interest
| Compound No. | Compound Structure |
|---|---|
| 33 | 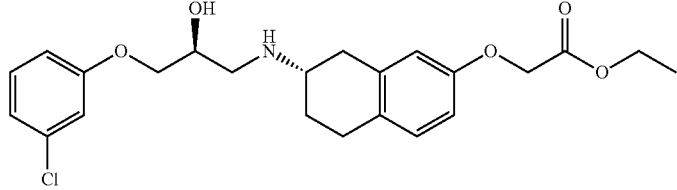 [SMILES: CCOC(=O)COc1ccc2c(c1)C[C@@H](NC[C@H](O)COc1cccc(Cl)c1)CC2] |
| 34 | 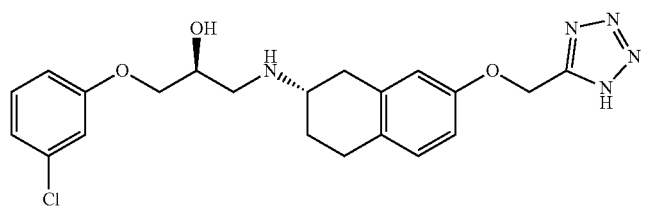 [SMILES: O[C@@H](CN[C@H]1CCc2ccc(OCc3nnn[nH]3)cc2C1)COc1cccc(Cl)c1] |
| 35 | 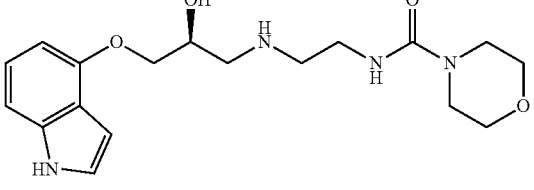 |
| 36 | 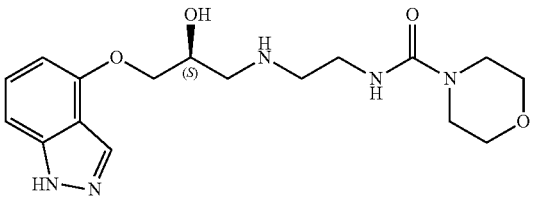 |
| 37 | 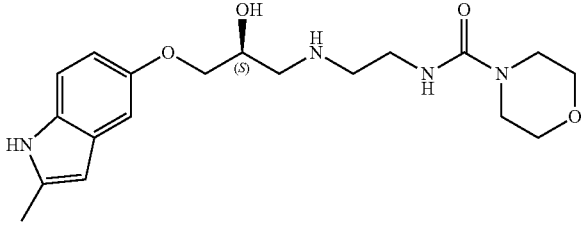 |
| 38 | 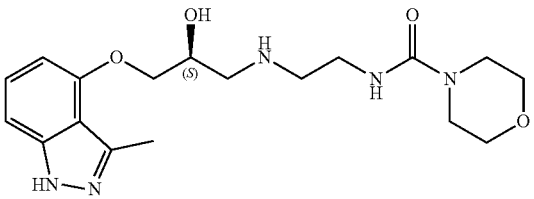 |
| 39 | 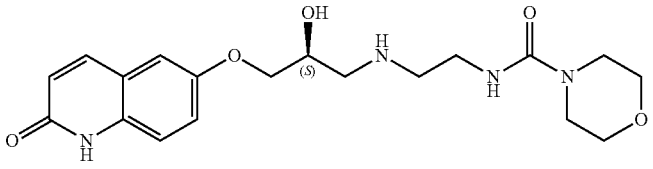 |

TABLE 1-continued

Compounds of interest

| Compound No. | Compound Structure |
| --- | --- |
| 40 | 2-methyl-1H-indol-4-yl connected via O-CH2-CH(OH)(S)-CH2-NH-CH2-CH2-NH-C(=O)-N(morpholine) |
| 41 | 1H-indazol-5-yl connected via O-CH2-CH(OH)(S)-CH2-NH-CH2-CH2-NH-C(=O)-N(morpholine) |
| 42 | 3-methyl-1H-indazol-5-yl connected via O-CH2-CH(OH)-CH2-NH-CH2-CH2-NH-C(=O)-N(morpholine) |
| 43 | 4-hydroxyphenyl-O-CH2-CH(OH)-CH2-NH-CH2-CH2-O-(2-methoxyphenyl) |
| 44 | 4-hydroxyphenyl-O-CH2-CH(OH)(S)-CH2-NH-CH2-CH2-O-CH2-CH2-(3,4-dimethoxyphenyl) |
| 45 | 4-hydroxyphenyl-O-CH2-CH(OH)-CH2-NH-CH2-CH2-CH2-C(=O)-N(morpholine) |
| 46 | 4-hydroxyphenyl-O-CH2-CH(OH)-CH2-NH-CH2-CH2-C(=O)-N(morpholine) |
| 47 | 4-hydroxyphenyl-O-CH2-CH(OH)-CH2-NH-CH2-CH2-NH-C(=O)-N(3-hydroxyazetidine) |

TABLE 1-continued

Compounds of interest

| Compound No. | Compound Structure |
| --- | --- |
| 48 | (structure: 4-hydroxyphenoxy-CH2-CH(OH)-CH2-NH-CH2CH2-NH-C(O)-N(azetidine-3-yl-CH2OH)) |
| 49 | (structure: 5-hydroxy-naphthalen-1-yloxy-CH2-CH(OH)-CH2-NH-CH2CH2-NH-C(O)-N(morpholine)) |
| 50 | (structure: 3,4-dihydroxyphenoxy-CH2-CH(OH)-CH2-NH-CH2CH2-(3,4-dimethoxyphenyl)) |
| 51 | (structure: 4-hydroxyphenoxy-CH2-CH(OH)-CH2-NH-CH2CH2-NH-C(O)-N(piperidine)) |
| 52 | (structure: 3-methyl-1H-indazol-4-yloxy-CH2-CH(OH)-CH2-NH-CH2CH2-O-(2-methoxyphenyl)) |
| 53 | (structure: 3-methyl-1H-indazol-4-yloxy-CH2-CH(OH)-CH2-NH-CH2CH2-O-(2-ethoxyphenyl)) |
| 54 | (structure: 3-methyl-1H-indazol-4-yloxy-CH2-CH(OH)-CH2-NH-CH2CH2-O-(2,3-dimethoxyphenyl)) |

TABLE 1-continued
Compounds of interest
| Compound No. | Compound Structure |
|---|---|
| 55 | 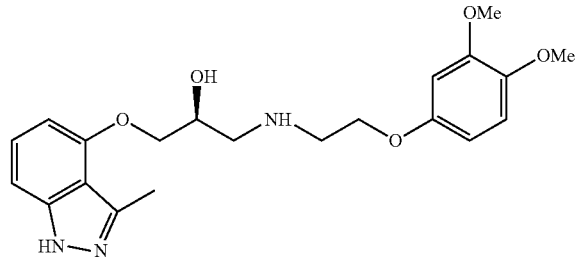 [SMILES: COc1ccc(OCCNC[C@H](O)COc2cccc3[nH]nc(C)c23)cc1OC] |
| 56 | 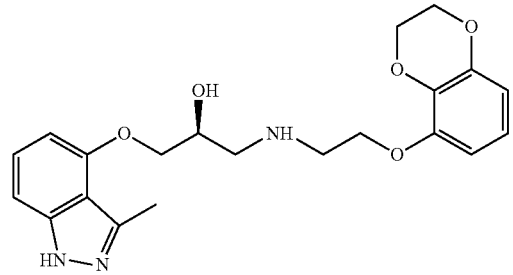 [SMILES: Cc1n[nH]c2cccc(OC[C@@H](O)CNCCOc3cccc4c3OCCO4)c12] |
| 57 | 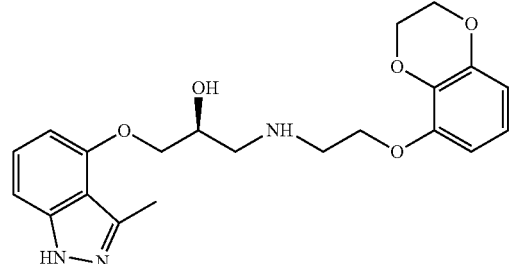 |
| 58 | 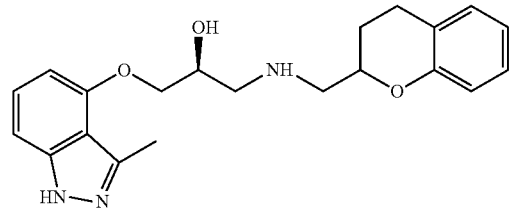 [SMILES: Cc1n[nH]c2cccc(OC[C@@H](O)CNCC3CCc4ccccc4O3)c12] |
| 59 | 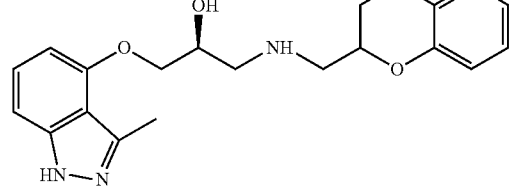 |
| 60 | 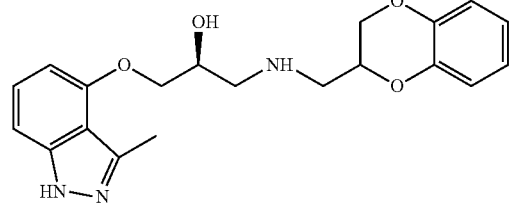 |

TABLE 1-continued

Compounds of interest

| Compound No. | Compound Structure |
|---|---|
| 61 | (3-methyl-1H-indazol-4-yl)oxy-CH2-CH(OH)-CH2-NH-CH2-(chroman-3-yl) |
| 62 | (3-methyl-1H-indazol-4-yl)oxy-CH2-CH(OH)-CH2-NH-(CH2)3-(2-methoxyphenyl) |
| 63 | (3-methyl-1H-indazol-4-yl)oxy-CH2-CH(OH)-CH2-NH-(CH2)2-(2-methoxyphenyl) |
| 64 | (3-methyl-1H-indazol-4-yl)oxy-CH2-CH(OH)-CH2-NH-(CH2)2-(2-methoxyphenyl) |
| 65 | (3-methyl-1H-indazol-4-yl)oxy-CH2-CH(OH)-CH2-NH-(CH2)2-(3,4-dimethoxyphenyl) |
| 66 | (3-methyl-1H-indazol-4-yl)oxy-CH2-CH(OH)-CH2-NH-(CH2)2-O-(7-methoxynaphthalen-1-yl) |

TABLE 1-continued
Compounds of interest
| Compound No. | Compound Structure |
|---|---|
| 67 | 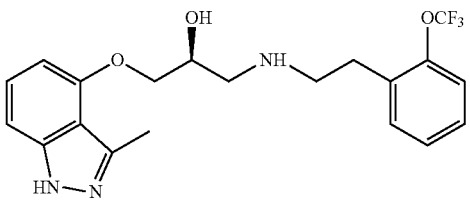 |
| 68 | 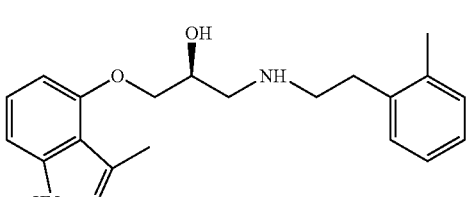 |
| 69 | 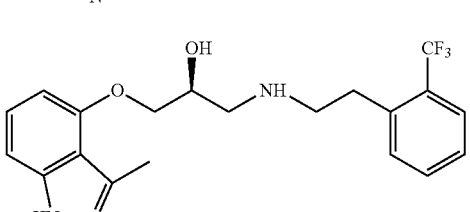 |
| 70 | 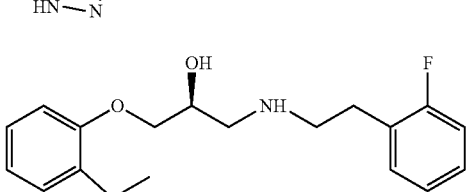 |
| 71 | 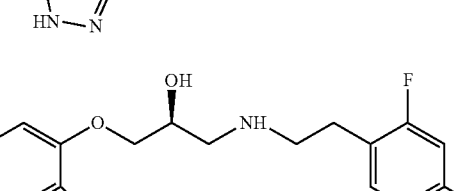 |
| 72 | 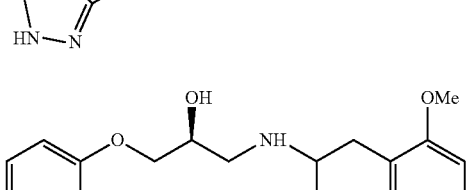 |
| 73 | 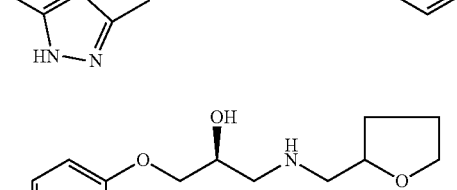 |

TABLE 1-continued

Compounds of interest

| Compound No. | Compound Structure |
|---|---|
| 74 | (S)-1-((3-methyl-1H-indazol-4-yl)oxy)-3-((cyclopropylmethyl)amino)propan-2-ol |
| 75 | (S)-1-((3-methyl-1H-indazol-4-yl)oxy)-3-(tert-butylamino)propan-2-ol |
| 76 | (S)-1-((3-methyl-1H-indazol-4-yl)oxy)-3-(neopentylamino)propan-2-ol |
| 77 | (S)-1-((3-methyl-1H-indazol-4-yl)oxy)-3-(((1-methyl-1H-pyrazol-3-yl)methyl)amino)propan-2-ol |
| 78 | (S)-1-((3-methyl-1H-indazol-4-yl)oxy)-3-((2-chlorophenethyl)amino)propan-2-ol |
| 79 | (S)-1-((3-methyl-1H-indazol-4-yl)oxy)-3-(((3-methylisoxazol-5-yl)methyl)amino)propan-2-ol |
| 80 | (S)-1-((3-methyl-1H-indazol-4-yl)oxy)-3-(((1-methyl-1H-imidazol-2-yl)methyl)amino)propan-2-ol |

TABLE 1-continued
Compounds of interest
| Compound No. | Compound Structure |
| --- | --- |
| 81 | 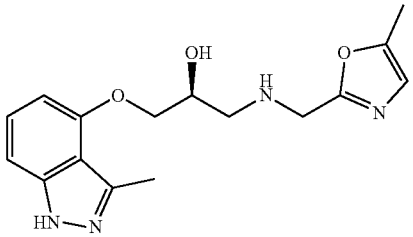 [SMILES: Cc1cnc(CNC[C@H](O)COc2cccc3[nH]nc(C)c23)o1] |
| 82 | 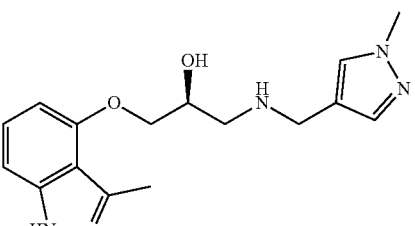 |
| 83 | 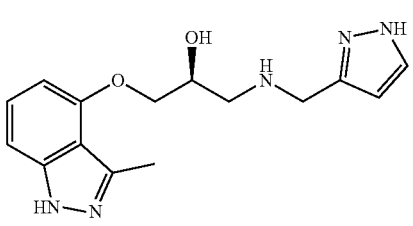 [SMILES: Cc1n[nH]c2cccc(OC[C@@H](O)CNCc3cc[nH]n3)c12] |
| 84 | 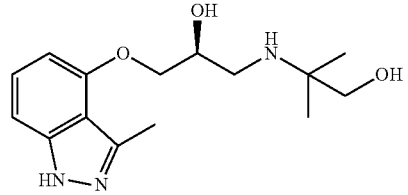 [SMILES: Cc1n[nH]c2cccc(OC[C@@H](O)CNC(C)(C)CO)c12] |
| 85 | 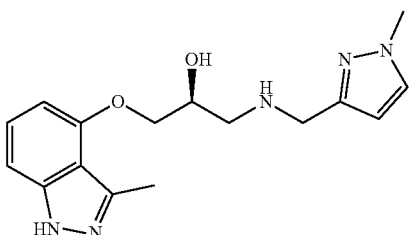 |
| 86 | 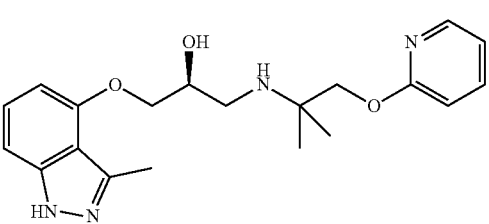 [SMILES: Cc1n[nH]c2cccc(OC[C@@H](O)CNC(C)(C)COc3ccccn3)c12] |

TABLE 1-continued
Compounds of interest
| Compound No. | Compound Structure |
|---|---|
| 87 | 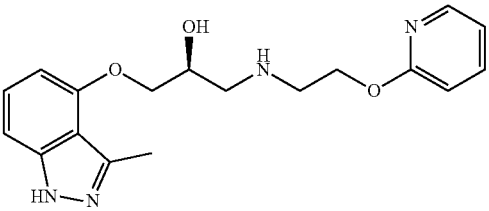 [SMILES: Cc1n[nH]c2cccc(OC[C@@H](O)CNCCOc3ccccn3)c12] |
| 88 | 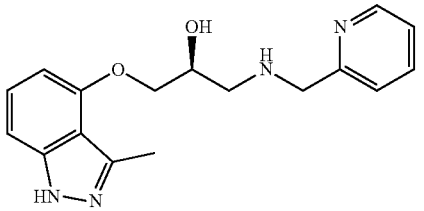 [SMILES: Cc1n[nH]c2cccc(OC[C@@H](O)CNCc3ccccn3)c12] |
| 89 | 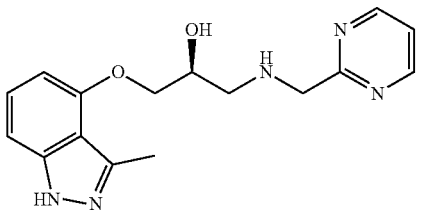 [SMILES: Cc1n[nH]c2cccc(OC[C@@H](O)CNCc3ncccn3)c12] |
| 90 | 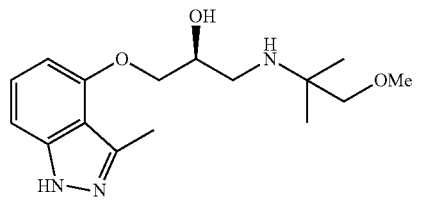 [SMILES: COCC(C)(C)NC[C@H](O)COc1cccc2[nH]nc(C)c12] |
| 91 | 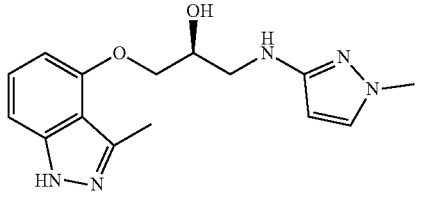 [SMILES: Cc1n[nH]c2cccc(OC[C@@H](O)CNc3ccn(C)n3)c12] |
| 92 | 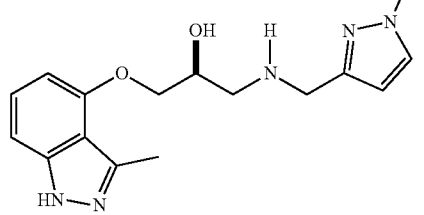 |
| 93 | 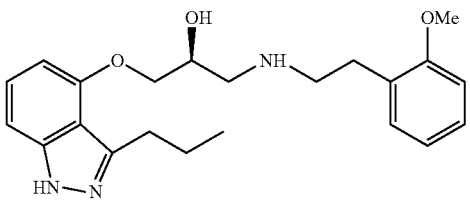 [SMILES: CCCc1n[nH]c2cccc(OC[C@@H](O)CNCCc3ccccc3OC)c12] |

TABLE 1-continued

Compounds of interest

| Compound No. | Compound Structure |
|---|---|
| 94 | 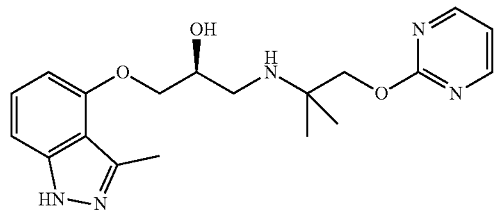 [SMILES: Cc1n[nH]c2cccc(OC[C@@H](O)CNC(C)(C)COc3ncccn3)c12] |
| 95 | 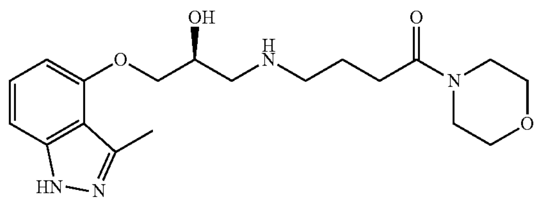 [SMILES: Cc1n[nH]c2cccc(OC[C@@H](O)CNCCCC(=O)N3CCOCC3)c12] |
| 96 | 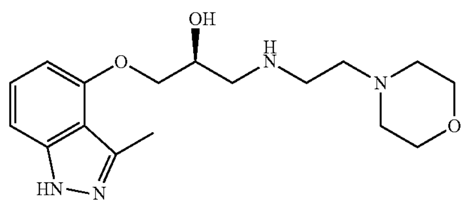 [SMILES: Cc1n[nH]c2cccc(OC[C@@H](O)CNCCN3CCOCC3)c12] |
| 97 | 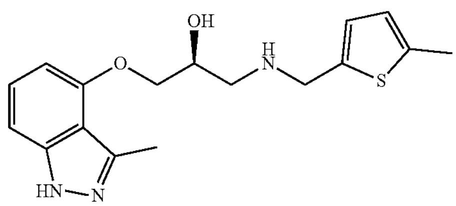 [SMILES: Cc1ccc(CNC[C@H](O)COc2cccc3[nH]nc(C)c23)s1] |
| 98 | 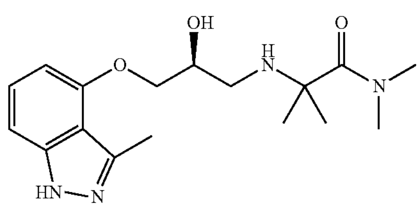 [SMILES: Cc1n[nH]c2cccc(OC[C@@H](O)CNC(C)(C)C(=O)N(C)C)c12] |
| 99 | 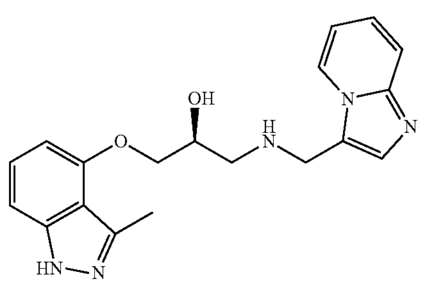 [SMILES: Cc1n[nH]c2cccc(OC[C@@H](O)CNCc3cnc4ccccn34)c12] |
| 100 | 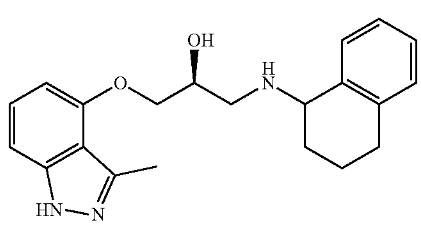 [SMILES: Cc1n[nH]c2cccc(OC[C@@H](O)CNC3CCCc4ccccc43)c12] |

TABLE 1-continued
Compounds of interest
| Compound No. | Compound Structure |
|---|---|
| 101 | 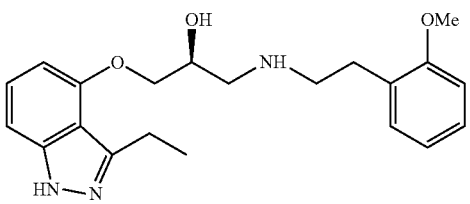 [SMILES: CCc1n[nH]c2cccc(OC[C@@H](O)CNCCc3ccccc3OC)c12] |
| 102 | 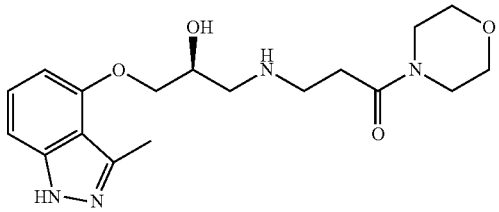 [SMILES: Cc1n[nH]c2cccc(OC[C@@H](O)CNCCC(=O)N3CCOCC3)c12] |
| 103 | 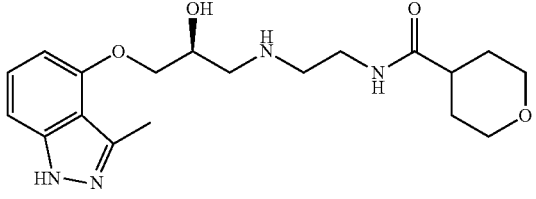 [SMILES: Cc1n[nH]c2cccc(OC[C@@H](O)CNCCNC(=O)C3CCOCC3)c12] |
| 104 | 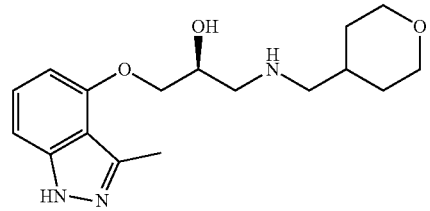 [SMILES: Cc1n[nH]c2cccc(OC[C@@H](O)CNCC3CCOCC3)c12] |
| 105 | 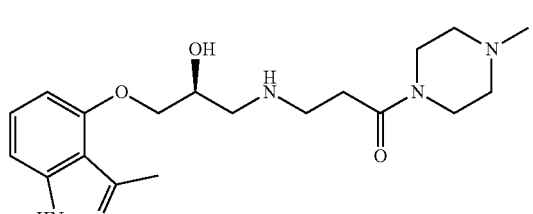 |
| 106 | 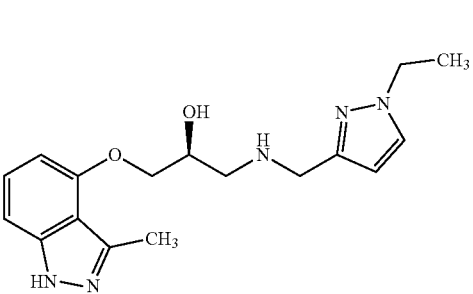 [SMILES: CCn1ccc(CNC[C@H](O)COc2cccc3[nH]nc(C)c23)n1] |

TABLE 1-continued

Compounds of interest

| Compound No. | Compound Structure |
| --- | --- |
| 107 | (3-methyl-1H-indazol-4-yl)oxy linked to (S)-2-hydroxypropyl-NH-CH2-(1-benzyl-1H-pyrazol-3-yl) |
| 108 | (3-methyl-1H-indazol-4-yl)oxy linked to (S)-2-hydroxypropyl-NH-CH2-(1-phenyl-1H-pyrazol-3-yl) |
| 109 | (3-methyl-1H-indazol-4-yl)oxy linked to (S)-2-hydroxypropyl-NH-CH(CH3)-(1-methyl-1H-pyrazol-3-yl) |
| 110 | (4-hydroxyphenoxy)-(S)-2-hydroxypropyl-NH-CH2CH2-N(cyclopropyl)-C(=O)-morpholine |
| 111 | (2,5-difluoro-4-hydroxyphenoxy)-(S)-2-hydroxypropyl-NH-CH2CH2-N(cyclopropyl)-C(=O)-morpholine |
| 112 | (4-hydroxyphenoxy)-(S)-2-hydroxypropyl-NH-CH2CH2-N(CH3)-C(=O)-morpholine |

TABLE 1-continued

Compounds of interest

| Compound No. | Compound Structure |
| --- | --- |
| 113 | 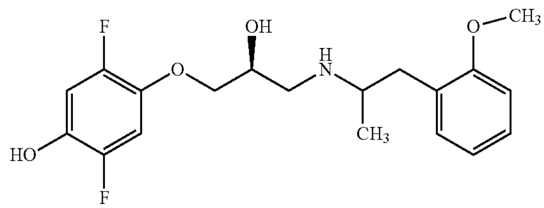 [SMILES: COc1ccccc1CC(C)NC[C@H](O)COc1cc(F)c(O)cc1F] |
| 114 | 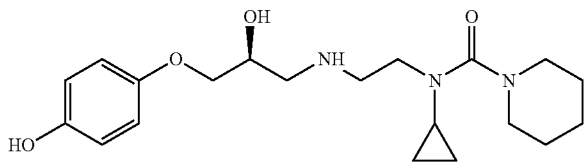 [SMILES: O=C(N1CCCCC1)N(CCNC[C@H](O)COc1ccc(O)cc1)C1CC1] |
| 115 | 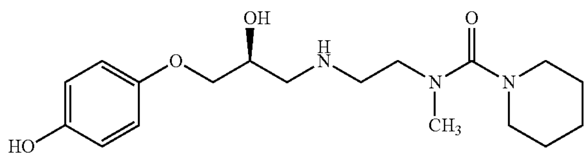 [SMILES: CN(CCNC[C@H](O)COc1ccc(O)cc1)C(=O)N1CCCCC1] |
| 116 | 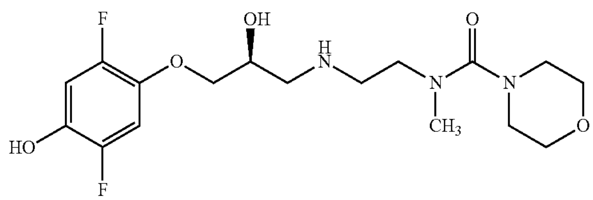 [SMILES: CN(CCNC[C@H](O)COc1cc(F)c(O)cc1F)C(=O)N1CCOCC1] |
| 117 | 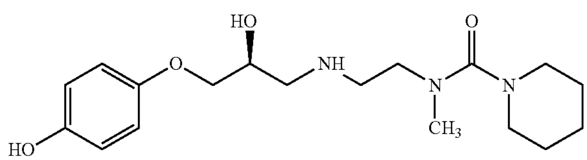 [SMILES: CN(CCNC[C@H](O)COc1ccc(O)cc1)C(=O)N1CCCCC1] |
| 118 | 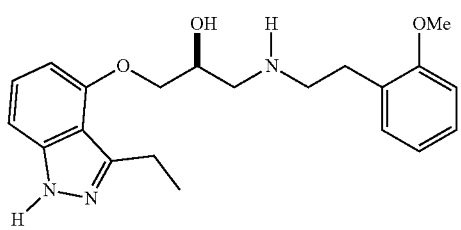 [SMILES: CCc1n[nH]c2cccc(OC[C@@H](O)CNCCc3ccccc3OC)c12] |

Aspects of the present disclosure include adrenergic receptor modulating compounds, salts thereof (e.g., pharmaceutically acceptable salts), and/or solvate, hydrate and/or prodrug forms thereof. In addition, it is understood that, in any compound described herein having one or more chiral centers, if an absolute stereochemistry is not expressly indicated, then each center may independently be of R-configuration or S-configuration or a mixture thereof. It will be appreciated that all permutations of salts, solvates, hydrates, prodrugs and stereoisomers are meant to be encompassed by the present disclosure.

Certain compounds of the present disclosure possess asymmetric carbon atoms (optical centers) or double bonds; the racemates, diastereomers, geometric isomers and individual isomers (e.g., separate enantiomers) are all intended to be encompassed within the scope of the present disclosure. The compounds of the present disclosure may also contain unnatural proportions of atomic isotopes at one or more of the atoms that constitute such compounds. For example, the subject compounds may be radiolabeled with radioactive isotopes, such as for example tritium, iodine-$^{125}$I or $^{14}$C. Examples of isotopes that can be incorporated into the compounds disclosed herein include, but are not limited to, $^2$H, $^3$H, $^{11}$C, $^{13}$C, $^{14}$C, $^{15}$N, $^{18}$O, $^{17}$O, etc. All isotopic variations of the subject compounds, whether radioactive or not, are intended to be encompassed within the scope of the present disclosure.

Deuteration of biologically active compounds of interest can produce analogs with improved pharmacokinetics (PK), pharmacodynamics (PD), and/or toxicity profiles. In some embodiments, compounds of interest (e.g., any one of the compounds described herein) include a deuterium substituent at any convenient location(s) of the moelcule. In certain instances of the subject compounds, the compound is further modified to include a deuterium, such as 2 or more deuterium substituents, such as 3 or more, 4 or more, or 5 or more deuterium substituents. In some cases, the deuterium substituents are located on carbon atoms of an alkyl or substituted alkyl group of the compound.

Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

Furthermore, except as otherwise noted, the chemical methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

In some embodiments, the subject compounds, or a prodrug form thereof, are provided in the form of pharmaceutically acceptable salts. Compounds containing an amine or nitrogen containing heteraryl group may be basic in nature and accordingly may react with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-I,4-dioate, hexyne-I,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid.

In some embodiments, the subject compounds are provided in a prodrug form. "Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent. "Promoiety" refers to a form of protecting group that, when used to mask a functional group within an active agent, converts the active agent into a prodrug. In some cases, the promoiety will be attached to the drug via bond(s) that are cleaved by enzymatic or non enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)).

In certain embodiments, the subject compound is a produg form of one of Formula (I)-(IX) that includes a promoiety attached to the aminoglycerol linker group as follows:

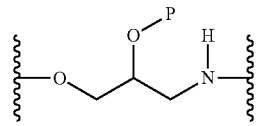

where P is the promoiety. In certain instances, —OP is an ether. In certain instances, —OP is a carbonate. In certain instances, —OP is an phosphate. In certain instances, —OP is an alkoxyphosphate. In certain instances, —OP is an ester. In certain embodiments, P is an acyl or a substituted acyl. In certain embodiments, P is —C(O)R$_{10}$, where R$_{10}$, R$_{20}$ and R$_{30}$ are each independently selected from hydrogen, unsubstituted or substituted C$_{1-6}$ haloalkyl, unsubstituted or substituted C$_{1-6}$ alkyl, unsubstituted or substituted C$_{3-6}$ cydoalkyl, unsubstituted or substituted C$_{2-6}$ alkenyl, unsubstituted or substituted C$_{2-6}$ alkynyl, unsubstituted or substituted C$_{6-10}$ aryl, unsubstituted or substituted 5- to 10-membered heteroaryl, unsubstituted or substituted aryl-C$_{1-4}$ alkyl, unsubstituted or substituted aryl-C$_{1-4}$ alkyl, and unsubstituted or substituted aryloxy-C$_{1-4}$ alkyl. In certain cases, P is selected from one of the following groups: —COCH$_3$: —COC$_2$H$_5$, —COC(CH$_3$)$_3$, —CO$_2$CH(CH$_3$)$_2$, —CO$_2$CH$_3$ and —CO$_2$CH$_5$.

In certain embodiments, the subject compound is a produg form of one of Formula (I)-(IX) that includes a promoiety attached to a phenolic substituent, e.g., Aryl-O—P, where P is the promoiety (e.g., as described herein). For example, in certain instances of formulae (IV) and (V), when one of R$^{11}$-R$^{15}$ is a hydroxy group, the subject compound can be present in a prodrug form where the hydroxy group is substituted with a promoiety P as defined above, such as an acyl or substituted acyl group.

In some embodiments, the subject compounds, prodrugs, stereoisomers or salts thereof are provided in the form of a solvate (e.g., a hydrate). The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

Pharmaceutical Preparations

Also provided are pharmaceutical preparations. Pharmaceutical preparations are compositions that include an adrenergic receptor modulating compound (for example one or more of the subject compounds, either alone or in the presence of one or more additional active agents) present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the present disclosure is formulated for administration to a mammal. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used.

When administered to a mammal, the compounds and compositions of the present disclosure and pharmaceutically acceptable vehicles, excipients, or diluents may be sterile. In some instances, an aqueous medium is employed as a vehicle when the subject compound is administered intravenously, such as water, saline solutions, and aqueous dextrose and glycerol solutions.

Pharmaceutical compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In some instances, the pharmaceutical compositions are formulated for administration in accordance with routine procedures as a pharmaceutical composition adapted for oral or intravenous administration to humans. Examples of suitable pharmaceutical vehicles and methods for formulation thereof are described in Remington: The Science and Practice of Pharmacy, Alfonso R. Gennaro ed., Mack Publishing Co. Easton, Pa., 19th ed., 1995, Chapters 86, 87, 88, 91, and 92, incorporated herein by reference. The choice of excipient will be determined in part by the particular compound, as well as by the particular method used to administer the composition. Accordingly, there is a wide variety of suitable formulations of the subject pharmaceutical compositions.

Administration of the subject compounds may be systemic or local. In certain embodiments administration to a mammal will result in systemic release of a compound of the present disclosure (for example, into the bloodstream). Methods of administration may include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. In certain embodiments, the compounds and compositions of the present disclosure are administered subcutaneously. In certain embodiments, the compounds and compositions of the present disclosure are administered orally. In certain embodiments, it may be desirable to administer one or more compounds of the present disclosure locally to the area in need of treatment. This may be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

For the treatment of eye disorders, the pharmaceutical formulations of the invention may be administered, e.g., by eye drops, subconjunctival injection, subconjunctival implant, intravitreal injection, intravitreal implant, sub-Tenon's injection or sub-Tenon's implant.

The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A subject compound may also be formulated for oral administration. For an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition may also contain minor amounts of non-toxic auxiliary substances such as wetting agents, emulsifying agents, or buffers. In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

The subject formulations can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

In some embodiments, formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freezedried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are appropriate. In some embodiments the topical formulation contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components, e.g., astringents, fragrances, pigments, skin penetration enhancing agents, sunscreens (e.g., sunblocking agents), etc.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms of the present disclosure depend on the particular compound employed and the effect to be achieved, and the pharmacodynamics associated with each compound in the host. In pharmaceutical dosage forms, the compounds may be administered in the form of a free base, their pharmaceutically acceptable salts, or they may also be used alone or in appropriate association, as well as in combination, with other pharmaceutically active compounds.

Dose levels can vary as a function of the specific compound, the nature of the delivery vehicle, and the like. Desired dosages for a given compound are readily determinable by a variety of means. The dose administered to an animal, particularly a human, in the context of the present disclosure should be sufficient to effect a prophylactic or therapeutic response in the animal over a reasonable time frame, e.g., as described in greater detail herein. Dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound.

Methods of Modulating Adranergic Receptors

The adrenergic receptor modulating compounds of the present disclosure find use in modulating the activity of a target adrenergic receptor in a sample. Aspects of the subject methods include contacting the sample with an effective amount of an adrenergic receptor modulating compound (e.g., as described herein).

The adrenergic receptor modulating compound can be an agonist of the target adrenergic receptor. In some cases, an effective amount of an adrenergic receptor modulating compound is an amount sufficient to activate an activity related to the adrenergic receptor in a cell by 10% or more, such as 20% or more, 30% or more, 40% or more, 50% or more, 60% or more, 70% or more, 80% or more, 90% or more, 100% or more, 200% or or even more relative to a control, e.g., a control cell exhibiting a known activity level of the receptor.

The adrenergic receptor modulating compound can be a partial agonist of the target adrenergic receptor. In some cases, an effective amount of an adrenergic receptor modulating compound is an amount sufficient to achieve partially agonism of the adrenergic receptor in a cell, e.g., where the subject compound achieves 10% activation or more of the receptor, such as 20% or more, 30% or more, 40% or more, 50% or more, 60% or more, 70% or more, 80% or more, or 90% or more, relative to a control, e.g., a receptor that is fully activated. Partial agonism may be assessed using any convenient methods, such as a cell based assay using a known full agonist as a 100% activation control, where the relative maximum activation of the receptor can be measured relative to the full agonist (see e.g., FIG. 2A).

The adrenergic receptor modulating compound can be an antagonist of the target adrenergic receptor. In some cases, an effective amount of an adrenergic receptor modulating compound is an amount sufficient to inhibit or decrease the activity of the target adrenergic receptor in a sample by 10% or more, such as 20% or more, 30% or more, 40% or more, 50% or more, 60% or more, 70% or more, 80% or more, 90% or more, or even more relative to a control, e.g., a sample not contacted with the compound of interest.

In some embodiments of the method, the target adrenergic receptor is a $\beta$1-adrenergic receptor. In some embodiments of the method, the target adrenergic receptor is a $\beta$2-adrenergic receptor. In some embodiments of the method, the target adrenergic receptor is a $\beta$3-adrenergic receptor. In some embodiments of the method, the target adrenergic receptor is an $\alpha$1-adrenergic receptor. In some embodiments of the method, the target adrenergic receptor is an $\alpha$2-adrenergic receptor. In certain instances, the compound is selective for the $\beta$1-adrenergic receptor over a $\beta$2-adrenergic receptor. In certain cases, the compound is selective for the $\beta$1-adrenergic receptor over a $\beta$3-adrenergic receptor.

As used herein, the term "sample" relates to a material or mixture of materials, in some cases in liquid form, containing one or more analytes of interest. In some embodiments, the term as used in its broadest sense, refers to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents. The term "sample" may also refer to a "biological sample". As used herein, the term "a biological sample" refers to a whole organism or a subset of its tissues, cells or component parts (e.g. body fluids, including, but not limited to, blood, mucus, lymphatic fluid, synovial fluid, cerebrospinal fluid, saliva, amniotic fluid, amniotic cord blood, urine, vaginal fluid and semen). A "biological sample" can also refer to a homogenate, lysate or extract prepared from a whole organism or a subset of its tissues, cells or component parts, or a fraction or portion thereof, including but not limited to, plasma, serum, spinal fluid, lymph fluid, the external sections of the skin, respiratory, intestinal, and genitourinary tracts, tears, saliva, milk, blood cells, tumors and organs. In certain embodiments, the sample has been removed from an animal or plant. Biological samples may include cells. The term "cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

The target adrenergic receptor may be one that is responsible for a mediating an intracellular signal or pathway in a cell. In certain instances, the sample includes a cell and modulating the adrenergic receptor modulates a physiological process in the cell. Any convenient physiological processes can be targeted for modulation in a cell using the subject methods. In some case, the physiological process is one that is implicated in cardiac function. In certain instances, the physiological process is one that is implicated in cognitive function. In certain instances, the physiological process is one that is implicated in an inflammatory pathway or condition. The subject methods can provide for mediation of the intracellular concentration of a signaling molecule in a cell, such as cAMP. The subject methods can provide for partial or full blockage of the target adrenergic receptor to result in modulation (e.g., activation) of cAMP in a sample. In certain embodiments, the method does not modulate beta-arrestin pathways of the cell. In some cases, the cells are inflammatory cells and the function of the cells is regulated. The subject methods can provide for inhibition of an inflammatory pathway in a cell. In some cases, TNF-alpha is inhibited in the cell, e.g., the concentration or production of TNF-alpha is reduced by practicing the subject method. In certain embodiments of the method, the cell is a neuron. In some cases, modulating the adrenergic receptor enhances neurogenesis.

In certain instances, the sample is a cellular sample. The sample can be in vitro or in vivo. Aspects of the subject methods include evaluating the activity of the target adrenergic receptor in the sample. As used herein, the terms "evaluating", "determining," "measuring," and "assessing," and "assaying" are used interchangeably and include both quantitative and qualitative determinations. Evaluating the activity of the target adrenergic receptor can be performed before and/or after the sample is contacted with the subject compound and can be achieved using any convenient methods, including both direct methods (e.g., assays of adrenergic receptor activity or inhibition assays of direct binding of the target adrenergic receptor) and indirect methods (e.g., measuring downstream signals produced by the target adrenergic receptor). A variety of methods for evaluating the activity of the target adrenergic receptor can be utilized, for example, any convenient functional GPCR cell based assay for an adrenergic receptor of interest and the assays of the Examples section.

Method of Modulating an Inflammatory Pathway in a cell

Aspects of the present disclosure include a method of modulating an Inflammatory pathway in a cell. Applicants discovered a method whereby selective activation of a β1-adrenergic receptor of interest in a cell can selectively activate the cAMP pathway related to receptor without also modulating the beta-arrestin pathway in the cell. In some cases, the subject method includes modulating an inflammatory response, e.g., an inflammatory response to an inflammatory signal or condition. In some cases, this method can be applied to modulate TNF-alpha in a cell (e.g., modulate production of TNF-alpha) of interest and finds use in a variety of therapeutic and research applications. As such, the method includes contacting a cell with a β1-selective adrenergic receptor modulating compound to selectively activate a cAMP pathway over a beta-arrestin pathway in the cell. In certain embodiments, the method does not modulate beta-arrestin pathways of the cell. The subject method can result in modulation of production of TNF-alpha in the cell. Modulating an inflammatory pathway refers to modulation of the concentration of any convenient member of the pathway of interest. In some cases, modulation reduces the concentration of the target member of the inflammatory pathway by 10% or more, such as 20% or more, 30% or more, 40% or more, 50% or more, 60% or more, 70% or more, 80% or more, 90% or more, or even more relative to a control, e.g., a cell not contacted with the compound of interest. In some cases, by "modulating TNF-alpha" is meant the concentration of production of TNF-alpha in the cell is reduced by 10% or more, such as 20% or more, 30% or more, 40% or more, 50% or more, 60% or more, 70% or more, 80% or more, 90% or more, or even more relative to a control, e.g., a cell not contacted with the compound of interest. In some cases of the method, an inflammatory pathway is inhibited in the cell. In certain instances, the cell is an inflammatory cell and the function of the cell is regulated.

Any convenient β1-selective adrenergic receptor modulating compounds can be utilized in the subject methods. In some cases, the compounds which find use in the subject method, are compounds of any one of Formula (I)-(IX) (e.g., as described herein). In some cases, the β1-selective adrenergic receptor modulating compound is a compound of Table 1. In some cases, the β1-selective adrenergic receptor modulating compound is one of compounds 43-48 (see Table 1).

In some embodiments of the method, the compound is a partial agonist of the β1-adrenergic receptor. In certain embodiments of the method, the compound is an antagonist of the β1-adrenergic receptor. In certain cases, the compound is selective for the β1-adrenergic receptor over a β2-adrenergic receptor. In certain instances, the compound is selective for the β1-adrenergic receptor over a β3-adrenergic receptor. In certain instances, the compound is selective for the β1-adrenergic receptor over both β2-adrenergic receptors and β3-adrenergic receptors in the cell.

The cell can be in vitro or in vivo. In certain instances, the cell is in vivo and the method includes treating a subject for an inflammatory condition. In certain instances, the inflammatory condition is psoriasis. In such instances, the contacting comprises administering the β1-selective adrenergic receptor modulating compound to a subject in need thereof. Any convenient route and methods of administration (e.g., as described herein) can be utilized in the subject methods. In some instances, the route of administration is oral. In some instances, the route of administration is dermal, e.g., via topical application of a suitable pharmaceutical composition. In certain instances, the route of administration is intranasal.

In some embodiments of the method, the target adrenergic receptor and cells are located in the brain of a subject, e.g., a subject in need of treatment for a neurodegenerative disease (e.g., as described herein). In such cases, the compound penetrates the blood brain barrier of the subject after administration. Compounds capable of penetrating across the blood-brain barrier find use in the subject method. In certain embodiments of the method, the target adrenergic receptor and cells are located in the peripheral organs of a subject, e.g. a subject in need of treatment for a cardiovascular disease. In such cases, compounds not capable of crossing the blood brain barrier (e.g., Compound 38) find use in the subject method without any CNS-related side effects.

Methods of Treatment

The adrenergic receptor modulating compounds of the present disclosure find use in treatment of a condition or disease in a subject in which the activity of an adrenergic receptor is implicated (e.g., as described herein). Aspects of the method include administering to a subject in need thereof a therapeutically effective amount of a adrenergic receptor modulating compound to treat the subject. By "a therapeutically effective amount" is meant the concentration of a compound that is sufficient to elicit the desired biological effect (e.g., treatment of the condition or disease). By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms.

Examples of diseases or conditions which may be treated with compounds of the invention include, but are not limited to: cardiac diseases, inflammatory diseases, neurodegenerative disease (e.g., Alzheimer's Disease), neuropsychiatric disorders, neurodevelopmental disorders (e.g., Down's syndrome or Autism), respiratory disorders, memory impairment, depression, stroke, ischemic brain or tissue injury and cancer.

In some instances, the subject compound is a β1-Adrenergic receptor agonist. In some instances, the subject compound is a β1-Adrenergic receptor partial agonist. In some instances, the subject compound is a β1-Adrenergic receptor agonist or partial agonist which finds use in a cardiac condition or disease, such as cardiogenic shock. In some instances, the subject compound is a β1-Adrenergic receptor antagonist which finds use in a cardiac condition or disease, e.g., hypertension, coronary heart disease, arrhythmias, myocardial infarction or ischemic heart diseases.

In some instances, the subject compound is a β1-Adrenergic receptor agonist or partial agonist which finds use in a neurodegenerative or neurodevelopmental disease, such as Alzheimer's Disease, memory impairment, depression, stroke and ischemic brain or tissue injury. In some instances, the subject compound is a β1-Adrenergic receptor antagonist which finds use in a neurodegenerative or neurodevelopmental disease.

In some instances, the subject compound is a β2-Adrenergic receptor agonist. In some instances, the subject compound is a β2-Adrenergic receptor partial agonist. In some instances, the subject compound is a β2-Adrenergic receptor agonist or partial agonist which finds use in a cardiac condition or disease, such as cardiogenic shock. In some instances, the subject compound is a β2-Adrenergic receptor antagonist which finds use in a cardiac condition or disease, e.g., hypertension, coronary heart disease, arrhythmias, myocardial infarction or ischemic heart diseases. In some instances, the subject compound is a β2-Adrenergic receptor agonist or partial agonist which finds use in a neurodegenerative or neurodevelopmental disease, such as Alzheimer's Disease, memory impairment, depression, stroke and ischemic brain or tissue injury. In some instances, the subject compound is a β2-Adrenergic receptor antagonist which finds use in a neurodegenerative or neurodevelopmental disease.

In the context of cancer, the term "treating" includes any or all of: reducing growth of a solid tumor, inhibiting replication of cancer cells, reducing overall tumor burden, and ameliorating one or more symptoms associated with a cancer.

In the context of a neurodegenerate disease, the term "treating" includes any or all of: reducing β-amyloid neuritic plaques, reducing intra neuronal neurofibrillary tangles, reducing amyloid angiopathy, prevention of neuronal degeneration, prevention of neuronal demyelination, prevention or inhibition of neuronal or extraneuronal accumulation of aberrant proteins or toxins and ameliorating one or more symptoms associated with a neurodegenerative disease.

In the context of a cardiac condition, the term "treating" includes any or all of reducing blood pressure in patients with hypertension, improving cardiac contractility in patients with cardiogenic shock or hypotension, and the like.

In the context of an inflammatory condition, the term "treating" includes any or all of: reducing amyloid beta plaque, changing microglia response to amyloid beta plaque, ameliorating neuronal loss in response to neuro-inflammatory response, improving cognitive function in people with neurodegenerative disorders, and the like. In some instances, the method results in modulation of Abeta-induced long-term potentiation (LTP) impairment (e.g., as described herein).

The subject to be treated can be one that is in need of therapy, where the host to be treated is one amenable to treatment using the adrenergic receptor modulating compound. In some embodiments, the subject is one that has a neurodegenerative disease or condition. In certain embodiments, the subject has Alzheimer's Disease. In some embodiments, the subject has, or is suspected of having, a cardiac disease or condition. In some embodiments, the subject is one that has an inflammatory disorder or condition. In some cases, the disease or condition treated by the subject method is selected from cancer, an inflammatory disorder, a neuropsychiatric disorder, a neurodevelopmental disorders (e.g., Down's syndrome or Autism), a respiratory disorder, memory impairment, depression, Stroke, Ischemic brain or tissue injury and cancer.

In some cases, the subject methods of treatment include a step of determining or diagnosing whether the subject has a disease or condition associated with a target adrenergic receptor. The determining step can be performed using any convenient methods. In some cases, the determining step includes obtaining a biological sample from the subject and assaying the sample for the presence of a cell comprising the target adrenergic receptor. The sample can be a cellular sample. In some cases, the sample is a biopsy (e.g., a tumor biopsy). The determining step can include identification, directly or indirectly, of an undesirable activity of a target adrenergic receptor.

Accordingly, a variety of subjects may be amenable to treatment using the adrenergic receptor modulating compounds and pharmaceutical compositions disclosed herein. As used herein, the terms "subject", "host" and "patient" are used interchangeably. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The amount of adrenergic receptor modulating compound administered can be determined using any convenient methods to be an amount sufficient to produce the desired effect in association with a pharmaceutically acceptable diluent, carrier or vehicle. The specifications for the unit dosage forms of the present disclosure will depend on the particular compound employed and the effect to be achieved, and the pharmacodynamics associated with each compound in the host.

In some embodiments, an effective amount of an adrenergic receptor modulating compound is an amount that ranges from about 50 ng/ml to about 50 µg/ml (e.g., from about 50 ng/ml to about 40 µg/ml, from about 30 ng/ml to about 20 µg/ml, from about 50 ng/ml to about 10 µg/ml, from about 50 ng/ml to about 1 µg/ml, from about 50 ng/ml to about 800 ng/ml, from about 50 ng/ml to about 700 ng/ml, from about 50 ng/ml to about 600 ng/ml, from about 50 ng/ml to about 500 ng/ml, from about 50 ng/ml to about 400 ng/ml, from about 60 ng/ml to about 400 ng/ml, from about 70 ng/ml to about 300 ng/ml, from about 60 ng/ml to about 100 ng/ml, from about 65 ng/ml to about 85 ng/ml, from about 70 ng/ml to about 90 ng/ml, from about 200 ng/ml to about 900 ng/ml, from about 200 ng/ml to about 800 ng/ml, from about 200 ng/ml to about 700 ng/ml, from about 200 ng/ml to about 600 ng/ml, from about 200 ng/ml to about 500 ng/ml, from about 200 ng/ml to about 400 ng/ml, or from about 200 ng/ml to about 300 ng/ml).

In some embodiments, an effective amount of an adrenergic receptor modulating compound is an amount that ranges from about 10 pg to about 100 mg, e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 µg, from about 1 µg to about 10 µg, from about 10 µg to about 50 µg, from about 50 µg to about 150 µg, from about 150 µg to about 250 µg, from about 250 µg to about 500 µg, from about 500 µg to about 750 µg, from about 750 µg to about 1 mg, from about 1 mg to about 50 mg, from about 1 mg to about 100 mg, or from about 50 mg to about 100 mg. The amount can be a single dose amount or can be a total daily amount. The total daily amount can range from 10 pg to 100 mg, or can range from 100 mg to about 500 mg, or can range from 500 mg to about 1000 mg.

In some embodiments, a single dose of the subject compound is administered. In other embodiments, multiple doses of the subject compound are administered. Where multiple doses are administered over a period of time, the adrenergic receptor modulating compound is administered twice daily (qid), daily (qd), every other day (qod), every third day, three times per week (tiw), or twice per week (biw) over a period of time. For example, a compound is administered qid, qd, qod, tiw, or biw over a period of from one day to about 2 years or more. For example, a compound is administered at any of the aforementioned frequencies for one week, two weeks, one month, two months, six months, one year, or two years, or more, depending on various factors.

Any of a variety of methods can be used to determine whether a treatment method is effective. For example, a biological sample obtained from an individual who has been treated with a subject method can be assayed for an activity or biological function related to a target adrenergic receptor. Assessment of the effectiveness of the methods of treatment on the subject can include assessment of the subject before, during and/or after treatment, using any convenient methods. Aspects of the subject methods further include a step of assessing the therapeutic response of the subject to the treatment.

In some embodiments, the method includes assessing the condition of the subject, including diagnosing or assessing one or more symptoms of the subject which are associated with the disease or condition of interest being treated (e.g., as described herein). In some embodiments, the method includes obtaining a biological sample from the subject and assaying the sample, e.g., for the presence of particular types of cells that are associated with the disease or condition of interest (e.g., as described herein). The sample can be a cellular sample. The assessment step(s) of the subject method can be performed at one or more times before, during and/or after administration of the subject compounds, using any convenient methods.

In certain cases, the assessment step includes identification of certain physiological characteristics or symptoms of the subject. In certain instances, assessing the subject include diagnosing whether the subject has a neurodegenerative disease or condition. In certain instances, the neurodegenerative condition is Alzheimer's Disease. In some cases, the assessment step includes assessing the spatial working memory of the subject. The subject methods of treatment can result in an improvement of the spatial working memory of a subject, e.g., via agonist stimulation of β1-adrenoreceptors.

Combination Therapy

Aspects of the present disclosure further include combination therapies. In certain embodiments, the subject method includes administering a therapeutically effective amount of one or more additional active agents. By combination therapy is meant that an adrenergic receptor modulating compound (e.g., as described herein) can be used in a combination with another therapeutic agent to treat a single disease or condition. In particular embodiments, a compound of the present disclosure is administered concurrently with the administration of another therapeutic agent, which can be administered as a component of a composition including the compound of the present disclosure or as a component of a different composition. In certain embodiments, a composition including a compound of the present disclosure is administered prior or subsequent to administration of another therapeutic agent.

The subject compounds can be administered in combination with other therapeutic agents in a variety of therapeutic applications. Therapeutic applications of interest for combination therapy include those applications in which activity of a target adrenergic receptor is the cause or a compounding factor in disease progression. As such, the subject compounds find use in combination therapies in which the inhibition of a target adrenergic receptor in the subject is desired. Examples of disease conditions which may be treated by a combination therapy including a subject compound include, but are not limited to, cardiac conditions or diseases, neurodegenerative or neurodevelopmental disease, respiratory disorders, asthma, memory impairment, depression, inflammatory diseases, stroke, ischemic brain or tissue injury and cancer. Agents of interest which can be used in jointly with the subject adrenergic receptor modulating compounds include, but are not limited to, antidepressants, antipsychotics, beta-blockers, vasoconstrictors, antihypotensives, decongestants, chemotherapeutic agents, agents used in Alzheimer's disease, and anti-inflammatory agents.

The subject adrenergic receptor modulating compounds can be used jointly with any agent useful in the treatment of a cardiac condition, such as cardiogenic shock, hypertension, congestive heart failure, coronary heart disease, arrhythmias, myocardial infarction or ischemic heart diseases. Agents of interest which can be used in jointly with the subject adrenergic receptor modulating compounds include, but are not limited to, denopamine, dobutamine, xamoterol, acebutolol, atenolol, betaxolol, bisoprolol, pindolol, esmolol, metoprolol, nebivolol, vortioxetine, Carvedilol, Labetalol, Phentolamine, Prazosin, Cirazoline, Methoxamine, Synephrine, Etilefrine, Metaraminol, Midodrine, and cumarin.

The subject adrenergic receptor modulating compounds can be used jointly with any agent useful in the treatment of a neurodegenerative or neurodevelopmental disease, such as such as Alzheimer's Disease, memory impairment, cognitive impairment, depression, stroke and ischemic brain or tissue injury, Down's syndrome or Autism. Agents of interest which can be used in jointly with the subject adrenergic receptor modulating compounds include, but are not limited to, acepromazine.

In some cases, the subject adrenergic receptor modulating compounds can be used in the treatment of a disease, such as a neurodegenerative or neurodevelopmental disease, in combination with a cholinesterase inhibitor or a NMDA receptor modulators. Agents of interest include, but are not limited to, Donepezil, Aricept, Galantamine, Razadyne, Memantine, Namenda, Rivastigmine, Exelon, Tacrine and Cognex.

Other agents of interest which can be used in jointly with the subject adrenergic receptor modulating compounds include, but are not limited to, 4-NEMD, 7-Me-marsanidine, Agmatine, Apraclonidine, Brimonidine, Cannabigerol, Clonidine, Detomidine, Dexmedetomidine, Fadolmidine, Guanabenz, Guanfacine, Lofexidine, Marsanidine, Medetomidine, Methamphetamine, Mivazerol, Rilmenidine, Romifidine, Talipexole, Tiamenidine, Tizanidine, Tolonidine, Xylazine, Xylometazoline, Aripiprazole, Asenapine, Atipamezole, Cirazoline, Clozapine, Efaroxan, Idazoxan, Lurasidone, Melperone, Mianserin, Mirtazapine, Napitane, Olanzapine, Paliperidone, Phenoxybenzamine, Phentolamine, Piribedil, Rauwolscine, Risperidone, Rotigotine, Quetiapine, Norquetiapine, Setiptiline, Tolazoline, Yohimbine, Ziprasidone and Zotepine.

Other agents of interest which can be used in jointly with the subject adrenergic receptor modulating compounds include, but are not limited to, bitolterol, fenoterol, hexoprenaline, isoprenaline or isoproterenol, levosalbutamol or levalbuterol, orciprenaline or metaproterenol, pirbuterol, procaterol, salbutamol or albuterol, terbutaline, bambuterol, denbuterol, formoterol, salmeterol, carmoterol, indacaterol, milveterol, olodaterol, vilanterol, fenoterol, hexoprenaline, isoxsuprine, ritodrine, salbutamol or albuterol, terbutaline, zilpaterol, ICI-118,551 and butoxamine.

Utility

The adrenergic receptor modulating compounds, e.g., as described herein, and methods of using the same find use in a variety of applications. Applications of interest include, but are not limited to: therapeutic applications, diagnostic applications and research applications.

Adrenergic receptor modulating compounds of the present disclosure and pharmaceutical compositions including the same find use in a variety of therapeutic applications. Therapeutic applications of interest include those applications in which a target adrenergic receptor activity is the cause or a compounding factor in disease progression. Adrenergic receptors are associated with a number of diseases. There are multiple subtypes of adrenergic receptors that are expressed in distinct patterns and involved in different physiological processes. In some cases, the subject compounds that can selectively target one subtype have therapeutic potential for multiple diseases. As such, the subject compounds find use in the treatment of a variety of different conditions in which the modulation of a target adrenergic receptor in the host is desired. Examples of diseases or conditions which may be treated with compounds of the invention include, but are not limited to: cardiac diseases, inflammatory diseases, neurodegenerative disease (e.g., Alzheimer's Disease), neuropsychiatric disorders, neurodevelopmental disorders (e.g., Down's syndrome or Autism), respiratory disorders, memory impairment, depression, stroke, ischemic brain or tissue injury and cancer.

In some instances, the subject compound is a β1-Adrenergic receptor agonist or partial agonist which finds use in a cardiac condition or disease, such as cardiogenic shock. In some instances, the subject compound is a β1-Adrenergic receptor antagonist which finds use in a cardiac condition or disease, e.g., hypertension, coronary heart disease, arrhythmias, myocardial infarction or ischemic heart diseases.

In some instances, the subject compound is a β1-Adrenergic receptor agonist or partial agonist which finds use in a neurodegenerative or neurodevelopmental disease, such as Alzheimer's Disease, memory impairment, depression, stroke and ischemic brain or tissue injury. In some instances, the subject compound is a β1-Adrenergic receptor antagonist which finds use in a neurodegenerative or neurodevelopmental disease.

In some instances, the subject compound is a β1-Adrenergic receptor agonist or partial agonist which finds use in a neurodegenerative or neurodevelopmental disease, such as Alzheimer's Disease, memory impairment, depression, stroke and ischemic brain or tissue injury, Down's syndrome or Autism. In some instances, the subject compound is a β1-Adrenergic receptor antagonist which finds use in a neurodegenerative or neurodevelopmental disease (e.g., as described herein).

The subject compounds find use in a variety of research applications including the identification and testing of candidate adrenergic receptor modulating compounds (e.g., for pharmaceutical development) and performing research on disease conditions of interest in which the activity of a target adrenergic receptor is implicated. Research applications of interest can involve use of the subject compounds in a variety of in vitro assays including high throughput screening assays, potency assays, and competitive inhibition assays where the subject compounds can be useful as a control compound or as a tool in the investigation the pathology of cells of interest.

Systems and Kits

Also provided are kits that include adrenergic receptor modulating compounds (e.g., as described herein). Systems of the present disclosure include collections of active agents brought together, e.g., by a health care practitioner, for administration to a subject, such as a patient. Such systems may include an adrenergic receptor modulating compound and one or more additional active agents (e.g., as described herein). Kits that include adrenergic receptor modulating compounds which are provided that may include one or more dosages of an adrenergic receptor modulating compound, and optionally one or more dosages of one or more additional active agents. Conveniently, the formulations may be provided in a unit dosage format. In such kits, in addition to the containers containing the formulation(s), e.g. unit doses, is an informational package insert describing the use of the subject formulations in the methods of the invention, e.g., instructions for using the subject unit doses to treat cellular proliferative disease conditions. These instructions may be present in the subject systems and kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Introduction

Among the many subtypes of ADRs, beta1-adrenergic receptor (ADRB1) is an important target in various therapeutic areas. For example, ADRB1 antagonists (beta-blockers) have been used to treat cardiovascular disease since the 1960s and remain one of the most commonly used drugs today. Our laboratory has also identified ADRB1 as a key player in the pathophysiology of Alzheimer's disease (AD) and one of the most underestimated therapeutic targets in AD. For example, we previously demonstrated that activation of ADRB1 reverses AD-like cognitive deficits in transgenic mice overexpressing human amyloid beta protein precursor (APP) (Coutellier et al. "Beta1-adrenergic receptor activation enhances memory in Alzheimer's disease model." Ann Clin Transl Neurol. 2014; 1(5):348-60). Similarly, we have shown that acute activation of ADRB1 rescues the contextual memory and spatial memory deficits observed in the Ts65Dn mouse model of Down syndrome, which displays an accelerated AD-like pathology (Faizi et al. "Comprehensive behavioral phenotyping of Ts65Dn mouse model of Down syndrome: activation of beta1-adrenergic receptor by xamoterol as a potential cognitive enhancer." Neurobiol Dis. 2011; 43(2):397-413). In addition to the cognitive enhancing effects, we also observed that activation of ADRB1 attenuated pathological features of AD including beta-amyloid burden, tau pathology, and neuroinflammation (Ardestani at al. "Modulation of neuroinflammation and pathology in the 5XFAD mouse model of Alzheimer's disease using a biased and selective beta-1 adrenergic receptor partial agonist." Neuropharmacology. 2017; 116:371-86).

ADRB1 agonist may have therapeutic potential for AD which can address both cognitive symptoms and AD pathology. In addition to its involvement in AD, accumulating evidence suggests that the NA system and ADRB1 play a critical role in regulating neuroimmune responses. The involvement of ADRB1 in immune system regulation is of great interest as neuroinflammation plays a major role in many chronic and acute pathological conditions including multiple sclerosis and Parkinson's disease. By regulating neuroinflammatory process, ADRB1 ligands in some cases can produce therapeutic benefits for the diseases associated with neuroinflammation. Thus, the present disclosure describes the development of ADRB1 agonists as therapeutic agents for AD and neuroinflammatory diseases.

In the classical view of GPCR signaling, activation of ADRB1 leads to stimulation of two ubiquitous and generic mechanisms: G-protein signaling and β-arrestin signaling. First, stimulation of ADRB1 with agonists leads to activation of heterotrimeric G-proteins and induces canonical second-messenger cAMP signaling. At the same time, ADRB1 activation stimulates the recruitment of β-arrestin to the receptor. The recruitment of β-arrestin to the receptor sterically interdicts further G-protein signaling, thereby limiting the G-protein signal duration. In addition, β-arrestin acts as a scaffold protein by mediating receptor internalization. Recently, however, it has become clear that agonists can show biased activation of signaling pathways. The ability of ligands to activate the receptor and produce responses in a pathway-dependent manner has been termed "signaling bias" or "functional selectivity". As G proteins and β-arrestins mediate distinct physiological processes, baised agonists can provide improved therapeutic selectivity with reduced adverse effects. In search of compounds having therapeutic potential for AD and neuroinflammatory diseases, we identified G-protein biased partial agonists of ADRB1. As partial agonists, these compounds have more subtle effects in the pheriphery compared to full agonists, yet be efficacious enough to produce therapeutic benefits for AD and neuroinflammatory disease. By selectively activating ADRB1 G-protein signaling with minimal to no activity on β-arrestin signaling, these compounds can also specifically target the disease relevant signaling pathways without causing the agonist induced tolerance.

Xamoterol (ICI118578) is a selective partial agonist of ADRB1. It is a partial agonist that produces approximately 50% efficacy compared to the full agonist isoproterenol, and was once used for the treatment of cardiovascular disease. However, xamoterol is an exceptionally polar compound (clogP=0.4) with only 5% oral bioavailability. In addition, its central nervous system (CNS) penetration is low due to its polarity. Thus, the focus of the present disclosure is ADRB1 ligands that (1) are partial agonists of ADRB1, (2) exhibit functional selectivity for the cAMP signaling cascade with minimal or no β-arrestin signaling, and (3) show improved brain penetration. The present disclosure includes a series of compounds including highly potent and selective drug-like ADRB1 partial agonists.

Example 1: Exemplary Syntheses of Compounds

The following representative synthetic methods and strategies can be adapted for use in preparation of the subject compounds.

Scheme 1

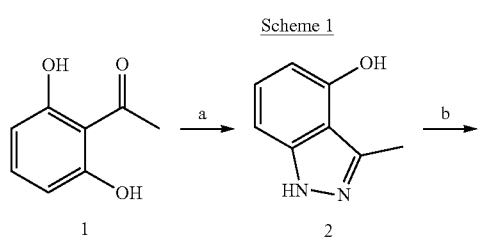

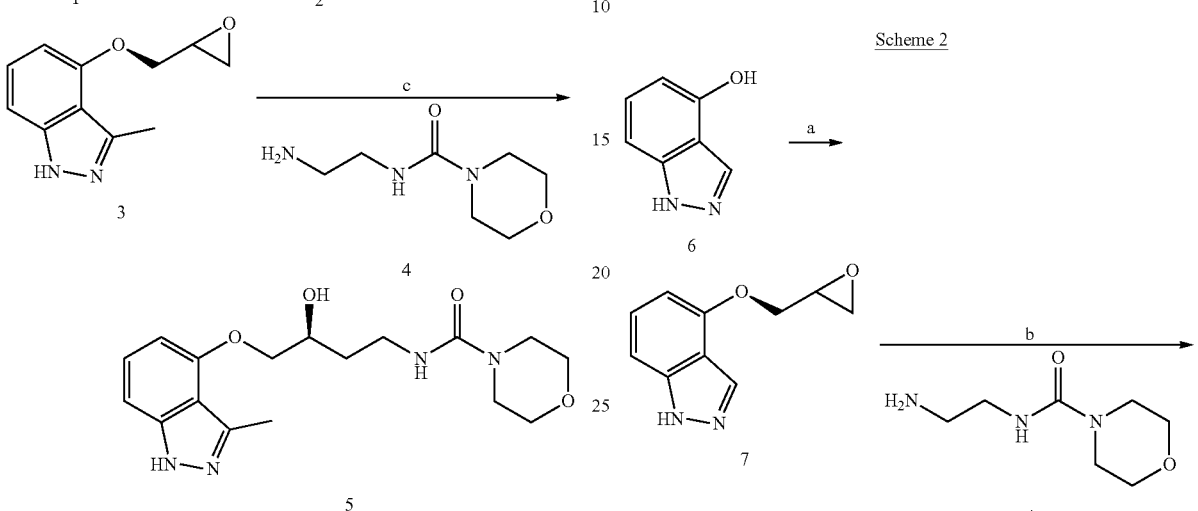

Reagents and conditions: a, Hydrazine hydrate, ethylene glycol, 25-160° C., 2.5 hr; b, (R)-epichlorohydrine, CsF, DMF, 50° C., 48 hr; c, 4, 2-propanol, 50° C., 12 hr.

3-methyl-1H-indazol-4-ol (2)

A mixture of 1-(2,6-dihydroxyphenyl)ethan-1-one (1) (5.0 g, 32.86 mmol) in ethylene glycol (70 ml) was added hydrazine hydrate (3.29 g, 65.72 mmol) in ethylene glycol (20 mL). The reaction mixture was stirred at room temperature for 20 min and then heated at 160° C. for additional 2 hr. After cooling to r.t. and dilution with water (200 mL), HOAc (2.5 ml) was added to adjust the pH=6. The resulting mixture was extracted with EtOAc (3×50 ml). The organic layer was washed with brine, dried over $Na_2SO_4$, filtered, and the filtrate was concentrated under reduced pressure. The crude product was purified by flash column (hexane:EtOAc=1:1) to give 3-methyl-1H-indazol-4-ol (2) (2.0 g, 41.1%) as brown solid.

(S)-3-methyl-4-(oxiran-2-ylmethoxy)-1H-indazole (3)

To a solution of 3-methyl-1H-indazol-4-ol (2) (1.0 g, 6.75 mmol) and (R)-2-(chloromethyl) oxirane (0.94 g, 10.12 mmol) in DMF (10 ml) was stirred at 0° C. Then to the mixture was added CsF (1.54 g, 10.12 mmol), and the resulting mixture was heated at 50° C. for 48 h. Then reaction mixture was partitioned between water and EtOAc. The organic layer was washed with water, brine, dried over $Na_2SO_4$, the filtrate was concentrated under reduced pressure and the crude product was purified by silica column, to give (S)-3-methyl-4-(oxiran-2-ylmethoxy)-1H-indazole (3) (0.8 g, 46.4%) as solid.

(S)—N-(3-hydroxy-4-((3-methyl-1H-indazol-4-yl)oxy)butyl)morpholine-4-carboxamide (5)

To a solution of 3 (0.8 g, 3.92 mmol) in 2-propanol (20 ml), was added N-(2-aminoethyl) morpholine-4-carboxamide (4)(2.04 g, 11.75 mmol). The reaction mixture was stirred under 50° C. for 5 h, and then cooled to R.T. and treated with water and extracted with EtOAc. The organic layer was washed with water, brine, dried over $Na_2SO_4$, the filtrate concentrated under reduced pressure and the crude product was purified by silica column, to give (S)—N-(3-hydroxy-4-((3-methyl-1H-indazol-4-yl) oxy)butyl)morpholine-4-carboxamide (5) (0.2 g, 13.5%) as a solid.

Scheme 2

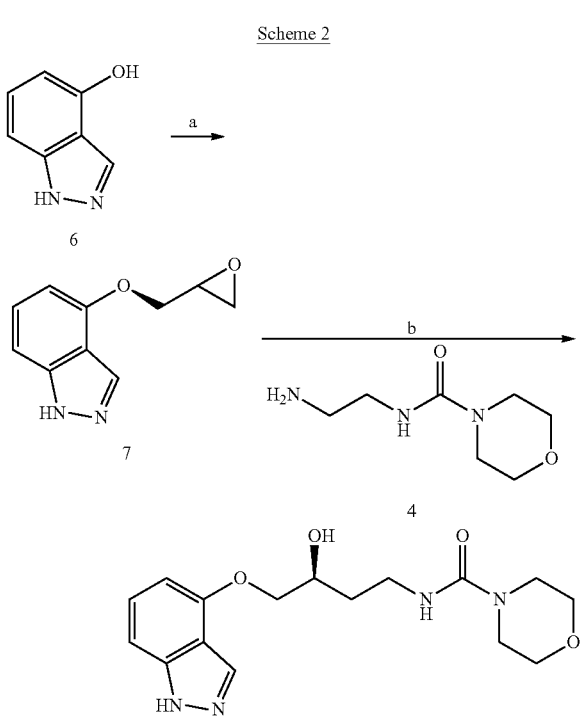

Reagents and conditions: a, (R)-epichlorohydrine, CsF, DMF, 50° C., 48 hr; c, 4, 2-propanol, 50° C., 12 hr.

(S)-4-(oxiran-2-ylmethoxy)-1H-indazole (7)

A procedure similar to that described above for the preparation of 3 was followed give (S)-4-(oxiran-2-ylmethoxy)-1H-indazole (7) (1.1 g, 38%) as colorless oil.

(S)—N-(4-((1H-indazol-4-yl)oxy)-3-hydroxybutyl) morpholine-4-carboxamide (8)

A procedure similar to that described above for the preparation of 5 was followed to give (S)—N-(4-((1H-indazol-4-yl)oxy)-3-hydroxybutyl)morpholine-4-carboxamide (20%) as yellowish oil.

Scheme 3

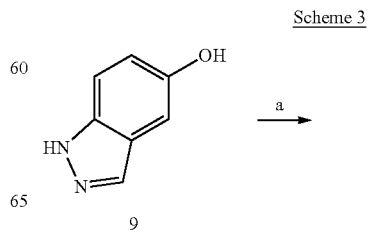

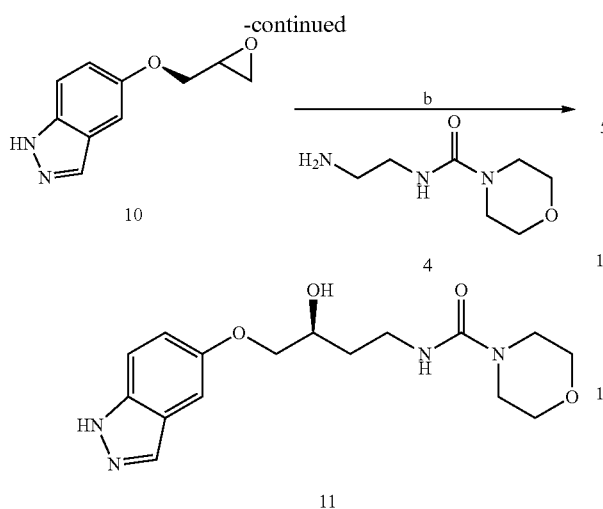

Reagents and conditions: a, (R)-epichlorohydrine, CsF, DMF, 50° C., 48 hr; c, 4, 2-propanol, 50° C., 12 hr.

(S) 5-(oxiran-2-ylmethoxy)-1H-indazole (10)

A procedure similar to that described above for the preparation of 3 was followed give (S)-5-(oxiran-2-yl-methoxy)-1H-indazole (10) as colorless oil.

(S)—N-(4-((1H-indazol-5-yl)oxy)-3-hydroxybutyl) morpholine-4-carboxamide (11)

A procedure similar to that described above for the preparation of 5 was followed to give (S)—N-(4-((1H-indazol-5-yl)oxy)-3-hydroxybutyl)morpholine-4-carboxamide (11) (19%) as yellowish oil.

Scheme 4

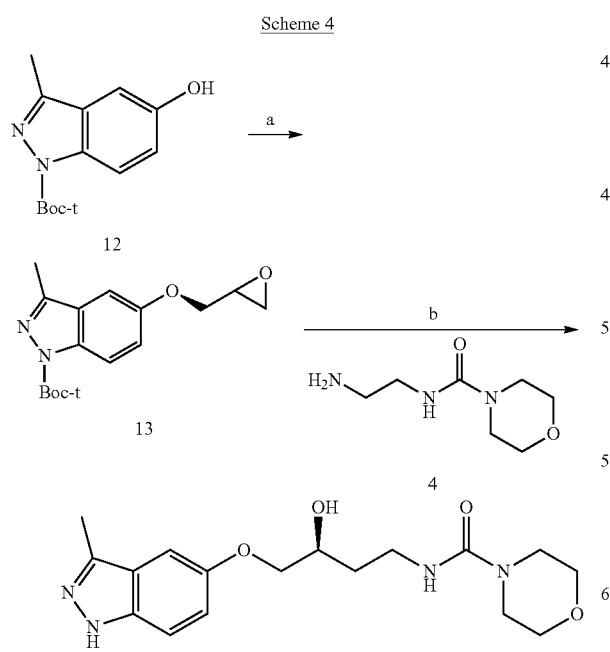

Reagents and conditions: a, (R)-epichlorohydrine, CsF, DMF, 50° C., 48 hr; c, (i) 4, 2-propanol, 50° C., 12 hr. (ii) HCl/EtOH, 2 hr, then pH 8.

(S)-tert-butyl 3-methyl-5-(oxiran-2-ylmethoxy)-1H-indazole-1-carboxylate (13)

To a solution of tert-butyl 5-hydroxy-3-methyl-1H-indazole-1-carboxylate (12) (0.80 g, 3.22 mmol) and (R)-2-(chloromethyl)oxirane (0.90 g, 9.72 mmol) in DMF (8 mL) CsF (1.47 g, 9.68 mmol) was added dropwise at 0° C. The mixture was stirred at 50° C. for 12 h, then diluted with water and extracted with EtOAc. The organic layer was washed with brine, dried over Na$_2$SO$_4$ and then concentrated under reduced pressure. The residue was purified by flash to provide 13 (0.5 g, 1.64 mmol) as a yellow solid. (10) as colorless oil.

(S)—N-(4-((1H-indazol-5-yl)oxy)-3-hydroxybutyl) morpholine-4-carboxamide (14)

A solution of 13 (0.5 g, 1.64 mmol) and N-(2-aminoethyl) morpholine-4-carboxamide (4) (0.71 g, 3.28 mmol) in IPA (5 mL) was stirred at 50° C. for 12 h, then diluted with water and extracted with EtOAc. The organic layer was washed with brine, dried over Na$_2$SO$_4$ and concentrated. The residue was dissolved in HCl/Et$_2$O and stirred at R.T. for 2 h. The mixture was concentrated, adjusted pH 8 with NaHCO$_3$ and purified by flash to 14 (0.35 g, 0.93 mmol) as a off-white solid.

Scheme 5

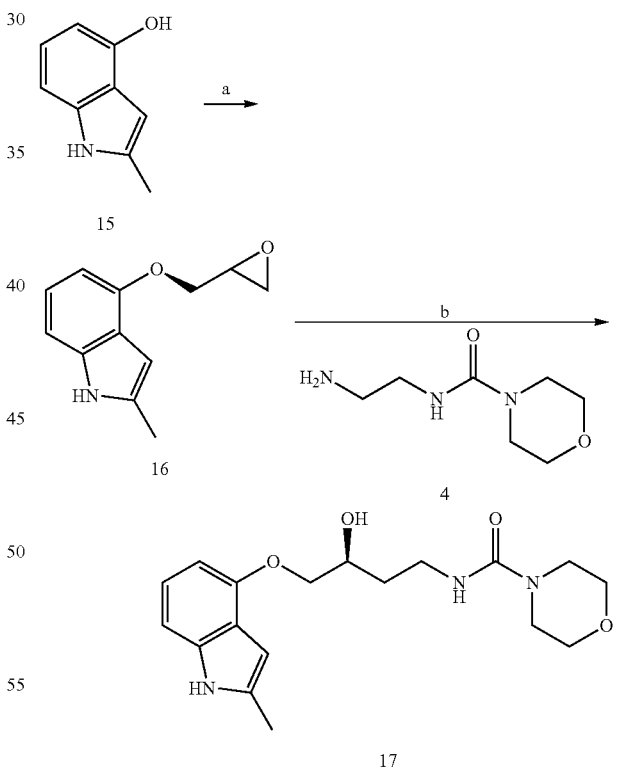

Reagents and conditions: a, (R)-epichlorohydrine, CsF, DMF, 50° C., 48 hr; c, 4, 2-propanol, 50° C., 12 hr.

(S)-2-methyl-4-(oxiran-2-ylmethoxy)-1H-indole (16)

This compound was prepared from 2-methyl-1H-indol-4-ol (15) by following the procedure described above.

(S)—N-(3-hydroxy-4-((2-methyl-1H-indol-4-yl)oxy)butyl)morpholine-4-carboxamide (17)

This compound was prepared from 16 following the procedure described above.

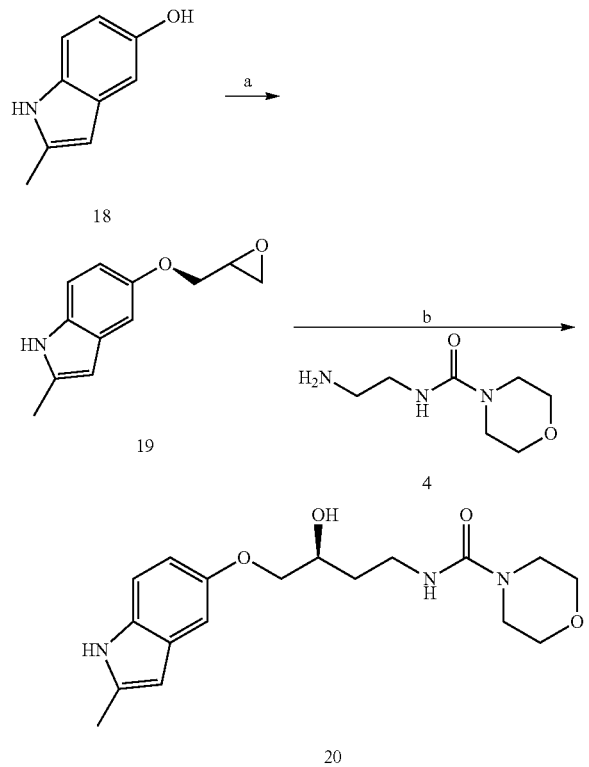

Reagents and conditions: a, (R)-epichlorohydrine, CsF, DMF, 50° C., 48 hr; c, 4, 2-propanol, 50° C., 12 hr.

(S)-2-methyl-5-(oxiran-2-ylmethoxy)-1H-indole (19)

This compound was prepared from 2-methyl-1H-indol-5-ol (18) following the procedure described above.

(S)—N-(3-hydroxy-4-((2-methyl-1H-indol-5-yl)oxy)butyl)morpholine-4-carboxamide (20)

This compound was prepared from 19 following the procedure described above.

Scheme 7

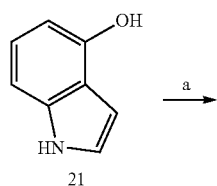

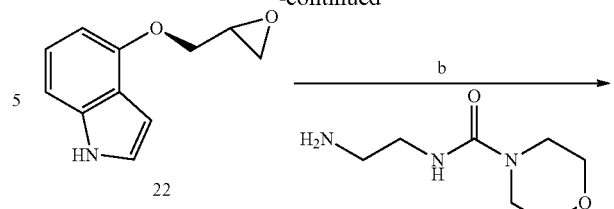

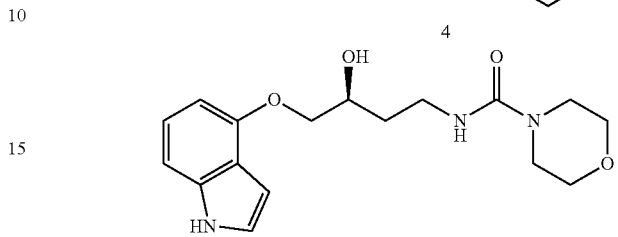

Reagents and conditions: a, (R)-epichlorohydrine, CsF, DMF, 50° C., 48 hr; c, 4, 2-propanol, 50° C., 12 hr.

(S)-4-(oxiran-2-ylmethoxy)-1H-indole (22)

This compound was prepared from 1H-indol-4-ol (21) following the procedure described herein to give 22 as white solid and was used in the next step.

(S)—N-(4-((1H-indol-4-yl)oxy)-3-hydroxybutyl)morpholine-4-carboxamide (23)

This compound was prepared from 22 following the procedure described herein to give 23.

Scheme 8

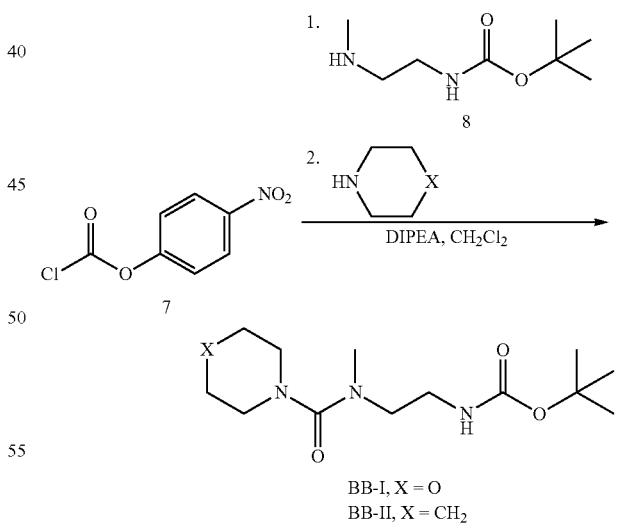

General Procedure C for Synthesis of BB-I and BB-II.

To a stirred solution of 4-nitrophenyl chloroformate (7) (1.39 g, 6.9 mmol, 1.2 equiv) in anhydrous $CH_2Cl_2$ (13 mL) was dropwise added a solution of tert-butyl (2-(methylamino)ethyl)carbamate (8) (1.0 g, 5.7 mmol, 1 equiv) and i-$PrNEt_2$ (1.49 mL, 8.6 mmol, 1.5 equiv) in $CH_2Cl_2$ (2 mL) at 0° C. The light greenish solution was warmed to room temperature and stirred for 1 hour, whereupon color changed to yellow. The reaction mixture was concentrated to one third of its original volume, appropriate amine (40 mmol, 7 equiv) was added and the resulting suspension was vigorously stirred at 100° C. for 8 hours. The suspension was cooled to room temperature and poured into water (25 mL). After basification to pH10 by addition of aqueous 1M NaOH, product was extracted with EtOAc (2×20 mL). The combined organic extracts were washed with 2:1 brine/aqueous 4M HCl (20 mL), dried over Na₂SO₄ and concentrated. The residue was purified by flash column chromatography on silica using EtOAc as a mobile phase.

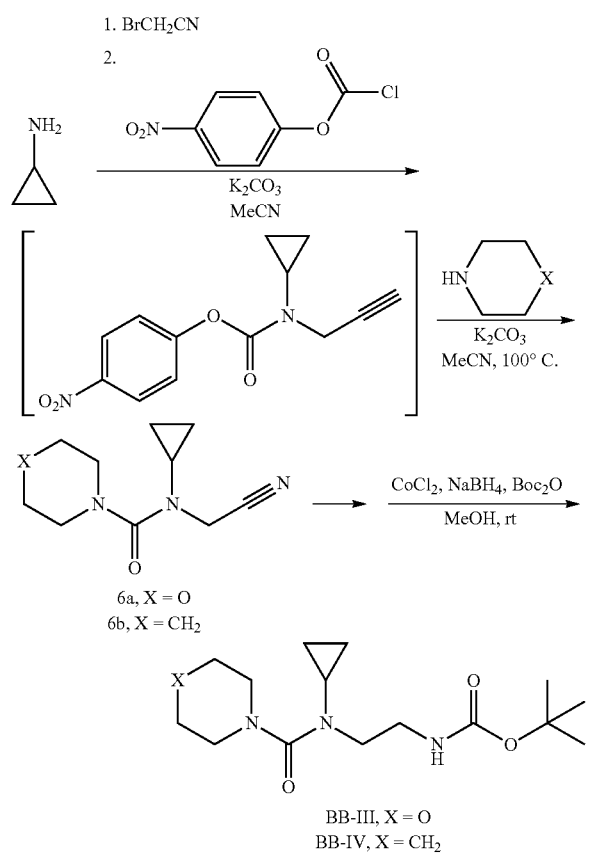

General Procedure a for Synthesis of Nitriles 6a,b

Pressure tube was charged with K₂CO₃ (2.0 g, 14.4 mmol, 1.2 equiv), cyclopropylamine (0.84 mL, 12 mmol, 1 equiv) bromoacetonitrile (0.85 mL, 12.6 mmol, 1.05 equiv) and anhydrous MeCN (20 mL), sealed with cap and the resulting suspension was stirred at 60° C. for 1 hour, whereupon color changed to yellow. The suspension was cooled to room temperature and seal was removed. Solid 4-nitrophenyl chloroformate (2.9 g, 14.4 mmol, 1.2 equiv) and K₂CO₃ (2.0 g, 14.4 mmol, 1.2 equiv) were added and the suspension was stirred for 1 h at room temperature. Appropriate amine (36 mmol, 3 equiv) was added next, the vial was sealed and the suspension was heated at 100° C. with stirring for 3 hours. The suspension was cooled to room temperature and poured into water (50 mL). After basification with 1M NaOH to pH10, the mixture was extracted with EtOAc (2×30 mL). Combined organic extracts were washed with 4:1 (v:v) brine/aqueous 4M HCl (20 mL), dried over Na₂SO₄ and concentrated. The oily residue was purified by flash column chromatography on silica using gradient elution from 1:1 (v:v) petroleum ether/EtOAc to pure EtOAc.

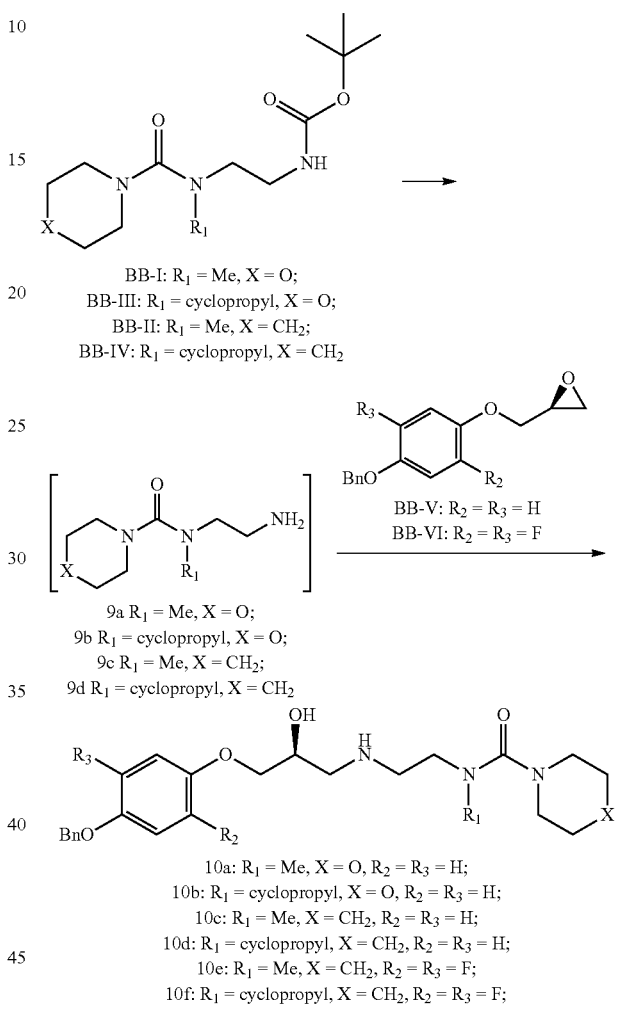

General Procedure for Epoxide Ring Opening.

A solution of N-Boc-amine BB-I-IV (2 equiv) in anhydrous DCM (3.4 mL/mmol) is cooled to 0° C. and neat TFA (10 equiv) is added dropwise. The solution is stirred at room temperature for 2 h, concentrated in vacuo and redissolved in DCM (3 mL). The resulting solution is concentrated again and the dissolution-concentration procedure is repeated twice. Final concentration afforded amine 9a-d, which is dissolved in isopropanol (1.3 mL/mmol) and NaHCO₃ (10 equiv) is added. The resulting yellowish solution is heated under reflux for approx 10 min, whereupon a solution of BB-V or BB-VI (1 equiv) in 2:1 (v:v) isopropanol/DMF (3.9 mL/mmol) is added dropwise (within 10-15 min) to the hot amine solution. Heating under reflux is continued for 3 hours. After cooling to room temperature water is added, and product is extracted with EtOAc (3×5 mL). Combined organic layers are washed with brine, dried over Na₂SO₄, concentrated under reduced pressure and purified by column chromatography on silica gel.

Example 2: Synthesis of Compounds

Reaction Scheme: Step 1

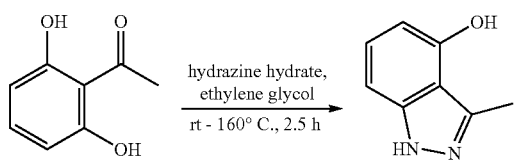

Procedure:

To a mixture of 1-(2,6-dihydroxyphenyl)ethanone (10 g, 65.7 mmol) in ethylene glycol (140 mL) was added hydrazine hydrate (6.58 g, 131.4 mmol) in ethylene glycol (40 mL). The reaction mixture was stirred at room temperature for 20 min and for an additional 2 h at 160° C. After cooling to ambient temperature RM was diluted with water (400 mL). Acetic acid (5 mL) was added to adjust the pH=6. The resulting mixture was extracted with EtOAc (3*100 mL). The organic layer was washed with brine, dried over $Na_2SO_4$, filtered, concentrated under reduced pressure and purified by crystallization (9.9 g, 100%) as brown solid.

Reaction Scheme: Step 2

Procedure:

To a mixture of Step-1 product (2 g, 13.5 mmol), TEA (5.61 mL, 40.4 mmol) and DMAP (100 mg) in dry THF (35 mL) was added drop wise $(BOC)_2O$ (2.94 g, 13.5 mmol) in THF (5 mL) at −15° C. The reaction mixture was stirred at −15° C. for 1 h. After cooling ambient temperature, RM was diluted with water (50 mL). Extracted with EtOAc (2*50 mL). The organic layer was washed with brine, dried over $Na_2SO_4$, filtered, concentrated under reduced pressure and purified by column chromatography using Ethyl acetate in hexane as the eluent (1.3 g, 38.80%) as brown solid.

Reaction Scheme: Step 3

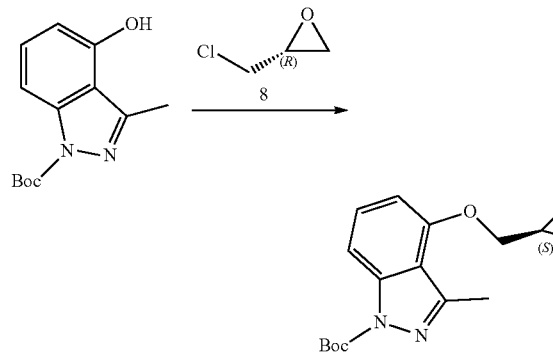

Procedure:

To a mixture of step-2 product (5.9 g, 23.7 mmol) and $Cs_2CO_3$ (14.98 g, 47.4 mmol) in dry DMF (59 mL) was added drop wise R-(+)-Epichoro hydrin (3.29 g, 35.6 mmol) at 10° C. The reaction mixture was stirred at 25-30° C. for 16 h. Filter the reaction mass and filtrate was quenched with water (100 mL). Extracted with EtOAc (2*50 mL). The combined organic layer was washed with water (50 mL) brine, dried over $Na_2SO_4$, filtered, concentrated under reduced pressure (6.1 g, 84.7%) and afforded brown oil (which was used as such in the next step).

Library Step:

Reaction Scheme: Step-1

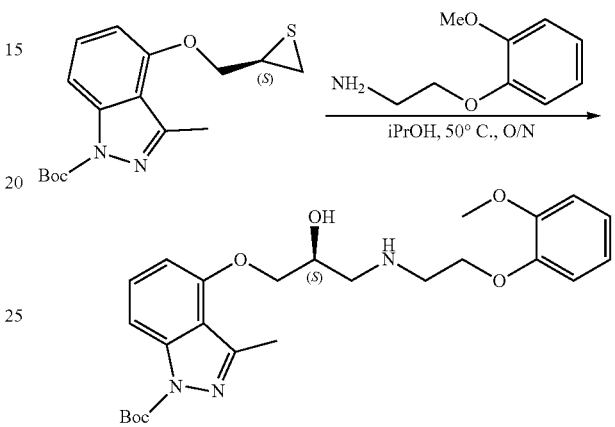

Procedure:

To a solution of Oxirane intermediate (0.44 g, 1.44 mmol) in iPrOH (10 mL), was added 2-methoxy phenoxyethylamine (0.24 g, 1.44 mmol). The reaction mixture was stirred under 60° C. for 12 h, concentrated under reduced pressure and purified by silica column chromatography using 1% methanol in ethyl acetate as eluent to give (0.35 g, 51%) as a thick liquid.

Reaction Scheme: Step 2

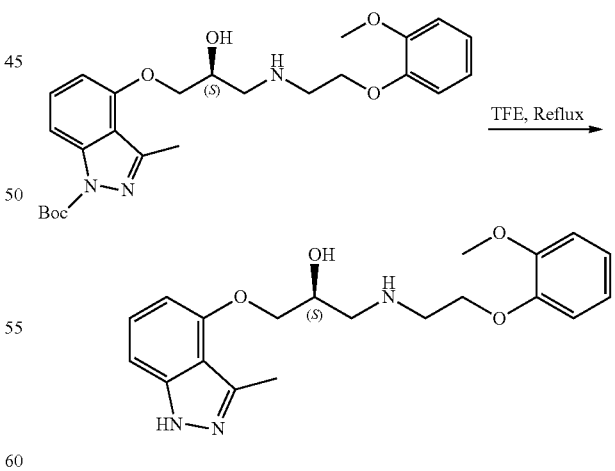

Procedure:

A solution of Boc indazole (0.35 g, 0.74 mmol) in trifluoro ethanol (5 mL) was stirred under 74° C. for 2 days, concentrated under reduced pressure and purified by silica column chromatography using 4% methanol in DCM as the eluent to give (0.11 g, 40%) as a solid.

Compound 02
Reaction Scheme: Step-1

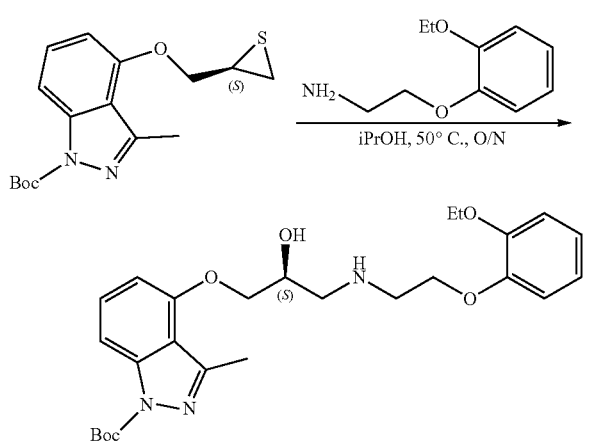

Procedure:

To a solution of Oxirane intermediate (1.0 g, 3.3 mmol) in iPrOH (20 ml), was added 2-ethoxy Phenoxy ethyl amine (0.89 g, 4.92 mmol). The reaction mixture was stirred under 60° C. for 16 h, after that RM was concentrated under reduced pressure and purified by silica column chromatography using 1% methanol in ethyl acetate as eluent to give (0.3 g, 18%) as a thick liquid.

Reaction Scheme: Step-2

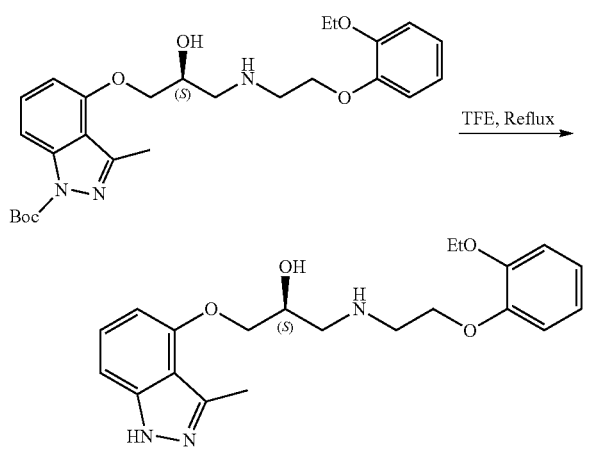

Procedure:

A solution of Boc indazole (0.3 g, 0.6 mol) in trifluoro ethanol (5 mL) was stirred under 74° C. for 2 days, concentrated under reduced pressure and purified by silica column chromatography using 4% methanol in DCM as the eluent to give (0.13 g, 40%) as a thick liquid, which was dissolved in 1 mL of methanol and added fumaric acid (19.5 mg, 0.16 mol). Clear solution was stirred at ambient temperature for 1 h, concentrated under vaccum, dried under high vacuum to get solid (0.13 g)

Compound 04
Reaction Scheme: Step-1

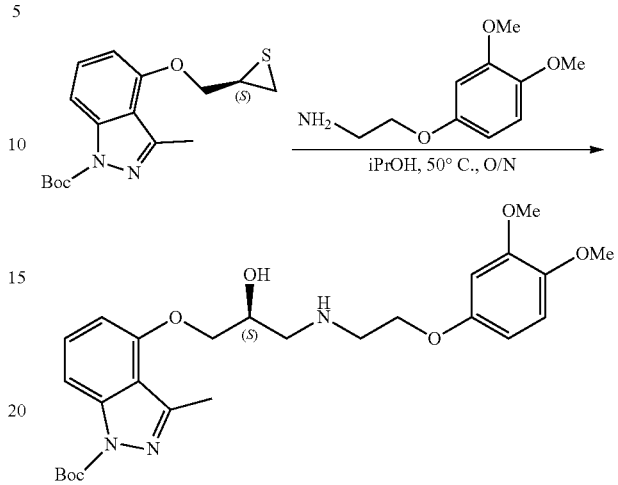

Procedure:

To a solution of Oxirane intermediate (1.0 g, 3.28 mol) in iPrOH (20 ml), was added 3,4-dimethoxy phenoxy ethyl amine(0.97 g, 4.92 mol). The reaction mixture was stirred under 60° C. for 16 h, after that RM was concentrated under reduced pressure and purified by silica column chromatography using 1% methanol in ethyl acetate as eluent to give (0.62 g, 37.8%) as a thick oil.

Reaction Scheme: Step-2

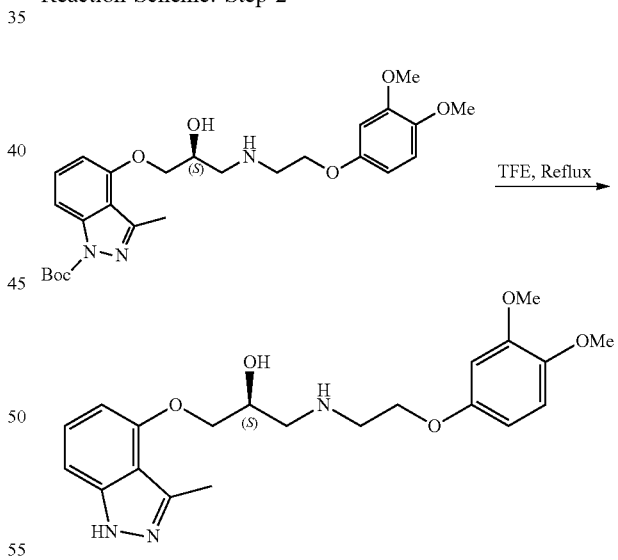

Procedure:

A solution of Boc Indazole (0.62 g, 1.2 mmol) in trifluoro ethanol (5 mL) was stirred under 74° C. for 2 days, concentrated under reduced pressure and purified by silica column chromatography using 4% methanol in DCM as the eluent to give (0.150 mg, 27.5%) as a thick liquid, which was dissolved in 1 mL of methanol. Then to the clear solution added Fumaric acid (21.7 mg, 0.18 mol) and stirred at ambient temperature for 1 h. Concentrated the RM under vacuum and dried under high vacuum to get solid (0.11 g)

Compound 05
Reaction Scheme: Step-1

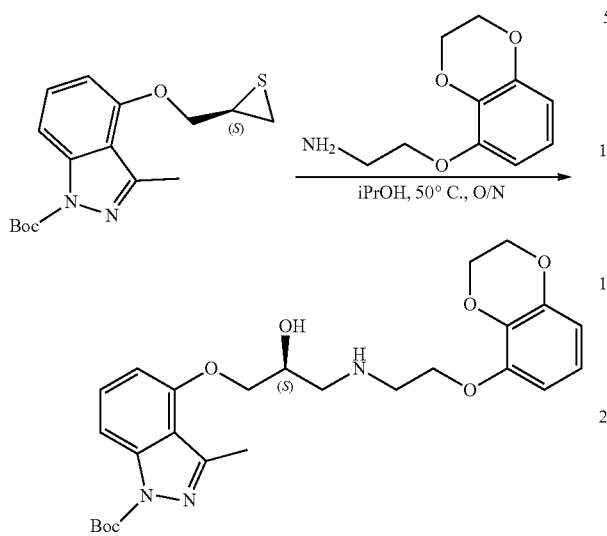

Procedure:

To a solution of Oxirane intermediate (1.1 g, 3.65 mmol) in iPrOH (22 mL), was added pyrogallol amine (0.7 g, 3.65 mmol). The reaction mixture was stirred under 60° C. for 8 h, after that RM was concentrated under reduced pressure and purified by silica column chromatography using 1% methanol in ethylacetate as eluent to give (0.6 g, 41%) as a thick liquid.

Reaction Scheme: Step-2

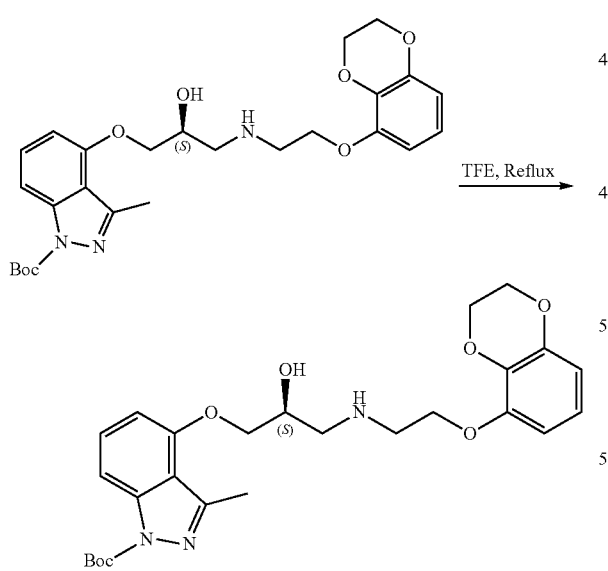

Procedure:

To a solution of Boc indazole (0.6 g, 1.2 mmol) in trifluoro ethanol (5 mL) was stirred under 74° C. for 2 days, concentrated under reduced pressure and purified by silica column chromatography using 4% methanol in DCM as the eluent to give (0.140 mg, 29%) as a solid.

Compound 06
Reaction Scheme: Step-1

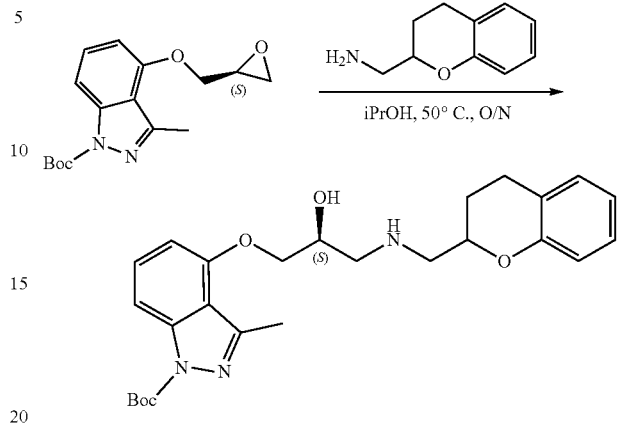

To a solution of Oxirane intermediate (1.0 g, 3.28 mmol) in iPrOH (20 mL), was added 2-chroman methyl amine (0.53 g, 3.28 mmol). The reaction mixture was stirred under 60° C. for 24 h, after that RM was concentrated under reduced pressure and purified by silica column chromatography using 1% methanol in ethyla acetate as the eluent to give (0.5 g, 32%) as a thick liquid.

Reaction Scheme: Step-2

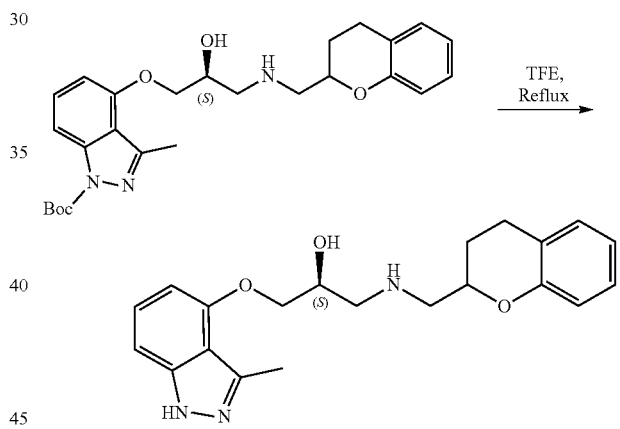

Procedure:

To a solution of Boc Indazole (0.5 g, 1.0 mmol) in trifluoro ethanol (5 mL) was stirred under 74° C. for 2 days, concentrated under reduced pressure and purified by silica column chromatography using 4% methanol in DCM as the eluent to give (240 mg, 61%) as a thick liquid, which was dissolved in 1 mL of methanol. And then added Fumaric acid (21.7 mg, 0.18 mol). Clear solution was stirred at ambient temperature for 1 h., concentrated, dried under high vacuum to get solid (0.11 g, 43%).

Compound 07
Reaction Scheme: Step-1

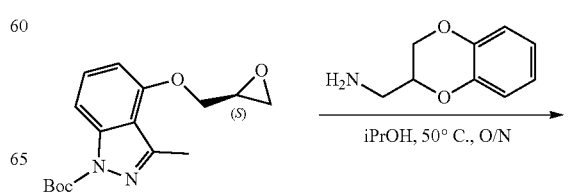

103
-continued

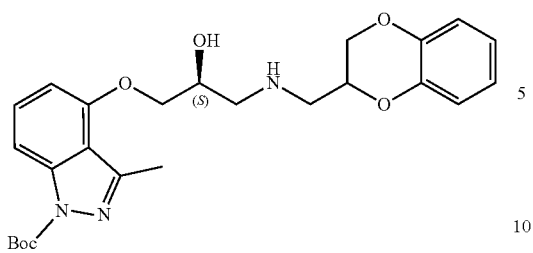

Procedure:

To a solution of Oxirane intermediate (1.0 g, 3.28 mmol) in iPrOH (20 mL), was added (2,3-dihydrobenzo[b][1,4]dioxin-2-yl)methanamine (0.54 g, 3.28 mmol). The reaction mixture was stirred under 60° C. for 24 h, after that RM was concentrated under reduced pressure and purified by silica column chromatography using 1% methanol in ethyl acetate as eluent to give (0.6 g, 38%) as a thick liquid.

Reaction Scheme: Step-2

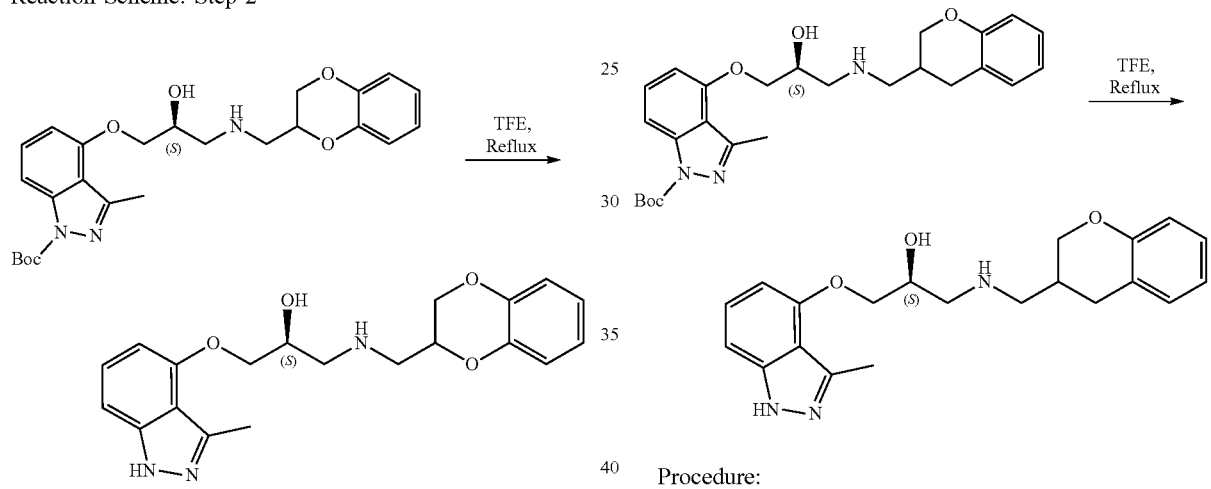

Procedure:

A solution of Boc indazole (0.6 g, 1.3 mmol) in trifluoro ethanol (5 mL) was stirred under 74° C. for 2 days, concentrated under reduced pressure and purified by silica column chromatography using 4% methanol in DCM as the eluent to give (240 mg, 61%) as a thick liquid, which was dissolved in 1 mL of methanol and then added fumaric acid (21.7 mg, 0.18 mol). Clear RM was stirred at ambient temperature for 1 h., concentrated under vacuum, dried under high vacuum to get solid (0.23 g, 43%)

Compound 08

Reaction Scheme: Step-1

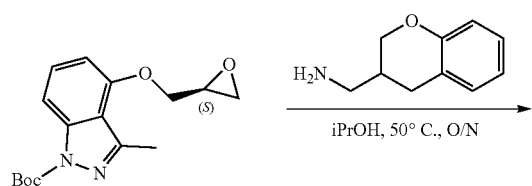

104
-continued

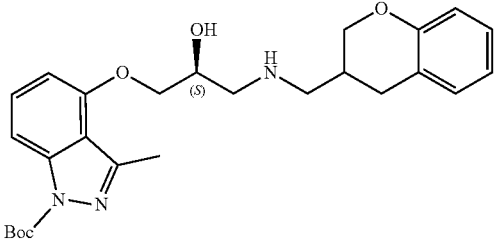

Procedure:

To a solution of Oxirane intermediate(1.0 g, 3.28 mmol) in iPrOH(20 ml), was added 2-chroman methyl amine(0.53 g, 3.28 mmol). The reaction mixture was stirred under 60° C. for 24 h, after that RM was concentrated under reduced pressure and purified by silica column chromatography using 1% Methanol in EA as the eluent to give (0.49 g, 32%) as a thick liquid.

Reaction Scheme: Step-2

Procedure:

A solution of Boc indazole (0.49 g, 1.0 mmol) in trifluoro ethanol (5 mL) was stirred under 74° C. for 2 days, concentrated under reduced pressure and purified by silica column chromatography using 4% Methanol in DCM as the eluent to give (130 mg, 34%) as a solid.

Compound 09

Reaction Scheme: Step-1

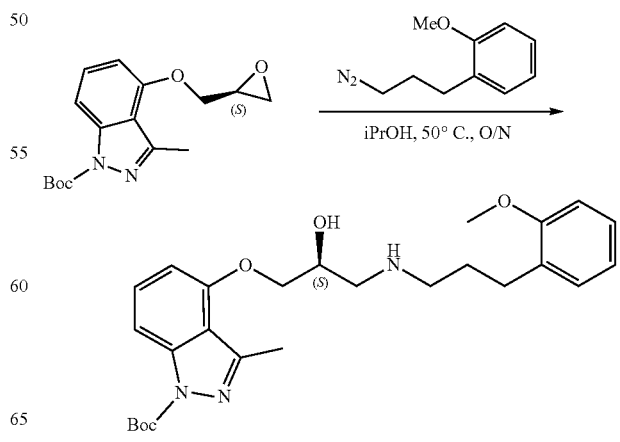

Procedure:

To a solution of Oxirane intermediate (1.0 g, 3.3 mmol) in iPrOH (200 mL), was added 2-methoxy Phenyl propyl amine (0.54 g, 3.3 mmol). The reaction mixture was stirred under 60° C. for 12 h, concentrated under reduced pressure and purified by silica column chromatography using 1% methanol in ethyl acetate as eluent to give (0.45 g, 29%) as a thick oil.

Reaction Scheme: Step-2

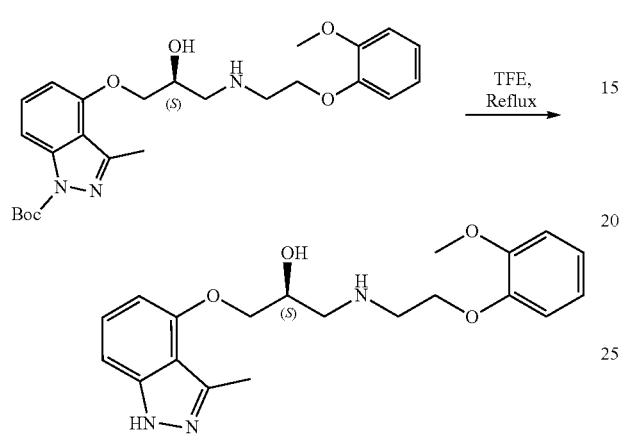

Procedure:

A solution of Boc indazole (0.45 g, 0.95 mmol) in trifluoro ethanol (5 mL) was stirred under 74° C. for 2 days, concentrated under reduced pressure and purified by silica column chromatography using 4% methanol in DCM as eluent to give (0.11 g, 31%) as a solid.

Compound 10

Reaction Scheme: Step-1

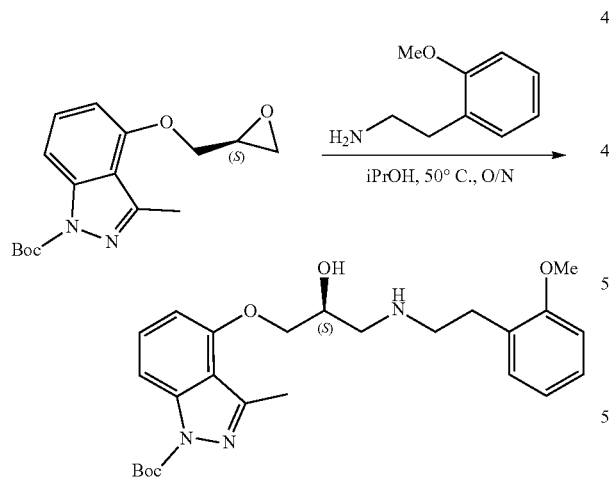

Procedure:

To a solution of Oxirane intermediate (1.0 g, 3.3 mmol) in iPrOH (200 mL), was added 2-methoxy Phenyl propyl amine (0.50 g, 3.3 mmol). The reaction mixture was stirred under 60° C. for 12 h, concentrated under reduced pressure and purified by silica column chromatography using 1% methanol in ethyl acetate as eluent to give (0.50 g, 33%) as thick oil.

Reaction Scheme: Step-2

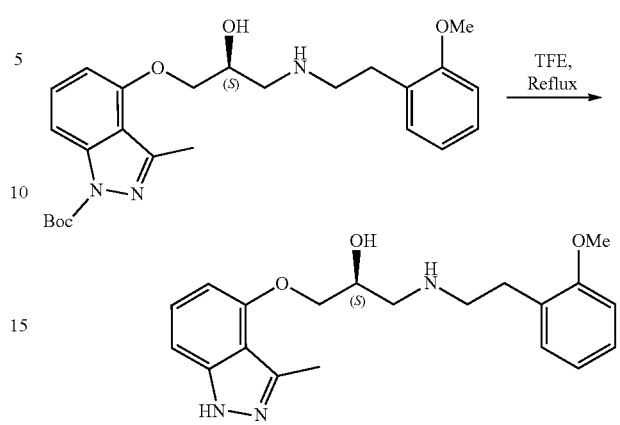

Procedure:

A solution of Boc indazole (0.45 g, 0.98 mmol) in trifluoro ethanol (5 mL) was stirred under 74° C. for 2 days, concentrated under reduced pressure and purified by silica column chromatography using 4% methanol in DCM as eluent to give (0.11 g, 31%) as solid.

Compound 11

Reaction Scheme: Step-1

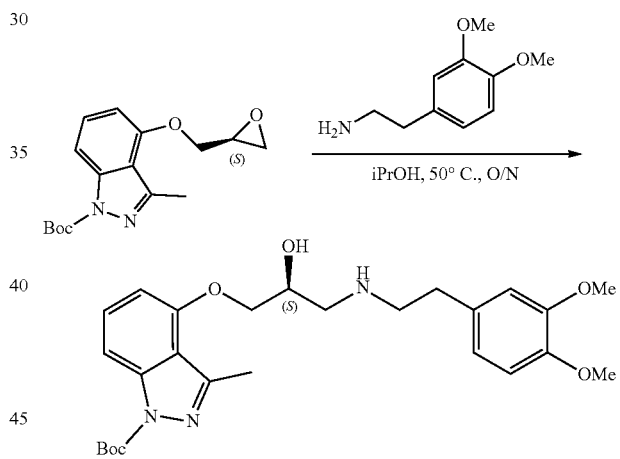

Procedure:

To a solution of Oxrane intermediate (1.0 g, 3.3 mmol) in iPrOH (200 mL), was added 2-methoxy Phenyl propyl amine (0.59 g, 3.3 mmol). The reaction mixture was stirred under 60° C. for 12 h, concentrated under reduced pressure and purified by silica column chromatography using 1% methanol in ethylacetate as eluent to give (0.6 g, 37%) as a thick oil.

Reaction Scheme: Step-2

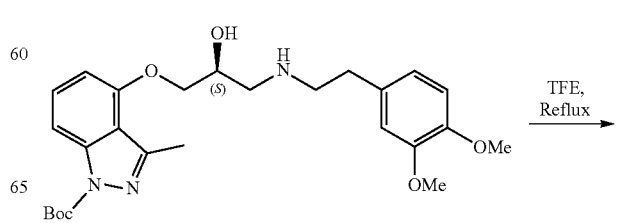

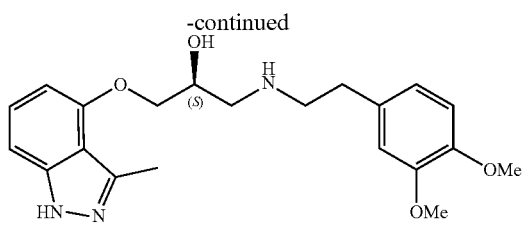

Procedure:

A solution of Boc indazole (0.45 g, 1.1 mmol) in trifluoro ethanol (5 mL) was stirred under 74° C. for 2 days, concentrated under reduced pressure and purified by silica column chromatography using 4% methanol in DCM as the eluent to give (180 mg, 41%) as a solid.

Compound 92 of Table 1

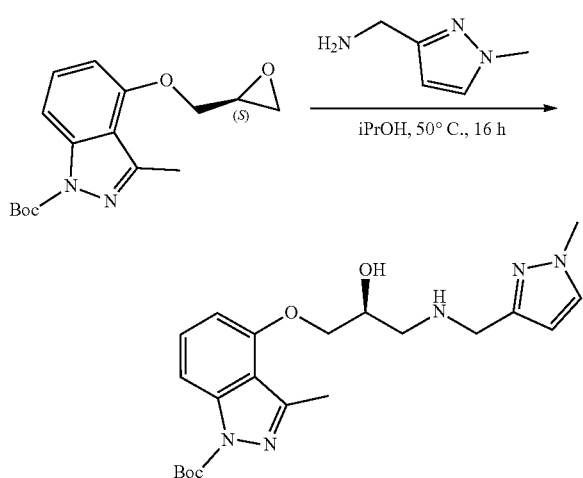

To a solution of Oxirane intermediate (16.0 g, 52.56 mmol) in iPrOH (200 ml), was added (1-methyl-1H-pyrazol-3-yl)methanamine (8.76 g, 78.84 mmol). The reaction mixture was stirred under 50° C. for 16 h, after that RM was concentrated under reduced pressure and purified by silica column chromatography using 100% ethyl acetate as eluent to give (8.8 g, 40%) as a thick liquid.

A solution of Boc indazole (8.8 g, 21.16 mmol) in trifluoro ethanol (100 mL) was stirred under 80° C. for 2 days, concentrated under reduced pressure and purified by silica column chromatography using 5% methanol: EtOAc as the eluent to give (4.26 g, 88%) as brown solid.

Example 3: Assays for Assessing Compounds

Assays which can be adapted to assess activities of the subject compounds include those described by Shamloo at al., Neurobiology of Disease 43 (2011) 397-413. In addition, the following materials and general methods can be adapted to assess activities of the subject compounds, e.g., modulation of neuroinflammation and pathology and activity in models of Alzheimer's Disease (AD).

Behavioral Testing

Open Field: General locomotor activity is assessed in a square arena (76 cm×76 cm×50 cm) under low light conditions. Mice are placed in one corner of the open field arena and allowed to freely explore for 10 minutes while being tracked by an automated tracking system (Ethovision) from a ceiling-mounted camera. At the end of each trial the surface of the arena is cleaned with 1% Virkon disinfectant.

Activity Chamber:

General locomotor activity is assessed as described previously (Shamloo et al. (2011) Comprehensive behavioral phenotyping of Ts65Dn mouse model of Down syndrome: . . . Neurobiol Dis 43, 397-413). Briefly, mice are placed in one corner of a square arena (43×43 cm2) located inside of a dark sound-attenuated chamber (66×55.9×55.9 cm3) and allowed to freely explore the arena. Movement is tracked by an automated tracking system with three planes of infrared detectors during a 10-min trial. Between each trial, the surface of the arena is cleaned with 1% Virkon disinfectant.

Y-maze:

Y-maze is performed to assess exploration and spatial memory. The symmetrical Y-maze is made of acrylic and consists of three arms separated by 120° angles. Each arm is 40 cm long and 8 cm wide with 15 cm high walls. Briefly, mice are placed in the center of the Y-maze and allowed to explore freely through the maze for 5 min. Arm entry is defined as having all four limbs inside an arm. The sequence and total number of arms entered are recorded. Between each trial, the surface of the arena is cleaned with 1% Virkon. A triad is defined as a set of 3 consecutive arm entries. An alternation is defined as a triad consisting of 3 unique arm entries (ex: ABC versus ABA). Percent alternation is calculated as the number of alternations divided by the total possible alternation (total entries—2).

Social Discrimination:

Recognition of a novel versus familiar juvenile conspecific is tested in a "homecage" social discrimination task (based upon Macbeth A H, Edds J S, Young W S, III (2009) Housing conditions and stimulus females: a robust social discrimination task for studying male rodent social recognition. Nat Protoc 4, 1574-1581). The test occurs in a dean cage and consists of three sessions without inter-trial intervals (ITIs), one habituation session of 20-min followed by two 10-min social sessions. During the first social session (learning), an unfamiliar juvenile (4-5 weeks old) male mouse (C57BL/6J) is placed under a stainless steel wire grid cup on one side of the cage while an empty similar cup is placed on the opposite side. The position of the stimulus mouse is altered between left and right between subjects. During the second social session (recognition), the now-familiar juvenile is placed under a cup in the side of the cage that was previously containing the empty cup and a new unfamiliar C57BL/6J juvenile (not a cage-mate of the familiar juvenile) is placed under a new cup in the opposite side of the cage. During each session, the testing animal is allowed to move freely in the entire arena for 10-min and the time spent sniffing each cup is recorded. The arena and cups are cleaned with 1% Virkon between mice. A discrimination index is calculated as (time with novel−time with familiar)/(time with novel+time with familiar).

Novel Object Recognition:

Mice are tested in a 20×40 cm arena to which they are habituated for 15-min the day prior to testing. On the first day of testing, mice are placed in the arena with 2 identical unfamiliar objects positioned 5 cm away from the walls. Mice are allowed to explore the arena and the objects during a 10-min trial (training session). Twenty-four hours later, one of the objects is changed for a new unfamiliar one while the other object is identical to the ones used during the training session. Again, mice are allowed to explore the arena and the objects during a 10-min trial (testing session). Each trial is recorded using an overhead camera. The amount of time spent sniffing and with the head within 1 cm of each object is scored as exploration of the object. At the end of each trial, the arena and the objects are cleaned using 1% Virkon. A discrimination index is calculated as (time with novel−time with familiar)/(time with novel+time with familiar).

Elevated Plus Maze:

Anxiety-related behavior is assessed in an elevated plus maze.

Without prior habituation, mice are placed in the center intersection of an elevated (50 cm) maze with 2 opposing "open" arms (lacking walls) and 2 opposing "closed" arms (with transparent plexiglass walls). Arms are 5 cm wide by 30 cm long, and walls of closed arms are 15 cm high. Mice are allowed to explore the maze for 8 minutes during which behavior is recorded from a ceiling-mounted camera and analyzed with Ethovision software. Duration in and entries into open and closed arms are analyzed for both the first 5 minutes and the full 8 minutes.

Morris Water Maze (MWM):

Mice are tested in a large water tank (178 cm in diameter; 22.0±1.5° C.) with a submerged 17 cm diameter circular platform (~1 cm below the water surface and ~50 cm away from the wall). Non-toxic tempera paints (Elmers) are used to make the water opaque. Privacy blinds with four different visual cues surrounded the tank and are located ~150 cm from the center of the tank. Testing is performed under dim white light (40 Lux at the water surface). Activity is monitored with Ethovision via an overhead video system. Mice complete 4-6 days of hidden platform training (60 seconds to locate the platform when released from a pseudorandomized drop location). Each day consists of 4 trials (30 min intertrial intervals), and each trial ends when the mice rest on the platform for 10 s or when the trial duration expires. If trial duration expires, mice are guided to the platform. After completion of 4-6 days of hidden platform training, at 24 hours after the last training session, a 60 s probe trial is conducted in the absence of the platform. Successful learning of MWM is determined by reduced escape latency and discriminative quadrant exploration during the probe trial. After the probe trial, the platform is moved to a new location and mice are given up to 3 days of reversal training. Following reversal training, visible platform training is performed to ensure that no gross sensorimotor or visual deficits are present. During the visible platform training, the platform is marked with a black-and-white Ping-Pong ball attached to a 10 cm wooden stick.

Fear Conditioning:

Conditioned fear-based learning and memory are assessed based on a previously described protocol (Shamloo et al., (2012) Thy1-hAPP(Lond/Swe+) mouse model of Alzheimer's disease displays broad behavioral deficits in sensorimotor, cognitive and social function. Brain Behav 2, 142-154) with modifications. Conditioning and testing are performed using Coulbourn Instruments fear conditioning chambers (Whitehall, Pa.). A trace fear conditioning protocol is used for the training day followed by tone-cued and contextual memory retrieval tests. On the first day (conditioning), mice are placed in the chamber for a 3-min baseline recording followed by five tone-shock pairings with intertrial intervals (ITIs) of 100 sec. The shocks (0.5 mA, 2 sec) are delivered 18 sec following the end of a tone (70 dB, 2 kHz, 20 sec). The 18 second period following the tone and preceding the shock is defined as the TRACE period for analysis of freezing in expectation of the shock. Increased freezing in consecutive TRACE periods is used as an indication of learning. On the second day (cued recall), a novel context is used for tone-cued testing (new olfactory environment, different shape of the chamber, new texture of the floor, blue plastic inserts for walls, extra source of blue light, and visual cues). After 3 min of baseline recording, three tones without shocks with ITIs of 100 sec are presented to the mice. Freezing during a TRACE period of 20 seconds following the tone is used as indication of cued recall. On the third day of the experiment (contextual recall), mice are placed in the same context as the first day for 5 min with no shocks or tones to test contextual memory retrieval (modified from the method described by Saxe et al. (2006) Ablation of hippocampal neurogenesis impairs contextual fear conditioning and synaptic plasticity in the dentate gyrus. Proc Natl Acad Sci USA 103, 17501-17506). The chambers are cleaned with 1% Virkon on days 1 and 3. On day 2, chambers are first cleaned by Alcid and then wiped with wet paper towels. Freezing is defined as the complete lack of motion for a minimum of 0.75 sec, as assessed by FreezeFrame software (Actimetrics, Evanston, Ill.).

Tissue Collection

Mice are deeply anesthetized with isoflurane. Prior to perfusion, whole blood is collected from the right ventricle via cardiac puncture into lithium heparin-containing vials (BD microtainer plasma tubes, Becton Dickinson 365958) for plasma collection. The right atrium is opened and mice are transcardially perfused with ice cold phosphate buffered saline (PBS. pH=7.4). Brains from half of the subjects are collected, flash-frozen on liquid nitrogen and stored at −80 for later analysis of protein and gene expression, while brains from the other half of the subjects are perfused with 4% paraformaldehyde (in PBS) and post-fixed for 24 hours in the same fixative at 4° C. Fixed brains are cryoprotected for at least 72 hours (until sunk) in 30% sucrose in PBS. Fixed brains are then rapidly frozen in isopentane on dry ice. All frozen brains and plasma are stored at −80° C.

Amyloid Beta ELISA

To determine the amount of soluble and insoluble amyloid beta isoforms, amyloid beta(1-40) (Aβ40) and amyloid beta(1-42) (Aβ42) in cortical tissue, samples of cortical tissues are processed as described previously (Lemere Calif. (2008) Complement C3 deficiency leads to accelerated amyloid beta plaque deposition and neurodegeneration and modulation of the microglia/macrophage phenotype in amyloid precursor protein transgenic mice. J Neurosci 28, 6333-634). In brief, frozen cortical tissue is dissected, weighed and homogenized in 10 volumes of tris-buffered saline (TBS) containing protease inhibitor cocktail. The samples are then centrifuged at 175,000 g for 30 min at 4° C. The supernatant (TBS-soluble homogenate) is collected and kept at −20° C. The pellets are re-homogenized in the same volume of TBS-T (TBS/1% Triton X-100 with protease inhibitor cocktail) at 4° C., centrifuged at 175,000 g for 30 min at 4° C., and resultant supernatant (TBS T-soluble homogenate), containing membrane bound Aβ, is collected and kept at −20° C. Subsequently, the pellets are homogenized in ice-cold 5M guanidine-HCl in 50 mM Tris (pH 8.0). The homogenates are then mixed for 4 hours at room temperature and used for measurement of insoluble Aβ40 and Aβ42. Finally, amounts of TBS-soluble and guanidine-soluble forms of Aβ are quantified using ELISA kits specific for human Aβ40 and Aβ42. The final values are normalized to the amount of loaded wet tissue.

Immunohistochemistry

Immunohistochemistry is performed for the microglia/macrophage marker ionized calcium-binding adapter molecule-1 (Iba1), amyloid beta (6E10), and the nucleic acid stain, 4',6-diamidino-2-phenylindole dihydrochloride (DAPI). Fixed brains are serially sectioned (at −18° C. using a Microm HM-550 cryostat) in a coronal plane across 6 series through the rostrocaudal extent of the brain (40 micrometer sections; 240 micrometers between sections within each series) and stored in cryoprotectant storage buffer (30% ethylene glycol, 20% glycerol in 0.05M phosphate buffer, pH 7.4). Multilabel fluorescent immunohistochemistry is used to stain 1 series of brain sections through the rostral hippocampus (from 0.26 to −2.92 mm Bregma). Free-floating sections are incubated at room temperature in 24-well tissue culture plates gently shaken on an orbital shaker throughout the procedure. All rinses are 15 minutes unless stated otherwise. Sections are rinsed three times in 0.05 M PBS, and then preincubated 1 hour in PBS containing 1% Triton X-100 (PBST) and 6% normal donkey serum. Sections are incubated 18 hours with rabbit anti-Iba1 primary antibody (019-19741, WACO Chemicals USA, Richmond, Va.) diluted 1:1000 and mouse anti-6E10 primary antibody (#803001, Biolegend, San Diego, Calif.; binds to amino acid residue 1-16 of amyloid beta) diluted 1:1000 in 0.3% PBST and 2% normal donkey serum, followed by 3 PBS rinses and a 2 hour incubation in CY3-conjugated donkey anti-rabbit (711-165-152, Jackson Immunoresearch, Maine USA) and AlexaFluor 488 donkey anti-mouse (715-545-151, Jackson Immunoresearch, Maine USA) IgG secondary antibodies diluted 1:200 in PBS. Sections are then rinsed 2 times prior to incubation for 30 minutes with DAPI (D9542, Sigma-Aldrich, St. Louis, Mo.) diluted 1:5000 in PBS. Free-floating sections are then rinsed 3 times in PBS, rinsed briefly in 0.15% gelatin in water, mounted on clean glass slides, and allowed to air-dry to affix sections to slides immediately prior to coverslipping with polyvinyl alcohol mounting medium with DABCO antifade (10981, Sigma-Aldrich, St. Louis, Mo.). Image analysis: Iba1-immunoreactivity (-ir) and 6E10-ir are assessed in retrosplenial cortex (RS), basolateral amygdala (BLA), CA3 of the hippocampus, dentate gyrus (DG), and subiculum (SUB) across 3-6 consecutive serial sections (depending on structure) throughout the respective structures (see FIG. 3 for depiction of regions of interest). Hippocampus, amygdala and retrosplenial cortex are selected based on evidence for dense terminal projections from LC and involvement in learning and memory. Immunostaining is quantified in both left and right hemispheres at each rostrocaudal level without differentiation of hemisphere for analysis. Images are captured at 5× using a Zeiss Axioscope M2 microscope with Stereo Investigator 10.0 Software (MicroBrightField Bioscience, Vermont). Images are quantified using NIH ImageJ 1.49. RGB images are converted to RGB monochrome stacks for image quantification. Regions are first outlined in the DAPI monochrome stack, and "mean gray value" is quantified within Iba1 and 6E10 stacks. Mean gray values from consecutive serial sections (6-12 values per subject; left and right hemispheres across 3-6 rostrocaudal levels) are entered as within subject replicates for analyses of variance in GraphPad Prism 5.0 software.

Single-label avidin-biotin-peroxidase (diaminobenzidine) immunohistochemistry was used to visual neuroblasts with a doublecortin (DCX) antibody (rabbit anti-DCX, 1:1000; Cell Signaling #4604S). Protocol was the same as above with the following exceptions. Prior to the initial blocking step, sections were incubated in 1% hydrogen peroxide in PBS for 15 min followed by 2×15 min washes. Following the overnight primary incubation, sections were incubated in biotinylated goat anti-rabbit secondary antibody (1:400; 90 min; Jackson Immunoresearch 111-065-003) followed by 2×15 min washes and an incubation with an avidin-biotin complex solution (Vector ABC, 1:200, 60 min). Sections were incubated in 0.05% diamobenzidine activated with 0.0075% hydrogen peroxide (10 min) to visualize the antibody complex. Slides were dehydrated through an ascending ethanol series and coverslipped with Cytoseal XYL (Richard-Allen Scientific, 8312-4). DCX Image analysis: DCX-immunoreactive cells were counted in serial sections through the dentate gyrus from images captured at 5× magnification on a Zeiss axioscope M2 microscope with StereoInvestigator 10.0 software.

Quantitative RT-PCR

Total RNA is isolated from 50 mg of cortex using the RNeasy Lipid Tissue Mini Kit (Qiagen). One mg of total RNA are transcribed into cDNAs (Superscript III, Invitrogen). PCR is performed in duplicate using TaqMan gene expression mastermix (Applied Biosystems) and validated TaqMan gene expression assays, Iba1 (Mm00479862_g1), CD14 (Mm00438094_g1), CD74 (Mm00658576_m1), CD68 (Mm03047340_m1), IL1β (Mm00434228_m1), IL6 (Mm00448190_m1), TNFα (Mm00443258_m1), TGFβ (Mm01178820_m1) and glyceraldehyde-3-phosphate dehydrogenase (GAPDH; Mm99999915_g1). Amplification is performed using StepOnePlus (Applied Biosystems). Fold changes of expression relative to control are determined after normalization to GAPDH. Relative quantification and fold change are calculated by the comparative CT method (Schmittgen T D, Livak K J (2008) Analyzing real-time PCR data by the comparative C(T)method. Nat Protoc 3, 1101-1108).

Measurement of Mean Aterial Blood Pressure (BP)

Adult rats are anesthetizes using isoflurane and are accommodated on a heated platform warmed to 36° C. A jugular catheter (for IV administration of the drug) and an intra-arterial catheter (tail artery, for blood pressure measurements) are implanted under 2.5% isoflurane. To avoid clotting, all animals received a single dose of heparin after intravenous cannulation. Intra-arterial catheter was then connected to a pressure transducer coupled to a computerized data acquisition system (PowerLab) and its application software (LabChart 8)[AD Instruments (Australia)]. Mean blood pressure and the hear rate was analyzed and plotted using prism software.

In Vitro Microglia Proliferation Assay

The effects of selected compounds on microglia proliferation are determined in primary microglia extracted from a rat. Briefly, mixed glial cells are obtained from the cerebral cortex of Sprague Dawley rat pups at postnatal days 1-3 and cultured in DMEM supplemented with 10% fetal bovine serum. After 8-14 days in vitro, microglia are harvested by gentle shaking of the growth flask and plated in a 96 well plate at the density of 7×104 cells/well. The cells are used following day. Effects of selected compounds on microglia proliferation are determined using BrdU cell proliferation assay kit (Roche Molecular Biochemicals; Mannheim, Germany). Briefly, microglia cells are treated with isoprenaline (positive control) or selected test compounds. After 24 hours of incubation, BrdU are added, and cells are incubated for an additional 2 hours. Following BrdU incubation, labeling medium are removed and cells are dry fixed overnight. BrdU incorporation are detected by incubation with anti-BrdD-peroxidase (POD) antibody solution followed by reaction with substrate solution. The incorporation of BrdU into DNA are quantified by the spectrophotometric absorbance of the chemiluminescent substrate reaction using the automated microplate reader.

cAMP Assay

Pharmacological effects of compounds at the cAMP pathway mediated by ADRB1 are evaluated by measuring cAMP production using the homogenous time-resolved fluorescence detection method with HEK-293 cells stably expressing human recombinant ADRB1. Briefly, cells are suspended in HBSS buffer completed with 20 mM HEPES (pH 7.4) and 500 µM IBMX (3-isobutyl-1-methylxanthine) and distributed at a density of $3\times10^3$ cells/well. Subsequently, cells are incubated with HBSS (basal control), the full agonist isoproterenol hydrochloride, xamoterol, or test compounds for 30 min. Following incubation, the cells are lysed and the fluorescence acceptor (D2-labeled cAMP) and fluorescence donor (anti-cAMP antibody labeled with europium cryptate) are added. After 60 min incubation with the fluorescence donor and acceptor at room temperature, the fluorescence transfer is measured at 337 nm (excitation) and 620 and 665 nm (emission) using a microplate reader. The cAMP concentration is determined by dividing the signal measured at 665 nm by that measured at 620 nm (ratio). The results are expressed as a percent of the maximum efficacy achieved with isoproterenol. Pharmacological effects of compounds at the cAMP pathway mediated by ADRB2 and ADRB3 are measured as described above using CHO cells stably expressing human recombinant ADRB2 and human SK-N-MC neurotumor cells endogenously expressing ADRB3, respectively.

β-Arrestin Assay

Pharmacological activity of compounds in the β-arrestin pathway mediated by ADRB1 are evaluated using an enzyme fragment complementation method with a β-galactosidase functional reporter. An engineered CHO-K1-ADRB1 PathHunter cell line (DiscoveRx) is used in the assay. In this cell line, enzyme acceptor (β-galactosidase fragment) is fused to β-arrestin and enzyme donor (β-galactosidase fragment) is fused to the ADRB1. Thus, activation of the ADRB1 stimulates binding of β-arrestin to the ProLink-tagged ADRB1 and forces complementation of the two enzyme fragments, resulting in the formation of an active β-galactosidase enzyme. Briefly, CHO-K1-ADRB1 PathHunter cell lines are plated in a total volume of 20 µL cell plating reagent (DiscoveRx, 93-0563R0A) at a density of 2,500 cells/well into 384 well microplates and incubated overnight at 37° C. in 5% $CO_2$. The following day, 5 µL of the full agonist isoproterenol, xamoterol (S), or test compounds is added to cells and incubated at 37° C. for 90 min. After the 90 min incubation, 15 µL of PathHunter Detection reagent cocktail (DiscoveRx, 93-0001) is added, followed by a 60 min incubation at room temperature. Chemiluminescent signal is then read with a PerkinElmer Envision™ instrument. The results are expressed as a percent of the maximum efficacy achieved with isoproterenol.

In Vitro Primary Microlia Tumor Necrosis Factor α (TNF-α) Assay

Mixed glial cells are obtained from the cerebral cortex of Sprague Dawley rat pups at postnatal days 1-3. Briefly, neonates are euthanized by decapitation and their brain tissues are collected for isolation of cortex. The isolated cortex was then trypsinized, triturated, and placed onto tissue culture flasks in DMEM supplemented with 10% fetal bovine serum and 1% Penicillin/Streptomycin. After 10 days in vitro, microglia are harvested by gentle shaking of the growth flask, plated in a 96 well plate at a density of 30,000 cells/well, and incubated at 37° C. overnight. The next day, microglia are stimulated with lipopolysaccharides (LPS) (10 ng/ml) along with isoproterenol, xamoterol (S), or compound 43 at the concentration of 10 µM for 4 h at 37° C. Following the 4 h incubation, cell media is collected and the concentration of TNF-α is measured by ELISA (Invitrogen, KRC3011) according to the manufacturer's instruction.

Microsomal Stability Assay

The test compound is pre-incubated with pooled human or mouse microsomes in 100 mM potassium phosphate buffer (pH 7.4) containing 10 mM $MgCl_2$ for 5 min in a 37° C. shaking waterbath. After the preincubation, the reaction is initiated by adding freshly prepared NADPH to a final concentration of 1 mM. Aliquots of the reaction samples are collected at 0 min, 15 min, 30 min, 45 min, and 60 min after the initiation of the reaction, and quenched with equal volume of acetonitrile. Samples are then mixed and centrifuged, and supernatants are diluted with equal volume of water and used for LC-MS/MS analysis to determine the concentrations of compound 43. Analyte peak areas at different time points are recorded, and the compound remaining is calculated by comparing the peak area at each time point to time zero. The half-life is calculated from the slope of the initial linear range of the logarithmic curve of compound remaining (%) vs. time, assuming first order kinetics.

Animals

For the in vivo LPS study, a total of 45 male C57BI/6J mice at the age of 10-12 weeks (Jackson Laboratory, Bar Harbor, Me., USA) are used. For the pharmacokinetic study, a total of 36 Sprague-Dawley male rats (Charles River, Wilmington, Mass., USA) weighing 280-380 g are used. All animals are kept under a reverse light-dark cycle with lights off at 8:30 AM and on at 8:30 PM in a temperature- and humidity-controlled environment and given food and water ad libitum. All experiments are conducted in accordance with protocols approved by the Stanford University Administrative Panel for Laboratory Animal Care and conformed to the U.S. National Institutes of Health Guide for the Care and Use of Laboratory Animals.

In Vivo LPS Assay

C57BI/6J mice (10-12 weeks old) are injected with xamoterol (3 mg/kg; subcutaneous; n=11), compound 43 (3 mg/kg; intraperitoneal; n=4) or vehicle (5% DMSO/20% PEG400/water intraperitoneal; n=12) 15 min prior to LPS (50 ug/kg; intraperitoneal). A control group is injected with vehicle 15 minutes prior to saline (n=18). Following injections, mice are single-housed. At 90 min post-LPS/saline, mice are deeply anesthetized with isoflurane and blood is collected from the right ventricle via cardiac puncture (23 g needle) into lithium heparin-containing vials (BD microtainer plasma tubes). Plasma is separated by centrifugation (11,000 rpm for 3 minutes) within 30 min of collection and stored at −80° C. until analysis. The concentration of TNF-α in the collected plasma is measured by ELISA (Invitrogen, KMC3012) according to the manufacturer's instruction.

Pharmacokinetic Studies

Two cohorts of Sprague-Dawley rats are used in two independent studies. All animals are fasted overnight before the experiment with free access to water. In study 1, a total of 18 rats are used for a 4 h time course pharmacokinetic (PK) study. Rats are anesthetized with 3% isoflurane and catheters are implanted into the jugular and/or portal veins for compound administration and/or blood sampling as previously described 1 to 2 days prior to the experiments. On the day of the experiment, xamoterol is freshly prepared in saline. The compound is freshly prepared in 5% DMSO, 20% PEG, and 75% distilled water. The prepared xamoterol or compound is administered to the cannulated rats at a dose of 10 mg/kg intravenously (IV), intraperitoneally (IP), or orally (PO) (n=3 per route). For IV and IP groups, approximately 150 μL aliquot of blood samples are collected via jugular vein catheters before drug administration, and 1, 5, 10, 45, 60, 90, 120, and 180 min after drug administration. For the PO group, approximately 150 μL aliquot of blood samples are collected via jugular and portal vein catheters before drug administration, and 1, 5, 10, 45, 60, 90, 120, and 180 min after drug administration. Four hours post-dose, rats are deeply anesthetized with isoflurane and blood samples are collected by cardiac puncture. In study 2, a total of 18 rats are used for a 20 min post-dose collection study. Xamoterol and compound are freshly prepared as described above and administered to rats at a dose of 10 mg/kg via IV, IP, or PO routes (n=3 per route). At 20 min post-dose, rats are deeply anesthetized with isoflurane and blood samples are collected by cardiac puncture. Brains are collected after perfusion with phosphate buffered saline. All plasma samples are immediately separated after collection by centrifugation (11,000 rpm for 3 minutes) and stored at −80° C. until analysis. The brain tissue samples are homogenized in distilled water at a ratio of 1:3 (weight of tissue:volume of water), and the homogenates are stored at −80° C. until analysis. The concentrations of xamoterol and compound 43 in plasma and brains are determined using LC-MS/MS. LC separation is carried out on a Phenomenex Synergi Polar-RP column (2.5 μm, 2 mm×50 mm) with a flow rate of 0.25 ml/min at room temperature. Mobile phase A consisted of 10 mM ammonium acetate and 0.1% formic acid in LCMS grade water. Mobile phase B consisted of 10 mM ammonium acetate and 0.1% formic acid in LCMS grade acetonitrile: water 90:10% (v/v). The HPLC elution program is as follows: 35% B (0.3 min)→85% B (linear increase in 1.2 min)→35% B (linear decrease in 0.1 min)→35% B (0.9 min). Five μl of the extracted samples is injected. The mass spectrometer is operated in the positive mode with multiple-reaction monitoring (MRM) with the transition m/z 334.1→210.1 and 334.1→100.2.

Cardiovascular Studies

Effects of compounds on heart rate and blood pressure are measured in Sprague-Dawley rats with fluid filled catheter-transducer system using disposable blood pressure transducer MLT 0699 connected to PowerLab 8/30 recording unit with Quad Bridge Amp (AD instruments). Briefly, rats are anesthetized with 3-4% isoflurane and 1 cm longitudinal incision is made on the ventral aspect of the tail exposing the tail artery. Polyethylene catheter (PE50) filled with heparinized saline is then inserted into the tail artery and connected to blood pressure transducer system. After assuring absence of any air bubbles, 5-10 min of baseline systolic and diastolic blood pressure along with heart rate are recorded using LabChart Pro (AD Instruments). After establishing the baseline, xamoterol or compound 43 is subcutaneously administred and changes in blood pressure and heart rate are recorded for additional 30 min. Effects of xamoterol or compound 43 on heart rate are calculated as the difference between average values recorded during the baseline recording and average values recorded during 10 min after the administration of compound. Effects of xamoterol or compound 43 on blood pressure are calculated as the difference between average values measured during the baseline recording and the lowest value measured during 10 min period after the administration of compound.

Calculation and Statistics

In vitro pharmacology data for the cAMP pathway represent 2-5 experiments performed singly or in duplicate. In vitro pharmacology data for the β-arrestin pathway represent technical replicates within a single experiment. Curve fitting is performed with GraphPad Prism 5.0 software using the equation for a single-site sigmoidal, dose-response curve with a variable slope. $EC_{50}$ values are expressed as geometric means (95% confidence limits). Statistical analyses are performed with GraphPad Prism 5.0. One-way analyses of variance, followed by Dunnett's test for post-hoc analysis, is performed for analyses of in vitro and in vivo TNF-α data. Pharmacokinetic analyses are performed using the Phoenix® WinNonlin® Professional Edition computer software version 2.0 (Certara, N.J.). Differences are considered to be significant at a level of $p<0.05$.

Example 3: Adrenergic Modulating Activities of Selected Compounds

The activity of several compounds of interest is assessed for modulation of the cAMP and β-arrestin pathways relative to control compound isoproterenol. Effects of compounds on cAMP signaling pathway are determined using Human Embryonic Kidney 293 (HEK 293) cells stably expressing human β1-adrenergic receptors with time-resolved FRET technology. Briefly, HEK 293 cells stably expressing human β1-adrenergic receptors are suspended in buffer complemented with 20 mM HEPES (pH 7.4) and 500 μM IBMX, whereupon they are distributed in microplates at a density of 3000 cells/well and incubated for 30 min in the presence of buffer (basal control), the test compound, or isoproterenol (the reference full agonist). After 30 minute incubation with compounds, the cells are lysed and the fluorescence donor (Europium-chelated-labeled cAMP tracer; Eu-cAMP tracer) and fluorescence acceptor (cAMP-specific monoclonal antibodies labeled with the ULight™ dye) are added. After 1 hour incubation with the fluorescence donor and acceptor, the fluorescence transfer is measured at 320 nm (excitation) and at 615 and 665 nm (emission) using a microplate reader. The results are expressed as a percent of the control response to 10 μM isoproterenol. For subtype selectivity determination, same procedure is performed using Chinese hamster ovary (CHO) cells stably expressing human β2-adrenergic receptors or SK-N-MC human neuroblastoma cell line expressing β3-adrenergic receptors.

Effects of compounds on β-arrestin signaling pathways are determined using CHO cells stably expressing human β1-adrenergic receptors or human β2-adrenergic receptors with PathHunter® β-Arrestin GPCR assay system (DiscoveRx). In this system, adrenergic receptor is fused in frame with the small enzyme fragment ProLink™ and co-expressed in cell stably expressing at fusion protein of β-arrestin and the larger, N-terminal deletion mutant of β-galactosidase enzyme. Activation of the adrenergic receptor stimulates binding of β-arrestin to the ProLink-tagged receptor and forces complementation of the two enzyme fragments, resulting in the formation of an active β-gal enzyme. This interaction leads to an increase in enzyme activity that can be measured using chemiluminescent detection reagents. The effects of compounds on β-arrestin signaling pathways are determined 90 minutes after incubating the cells with the test compounds.

Table 2 shows the structures of the compounds listed in FIGS. 1 to 3F. The receptor subtype selectivity of exemplary compounds of interest was assessed for adrenergic receptor beta 1 (ADRB1) over adrenergic receptor beta 2 (ADRB2). Table 2 shows the structures of the compounds listed in FIGS. 4A to 5F. The receptor subtype selectivity of exemplary compounds of interest was assessed for adrenergic receptor beta 1 (ADRB1) over adrenergic receptor beta 3 (ADRB3). Table 2 shows the structures of the compounds listed in FIGS. 6A-7F.

The concentration of selected compounds in plasma (FIG. 8A) versus concentration in brain (FIG. 8A) was assessed after administration in a mice. Briefly, mice are administered with selected compounds via subcutaneous route. Thirty minutes after the compound administration, plasma and brain samples are collected. Concentrations of the selected compounds in plasma and brains are determined by LC/MS/MS. Panel C shows the ratio of brain to plasma concentration demonstrating the compound compound 43 has improved brain exposure with up to 5 times more brain concentration. Table 2 shows the structures of the compounds listed in FIG. 8, panels A-C.

Figure 9:
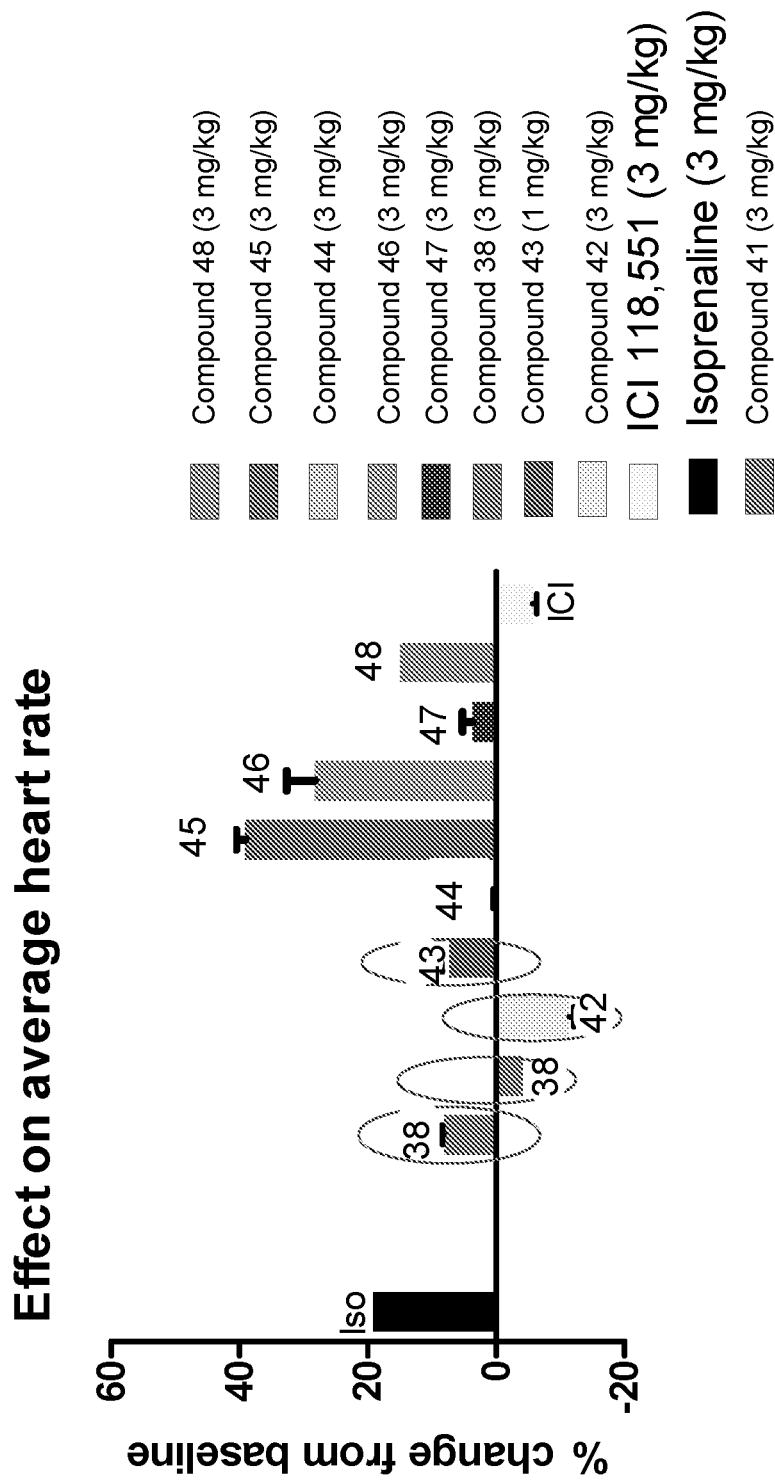
FIG. 9 illustrates the effect of exemplary compounds on average heart rate in a rat in comparison with reference compounds isoprenaline and ICI 118,551.
Figure 10:
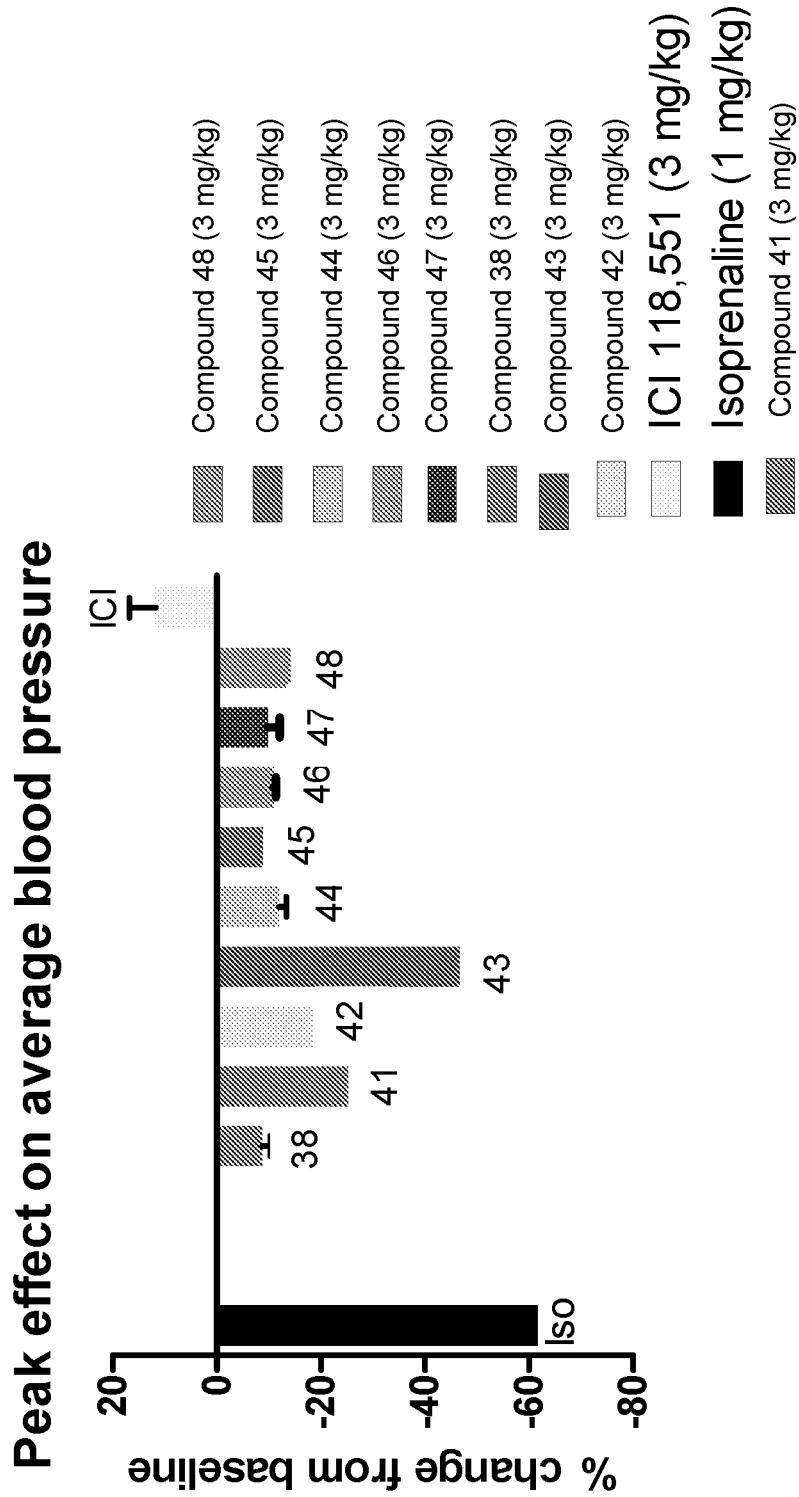
FIG. 10 illustrates the effect of exemplary compounds on blood pressure in a rat in comparison with reference compounds isoprenaline and ICI 118,551.

FIG. 9 illustrates the effect of exemplary compounds on average heart rate in a rat in comparison with reference compounds isoprenaline and ICI 118,551. FIG. 10 illustrates the effect of exemplary compounds on blood pressure in a rat in comparison with reference compounds isoprenaline and ICI 118,551. Intra-arterial measurement of heart rate and blood pressure are recorded in tail artery of a rat using Labchart software when rats are anesthetized with 2.5% isoflurane.

Figure 11:
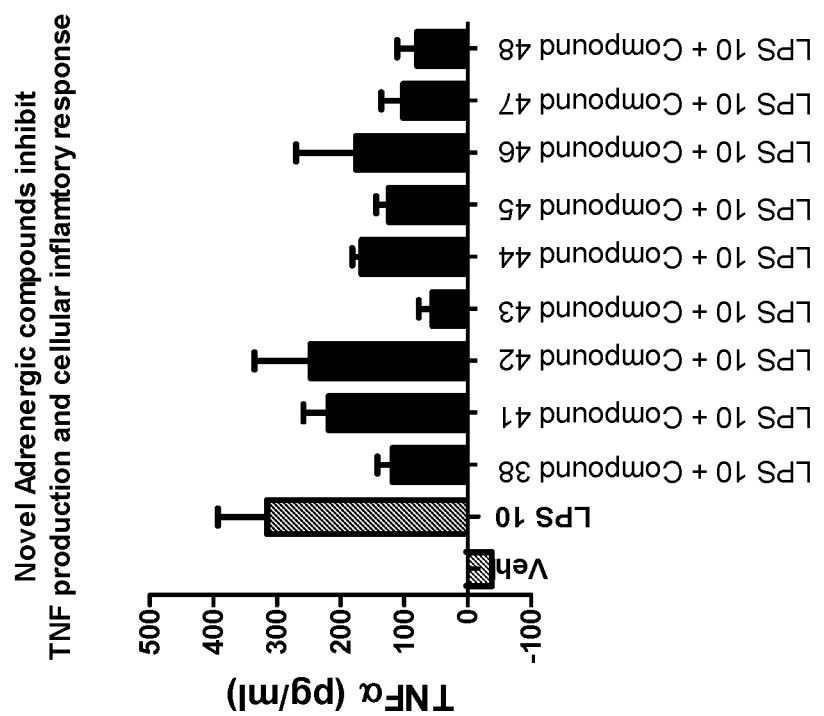
FIG. 11 illustrates the inhibitory effect of exemplary compounds on Tumor necrosis factor (TNFα) production and inflammatory response to lipopolysaccharide (LPS).

FIG. 11 illustrates the inhibition of Tumor necrosis factor (TNFα) production and cellular inflammatory response to lipopolysaccharide (LPS 10) by selected exemplary compounds. The effects of selected compounds on cellular inflammatory response to LPS are determined in primary microglia extracted from a rat. Briefly, mixed glial cells are obtained from the cerebral cortex of Sprague Dawley rat pups at postnatal days 1-3 and cultured in DMEM supplemented with 10% fetal bovine serum. After 7 days in vitro, microglia are harvested by gentle shaking of the growth flask and plated in a 96 well plate at the density of $3 \times 10^4$ cells/well. The cells are used following day. Effects of compounds on LPS-induced TNFα production are determined by incubating cells with LPS along with or without test compounds for 4 hours. Following the 4 hour incubation, cell media are collected and concentration of TNFα was measured by EUSA.

Table 2 shows the structures of the compounds listed in FIGS. 9-11.

TABLE 2

Figure 2A:
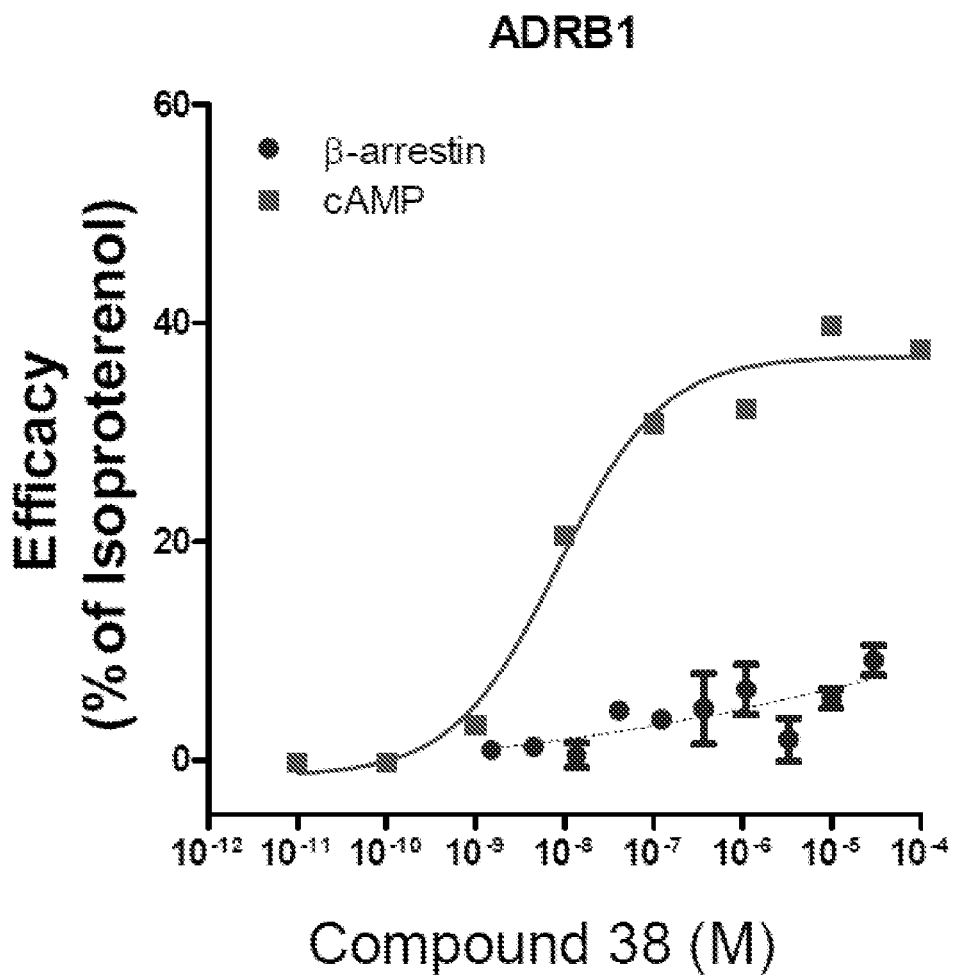
FIGS. 2A-2C illustrate the activity of compounds of interest on the cAMP and beta-arrestin pathways, relative to isoproterenol.
Figure 2B:
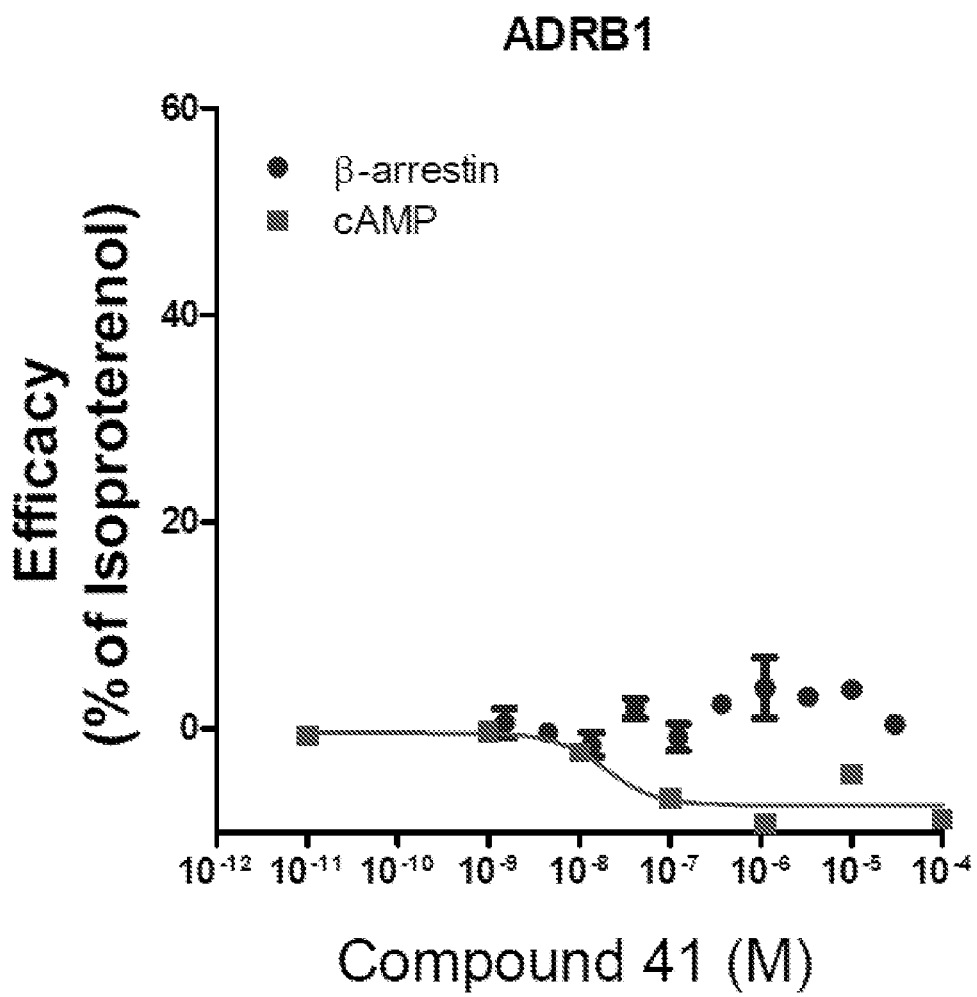
Figure 2C:
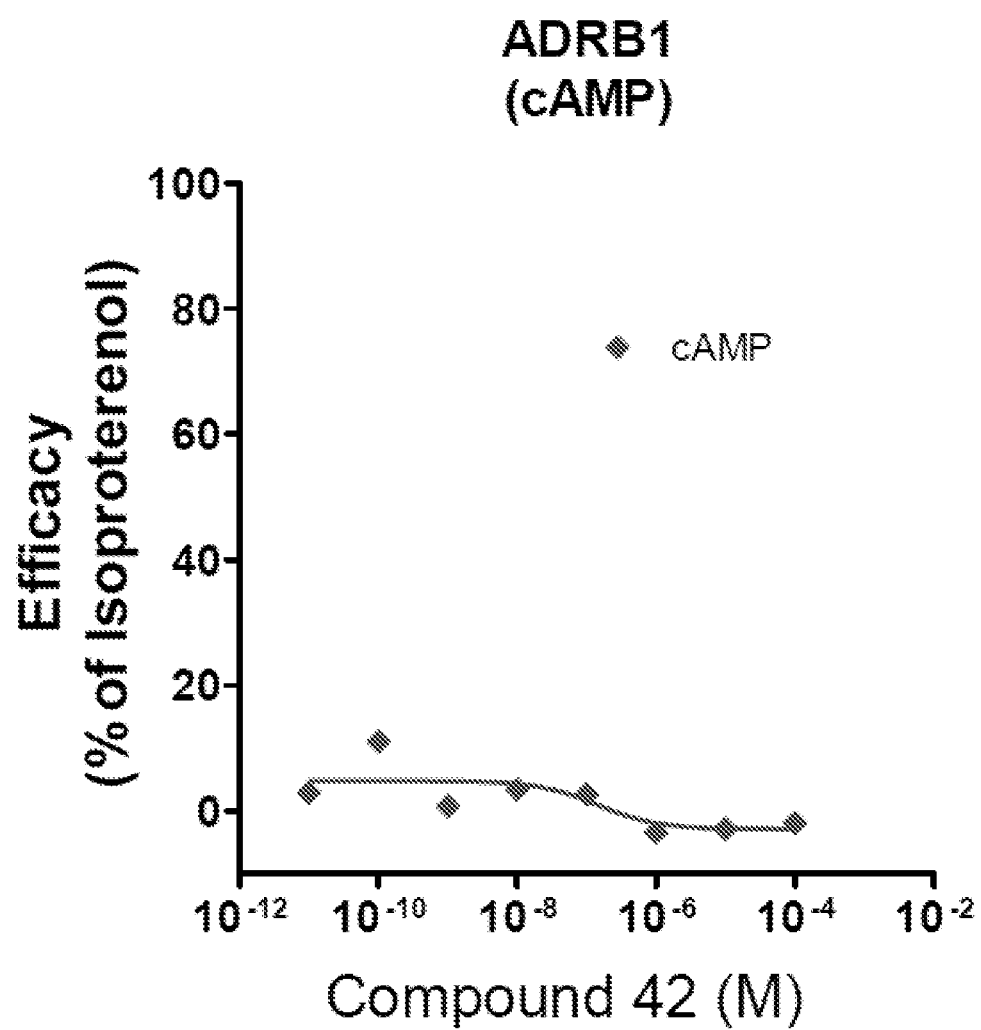
Figure 3A:
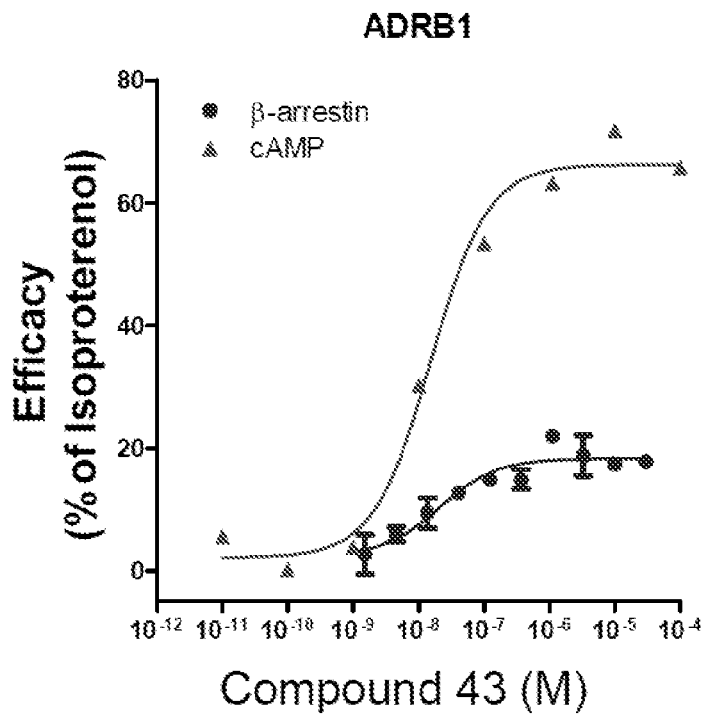
FIGS. 3A-3F illustrate the efficacy of exemplary compounds of interest for activation of cAMP pathway over β-arrestin pathway, relative to isoproterenol.
Figure 4A:
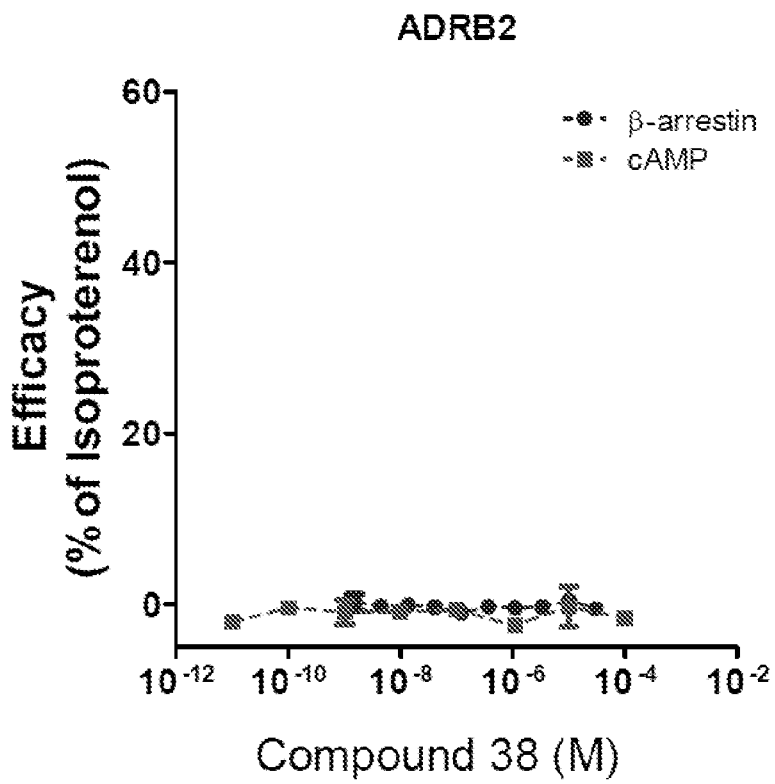
FIGS. 4A-4C show graphs of data for exemplary compounds of interest which demonstrate the compounds have subtype selectivity for adrenergic receptor beta 1 (ADRB1) over adrenergic receptor beta 2 (ADRB2).
Figure 4B:
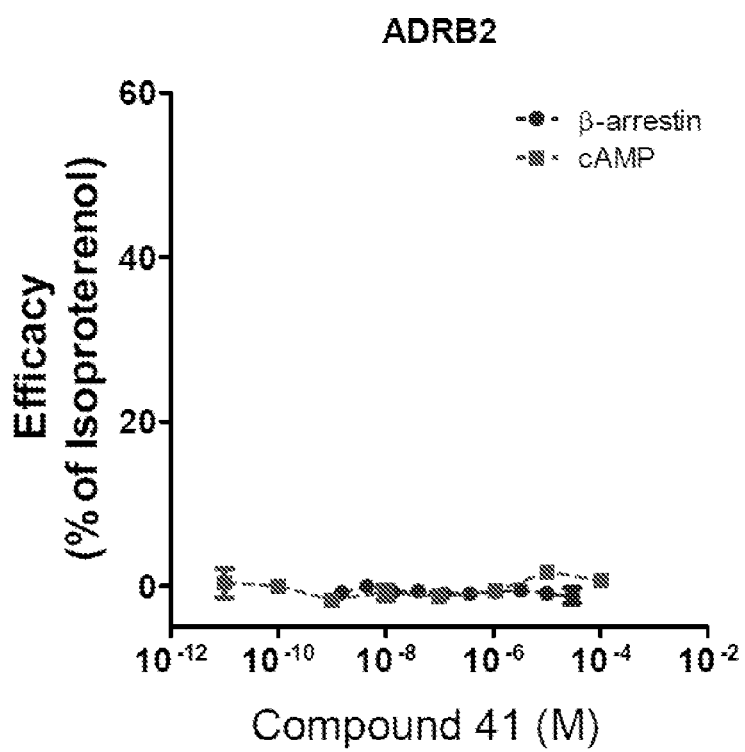
Figure 4C:
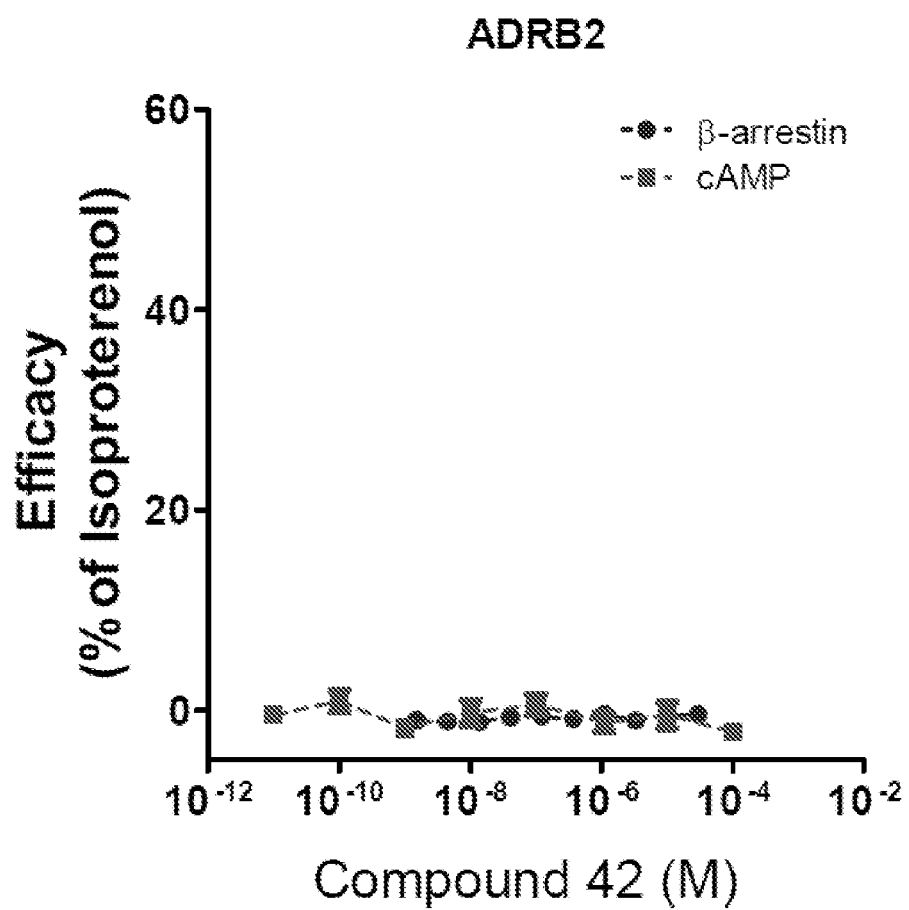
Figure 5A:
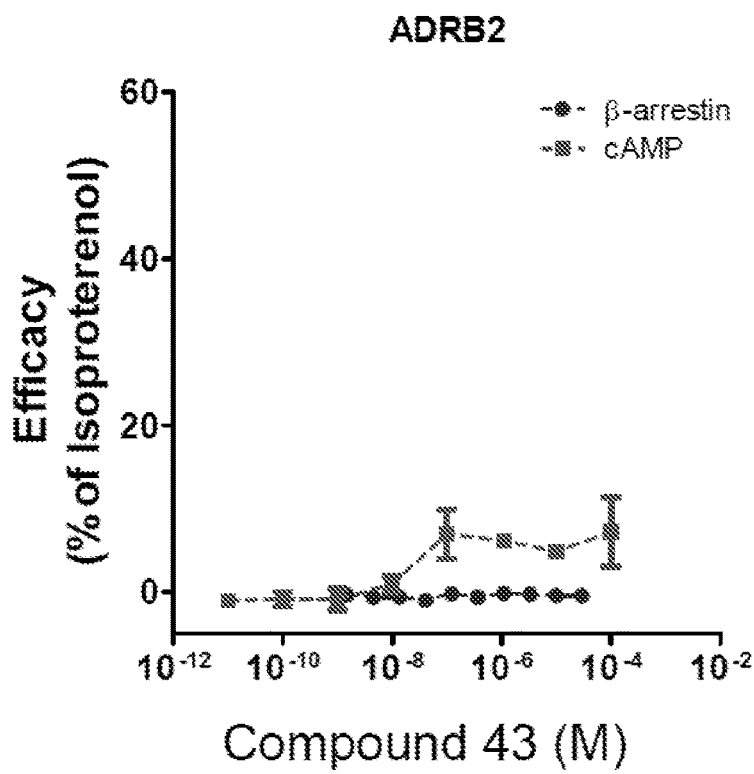
FIGS. 5A-5F show graphs of data for exemplary compounds of interest which demonstrate the compounds have subtype selectivity for adrenergic receptor beta 1 (ADRB1) over adrenergic receptor beta 2 (ADRB2).
Figure 6A:
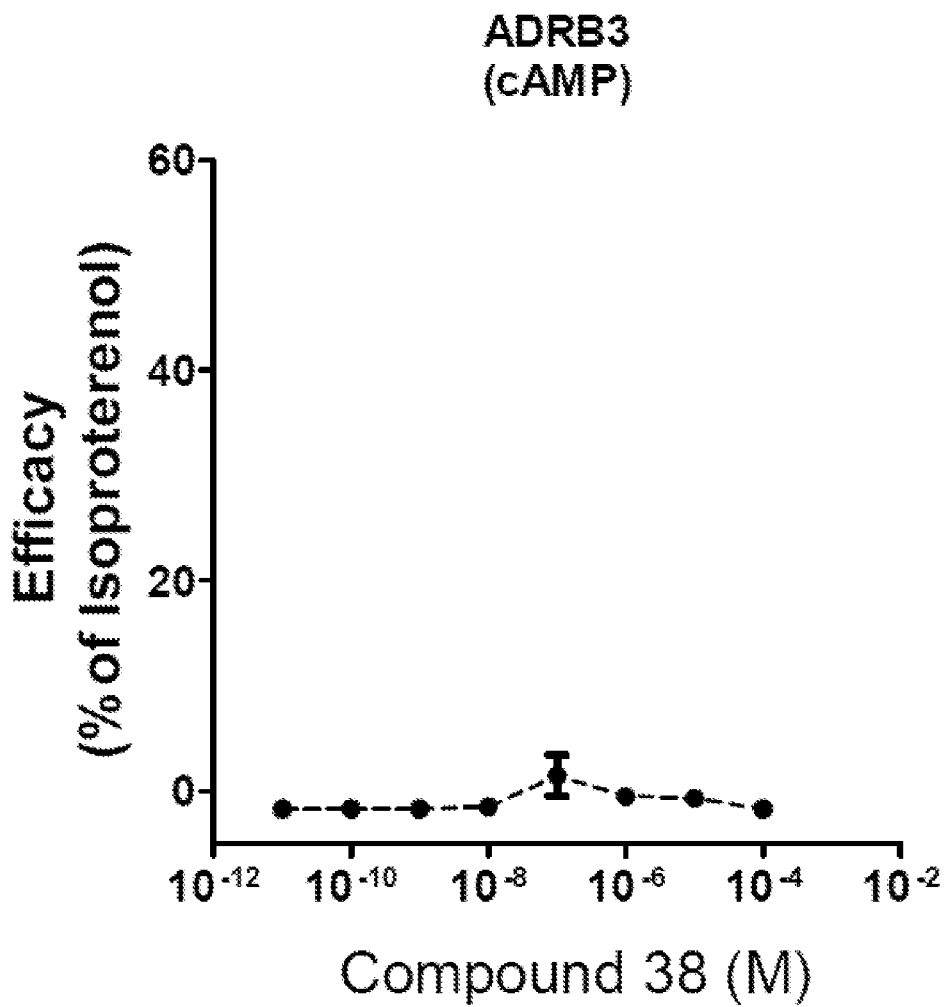
FIGS. 6A-6C show graphs of data for exemplary compounds of interest which demonstrate the compounds have subtype selectivity for adrenergic receptor beta 1 (ADRB1) over adrenergic receptor beta 3 (ADRB3).
Figure 6B:
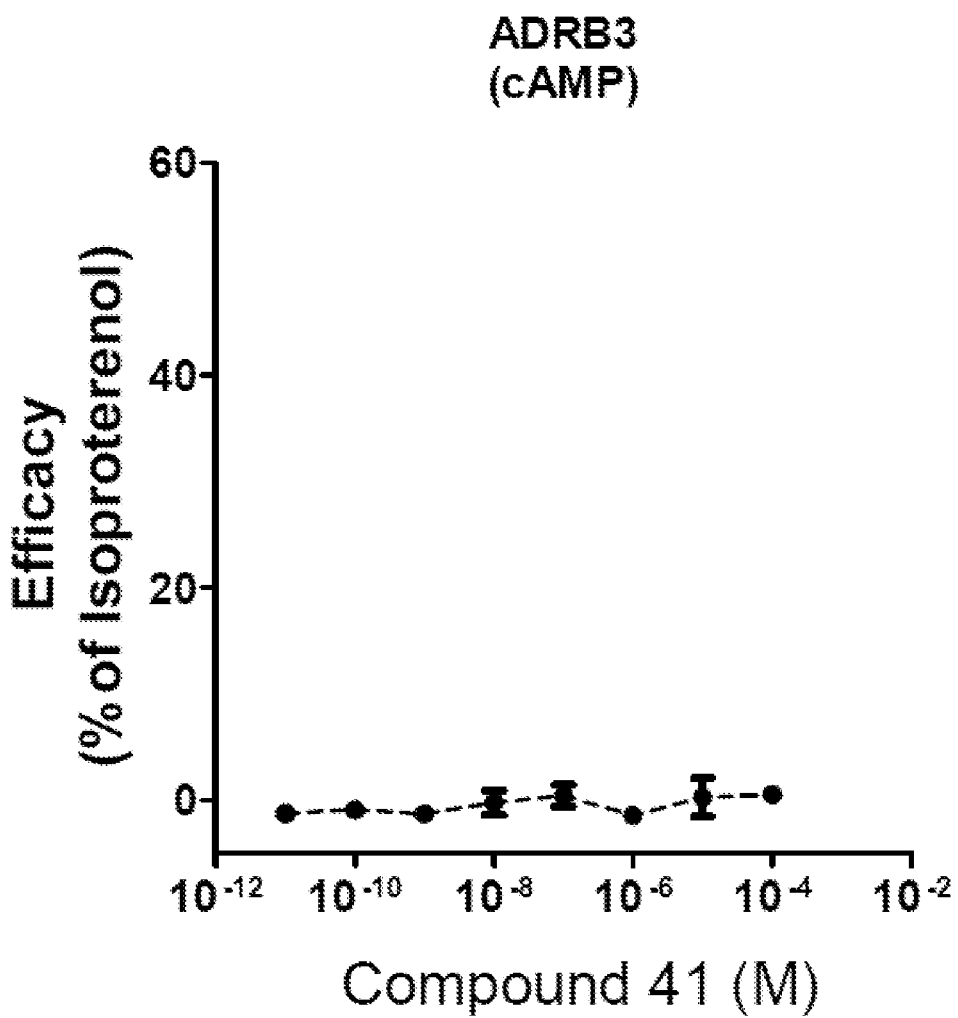
Figure 6C:
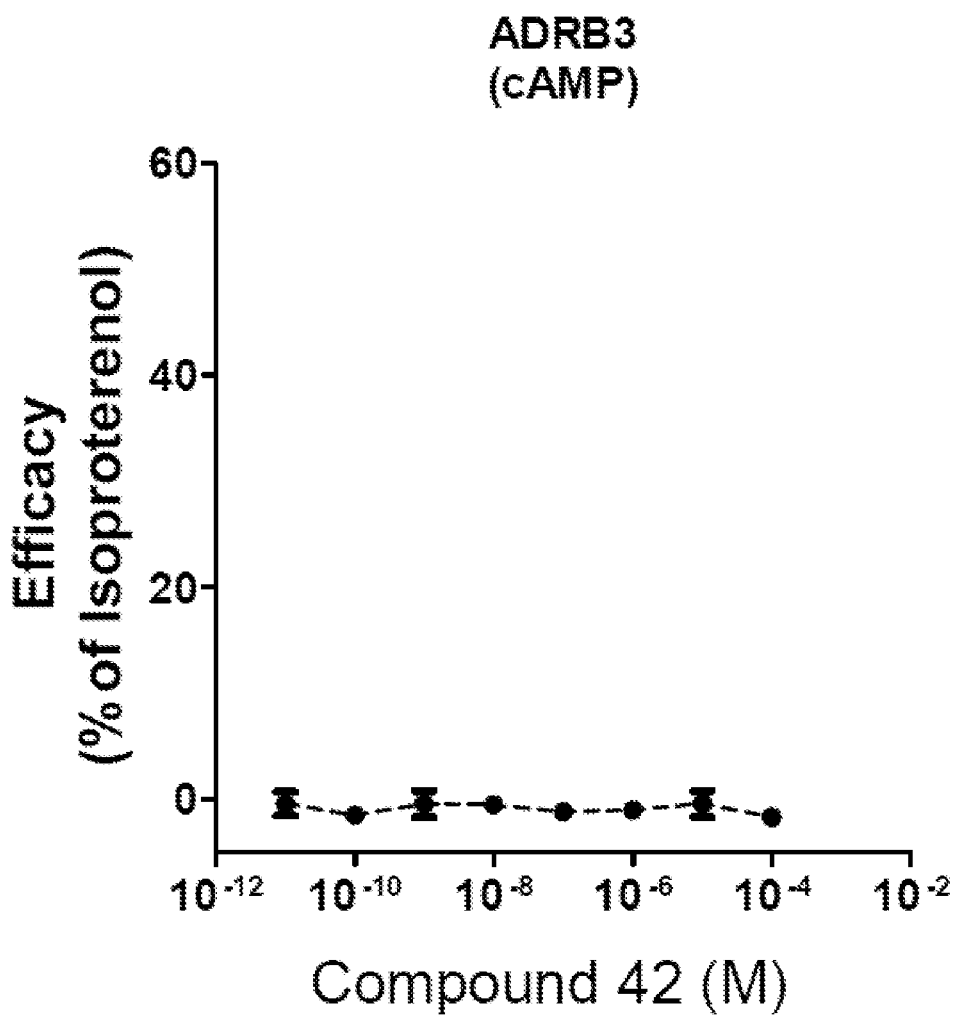
Figure 7A:
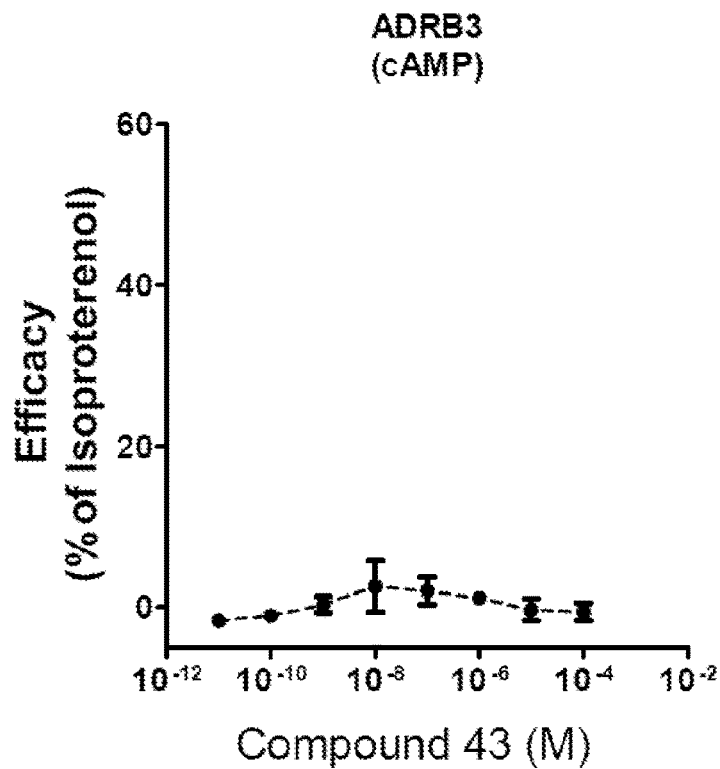
FIGS. 7A-7F show graphs of data for exemplary compounds of interest which demonstrate the compounds have subtype selectivity for adrenergic receptor beta 1 (ADRB1) over adrenergic receptor beta 3 (ADRB3).
Figure 8:
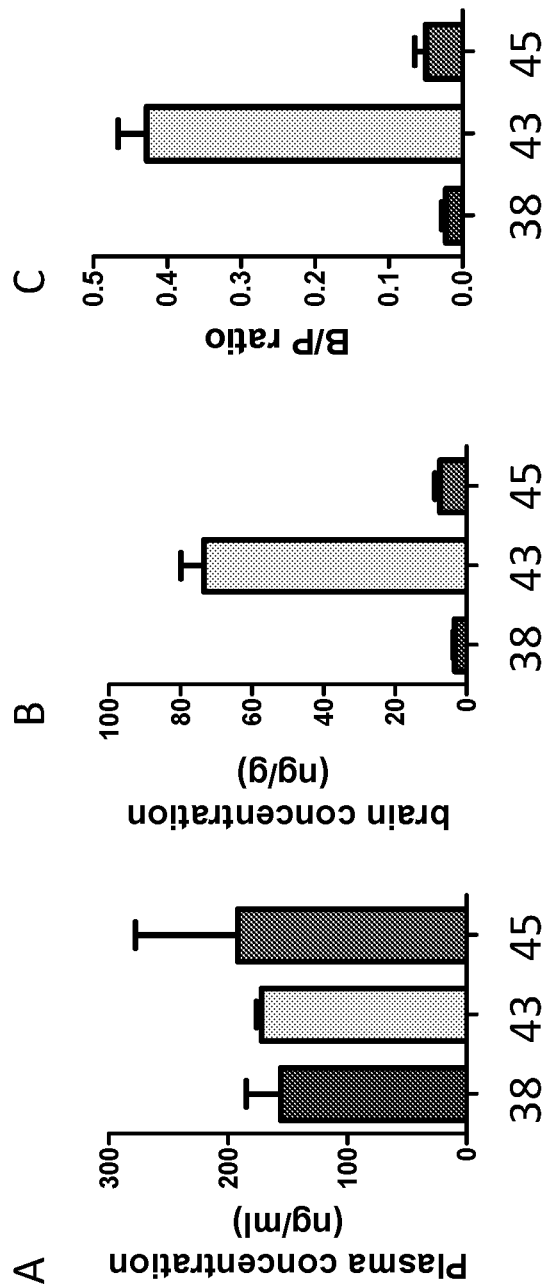
FIG. 8, panels A-C, shows data for selected compounds illustrating concentration in plasma (panel A) versus concentration in brain (panel B) after administration in a mouse. Panel C shows the ratio of brain to plasma concentration demonstrating that compound compound 43 has higher brain exposure with up to 5 times more brain concentration.

| Compound ID | Structure/name | Data |
|---|---|---|
| | isoproterenol/isoprenaline | FIG. 1<br>FIG. 9<br>FIG. 10 |
| ICI 118,551 | (RS,SR)-3-(Isopropylamino)-1-[(7-methyl-4-indanyl)oxy]butan-2-ol | FIG. 9<br>FIG. 10 |
| 38 | (structure) | FIG. 2A<br>FIG. 4A<br>FIG. 6A<br>FIG. 8<br>FIG. 9<br>FIG. 10 |
| 41 | (structure) | FIG. 2B<br>FIG. 4B<br>FIG. 6B<br>FIG. 9<br>FIG. 10 |
| 42 | (structure) | FIG. 2C<br>FIG. 4C<br>FIG. 6C<br>FIG. 9<br>FIG. 10 |
| 43 | (structure) | FIG. 3A<br>FIG. 5A<br>FIG. 7A<br>FIG. 8<br>FIG. 9<br>FIG. 10 |

TABLE 2-continued

Figure 3B:
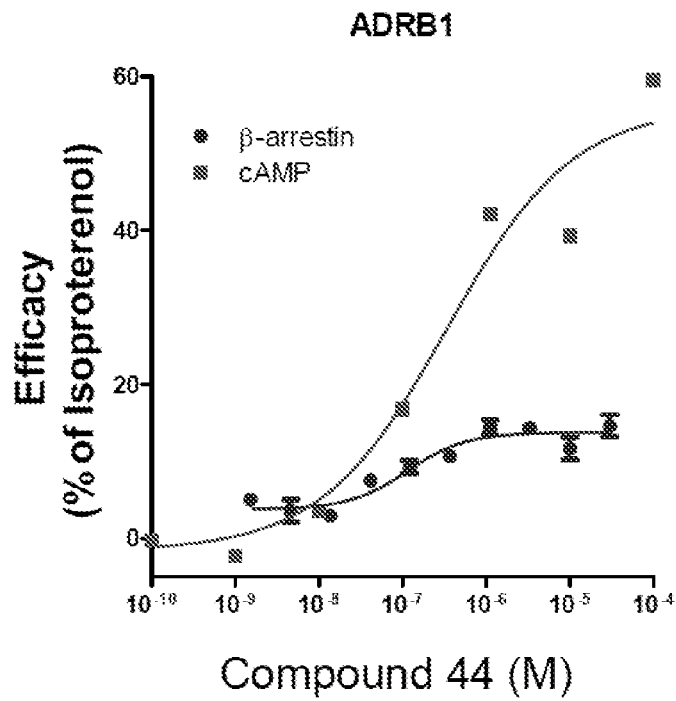
Figure 3C:
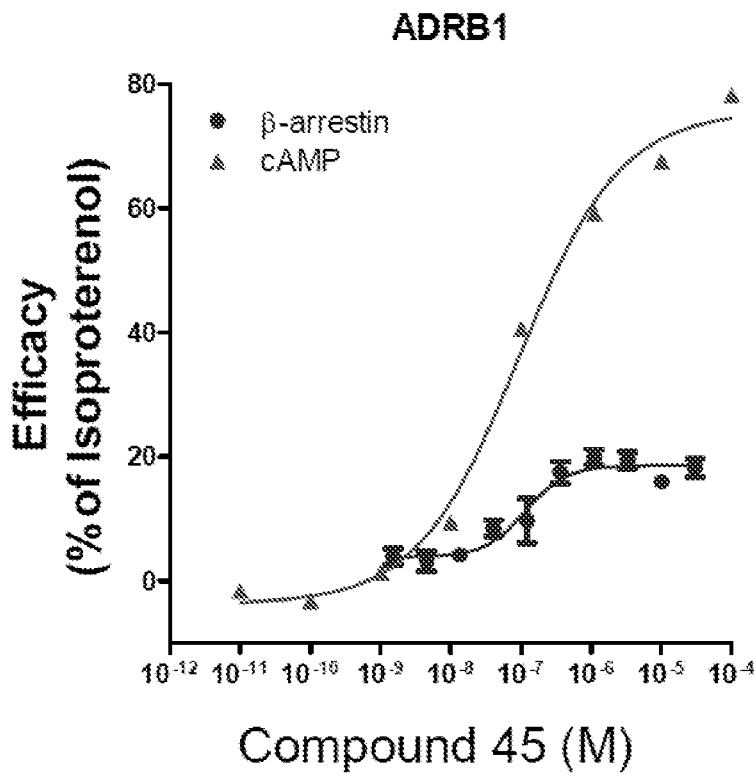
Figure 3D:
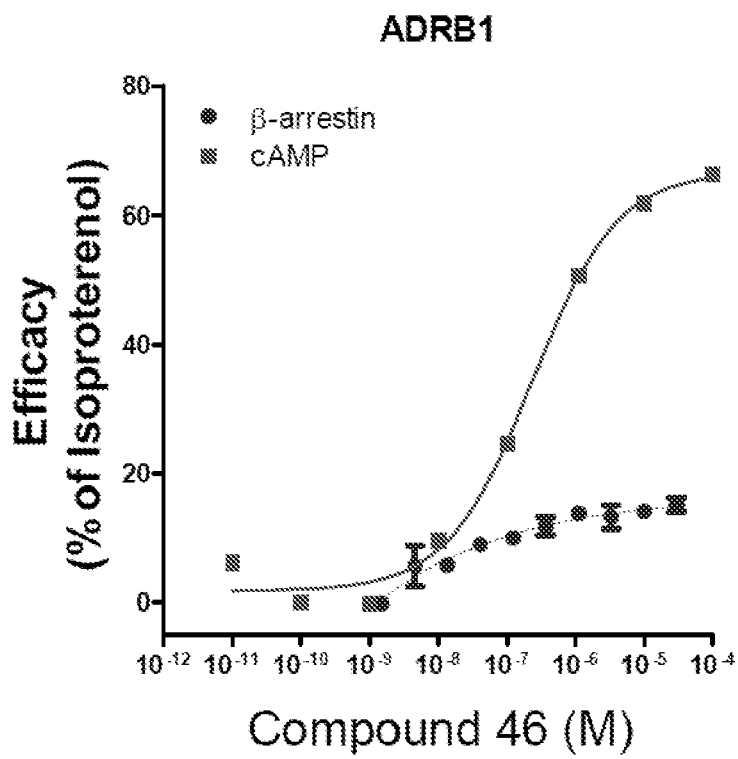
Figure 3E:
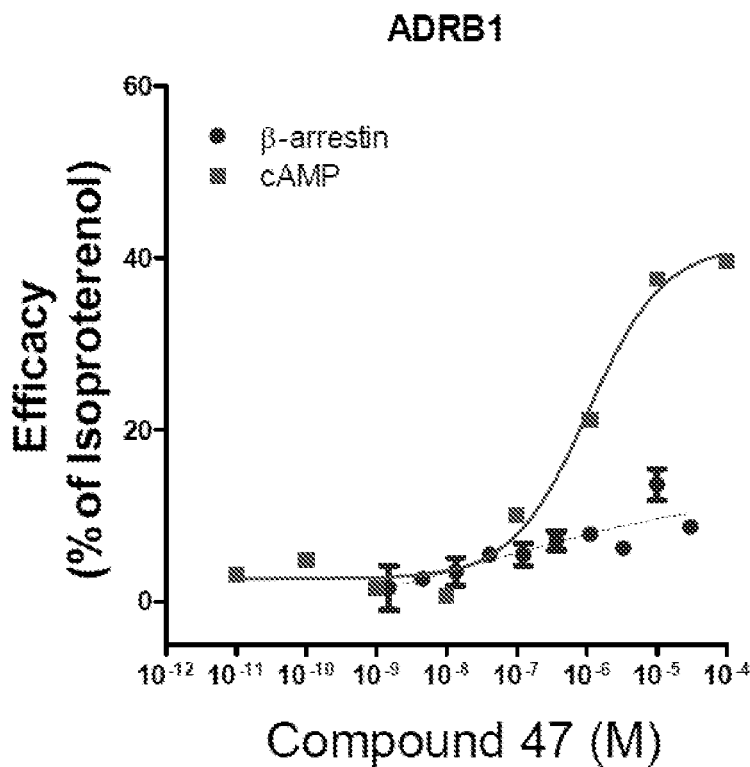
Figure 3F:
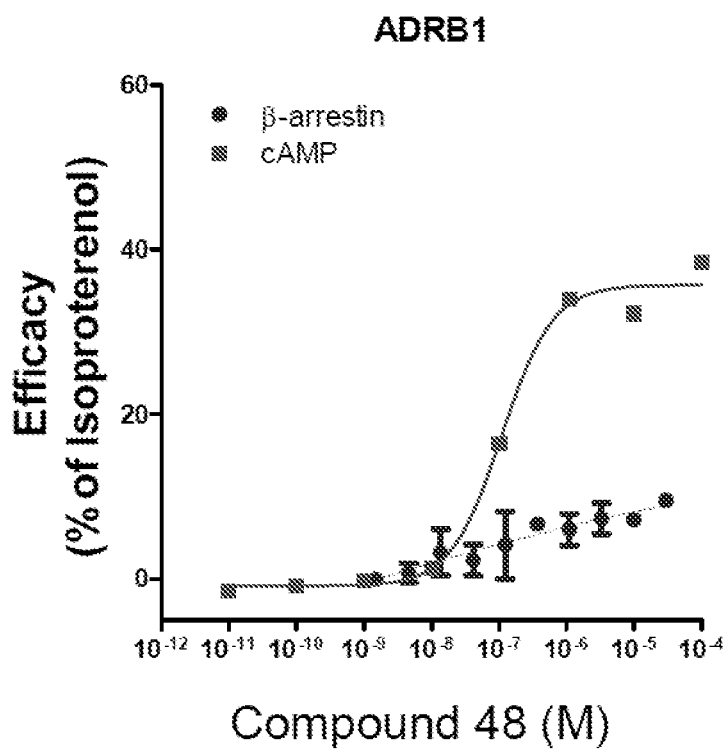
Figure 5B:
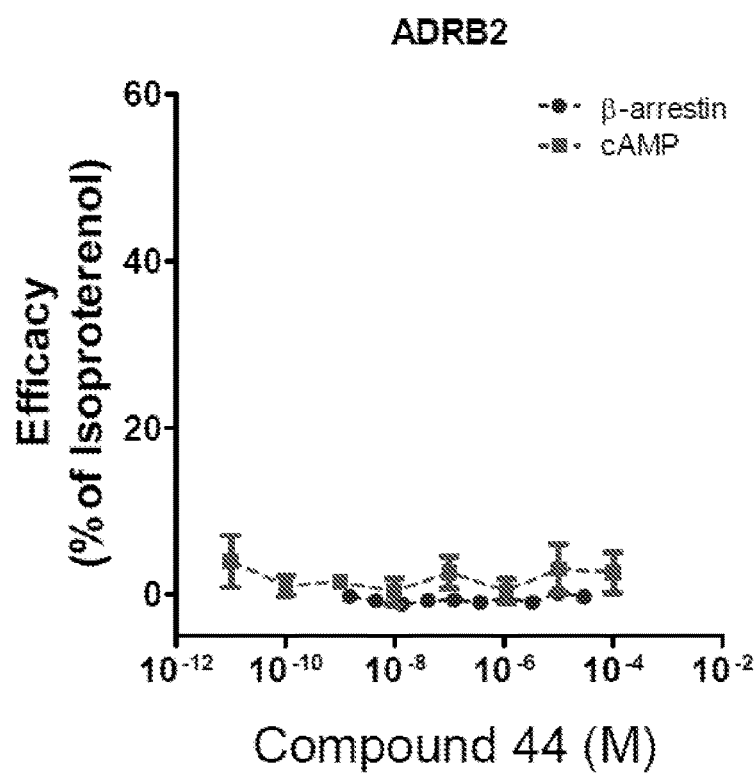
Figure 5C:
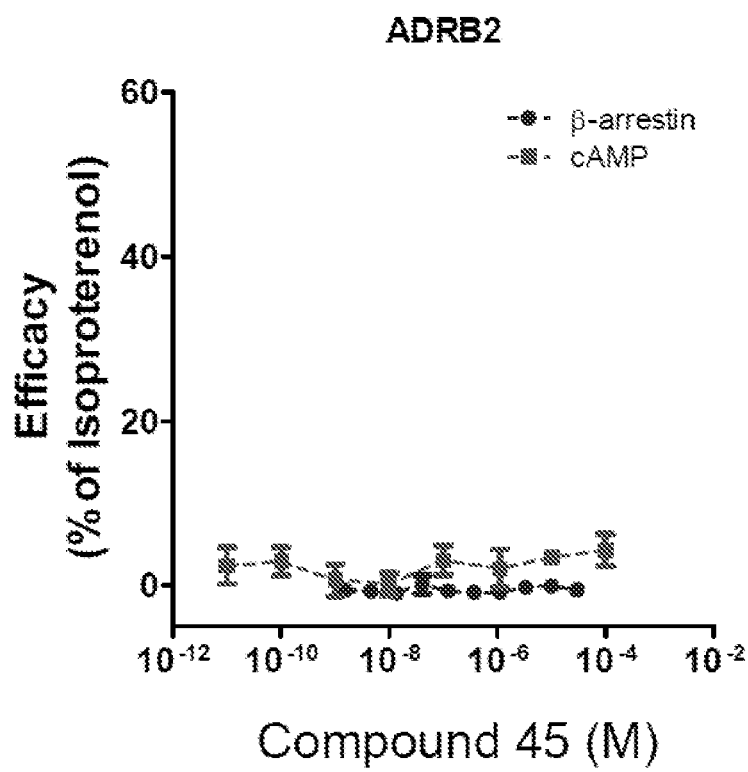
Figure 5D:
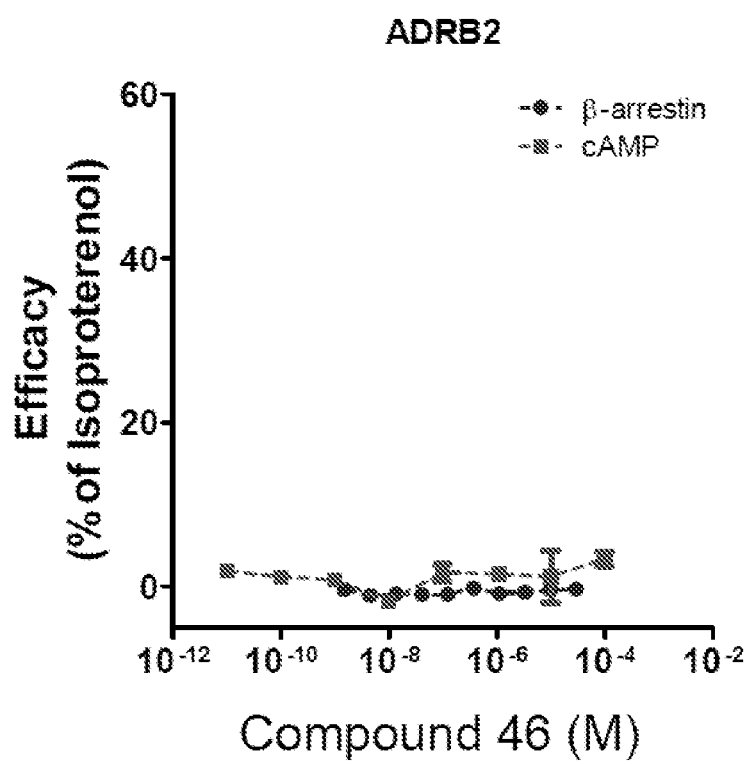
Figure 5E:
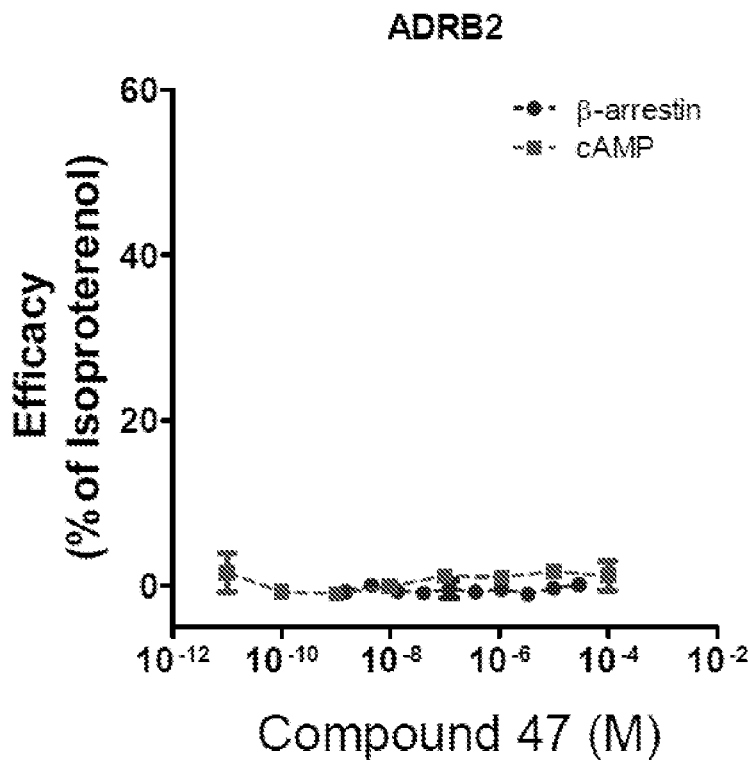
Figure 5F:
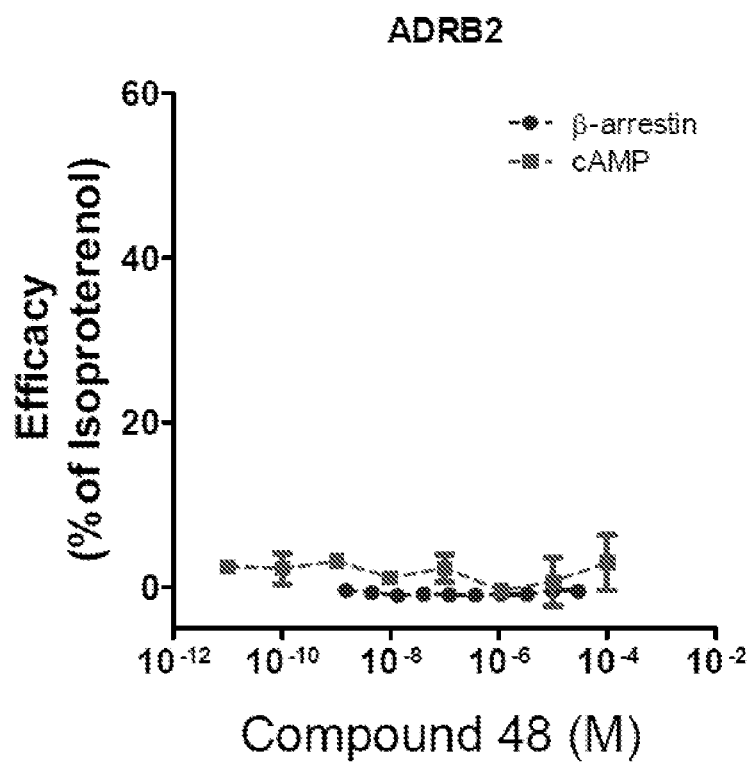
Figure 7B:
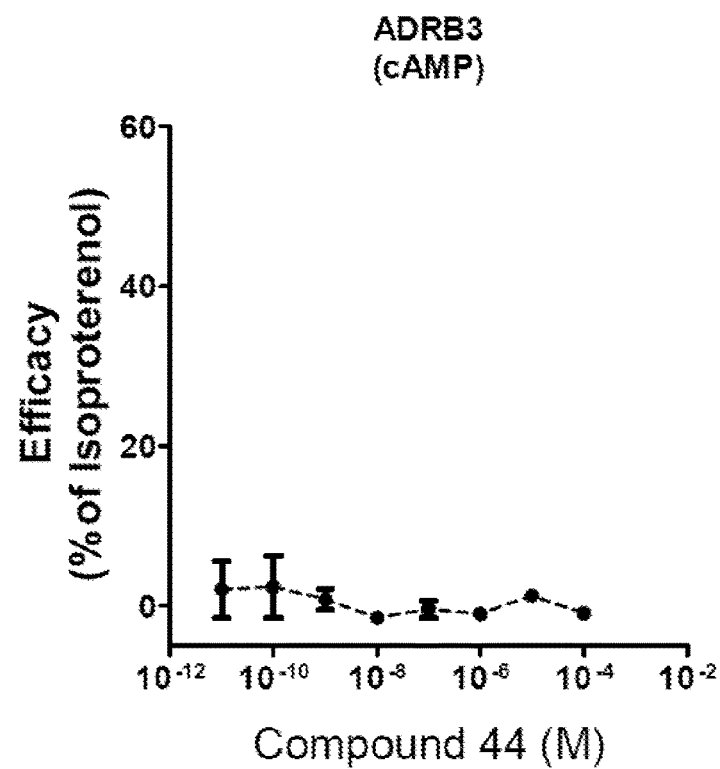
Figure 7C:
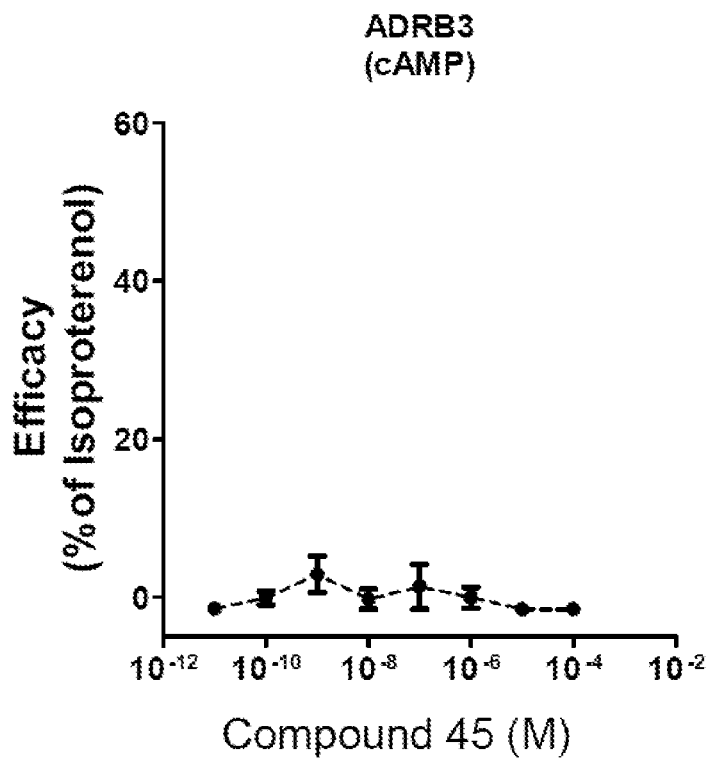
Figure 7D:
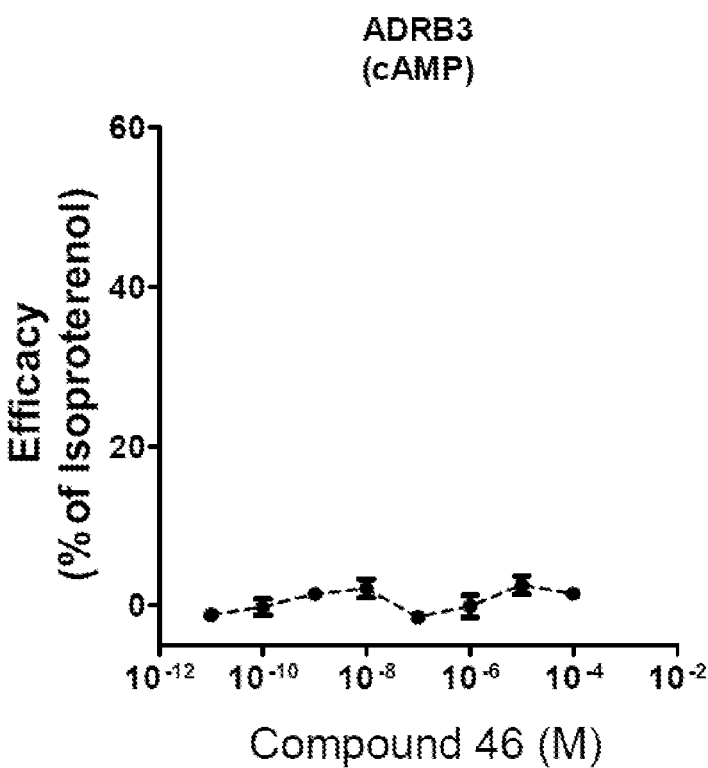
Figure 7E:
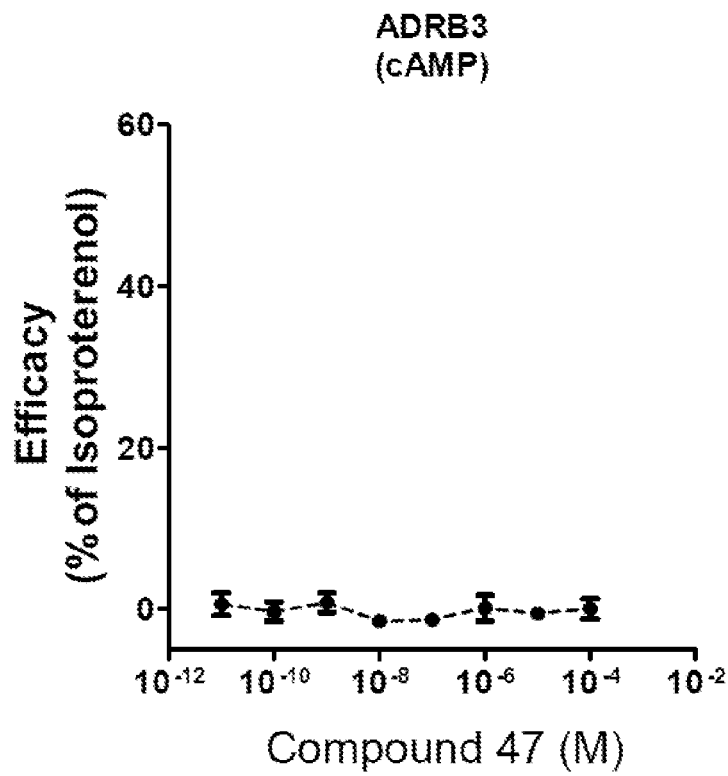
Figure 7F:
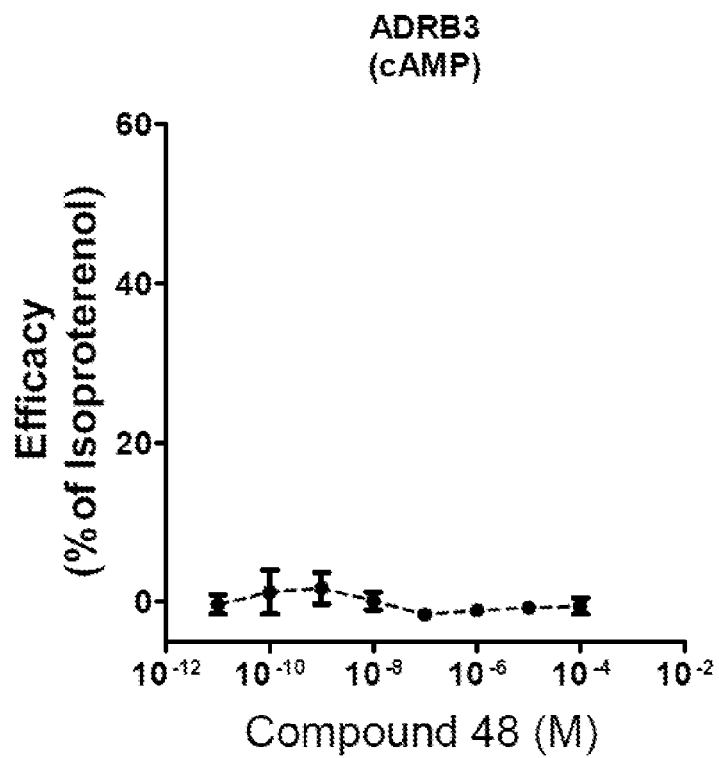

| Compound ID | Structure/name | Data |
|---|---|---|
| 44 | 4-hydroxyphenoxy-propanol-NH-CH2CH2-O-CH2CH2-(3,4-dimethoxyphenyl) | FIG. 3B<br>FIG. 5B<br>FIG. 7B<br>FIG. 9<br>FIG. 10 |
| 45 | 4-hydroxyphenoxy-propanol-NH-(CH2)3-C(O)-morpholine | FIG. 3C<br>FIG. 5C<br>FIG. 7C<br>FIG. 8<br>FIG. 9<br>FIG. 10 |
| 46 | 4-hydroxyphenoxy-propanol-NH-CH2-C(O)-morpholine | FIG. 3D<br>FIG. 5D<br>FIG. 7D<br>FIG. 9<br>FIG. 10 |
| 47 | 4-hydroxyphenoxy-propanol-NH-CH2CH2-NH-C(O)-N(azetidin-3-ol) | FIG. 3E<br>FIG. 5E<br>FIG. 7E<br>FIG. 9<br>FIG. 10 |
| 48 | 4-hydroxyphenoxy-propanol-NH-CH2CH2-NH-C(O)-N(3-hydroxymethyl-azetidine) | FIG. 3F<br>FIG. 5F<br>FIG. 7F<br>FIG. 9<br>FIG. 10 |

Example 4: Structure-Activity Relationship of Compounds at the cAMP Pathway Mediated by ADRB1

The β-aminoalcohol linking moiety is a pharmacophoric element of most ADRB1 binding compounds, including xamoterol. Consequently, structure-activity relationship (SAR) studies and drug discovery programs have focused upon making structural changes at the two terminal sites of ADRB1 binding molecules. Affinity and selectivity at ADRB1 can be significantly improved and manipulated by making the appropriate structural changes to xamoterol at the phenolic and morpholino subsites. As such, we prepared 18 analogs of xamoterol with the objective of (1) maintaining affinity and efficacy for ADRB1, and (2) increasing brain penetration. Pharmacological effects of the analogs on ADRB1 were then evaluated by measuring cAMP production.

Figure 12:
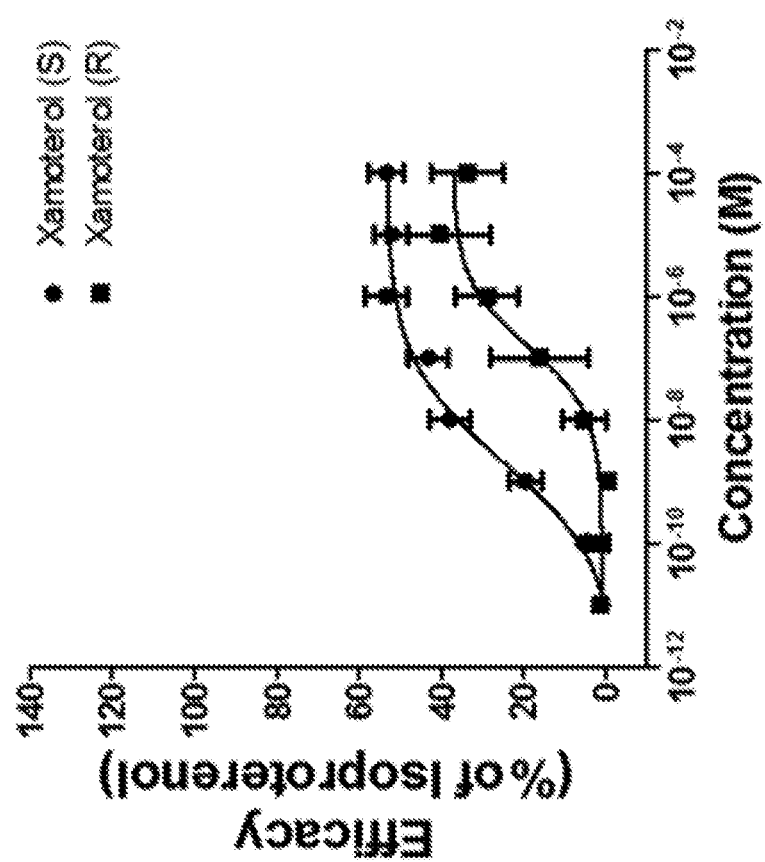
FIG. 12 shows concentration-response effects of (S) and (R)-xamoterol on the cAMP pathway via ADRB1. Data are expressed as a percentage of maximum efficacy obtained with the full agonist isoproterenol. Values represents means±S.E.M.s (1-2 experiments with n=1-2).

The major shortcomings of xamoterol for CNS indications are its poor oral bioavailability (approximately 5%) and rapid clearance. Most of the absorbed drug in humans are excreted in the urine unchanged, with a substantial amount also excreted as the sulfate after first pass by the liver. It was envisioned that structural modifications of the phenol group could enhance PK properties of the molecules. In the first series of compounds, the phenol group in xamoterol is substituted with a variety of electron donating and electron withdrawing groups (Table 3). These diverse structural modifications also alter the lipophilicity of the compounds and modulate other molecular properties, such as tPSA, which can enhance oral absorption. As the (S)-enantiomer of xamoterol was more potent and efficacious than the (R)-enantiomer, all structural modifications were made on the (S)-enantiomer (FIG. 12, Table 3).

TABLE 3

Effects of structural modifications of the phenolic OH moiety of xamoterol on the cAMP pathway mediated by ADRB1.

| | | cAMP pathway | | β-arrestin pathway | |
|---|---|---|---|---|---|
| Compound | clogP[a] | ADRB1 EC$_{50}$ (nM)[b] | % Iso max[c] | ADRB1 EC$_{50}$ (nM)[b] | % Iso max[c] |
| (S)-Xamoterol | 0.44 | A | 50.9 ± 3.9 | no response | ~[d] |
| (R)-Xamoterol | 0.44 | C | 40.4 ± 13.9 | — | — |
| 24 | 0.88 | no response | ~[d] | — | — |
| 25 | 1.04 | no response | ~[d] | — | — |
| 26 | 1.41 | no response | ~[d] | — | — |
| 29 | 0.54 | A | 25.1 ± 4.7 | — | — |
| 28 | 0.62 | A | 21.5 ± 0.5 | — | — |

TABLE 3-continued

Effects of structural modifications of the phenolic OH moiety of xamoterol on the cAMP pathway mediated by ADRB1.

| | | cAMP pathway | | β-arrestin pathway | |
|---|---|---|---|---|---|
| Compound | clogP$^a$ | ADRB1 EC$_{50}$ (nM)$^b$ | % Iso max$^c$ | ADRB1 EC$_{50}$ (nM)$^b$ | % Iso max$^c$ |
| 30 | 0.62 | no response | ~$^d$ | — | — |
| 27 | 1.06 | no response | ~$^d$ | — | — |
| 31 | 0.56 | no response | ~$^d$ | — | — |
| 32 | 0.17 | no response | ~$^d$ | — | — |
| 49 | 1.56 | no response | ~$^d$ | — | — | clogP$^a$, Calculated with ChemDraw Pro Version 16.0 (PerkinElmer Health Sciences, CT; EC$_{50}$ (nM)$^b$,
A = 1-10 nM,
B = 10-100 nM,
C = 100 nM-1 uM;
% Iso max$^c$, Percent efficacy compared to the maximum response achieved with isoproterenol;
~$^d$, Could not be determined.

In the second series of compounds, analogs incorporated structural modifications of the morpholino urea moiety of xamoterol (Table 4). Importantly, none of the second series of compounds having partial agonist activity on the cAMP pathway via ADRB1 show activity on cAMP pathways via ADRB2 or ADRB3, suggesting that they are partial agonists selective for ADRB1 versus ADRB2 and ADRB3 (data not shown).

TABLE 4

Effects of structural modifications of the morpholino urea moiety of xamoterol on the cAMP pathway mediated by ADRB1.

| | | cAMP pathway | | β-arrestin pathway | |
|---|---|---|---|---|---|
| Compound | clogP$^a$ | ADRB1 EC$_{50}$ (nM)$^b$ | % Iso max$^c$ | ADRB1 EC$_{50}$ (nM)$^b$ | % Iso max$^c$ |
| (S)-Xamoterol | 0.44 | A | 50.9 ± 3.9 | no response | ~$^d$ |
| 43 | 2.08 | B | 83.3 ± 15.65 | B | 18.3 |
| 44 | 2.16 | C | 60.2 ± 9.3 | C | 14 |
| 45 | 0.43 | B | 71.9 ± 1.3 | C | 18.6 |
| 46 | 0.24 | C | 73.9 ± 10.2 | B | 13.7 |
| 47 | 0.31 | C | 42.0 ± 2.4 | no response | ~$^d$ |
| 48 | -1.12 | B | 40.12 ± 3.9 | no response | ~$^d$ |
| 50 | 1.47 | A | 104.2 ± 23.9 | B | 36.5 | clogP$^a$, Calculated with ChemDraw Pro Version 16.0;
EC$_{50}$ (nM)$^b$,
A = 1-10 nM,
B = 10-100 nM,
C = 100 nM-1 uM;
% Iso max$^c$, Percent efficacy compared to the maximum response achieved with isoproterenol;
~$^d$, Could not be determined.

Signaling Bias of the Key Compound

Figure 13:
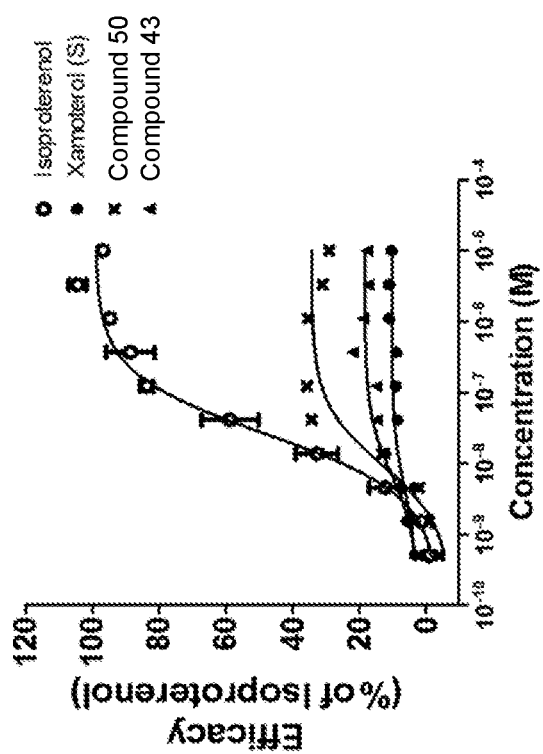
FIG. 13 shows concentration-response effects of compounds on the β-arrestin pathway via ADRB1. Data are expressed as a percentage of maximum efficacy obtained with the full agonist isoproterenol. Values represents means±S.E.M.s (1-2 experiments with n=1-2).
Figure 14:
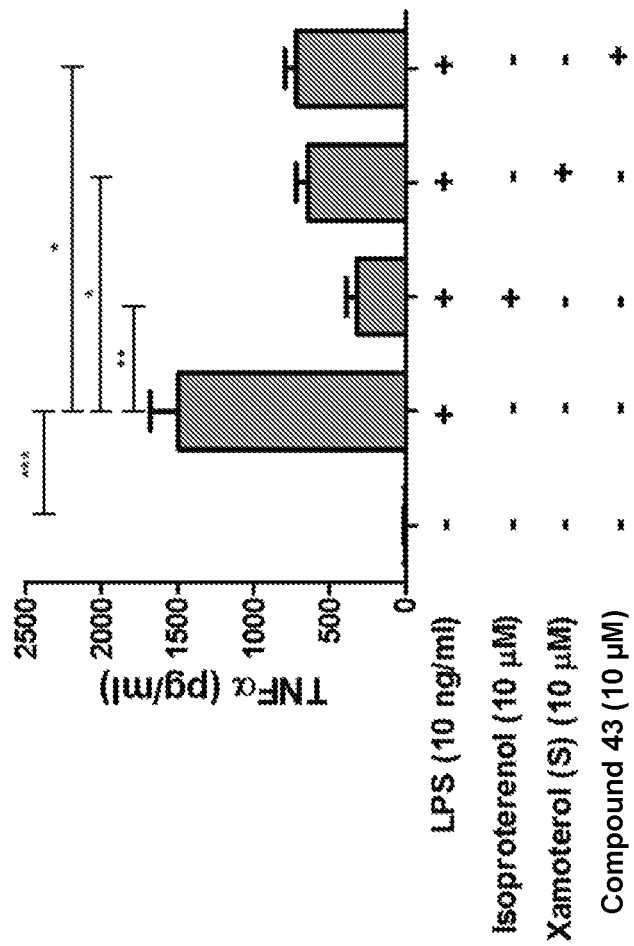
FIG. 14. shows inhibitory effects of ADRB1 ligands on LPS-induced TNF-α response in primary microglia. Data are represented as mean±S.E.M.s of two independent experiments (one-way ANOVA followed by Dunnett's multiple comparison against LPS exposure alone).

To identify G-protein-biased agonists of ADRB1, we assessed the pharmacological activity of the compounds that showed significant agonistic activity at the cAMP pathway (e.g. Compounds 43-48 and 50) on the ADRB1-mediated β-arrestin pathway. As a classical unbiased agonist, isoproterenol produced concentration-dependent responses at the β-arrestin pathway via ADRB1 with an EC$_{50}$ value of 31.3 nM (FIG. 13). In contrast, xamoterol (S) did not produce concentration-dependent responses up to 30 µM, indicating that it has a very high level of functional selectivity toward the cAMP pathway (FIG. 13). The partial agonists Compound 43 through Compound 46 displayed very weak partial agonist activity at the β-arrestin pathway, producing less than 20% efficacy compared to the full agonist isoproterenol (Table 4, FIG. 13). The other two compounds Compound 47 and 48 did not produce concentration-dependent response up to 30 µM (Table 4). On the other hand, Compound 50, which showed full agonistic activity on the ADRB1-mediated cAMP pathway, produced partial agonistic activity on the ADRB1-mediated β-arrestin pathway, achieving 36.5% efficacy with an EC$_{50}$ value of 32.2 nM. On the basis of potency and partial agonistic activity on the cAMP pathway and functional selectivity for cAMP pathway over β-arrestin pathway, the compound Compound 43 was selected for further in vitro and in vivo testing.

Pharmacological Specificity of the Key Compound

From a drug development perspective, characterizing the off-target effects of lead compounds is an important issue, as interactions with off-target molecules may lead to undesirable side effects. Thus we screened xamoterol (S) and the key compound compound 43 against a panel of CNS relevant targets, including G-protein coupled receptor and transporters. Xamoterol (S) displays a distinct preference for ADRB1 and shows low off-target affinity ($K_i$>10 µM) for a broad range of neurotransmitter transporters, ion channels and other CNS proteins (including opioid, dopamine, serotonin, nicotinic acetylcholine, muscarinic acetylcholine, and N-methyl-D-aspartate receptors) (data not shown). In contrast, compound 43 displays significant affinity for non-ADRB1 binding including 5-HT$_{1A}$, 5-HT$_{2B}$, $\alpha_{1A}$ adrenergic, $\alpha_{1D}$ adrenergic, and D$_3$ dopaminergic receptors, while maintaining nominal affinity for several other CNS proteins including opioid, histamine, and muscarinic acetylcholine receptors.

Neuroimmuno-Modulatory Effects of the Key Compound

Figure 15:
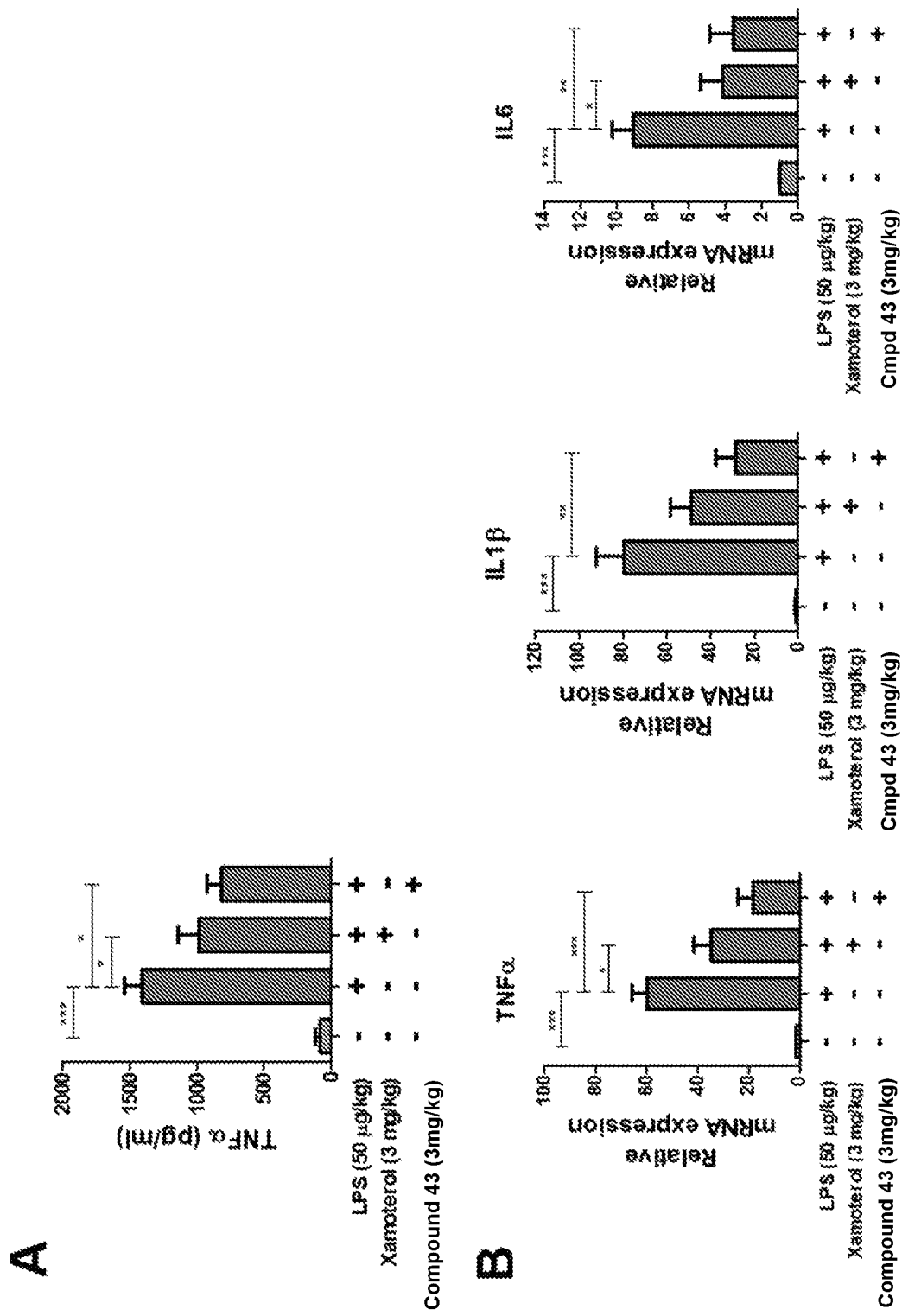
FIG. 15, panels A-B, shows inhibitory effects of ADRB1 ligands on LPS induced plasma TNF-α response in mice. (Panel A) Plasma TNFα concentrations in control animals and animals pretreated with xamoterol or compound 43 90 min after LPS injection. (Panel B) TNFα, IL1β, and IL6 mRNA expression in homogenized cortial tissue from control mice and animals pretreated with xamoterol or compound 43 90 min after LPS injection. Data are represented as mean±S.E.M.s of three independent experiments. (### $p<0.001$ versus no LPS control. * $p<0.05$ and *** $p<0.001$ versus LPS alone, one-way ANOVA followed by Dunnett's multiple comparison).
Figure 16:
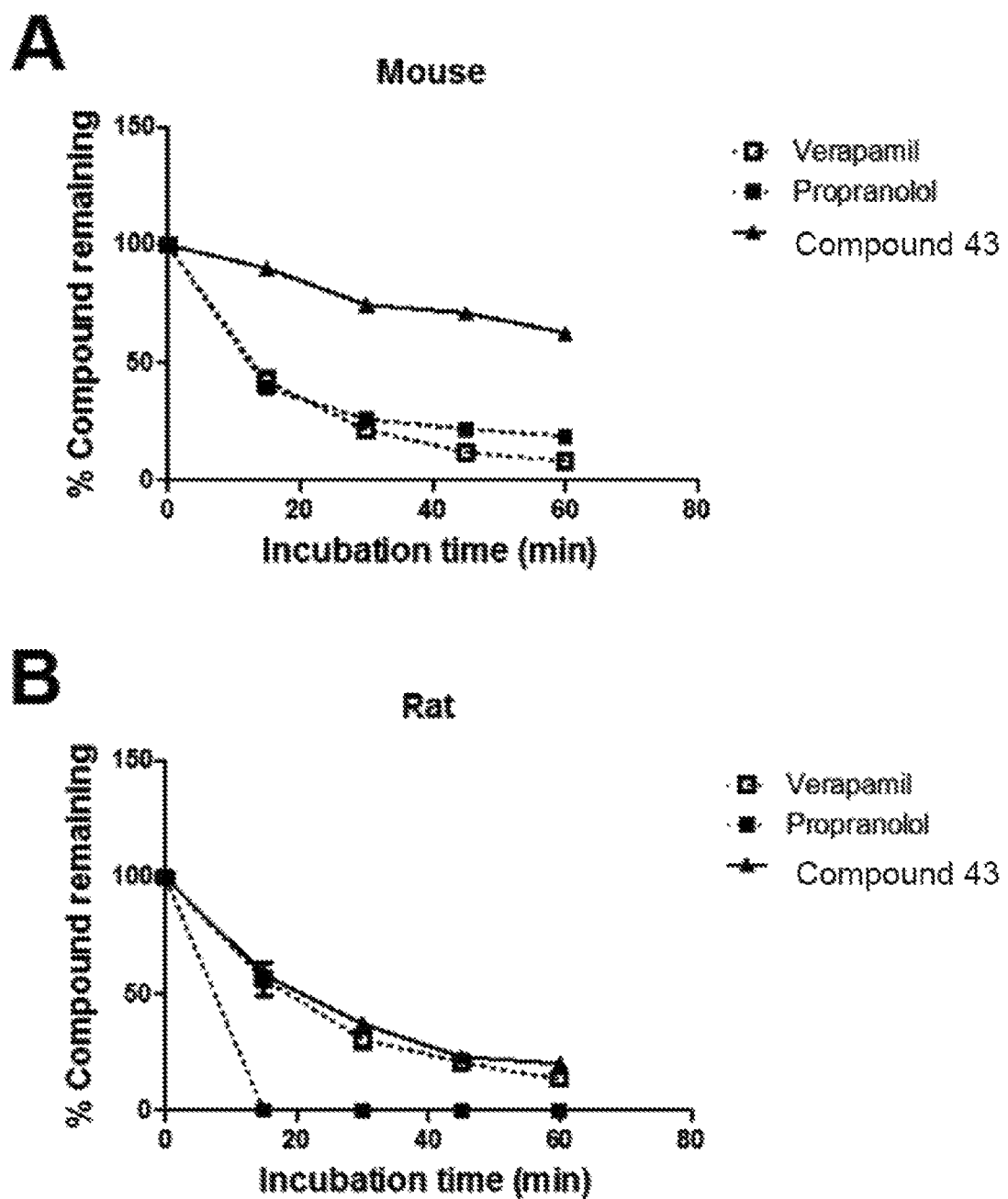
FIG. 16, panels A-C, shows metabolic stability in mouse and human microsomes. Compound 43 and two reference compounds verapamil and propranolol were incubated at 0.1 uM in mouse (Panel A), rat (Panel B), or human (Panel C) liver microsomes. Serial samples were removed up until 60 min. All experiments were performed in duplicate, and data are represented as mean±S.E.M.
Figure 16:
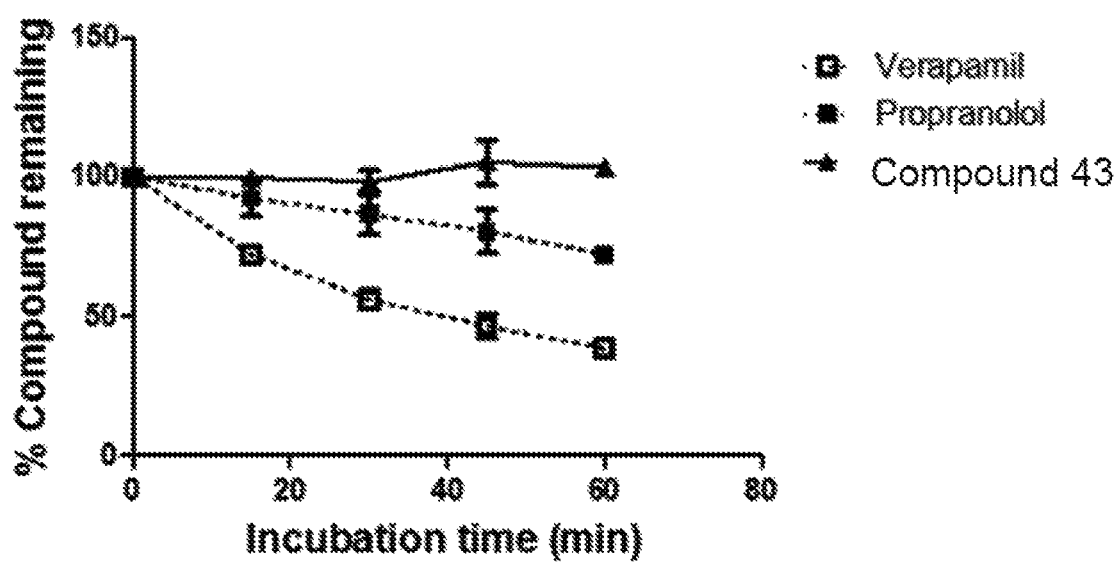

The TNF-α signaling pathway has been strongly implicated in AD pathology and neuroinflammatory diseases. With the aim of identifying compounds that have therapeutic potential for AD and neuroinflammatory diseases, we assessed if our key compound Compound 43 could modulate the TNF-α signaling pathway. First, the effects of Compound 43 on the TNF-α signaling pathway were assessed in vitro by stimulating primary microglia with the bacterial endotoxin LPS for 4 hours in the absence or presence of the test compounds. Previous studies with this model have shown that the effects of xamoterol on the LPS induced TNF-α response are dependent on ADRB1, as its effects were reversed by the selective ADRB1 antagonist, CGP 20712A or betaxolo, but not by the selective ADRB2 antagonist ICI-118551 (Ardestani et al. "Modulation of neuroinflammation and pathology in the 5XFAD mouse model of Alzheimer's disease using a biased and selective beta-1 adrenergic receptor partial agonist." Neuropharmacology. 2017; 116:371-86). As shown in FIG. 15, stimulation of primary microglia cells with LPS led to a significant increase in TNF-α levels. Treatment with the unbiased full agonist of ADRB1, isoproterenol, inhibited the LPS-induced TNF-α production by 85%, whereas xamoterol (S) inhibited LPS-induced TNF-α production by approximately 60%. Compound 43 reduced LPS-induced TNF-α production by approximately 55%. In order to investigate whether Compound 43 could also inhibit the TNF-α response in vivo, the effects of Compound 43 on mice exposed to LPS were also examined. Administration of LPS resulted in inflammatory response in periphery as measured by increased levels of TNF-α in plasma (FIG. 16, panel A). The LPS-induced TNF-α response in periphery was markedly inhibited by pre-treating mice with xamoterol (S) or Compound 43 (FIG. 16, panel A). Administration of LPS also led to inflammatory response in the CNS. Brain tissues from LPS-injected mice showed increased gene expression of proinflammatory cytokines such as TNF-α, IL-1β, and IL-6 (FIG. 16, panel B). The LPS-induced inflammatory response in the brain was attenuated by pre-treating mice with xamoterol (S) or Compound 43 (FIG. 16, panel B).

Pharmacokinetic Properties of the Key Compound

Figure 17:
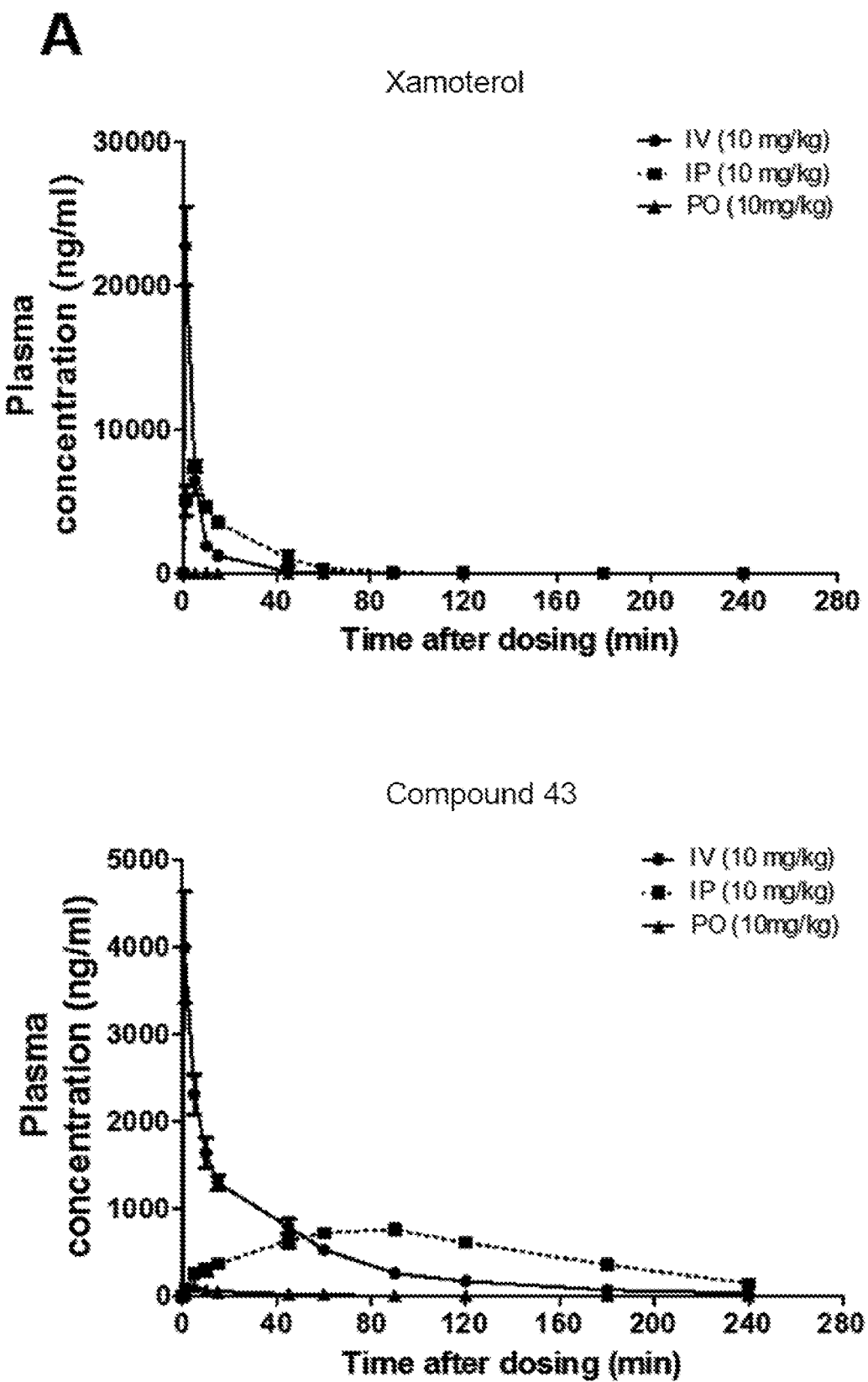
FIG. 17, panels A-B, show pharmacokinetics of compound 43 in comparison to xamoterol. Systemic (Panel A) and portal vein (Panel B) plasma concentrations of xamoterol and compound 43 as a function of time after a single injection of xamoterol (10 mg/kg) or compound 43 (10 mg/kg) via intravenous (IV), intraperitoneal (IP) and oral (PO) administration.
Figure 17:
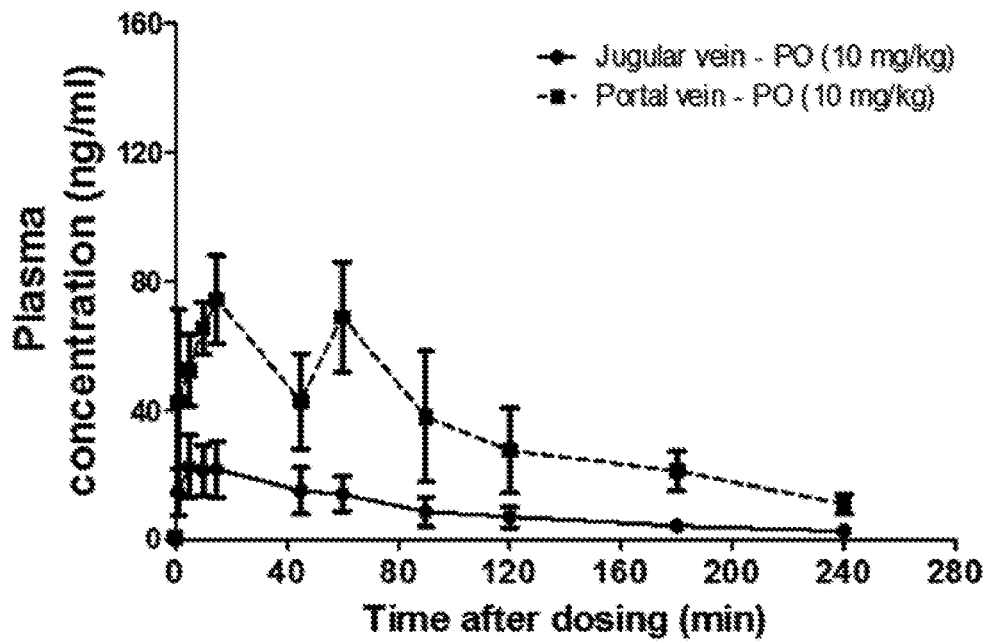
Figure 17:
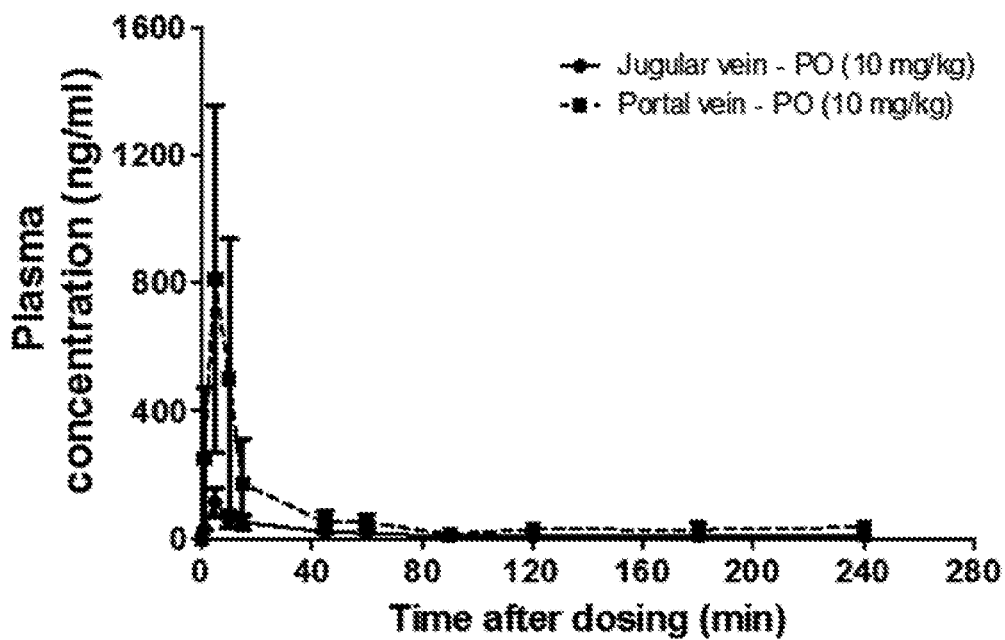

In light of its promising in vitro pharmacology profiles, Compound 43 was further profiled using an in vitro microsomal stability assay and in vivo pharmacokinetic studies. First, the metabolic stability of Compound 43 was assessed together with the reference compounds verapamil (calcium channel blocker) and propranolol (beta blocker) using microsomes from mouse, rat, and human. In mouse microsomes, both verapamil and propranolol were readily metabolized, showing half-lives of less than 30 minutes (FIG. 17, panel A). In comparison, Compound 43 was stable in mouse liver microsomes, with 62.8% of the compound remaining after 60 minutes (FIG. 17, panel A). Rates of disappreance of verapamil, propranolol, and Compound 43 were greater in microsomes prepared from rat compared with that observed with mouse microsomes (FIG. 17, panel B). Verapamil and propranolol were readily metabolized with half-lifes of 20.9 min and 7 min, respectively. Compound 43 was metabolized with a half-life of 25.2 min in rat microsomes. In human microsomes, verapamil was metabolized with a half-life of 44.1 minutes; propranolol was stable with 72.2% of compound remaining after 60 minutes (FIG. 17, panel C). Compound 43 was very stable in human microsomes, with almost no reduction after 60 min. (FIG. 17, panel C).

Figure 18:
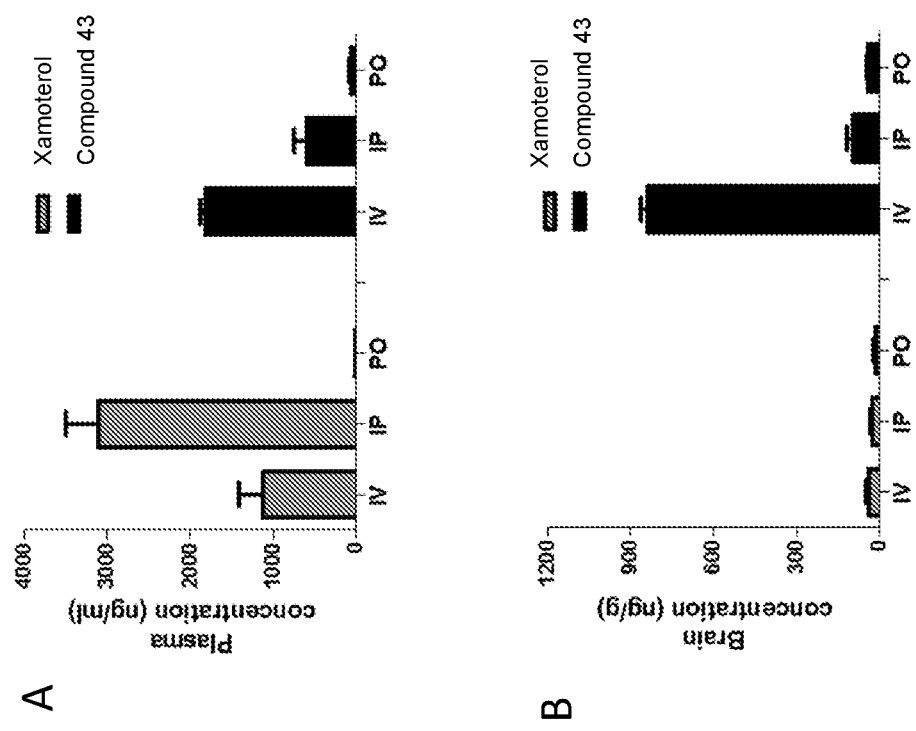
FIG. 18, panels A-B, show plasma and brain concentrations of xamoterol and compound 43 in rats collected 20 min after a single injection of xamoterol or compound (10 mg/kg) via IV, IP, and PO administration. Data are represented as mean±SEM (N=3 per route).

In vivo pharmacokinetic properties of Compound 43 were also evaluated in male Sprague-Dawley rats in 4 hour time-course PK and 20 minutes post-dose collection studies after IV, IP, and PO administration of Compound 43 at a 10 mg/kg dose. In comparison, the pharmacokinetic properties of xamoterol were also determined. The 4 hour time-course PK study revealed that xamoterol was cleared rapidly (FIG. 18, panel A, Table 5). Xamoterol's oral bioavailability was low (1.7%). Concentrations of xamoterol in the jugular and portal veins were consistently low, indicating that the low absolute oral bioavailability of xamoterol is due to poor absorption. Compared to xamoterol, Compound 43 was cleared more slowly and remained in the system for a longer period of time (FIG. 18, panel A, Table 5). Following IP injection, Compound 43 was rapidly and very significantly absorbed, as evidenced by the systemic plasma concentrations (FIG. 18, panel A). The maximum concentration (C) of 762 ng/mL was achieved in systemic plasma following IP administration at 90 minutes post-dose (Table 5). After oral administration, the concentration of Compound 43 in plasma collected from the jugular and portal veins were consistently low similar to xamoterol, resulting in low absolute oral bioavailability (6%) (FIG. 18, panels A-B). In systemic (jugular vein) circulation, the $C_{max}$ of Compound 43 was 116 ng/ml after oral administration. The corresponding $C_{max}$ of Compound 43 in portal veins was 946 ng/ml (Table 5).

Figure 19:
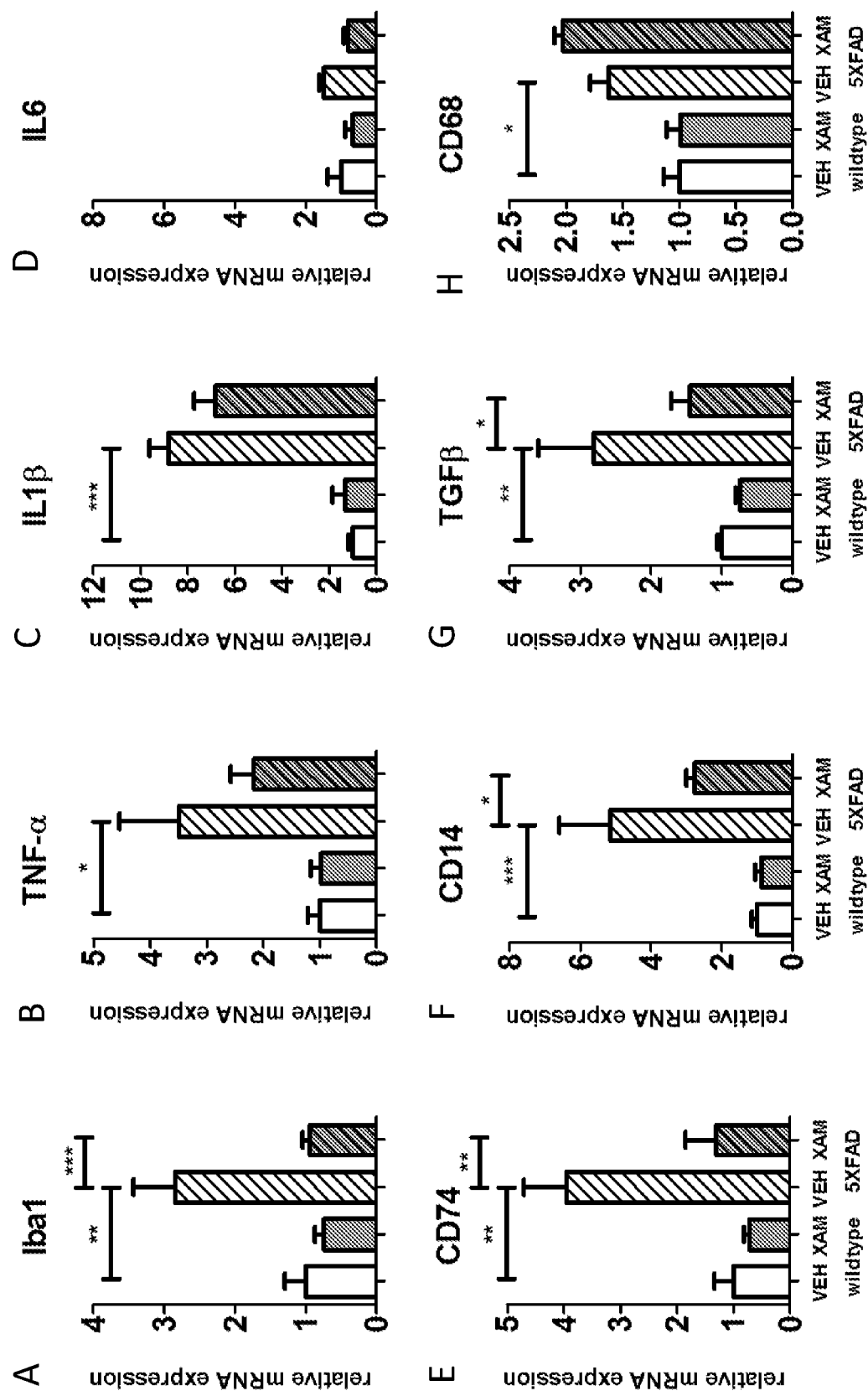
FIG. 19, panels A-H, illustrates the anti-inflammatory effects of xamoterol shown in 5XFAD mouse model of Alzheimer's disease. All genes (Iba1, TNFa, IL1b, CD14, CD74, TGFb, and CD68) with the exception of IL6, were elevated in 5XFAD-vehicle treated mice relative to wild-type-vehicle. Chronic treatment with xamoterol attenuated elevated expression of Iba1, CD74, CD14 and TGFb.

The 20 minutes post-dose collection study revealed that absorption of xamoterol was poor after oral administration, in line with its low oral bioavaiblity. Plasma concentration of xamoterol at 20 minutes post-dose following PO administration was 0.7% and 0.2% of the plasma concentrations achieved via IV and IP administration, respectively (FIG. 19, Table 6). Adminstration of Compound 43 led to plasma concentrations comparable with those obtained from administration of xamoterol. On the other hand, Compound 43 showed higher CNS penetration. Following IV, brain concentrations of Compound 43 were 22-fold higher than that of xamoterol (FIG. 19, Table 6).

TABLE 5

Pharmacokinetic parameters of Xamoterol and Compound 43 determined in the 4 hour time course study.

|  | Route | $C_{max}$ (ng/mL) | $AUC_{inf}$ (h*ng/mL) |
|---|---|---|---|
| Xamoterol | IV | 22200 ± 4029 | 2446 ± 601 |
|  | IP | 7443 ± 730 | 2834 ± 517 |
|  | PO - Systemic | 23 ± 16 | 42.5 ± 29.5 |
|  | PO - Portal | 79.8 ± 23.8 | 175.9 ± 53.4 |
| Compound 43 | IV | 3997 ± 1107 | 1796 ± 256 |
|  | IP | 762 ± 67 | 2159 ± 310 |
|  | PO - Systemic | 116 ± 78 | 101 ± 29 |
|  | PO - Portal | 946 ± 867 | 362 ± 367 |

TABLE 6

Pharmacokinetic parameters of Xamoterol and Compound 43 determined in the 20 min post-dose collection study.

|  |  | Plasma concentration (ng/ml) | Brain concentration (ng/g) |
|---|---|---|---|
| Xamoterol | IV | 1121 ± 297.1 | 38.3 ± 9.3 |
|  | IP | 3113 ± 388.6 | 26.5 ± 8.4 |
|  | PO | 8.1 ± 2.0 | 15.8 ± 5.7 |
| Compound 43 | IV | 1813 ± 67.41 | 838.7 ± 23.6 |
|  | IP | 597.7 ± 149.8 | 96.0 ± 22.6 |
|  | PO | 56.9 ± 29.2 | 41.7 ± 5.3 |

Cardiovascular Effects of the Key Compound

To assess the peripheral effects of xamoterol and Compound 43, we evaluated the cardiovascular response to xamoterol or Compound 43 in anesthetized rats. At a dose of 3 mg/kg, xamoterol and Compound 43 did not produce significant effects on heart rate, a process known to be mediated by ADRB1 expressed in heart. However, the same dose of xamoterol and Compound 43 led to a significant reduction in blood pressure.

DISCUSSION

In this study, we established SARs for a novel chemotype targeting the ADRB1. Exemplary compound 43 was shown to have partial agonistic activity on G-protein signaling with an $EC_{50}$ value in the low nanomolar range, but engaged very little β-arrestin signaling compared to the unbiased agonist isoproterenol. This biased ligand represents a new mode for ADRB1 activation and is distinctly different compared to isoproterenol—a full and unbiased agonist.

ADRB1 has been known to play an important role in learning and memory functions. For example, the ADRB1 selective antagonist betaxolol has been shown to induce contextual memory impairment in mice, which was reversed by the ADRB1 selective partial agonist xamoterol in a dose-dependent manner. Similarly, the retrieval deficits exhibited by mice with NA deficiency have been rescued by the ADRB1 selective partial agonist xamoterol. The involvement of ADRB1 in learning and memory has important clinical and therapeutic implications for AD, as severe neurodegeneration of the NA system begins in the early stages of AD. It is believed that loss of NA signaling and the resulting hypoactivation of ADRB1 may partially contribute to the cognitive symptoms in AD. Therefore, ADRB1 agonists may provide a promising therapeutic strategy to improve cognitive function in AD by restoring the lost NA signaling. Given the well-characterized role of protein kinase A (PKA)/cAMP response element-binding protein (CREB) signaling in learning and memory, the cyclic adenosine monophosphate (cAMP) signaling pathway downstream of ADRB1 is believed to mediate the cognitive enhancing effects of ADRB1. Toward our goal of modulating ADRB1 to produce therapeutic benefits in AD, we specifically sought to discover partial agonists; these would have more subtle effects in the periphery yet be efficacious enough to restore the decreased NA signaling in the context of AD. Accordingly, we chose xamoterol as our lead compound and exploited structure-activity relationships (SAR) around its analogs.

The SAR studies described herein showed that, in general, substitution of the phenol ring of xamoterol was not well tolerated. This was especially true for the ortho position to the phenolic OH group, where alkyl groups and Cl led to a complete loss of activity. This appeared to be largely a steric effect, as substitution with the small F atom ortho to the OH group gave a compound with only a small diminution in potency. On the other hand, substitutions at the morpholino urea site were relatively well tolerated although all were less potent than xamoterol. Aside from the two azetidine urea analogs, all of the compounds showed greater efficacy at the cAMP pathway via ADRB1 compared to xamoterol (S). This effect did not correlate with lipophilicity (clogP), nor any other obvious structural features of this subset of molecules. It is therefore interesting to speculate that the observed higher efficacy is due to the increased conformational flexibility of the side chains of the non-urea compounds and their consequent ability to fit more readily into the binding sites of the receptor.

Biased agonism, the notion that ligands at GPCRs can preferentially stimulate one intracellular signaling pathway over another, is of interest in GPCR signaling. In some cases, biased GPCR ligands can provide safer and more efficacious therapeutic benefits compared to non-biased ligands by selectively targeting a subset of the receptor-mediated signaling. GPCRs of interest include the dopamine D2 receptor, serotonin 5-HT2A, cannabinoid CB1, and κ-opioid receptors. A property of interest of the subject compounds is the functional bias toward the G-protein mediated cAMP pathway. G-protein-mediated signaling of ADRB1 is implicated in cognitive function and neuroinflammation, and β-arrestin mediated signaling is implicated in development of drug-induced tolerance. Therefore, in some cases, the development of a G-protein biased agonist of ADRB1 can provide a means to optimally tune ADRB1 therapeutics that will ameliorate the cognitive deficits and pathology underlying AD, as well as other neuroinflammatory diseases, without producing significant tachyphylaxis. The biased ligands can be used as pharmacological tools to aid in the elucidation of ADRB1-mediated signaling cascades in cellular systems and in vivo.

Accumulating data suggests a close association exists between neuroinflammation and AD pathogenesis. Prominent activation of immune responses characterized by activated microglia, reactive astrocytes, and increased expression of complement factors and proinflammatory cytokines associated with Aβ deposits, have been observed in the brains of AD patients as well as in transgenic mouse models of AD. TNF-α is one of the main proinflammatory cytokines known to be elevated in the brains from AD patients and animal models of AD, and has been strongly implicated in AD pathology. For example, elevated levels of TNF-α are observed in serum and cerebrospinal fluid (CSF) from AD patients compared to their normal subjects. Similarly, overexpression of TNF-α has been shown in several animal models of AD including 3×Tg-AD and 5XFAD mouse models. More importantly, increased levels of TNF-α in AD models was correlated with disease progression. At the molecular level, TNF-α has been shown to exacerbate Aβ-induced apoptosis in neurons and increase Aβ production by upregulating both β-secretase expression and γ-secretase activity, as well as the expression of APP. It has also been demonstrated that TNF-α inhibits phagocytosis of toxic Aβ species, which may lead to the hindering of efficient plaque removal by brain resident microglia. Excessive expression of TNF-α may contribute to and accelerate the progression of AD. Targeted inhibition of TNF-α signaling in AD may be an effective therapeutic approach to halt or attenuate the progression of AD. In support of this idea, inhibition of TNF-α signaling prevents pre-plaque amyloid-associated neuropathology and reduces plaque accumulation and tau phosphorylation in transgenic mouse models of AD. The adrenergic system has been shown to be involved in the regulation of TNF-α signaling as well as general inflammatory responses both in periphery and CNS. In our previous in vitro study with primary microglia, we have shown that the highly selective ADRB1 agonists xamoterol inhibited the LPS-induced TNFα response. Its effects were reversed by the ADRB1 selective antagonist, CGP 20712A or betaxolol, but not by the ADRB2 selective antagonist ICI-118551, suggesting that xamoterol produces its anti-inflammatory effects on TNFα response via ADRB1. When chronically administered to the 5×FAD mouse model of AD, xamoterol also produced anti-inflammatory effects and attenuated increased expressions of pro-inflamatory markers including TNFα shown in the brains of the transgenic mice. This suggest that ADRB1 is an important player in regulating immune response, and modulating ADRB1 activity has therapeutic potential for AD as well as other neuroinflammatory diseases. Notably, the exemplary compound 43 was found to suppress TNF-α production in rat primary microglia challenged with LPS. When administered to mice before the LPS challenge, compound 43 as well as xamoterol also attenuated the peripheral and CNS TNF-α response induced by LPS. Given the fact that compound 43 has non-specific activity on other receptors and bind to several receptors such as 5-HT 1A and 5-HT 2B with comparable affinity as for ADRB1, it is possible that its anti-inflammaotry effects shown in in vitro and in vivo studies could be mediated by non-ADRB1.

In order to evaluate the drug-like properties of the subject compounds, we conducted in vitro microsomal stability tests and in vivo PK studies. In the microsome stability test, exemplary compound 43 was shown to be very stable with half-lives greater than 60 minutes both in mouse and human microsomes. In rat microsomes, however, compound 43 was relatively less stable, and metabolized with a half-life of 25.2 min. The 20 minute one-time point in vivo study also revealed that a high concentration of compound 43 was detected in brain tissue, particularly when compound 43 was given intravenously or intraperitoneally. This suggests a possible beneficial therapeutic value of compound 43 for CNS indications. However, its bioavailability was very low (6%) when compound 43 was administered orally, which could be as a result of poor absorption through the gut membrane or permeability glycoprotein efflux.

Example 5

The subtype selective activity of some compounds of interest was assessed for adrenergic receptor beta 1 (ADRB1) versus adrenergic receptor beta 2 (ADRB2). ADRB1 EC50 from functional assay (nM)[a], Determined using the homogenous time-resolved fluorescence detection method with HEK-293 cells stably expressing human recombinant ADRB1. ADRB2 IC50 from binding assay (nM)[b], Determined using the Tag-lite Adrenoceptor Beta2 receptor ligand binding assay.

TABLE 7

Subtype selective activity for ADRB1 versus ADRB2.

| Compound ID | Structure | ADRB1 EC50 from functional assay (nM)[a] | ADRB2 IC50 from binding assay (nM)[b] |
|---|---|---|---|
| 72 | 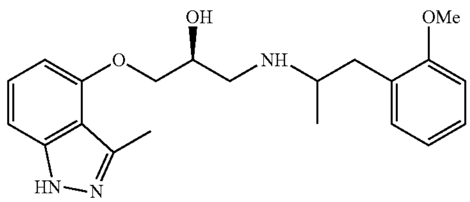 [SMILES: COc1ccccc1CC(C)NC[C@H](O)COc1cccc2[nH]nc(C)c12] | 0.8 | 0.009 |
| 69 | 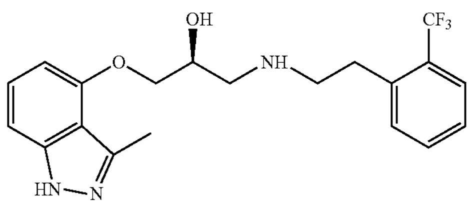 [SMILES: Cc1n[nH]c2cccc(OC[C@@H](O)CNCCc3ccccc3C(F)(F)F)c12] | 1.0 | 0.048 |
| 90 | 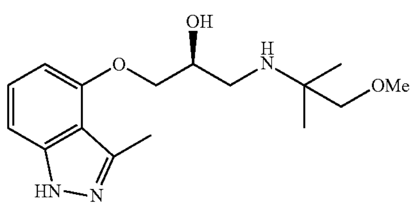 [SMILES: COCC(C)(C)NC[C@H](O)COc1cccc2[nH]nc(C)c12] | 3.4 | 0.019 |
| 75 | 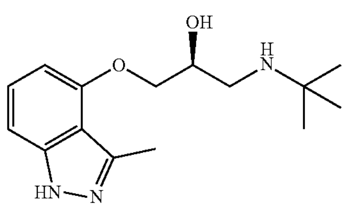 [SMILES: Cc1n[nH]c2cccc(OC[C@@H](O)CNC(C)(C)C)c12] | 3.5 | 0.065 |
| 87 | 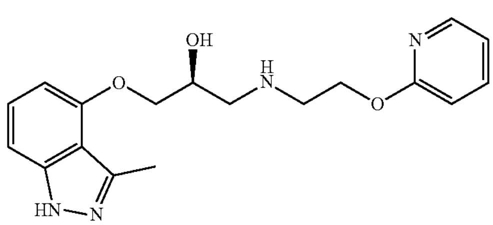 [SMILES: Cc1n[nH]c2cccc(OC[C@@H](O)CNCCOc3ccccn3)c12] | 5.0 | 0.23 |
| 52 | 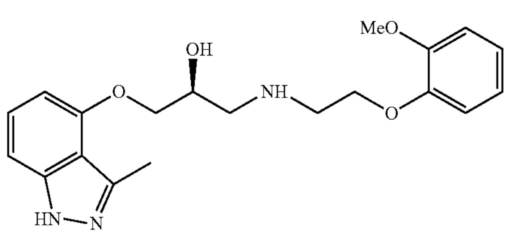 [SMILES: COc1ccccc1OCCNC[C@H](O)COc1cccc2[nH]nc(C)c12] | 9.2 | 0.024 |

TABLE 7-continued

Subtype selective activity for ADRB1 versus ADRB2.

| Compound ID | Structure | ADRB1 EC50 from functional assay (nM)[a] | ADRB2 IC50 from binding assay (nM)[b] |
|---|---|---|---|
| 55 | (structure shown) | 35.4 | 0.38 |
| 86 | (structure shown) | 44.7 | 0.1442 |

Example 6

Experimental A

Wild-type mice and transgenic mice expressing 5 gene mutations related to Familial Alzheimer's Disease (5XFAD mice) were administered xamoterol (3 mg/kg/day) or vehicle by use of a mini-osmotic pump from 7.0 to 9.5 months of age. Pumps (model 2006, Alzet, Cupertino, Calif.) were inserted subcutaneously in the back of each mouse under anesthesia. Following 2.5 months of xamoterol administration, mice were sacrificed and their brain tissues were collected. Total RNA was extracted from cortex using the Rneasy Lipid tissue mini kit, and qRT-PCR were ran to measure the expression of genes related to inflammation.

FIG. 19 shows the G-protein biased partial agonist of ADRB1 (xamoterol) produces inhibitory effects on neuroinflammation associated with Alzheimer's disease. This suggests that this class of ligands has therapeutic value for diseases associated with neuroinflammation. Specifically, FIG. 19 illustrates the anti-inflammatory effects of xamoterol shown in 5XFAD mouse model of Alzheimer's disease. All genes (Iba1, TNFa, IL1b, CD14, CD74, TGFb, and CD68) with the exception of IL6, were elevated in 5XFAD-vehicle treated mice relative to wildtype-vehicle. Chronic treatment with xamoterol attenuated elevated expression of Iba1, CD74, CD14 and TGFb. One-way ANOVA followed by Dunnett's test for post-hoc analysis (One way ANOVA; p<*0.050.01 *0.001). Veh, vehicle; Xam, xamoterol.

Experimental B

Transgenic mice expressing amyloid beta protein precursor (APP) and wild-type mice were chronically administered with KSN01-01-18 (10 mg/kg, subcutaneous). Changes on body weight were recorded. Effects of KSN01-01-18 on cognitive function were evaluated in Morris water maze (MWM). Briefly, In the MWM, a large water tank (178 cm in diameter) filled with water was used. A circular platform was placed about 1 cm below the water surface approximately 17 cm away from the wall in one 20 quadrant of the tank. Nontoxic tempera paints were used to make the water opaque. During the consecutive days of hidden platform training, mice were released from drop locations and given 60 sec to find the platform. Upon completion of the hidden platform training, the platform was removed and a 60-sec probe trial was conducted. Successful learning of MWM was determined by the gradual decrease in escape latency during the hidden platform training and discriminative quadrant exploration and latency to reach virtual platform during the probe trial.

Figure 20:
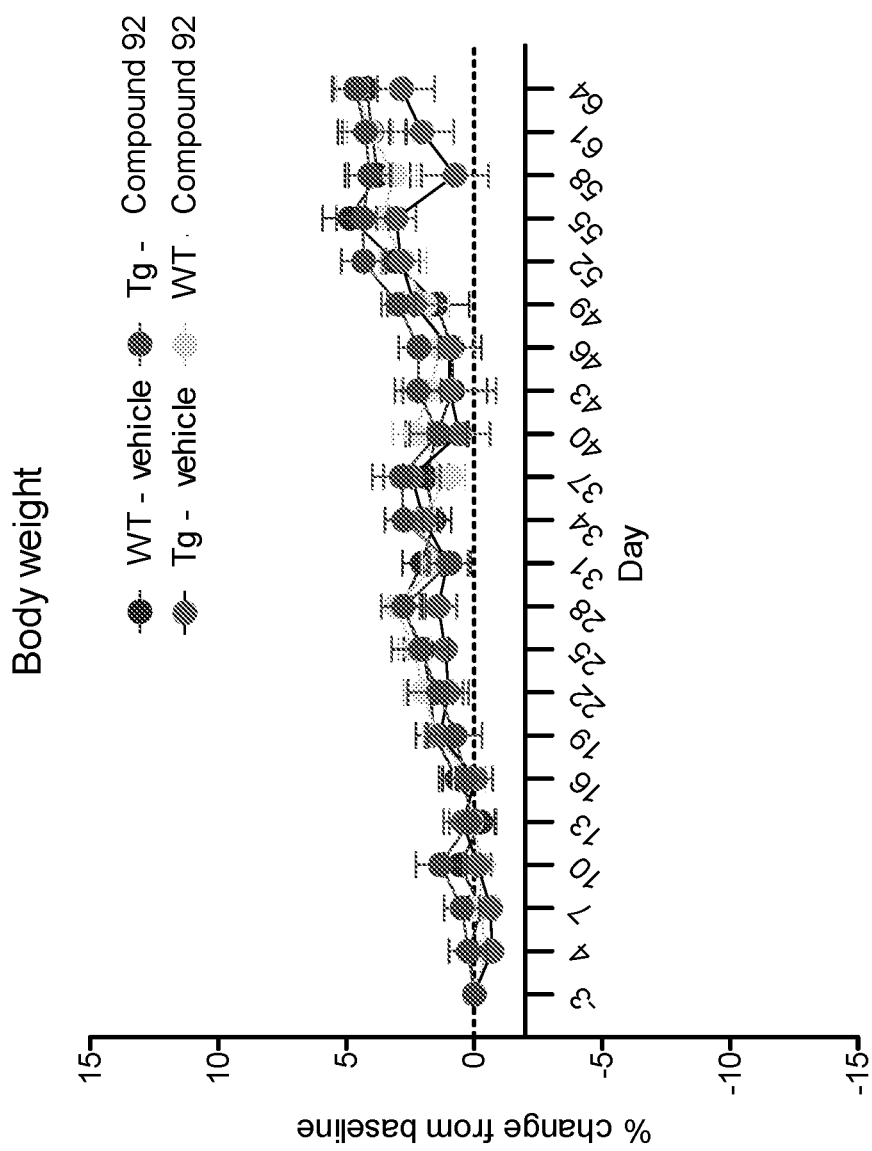
FIG. 20 shows data illustrating that administration of exemplary compound 92 in mice does not cause general toxicity, as measured by changes in body weight.
Figure 21:
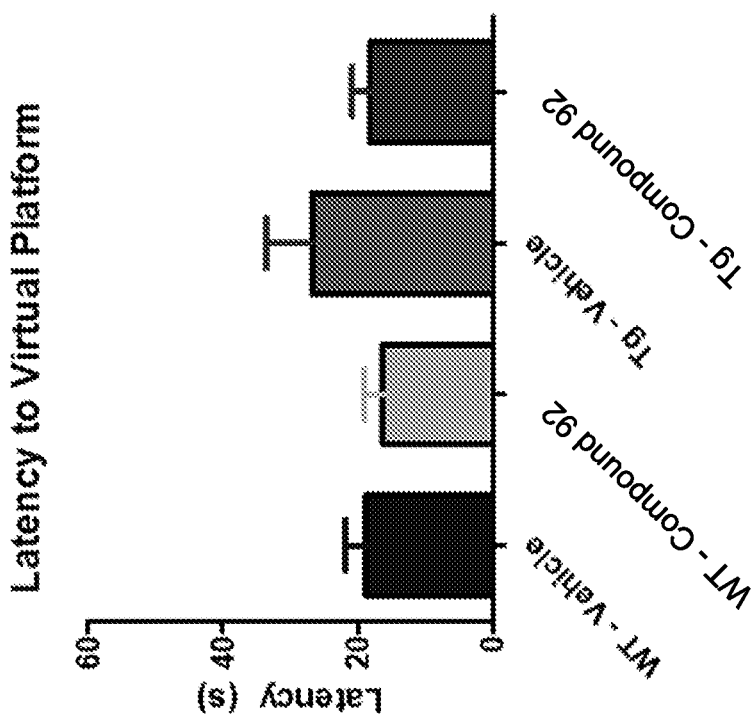
FIG. 21 shows data demonstrating that compound 92 produces cognitive enhancing effects in morris water maze test. Transgenic mice treated with 92 took less time to find the virtual platform compared to the transgenic mice treated with vehicle. WT, wild-type; Tg, transgenic.

FIG. 20 shows data illustrating that administration of KSN01-01-18 in mice does not cause general toxicity, as measured by changes in body weight. FIG. 21 shows data demonstrating that compound 92 produces cognitive enhancing effects in morris water maze test Transgenic mice treated with 92 took less time to find the virtual platform compared to the transgenic mice treated with vehicle. WT, wild-type; Tg, transgenic.

Experimental C

Mice were anesthetized with isoflurane before decapitation. The brain was quickly removed and immersed for 2 min in ice-cold low-calcium modified artificial cerebrospinal fluid (mACSF) composed of (in mM): 119 NaCl, 2.5 KCl, 1 $CaCl_2$, 3 $MgSO_4$, 1 $NaH_2PO_4$, 26 $NaHCO_3$ and 10 glucose, osmolarity ~305 mOsm, continuously bubbled with 95% O2-5% CO2, pH=7.4. The hippocampus was dissected out and cut in ice-cold mACSF with a vibratome (Leica VT1000S; Nussloch, Germany) into 350 mm-thick slices from the middle part of the hippocampus. The slices were allowed to recover in oxygenated mACSF at 33° C. for 10 min, and then at room temperature for an additional 2-3 hr before experimental recordings. Slices were transferred into the recording chamber and superfused with regular ACSF containing (in mM): 119 NaCl, 2.5 KCl, 2.5 $CaCl_2$, 1.3 $MgSO_4$, 1 $NaH_2PO_4$, 26 $NaHCO_3$ and 10 glucose, continuously bubbled with 95% O2-5% C02, pH=7.4, osmolarity ~305 mOsm, at a constant rate of 2.7 mL/min at 32° C. Recording electrodes were made of borosilicate glass capillaries (1B150F, World Precision Instruments, Sarasota, Fla.) using a Sutter P-87 electrode puller (Sutter Instruments, Novato, Calif.) and filled with ACSF (resistance ~0.8-1 MΩ). Monopolar stimulating electrodes were made of Pt/Ir (Platinum/Iridium) wires of diameter 25.4 μm (PTT0110, World Precision Instruments, Sarasota, Fla.) with 100-μm-long exposed tips. Both the stimulating and recording electrodes were inserted under visual control perpendicular to the slice surface into the CA1 stratum radiatum at a distance 250-300 mm from each other. The initial slope of field excitatory postsynaptic potentials (fEPSP) was measured at latencies 0.1-0.9 ms. Testing stimuli (duration 100 μs, current 70 mA) evoked field responses with amplitudes of 70-80% of maximum. After stabilization of responses, input-output dependences were measured using series of stimulation intensities (range 30-150 μA). Xamoterol (10 uM) or vehicle was applied at the period 3 h before the tetanus until the end of the recordings. Amyloid beta or vehicle was applied at the period 2.5 h before the tetanus until the end of the recordings. LTP was induced by high-frequency tetanization (70 mA, 100 Hz for 1 sec), and the responses were recorded for the period of 1.5 h after the tetanus.

The responses show that amyloid beta (Ab) induces long-term potentiation (LTP) impairment in hippocampal slices. The responses show that Xamoterol (10 uM) blocks the LTP impairment induced by Ab. As such, xamoterol attenuates Abeta-induced LTP Impairment in Hippocampal Slices. A balance of synaptic excitation and inhibition and the ability of synapses to strengthen or weaken over time in response to synaptic input (synaptic plasticity) are important for cognitive functions. One hypothesis for the cognitive impairment associated with AD is that there is an imbalance in these dynamic processes in which weakening (i.e., depression) of synaptic connections is enhanced while strengthening (i.e., potentiation) of connections is suppressed. This hypothesis is supported by the findings that amyloid beta disrupt synaptic function and inhibit long-term potentiation (LTP) in hippocampal slices.

The figures demonstrate that amyloid beta (Ab) induces impairment in LTP in mouse hippocampal slices. Xamoterol (10 uM) blocks the Ab-induced LTP in impairment. Short-term potentiation (STP) was measured by comparing baseline value and slices' response between 2-15 min after tetanus. Long-term potentiation (LTP) was measured by comparing baseline value and slices' response between 60-90 min after tetanus.

Figure 25:
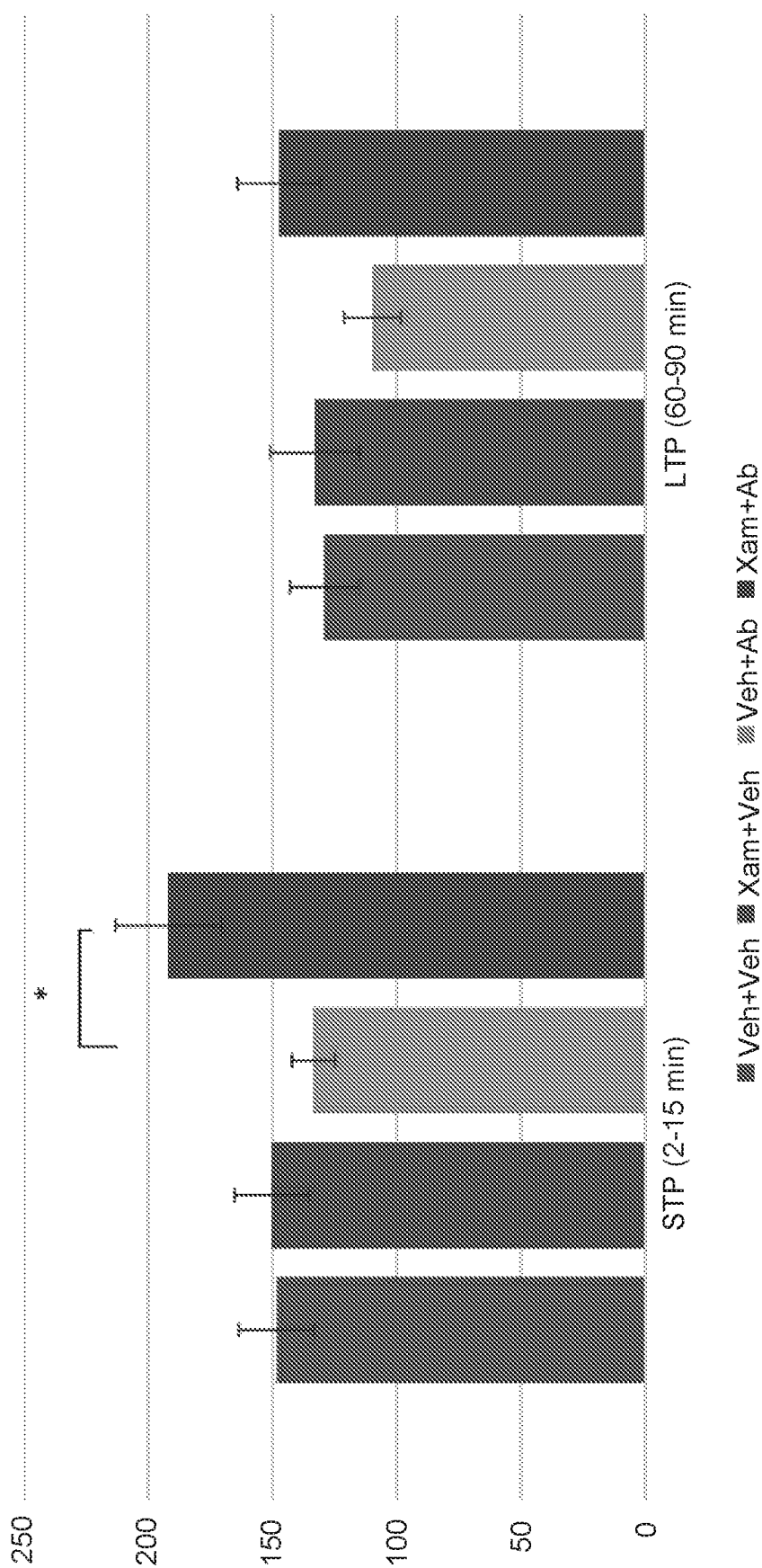
FIG. 25 shows effects of xamoterol and amyloid beta (1-42) on Short-Term Potentiation (STP) and Long-Term Potentiation (LTP).

FIG. 25 shows the results of short-term (2-15 min after the tetanus) and long-term (60-90 min after the tetanus) potentiation for the four groups. p*=0.026—difference in STP between Veh+Ab vs. Xam+Ab gropus. Same comparison for LTP gives p=0.075, n.s. n=4 per group. The data do not include the results of the last two experiments (n=2 per group), which did not show any difference between the groups.

Experimental D

C57Bl/6J female mice were administered with isoproterenol, KSN01-01-15, or KSN01-01-18 at 10 mg/kg for 24 days. After 24 days of treatment, mice were sacrificed, and lung and heart weight were measured. Hearts were then fixed in 10% formalin, and stained with Masson trichrome for evaluation of fibrosis.

Figure 22:
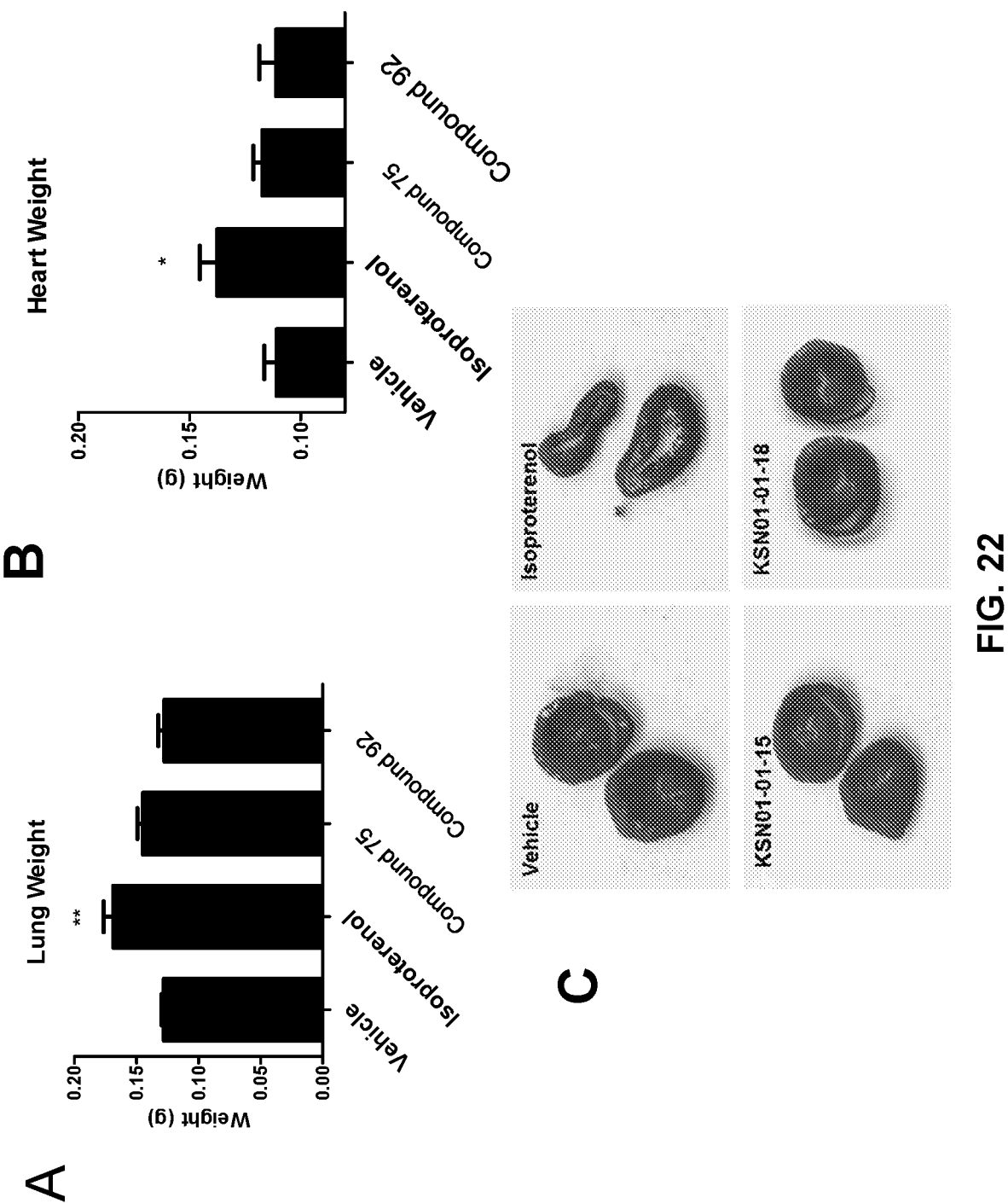
FIG. 22, panels A-C, illustrate that G-protein biased agonists of ADRB1 (antagonists for β-arrestin signaling) can be used for diseases associated with fibrosis by antagonizing β-arrestin signaling. Panel A shows data illustrating that unbiased agonist isoproterenol induces fibrotic changes in lung and increases lung weight following 24 days of administration. G-protein biased agonists (exemplary compounds 75 and 92) did not induce these changes. Panel B shows data illustrating that unbiased agonist isoproterenol induces fibrotic changes in heart and increases heart weight following 24 days of administration. G-protein biased agonists (exemplary compounds 75 and 92) did not induce these changes. Panel C demonstrated that chronic administration of the unbiased agonist isoproterenol produces morphological changes in heart. The G-protein biased agonists, exemplary compounds 75 and 92, did not induce these changes.

FIG. 22, panels A-C illustrate that G-protein biased agonists of ADRB1 (antagonists for β-arrestin signaling) can be used for diseases associated with fibrosis by antagonizing β-arrestin signaling. Panel A shows data illustrating that unbiased agonist isoproterenol induces fibrotic changes in lung and increases lung weight following 24 days of administration. G-protein biased agonists (exemplary compounds 75 and 92) did not induce these changes. Panel B shows data illustrating that unbiased agonist isoproterenol induces fibrotic changes in heart and increases heart weight following 24 days of administration. G-protein biased agonists (exemplary compounds 75 and 92) did not induce these changes. Panel C demonstrated that chronic administration of the unbiased agonist isoproterenol produces morphological changes in heart. The G-protein biased agonists, exemplary compounds 75 and 92, did not induce these changes. Unbiased agonist isoproterenol induces fibrotic changes following chronic administration, whereas G-protein biased agonists of ADRB1 do not cause these changes. This suggests that G-protein biased agonists of ADRB1 (antagonists for β-arrestin signaling) can be used for diseases associated with fibrosis by antagonizing β-arrestin signaling.

Experimental E

Figure 23:
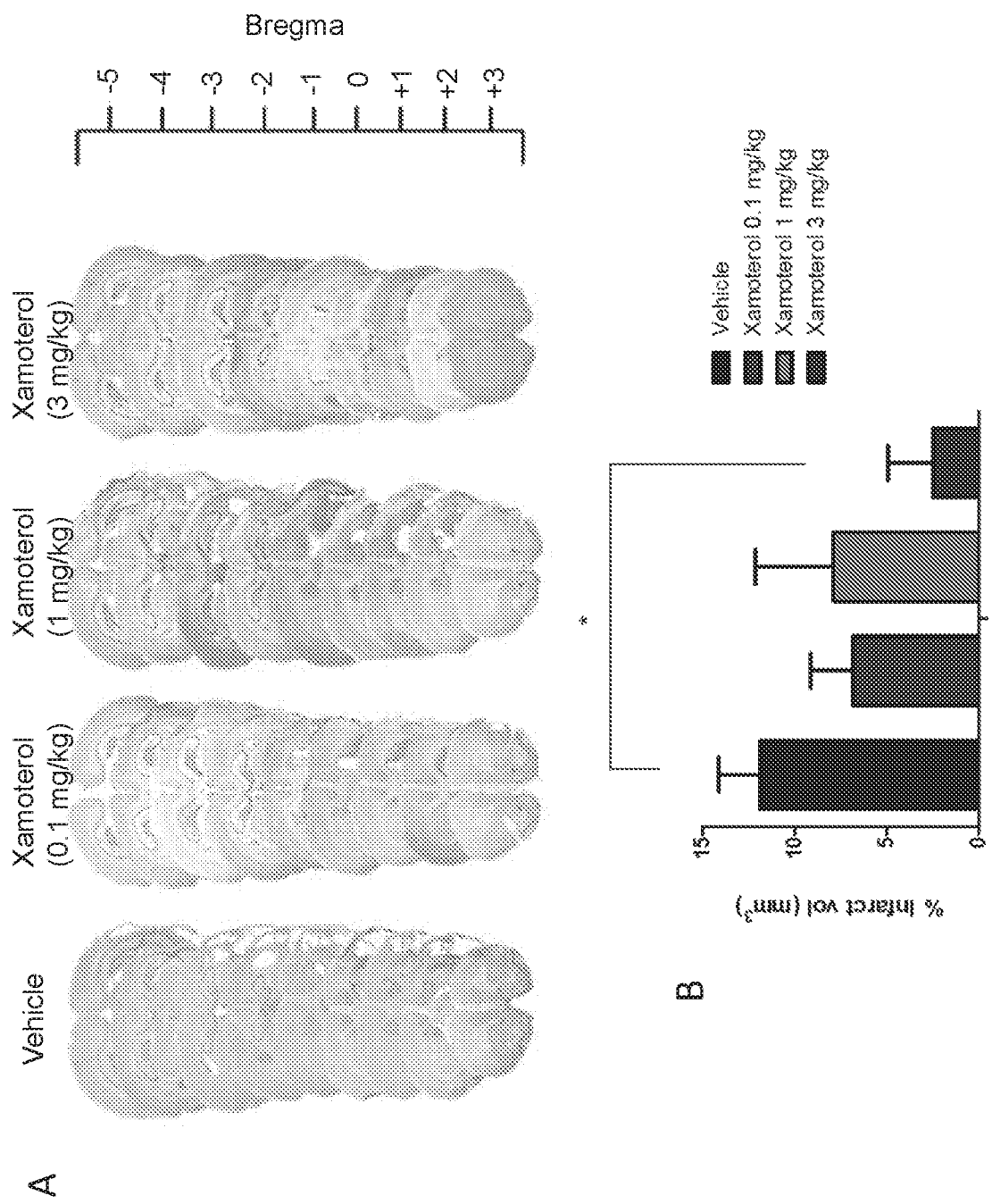
FIG. 23, panels A and B, illustrates that xamoterol (3 mg/kg) reduces infarction volume in transient middle cerebral artery occlusion (tMCAO) model of stroke in rat.

The tMCAO is performed on animal under isoflurane inhalation anesthesia (4% for induction and 1.5-2.5% for maintenance) in airoxygen mixture ratio 3:1. Ventral neck area is shaved by electric razor and disinfected using betadine followed by 70% ethanol solution. Subsequently, a midline incision is made in the ventral neck area, sharp and blunt dissection techniques are used to isolate left common carotid artery (CCA) and the internal and external carotid arteries (ICA and ECA, respectively). The proximal CCA is ligated below the bifurcation using 3-0 braided silk suture allowing enough room for filament insertion in the area between the ligation and bifurcation. Subsequently, ECA is ligated at its origin dose to the CCA bifurcation, so that the occipital artery stays proximal to the ligature. A microvessel dip is placed on ICA temporarily to avoid excessive bleeding during filament insertion. In order to occlude the origin of middle cerebral artery (MCA), a monofilament with silicon coated tip (0.39 mm diameter, 5-6 mm long) is then inserted into the CCA, the microvessel dip removed following filament advancement into the ICA 20 mm from the bifurcation through small, horizontal incision. The filament is secured in its place by a suture knot placed between the bifurcation and proximal CCA ligature. After 90 minutes, to induce reperfusion to the ischemic brain area, filament is removed until the silicone tip touches the security knot on CCA and cut. The incision is closed with wound dips. Xamoterol was administered 24 h post-tMCAO at 0.1, 1, or 3 mg/kg and continued for 21 days. After 21 days of the treatment with xamoterol, rats were sacrificed and brain tissues were collected. The sectioned brain tissues were then stained with cresyl violet stain to identify regions of ischemic damage. FIG. 23 illustrates that xamoterol (3 mg/kg) reduces infarction volume in transient middle cerebral artery occlusion (tMCAO) model of stroke in rat.

Experimental F

Figure 24:
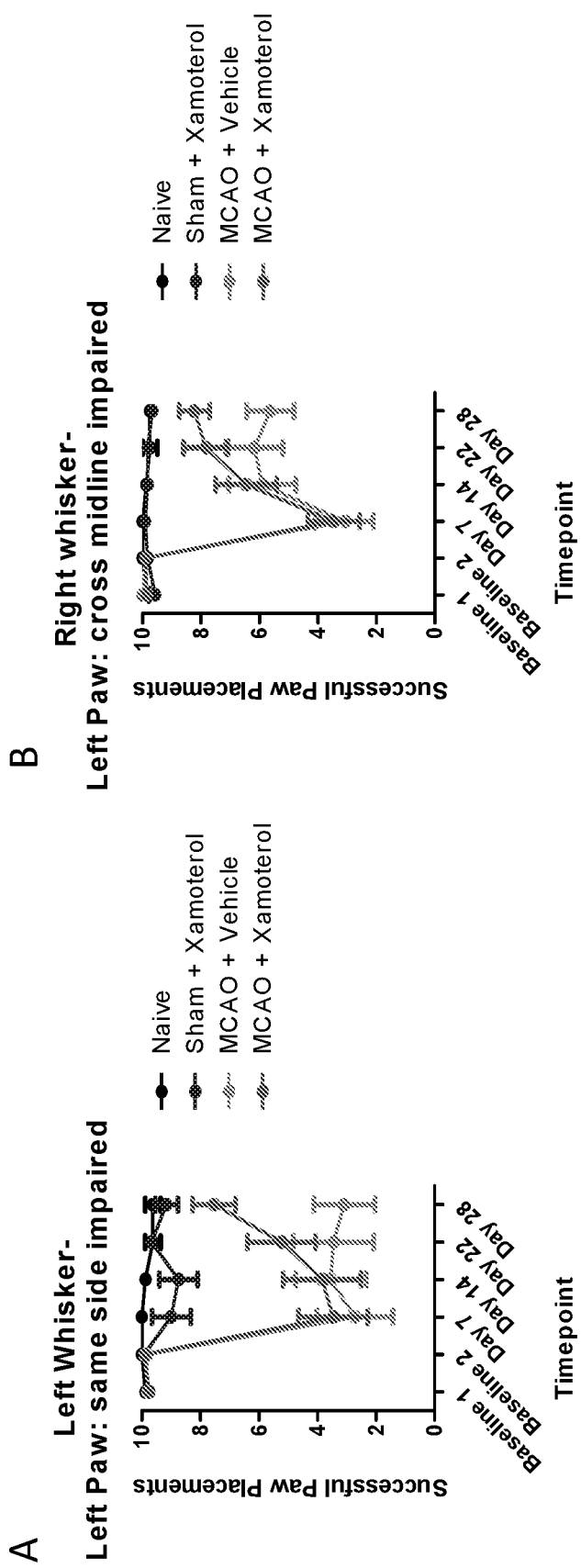
FIG. 24, panels A and B, illustrates that xamoterol improves sensorimotor function in tMCAO rat model of stroke.

The tMCAO is performed on animal under isoflurane inhalation anesthesia (4% for induction and 1.5-2.5% for maintenance) in airoxygen mixture ratio 3:1. Ventral neck area is shaved by electric razor and disinfected using betadine followed by 70% ethanol solution. Subsequently, a midline incision is made in the ventral neck area, sharp and blunt dissection techniques are used to isolate left common carotid artery (CCA) and the internal and external carotid arteries (ICA and ECA, respectively). The proximal CCA is ligated below the bifurcation using 3-0 braided silk suture allowing enough room for filament insertion in the area between the ligation and bifurcation. Subsequently, ECA is ligated at its origin dose to the CCA bifurcation, so that the occipital artery stays proximal to the ligature. A microvessel dip is placed on ICA temporarily to avoid excessive bleeding during filament insertion. In order to occlude the origin of middle cerebral artery (MCA), a monofilament with silicon coated tip (0.39 mm diameter, 5-6 mm long) is then inserted into the CCA, the microvessel dip removed following filament advancement into the ICA 20 mm from the bifurcation through small, horizontal incision. The filament is secured in its place by a suture knot placed between the bifurcation and proximal CCA ligature. After 75 minutes, to induce reperfusion to the ischemic brain area, filament is removed until the silicone tip touches the security knot on CCA and cut. The incision is closed with wound dips. Xamoterol was administered 24 h post-tMCAO (3 mg/kg, subcutaneous) and continued daily (0.3 mg/kg, subcutaneous) for 28 days. Sensorimotor function was measured by the Paw-Whisker test (vibrissae-evoked forelimb placing) once a week until 4 weeks post stroke. FIG. 24 illustrates that xamoterol improves sensorimotor function in tMCAO rat model of stroke. This suggests that this class of ligand has therapeutic value for stroke.

Experimental G

C57bl/6J mice were administered xamoterol (0.3 mg/kg; subcutaneous) or vehicle daily from 3.5 to 6.0 months of age. Mice were sacrificed and their brain tissues were collected. Immunohistochemistry was performed on 40 micrometer paraformaldehyde-fixed brain sections for counting cells immunoreactive for the neuroblast marker, doublecortin (DCX), which labels newly bom immature neuroblasts in the dentate gyrus.

Figure 26:
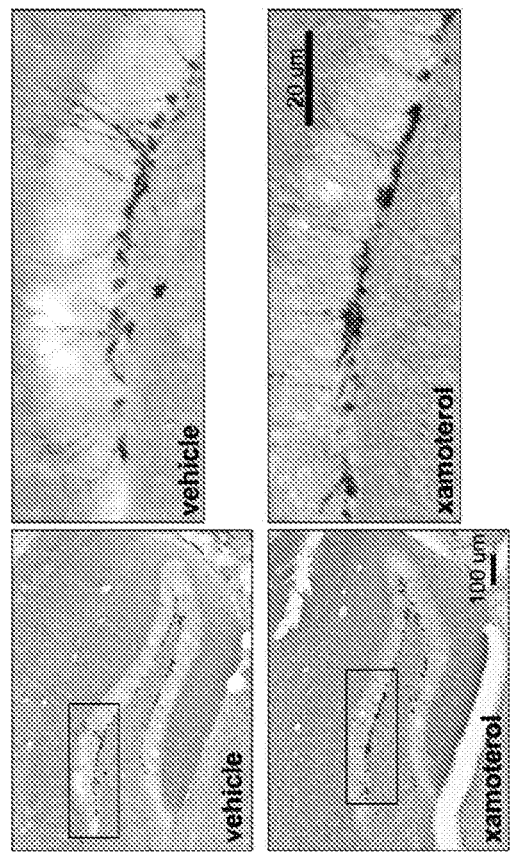
FIG. 26. panels A-C, illustrates that the G-protein biased partial agonist of ADRB1 (xamoterol) increases neurogenesis in mice. Neuroblast counts were elevated in dentate gyrus of the hippocampus of xamoterol-treated mice relative to vehicle treatment. (*$p<0.05$; t-test). DG, dentate gyrus.
Figure 26:
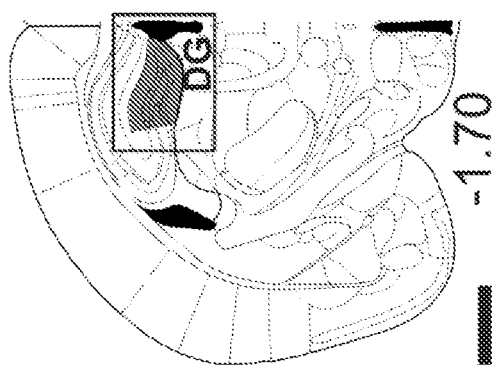
Figure 26:
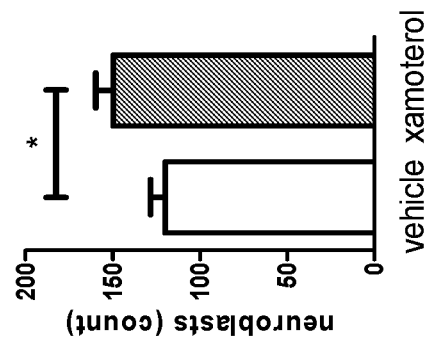

FIG. 26 shows that the G-protein biased partial agonist of ADRB1 (xamoterol) increases neurogenesis in mice. This suggests that partial agonists of ADRB1 can increase neural plasticity and have therapeutic value in diseases where neural plasticity is compromised. This figure illustrates effects of xamoterol on neurogenesis in c57bl/6J mice. Neuroblast counts were elevated in dentate gyrus of the hippocampus of xamoterol-treated mice relative to vehicle treatment. (*p<0.05; t-test). DG, dentate gyrus.

Notwithstanding the appended claims, the disclosure set forth herein is also described by the following clauses:

1. An adrenergic receptor modulating compound of formula (I):

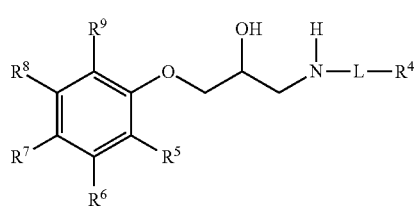

wherein:

L is a linker;

$R^4$ is an alkyl, a substituted alkyl, a cydoalkyl, a substituted cycloalkyl, an aryl, a substituted aryl, a heterocycle, a substituted heterocycle, a heteroaryl or a substituted heteroaryl; and EITHER:

a) $R^5$ and $R^6$ are cyclically linked to form a fused 5 membered heterocycle ring comprising at least one nitrogen and optionally substituted with alkyl or substituted alkyl; and $R^7$-$R^9$ are independently selected from H, alkyl, substituted alkyl, halogen, hydroxyl, cyano, a fluorinated alkyl group (e.g., an alkyl group substituted with 1-6 fluoro, such as $CF_3$), alkoxyl, substituted alkoxy, OCOR', OCONR'R", where R' and R" are independently $R^5$, aryl, substituted aryl, alkyl or cycloalkyl, optionally further substituted with 1-6 fluoros, or R' and R" together with the connected N form a heterocycle or substituted heterocycle;

OR b) $R^7$ is hydroxyl, alkoxy, substituted alkoxy, OCOR', OCONR'R", where R' and R" are independently $R^5$, aryl, substituted aryl, alkyl or cydoalkyl, optionally further substituted with 1-6 fluoros, or R' and R" together with the connected N form a heterocyde or substituted heterocycle;

$R^6$ and $R^9$ are independently fluoro or H; and $R^5$ and $R^8$ are hydrogen; wherein the compound is not xamoterol or compounds 43 or 44 of Table 1;

or a prodrug thereof, or a salt thereof.

2. The compound of clause 1, wherein the compound is of Formula (III):

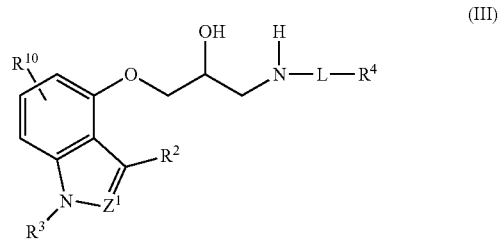

wherein: $Z^1$ is N or $CR^1$; $R^1$, $R^2$ and $R^3$ are each independently H, an alkyl or a substituted alkyl; $R^{10}$ is one or more substituents selected from H and $R^7$; or a prodrug thereof, or a salt thereof.

3. The compound of clause 2, wherein $Z^1$ is N.

4. The compound of clause 2, wherein $Z^1$ is $CR^1$.

5. The compound of any one of clauses 2-4, wherein $R^3$ is H and $R^2$ is C1-C6 alkyl.

6. The compound of clause 1, wherein: $R^7$ is hydroxyl, alkoxy, substituted alkoxy, OCOR', OCONR'R", where R' and R" are independently $R^5$, aryl, substituted aryl, alkyl or cydoalkyl, optionally further substituted with 1-6 fluoros, or R' and R" together with the connected N form a heterocycle or substituted heterocycle; $R^6$ and $R^9$ are independently fluoro or H, wherein at least one of $R^6$ and $R^9$ is fluoro; and $R^5$ and $R^8$ are hydrogen.

7. The compound of any one of clauses 1-6, wherein the compound is of formula (IV) or (v):

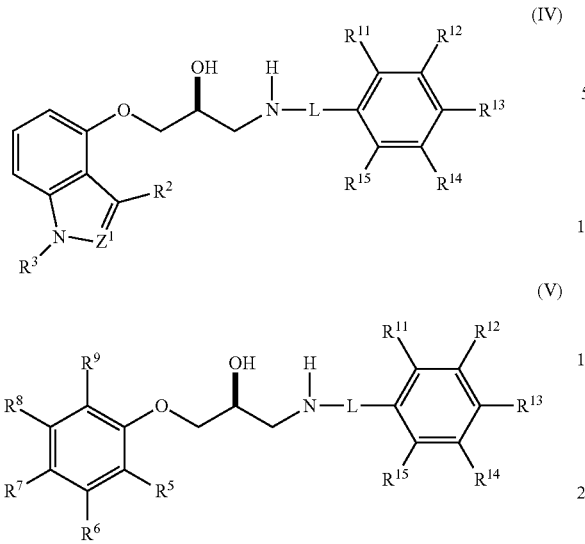

(IV)

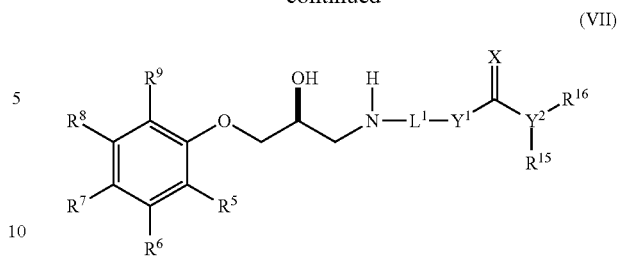

(VII)

wherein:

$R^{10}$ is one or more optional substituents selected from halogen, C1-C6 alkyl, substituted C1-C6 alkyl, hydroxyl, C1-C6 alkoxy and substituted C1-C6 alkoxy;

$L^1$ is a linker;

$Y^1$ is absent or NR, wherein each R is independently H, an alkyl, a substituted alkyl, a cycloalkyl or a substituted cycloalkyl;

X is O or S;

$Y^2$ is CH or N; and $R^{15}$ and $R^{16}$ are independently selected from H, an alkyl and a substituted alkyl, or $R^{15}$ and $R^{16}$ are cyclically linked and together with $Y^2$ form an optionally substituted cycloalkyl or heterocycle.

11. The compound of clause 10, wherein the compound has formula (VI), wherein $Z^1$ is N, $R^2$ is C1-C6 alkyl and $R^3$ is hydrogen.

12. The compound of clause 10, wherein the compound has formula (VII) wherein $R^7$ is hydroxyl, $R^6$ and $R^9$ are independently fluoro or H, and $R^5$ and $R^8$ are hydrogen;

wherein at least one of $R^6$ and $R^9$ is fluoro, or $Y^1$ is NR where R is alkyl, cycloalkyl, substituted alkyl or substituted cydoalkyl.

13. The compound of clause 12, wherein the compound has the structure:

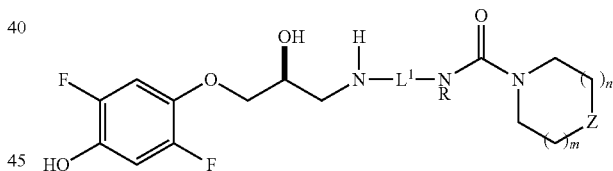

wherein: Z is O, NR or CHR wherein R is H, alkyl, substituted alkyl, cycloalkyl or substituted cycloalkyl; m and n are independently 0 or 1; and $L^1$ is a C2-C6 alkyl linker.

14. The compound of clause 10, wherein the compound has the structure:

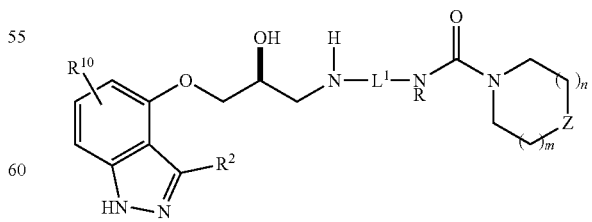

wherein: Z is O, NR or CHR wherein R is H, hydroxyl, alkoxy, substituted alkoxy, alkyl, substituted alkyl, cycloalkyl or substituted cycloalkyl; m and n are independently 0 or 1; and $L^1$ is a C2-C6 alkyl linker.

(V)

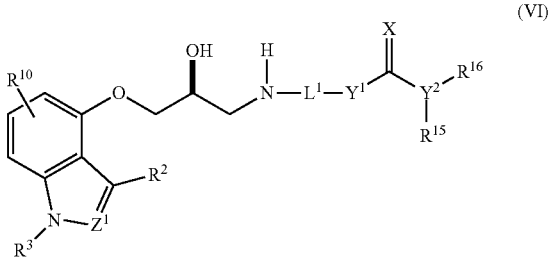

wherein:

$R^{11}$-$R^{15}$ are each independently selected from H, halogen, —CN, —$NO_2$, —OH, —$OR_{10}$, —C(O)$R_{10}$, —$CO_2R_{10}$, —O(CO)$R_{10}$, —C(O)$NR_{10}R_{20}$, —OC(O)$NR_{10}R_{20}$, —$SR_{10}$, —$SOR_{10}$, —$SO_2R_{10}$, —$SO_2NR_{10}R_{20}$, —$NR_{10}R_{20}$, —$NR_{10}C(O)R_{20}$, —$NR_1C(O)_2R_{20}$, —$NR_1SO_2R_{20}$, —$NR_1$(CO)$NR_{20}R_{30}$, unsubstituted or substituted $C_{1-8}$ alkyl, unsubstituted or substituted $C_{2-8}$ alkenyl, unsubstituted or substituted $C_{2-8}$ alkynyl, unsubstituted or substituted $C_{3-8}$ cycloalkyl, unsubstituted or substituted $C_{6-10}$ aryl, unsubstituted or substituted 5- to 10-membered heteroaryl, and unsubstituted or substituted 3- to 10-membered heterocydyl; where $R_{10}$, $R_{20}$ and $R_{30}$ are each independently selected from hydrogen, unsubstituted or substituted $C_{1-6}$ haloalkyl, unsubstituted or substituted $C_{1-6}$ alkyl, unsubstituted or substituted $C_{3-6}$ cycloalkyl, unsubstituted or substituted $C_{2-6}$ alkenyl, unsubstituted or substituted $C_{2-6}$ alkynyl, unsubstituted or substituted $C_{6-10}$ aryl, unsubstituted or substituted 5- to 10-membered heteroaryl, unsubstituted or substituted aryl-$C_{1-4}$ alkyl, unsubstituted or substituted aryl-$C_{14}$ alkyl, and unsubstituted or substituted aryloxy-$C_{1-4}$ alkyl; or two of $R_{10}$, $R_{20}$ together or $R_{10}$ and $R_{30}$ together with the atom(s) to which they are attached, may form an unsubstituted or substituted 5-, 6- or 7-membered ring.

8. The compound of clause 7, wherein the compound has formula (IV) wherein $Z^1$ is N, $R^2$ is C1-C6 alkyl and $R^3$ is hydrogen.

9. The compound of clause 7, wherein the compound has formula (V) wherein $R^7$ is hydroxyl, $R^6$ and $R^9$ are each fluoro and $R^5$ and $R^8$ are hydrogen.

10. The compound of any one of clauses 1-6, wherein the compound is of formula (VI) or (VII):

(VI)

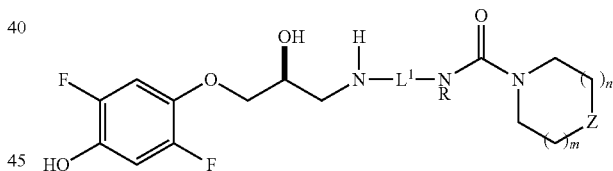

15. The compound of any one of clauses 1-6, wherein $R^4$ is of Formula (XII) or (XIII):

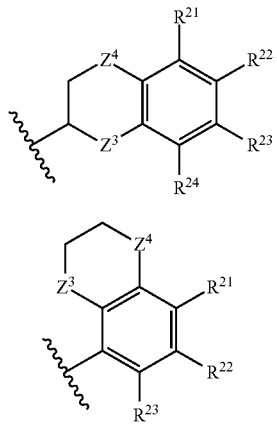

(XII)

(XIII)

wherein:
$Z^3$ and $Z^4$ are independently O, $CH_2$ or NR, wherein R is H, an alkyl or a substituted alkyl; and
$R^{21}$—$R^{24}$ are each independently selected from H, halogen, —CN, —$NO_2$, —OH, —$OR_{10}$, —C(O)$R_{10}$, —$CO_2R_{10}$, —O(CO)$R_{10}$, —C(O)$NR_{10}R_{20}$, —OC(O)$NR_{10}R_{20}$, —$SR_{10}$, —$SOR_{10}$, —$SO_2R_{10}$, —$SO_2NR_{10}R_{20}$, —$NR_{10}R_{20}$, —$NR_{10}$C(O)$R_{20}$, —$NR_1$C(O)$_2R_{20}$, —$NR_1SO_2R_{20}$, —$NR_1$(CO)$NR_{20}R_{30}$, unsubstituted or substituted $C_{1-8}$ alkyl, unsubstituted or substituted $C_{2-8}$ alkenyl, unsubstituted or substituted $C_{2-8}$ alkynyl, unsubstituted or substituted $C_{3-8}$ cycloalkyl, unsubstituted or substituted $C_{6-10}$ aryl, unsubstituted or substituted 5- to 10-membered heteroaryl, and unsubstituted or substituted 3- to 10-membered heterocydyl; where $R_{10}$, $R_{20}$ and $R_{30}$ are each independently selected from hydrogen, unsubstituted or substituted $C_{1-6}$ haloalkyl, unsubstituted or substituted $C_{1-6}$ alkyl, unsubstituted or substituted $C_{3-6}$ cycloalkyl, unsubstituted or substituted $C_{2-6}$ alkenyl, unsubstituted or substituted $C_{2-6}$ alkynyl, unsubstituted or substituted $C_{6-10}$ aryl, unsubstituted or substituted 5- to 10-membered heteroaryl, unsubstituted or substituted aryl-$C_{1-4}$ alkyl, unsubstituted or substituted aryl-$C_{1-4}$ alkyl, and unsubstituted or substituted aryloxy-$C_{1-4}$ alkyl; or two of $R_{10}$, $R_{20}$ together or $R_{10}$ and $R_{30}$ together with the atom(s) to which they are attached, may form an unsubstituted or substituted 5-, 6- or 7-membered ring 16. The compound of clause 15, wherein $Z^4$ is O and $Z^3$ is $CH_2$.

17. The compound of clause 15, wherein $Z^4$ and $Z^3$ are each O.

18. The compound of clause 15, wherein $Z^4$ is $CH_2$ and $Z^3$ is O.

19. The compound of any one of clauses 1-6, wherein $R^4$ is selected from one of the following:

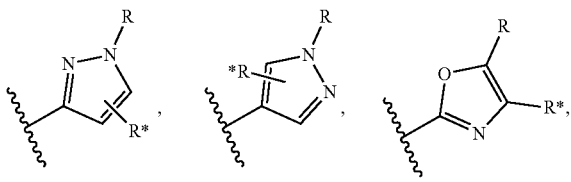

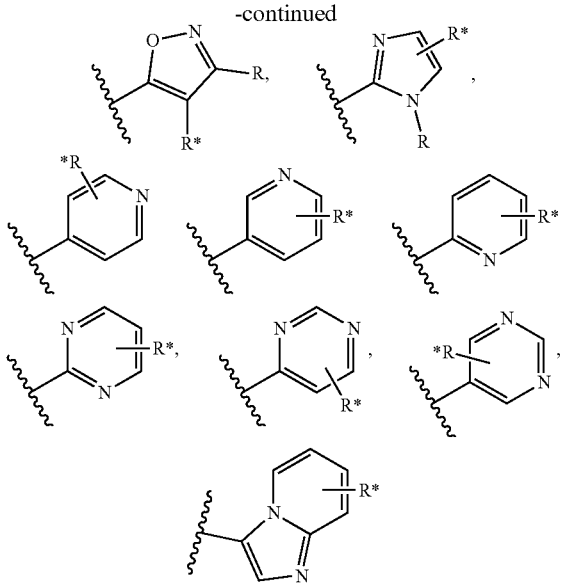

wherein R is H, alkyl, substituted alkyl, halogen, cyano, alkoxy, substituted alkoxy; and R* is one or more optional substituents selected from alkyl, substituted alkyl, halogen, hydroxy, cyano, alkoxy, and substituted alkoxy.

20. The compound of clause 19, wherein:
L is a covalent bond, C1-C6 alkyl or substituted C1-C6 alkyl;
$R^7$ is hydroxyl, alkoxy, substituted alkoxy, OCOR', OCONR'R", where R' and R" are independently $R^5$, aryl, substituted aryl, alkyl or cydoalkyl, optionally further substituted with 1-6 fluoros, or R' and R" together with the connected N form a heterocycle or substituted heterocycle;
$R^6$ and $R^9$ are independently fluoro or H, wherein at least one of $R^6$ and $R^9$ is fluoro; and
$R^5$ and $R^8$ are hydrogen.

21. The compound of clause 19, wherein the compound is of Formula (III) and L is a covalent bond, C1-C6 alkyl or substituted C1-C6 alkyl.

22. The compound of clause 21, wherein the compound has the formula:

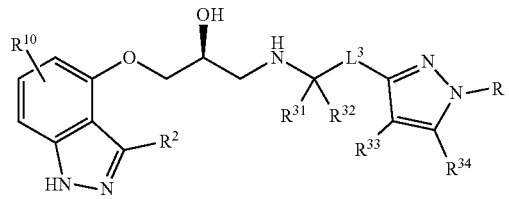

wherein:
$R^{33}$ and $R^{34}$ are independently selected from H, alkyl, substituted alkyl, halogen, hydroxy, cyano, alkoxy, and substituted alkoxy;
$R^{31}$ and $R^{32}$ are independently selected from H, deuterium, C1-C6 alkyl, substituted C1-C6 alkyl;
$R^2$ is a C1-C6 alkyl linker or a substituted C1-C6 alkyl linker; and
$L^3$ is a covalent bond, a C1-C5 alkyl linker or a substituted C1-C5 alkyl linker.

21. The compounds of clause 20, where the compound has the structure:

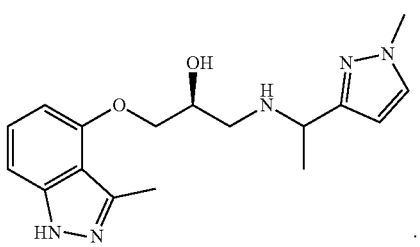 [SMILES: Cc1n[nH]c2cccc(OC[C@@H](O)CNC(C)c3ccn(C)n3)c12]

22. The compound of any one of clauses 1-20, wherein the linker L or L¹ is selected from: a covalent bond, —CH₂—, —(CH₂)$_n$—, —(CR₂)$_n$—, —(CH₂)$_n$—O—, —(CR₂)$_n$—O—(CR₂)$_m$—, —(CH₂CH₂O)$_p$—(CH₂)$_m$—, —(CH₂CH₂O)$_p$—, —(CR₂)$_n$—CO—, —(CR₂)$_n$—O—(CH₂)$_m$CO—, —(CH₂CH₂O)$_p$—(CH₂)$_m$—CO—, —(CR₂)$_n$—NHCO—, —(CR₂)$_n$—O—(CH₂)$_m$—NHCO— and —(CH₂CH₂O)$_p$—(CH₂)$_m$—NHCO—, wherein each R is independently H, C1-C6 alkyl or C1-C6 substituted alkyl, n is an integer from 1-6 and m and p are each independently an integer from 1-6.

23. The compound of any one of clauses 1-22, wherein the compound is a compound of Table 1.

24. The compound of clause 1, wherein the compound has one of the following structures:

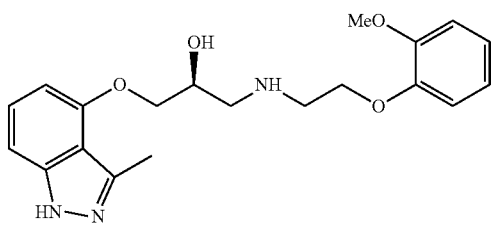

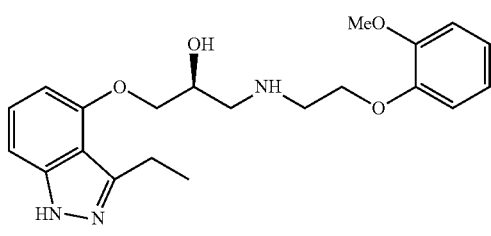

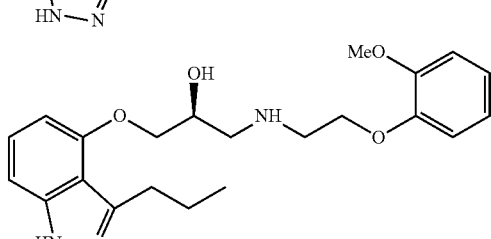

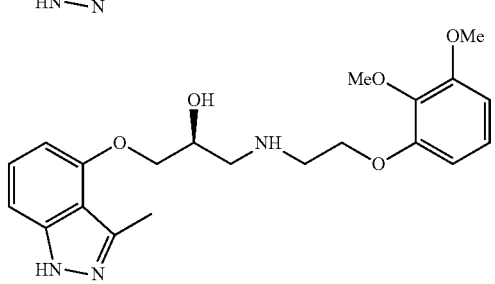

-continued

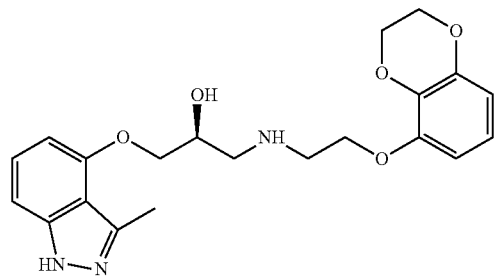

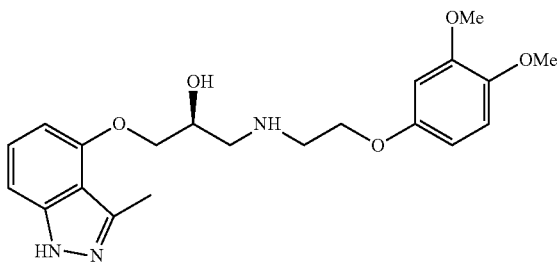

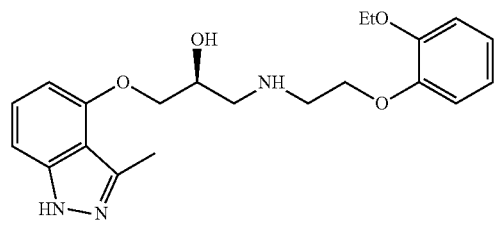

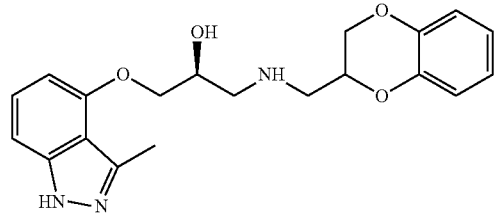

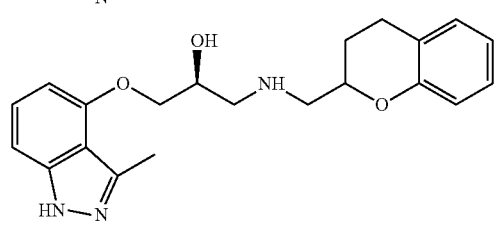

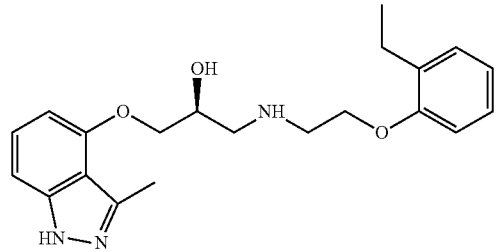

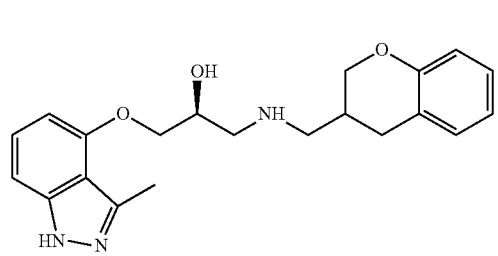

-continued

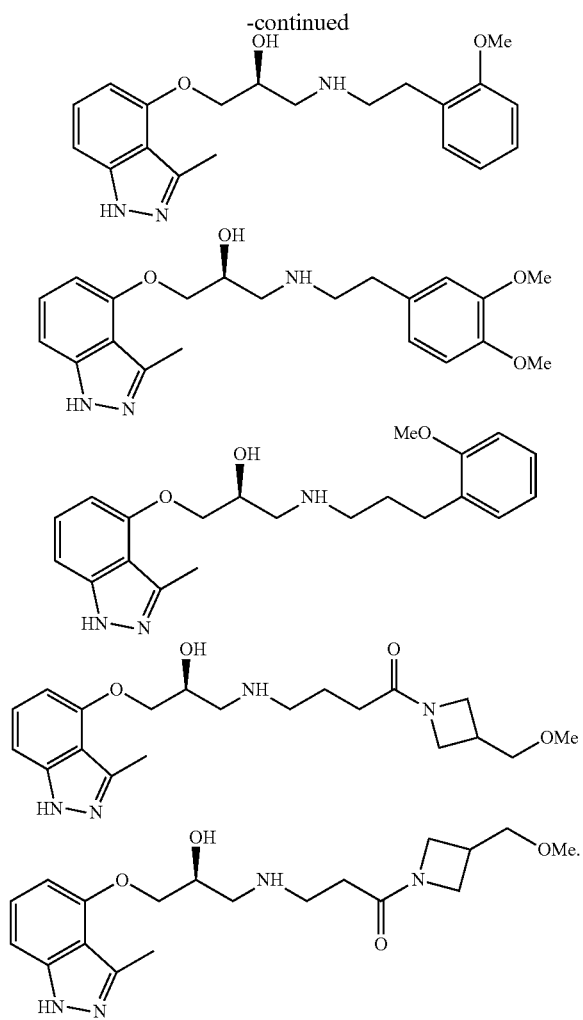

25. The compound of clause 1, wherein the compound has one of the following structures:

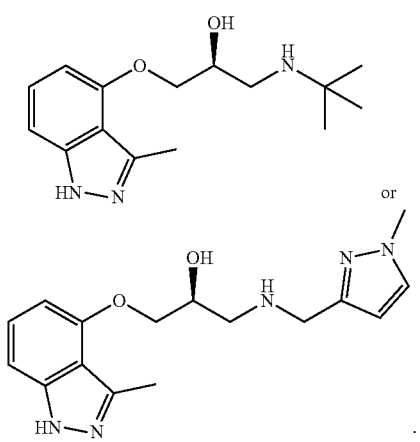

26. A pharmaceutical composition comprising: the compound of any one of clauses 1-25 or a pharmaceutically acceptable salt thereof; and a pharmaceutically acceptable excipient.

27. A method of modulating an adrenergic receptor, the method comprising: contacting a sample comprising the adrenergic receptor with an adrenergic receptor modulating compound of any one of clauses 1-23 or a pharmaceutical composition of clause 24.

28. The method of clause 27, wherein the compound is an agonist of the adrenergic receptor.

29. The method of clause 27, wherein the compound is a partial agonist of the adrenergic receptor.

30. The method of clause 27, wherein the compound is an antagonist of the adrenergic receptor.

31. The method of any one of clauses 27-30, wherein the adrenergic receptor is a β1-adrenergic receptor.

32. The method of clause 31, wherein the compound is selective for the β1-adrenergic receptor over a β2-adrenergic receptor.

33. The method of clause 31 or 32, wherein the compound is selective for the β1-adrenergic receptor over a β3-adrenergic receptor.

34. The method of any one of clauses 27-30, wherein the adrenergic receptor is a β2-adrenergic receptor.

35. The method of clause 34, wherein the compound is selective for the β2-adrenergic receptor over a β1-adrenergic receptor.

36. The method of any one of clauses 27-35, wherein the sample comprises a cell and modulating the adrenergic receptor modulates a physiological process in the cell.

37. The method of clause 36, wherein the physiological process is implicated in cardiac function.

38. The method of clause 36, wherein the physiological process is implicated in cognitive function.

39. The method of clause 36, wherein a cAMP pathway is activated in the cell.

40. The method of clause 36, wherein an inflammatory pathway is inhibited in the cell.

41. The method of clause 36, wherein TNF-alpha is inhibited in the cell.

42. The method of clause 36, wherein the cells are inflammatory cells and the function of the cells is regulated.

43. The method of clause 36, wherein a beta-arrestin pathway is not modulated in the cell.

44. The method of clause 36, wherein the cell is a neuron and modulating the adrenergic receptor enhances neurogenesis.

45. A method of treating a subject for a disease or condition associated with an adrenergic receptor, the method comprising: administering to the subject a pharmaceutical composition comprising a therapeutically effective amount of the adrenergic receptor modulating compound of any one of clauses 1-23, or a pharmaceutically acceptable salt thereof, or a pharmaceutical composition of clause 24.

46. The method of clause 45, wherein the disease or condition is a neurodegenerative disease or condition.

47. The method of clause 46, wherein the neurodegenerative condition is Alzheimer's Disease.

48. The method of any one of clauses 45-47, wherein Abeta-induced long-term potentiation (LTP) impairment is modulated.

49. The method of any one of clauses 45-48, wherein spatial working memory of the subject is improved by agonist stimulation of β1-adrenoreceptors.

50. The method of clause 45, wherein the disease or condition is a cardiac disease or condition.

51. The method of clause 45, wherein the disease or condition is selected from cancer, an inflammatory disorder, a neuropsychiatric disorder, a neurodevelopmental disorders (e.g., Down's syndrome or Autism), a respiratory disorder, memory impairment, depression, Stroke, Ischemic brain or tissue injury and cancer.

52. The method of any one of clauses 45-51, further comprising administering to the subject a a therapeutically effective amount of a second active agent.
53. The method of clause 51, wherein the second active agent is a cholinesterase inhibitor or a NMDA receptor modulator
54. The method of clause 53, wherein the second active agent is selected from Donepezil, Aricept, Galantamine, Razadyne, Memantine, Namenda, Rivastigmine, Exelon, Tacrine and Cognex.
55. A method of modulating an inflammatory pathway in a cell, the method comprising:
contacting a cell with a selective adrenergic receptor modulating compound to selectively activate a cAMP pathway over a beta-arrestin pathway in the cell thereby modulating TNF-alpha in the cell.
56. The method of clause 55, wherein modulating an inflammatory pathway in a cell comprises modulating production of TNF-alpha in the cell.
57. The method of clause 55, wherein the compound is a partial agonist of the β1-adrenergic receptor.
58. The method of clause 55, wherein the compound is an antagonist of the β1-adrenergic receptor.
59. The method of any one of clauses 55-58, wherein the compound is selective for the β1-adrenergic receptor over a β2-adrenergic receptor.
60. The method of any one of clauses 55-59, wherein the compound is selective for the β1-adrenergic receptor over a β3-adrenergic receptor.
61. The method of any one of clauses 55-56, wherein the compound is selective for the β2-adrenergic receptor over a β1-adrenergic receptor.
62. The method of any one of clauses 55-61, wherein an inflammatory pathway is inhibited in the cell.
63. The method of clause 62, wherein the cell is an inflammatory cell and the function of the cell is regulated.
64. The method of any one of clauses 55-63, wherein the cell is in vitro.
65. The method of any one of clauses 55-63, wherein the cell is in vivo.
66. The method of clause 65, wherein the method comprises treating a subject for an inflammatory condition and the contacting comprises administering (e.g., oral, dermal, intranasal administration) the β1-selective adrenergic receptor modulating compound to a subject in need thereof.
67. The method of clause 65, wherein the compound penetrates the blood brain barrier of the subject after administration.
68. The method of clause 66, wherein the inflammatory condition is psoriasis.
69. The method of any one of clauses 55-68, wherein the compound is an adrenergic receptor binding compound of any one of clauses 1-25 or a pharmaceutical composition of clause 26.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the following.

What is claimed is:
1. A compound having the structure of formula:

or a prodrug, solvate, hydrate, or a pharmaceutically acceptable salt thereof, wherein:
R is selected from H, alkyl, substituted alkyl, halogen, cyano, alkoxy, and substituted alkoxy;
$R^{10}$ is one or more substituents independently selected from H, alkyl, substituted alkyl, halogen, hydroxyl, cyano, alkoxyl, substituted alkoxy, OCOR', and OCONR'R", wherein R' and R" are each independently H, aryl, substituted aryl, alkyl or cycloalkyl, optionally further substituted with 1-6 fluoros, or R' and R" together with the connected N form a heterocycle or substituted heterocycle;
$R^{33}$ and $R^{34}$ are independently selected from H, alkyl, substituted alkyl, halogen, hydroxy, cyano, alkoxy, and substituted alkoxy;
$R^{31}$ and $R^{32}$ are independently selected from H, deuterium, C1-C6 alkyl, substituted C1-C6 alkyl;
$R^2$ is selected from H, an alkyl and a substituted alkyl; and
$L^3$ is a covalent bond, a C1-C5 alkyl linker or a substituted C1-C5 alkyl linker.
2. A compound having the structure:

3. A pharmaceutical composition comprising:
the compound of claim 1 or 2 or a pharmaceutically acceptable salt thereof; and
a pharmaceutically acceptable excipient.

4. A method of modulating an adrenergic receptor, the method comprising: contacting a sample comprising the adrenergic receptor with an adrenergic receptor modulating compound of claim 1.

5. The method of claim 4, wherein the adrenergic receptor is β1-adrenergic receptor.

6. The method of claim 4, wherein the adrenergic receptor is a β2-adrenergic receptor.

7. The method of claim 4, wherein the sample comprises a cell and modulating the adrenergic receptor modulates a physiological process in the cell.

8. A method of ameliorating, suppressing or alleviating symptoms of a disease or condition associated with an adrenergic receptor in a subject comprising:
   administering to the subject a pharmaceutical composition comprising a therapeutically effective amount of the adrenergic receptor modulating compound of claim 1 or a pharmaceutically acceptable salt thereof.

9. The method of claim 8, wherein the disease or condition is a neurodegenerative disease or condition.

10. The method of claim 8, wherein the disease or condition is selected from an inflammatory disorder, a neuropsychiatric disorder, a neurodevelopmental disorders, a respiratory disorder, memory impairment, depression, stroke, ischemic brain or tissue injury and cancer.

11. The method of claim 8, further comprising administering to the subject a therapeutically effective amount of a second active agent.

* * * * *